United States Patent
Brown et al.

(10) Patent No.: US 10,329,278 B2
(45) Date of Patent: Jun. 25, 2019

(54) PHARMACEUTICAL COMPOUNDS

(71) Applicant: Heptares Therapeutics Limited, Cambridge (GB)

(72) Inventors: Giles Albert Brown, Cambridge (GB); Julie Elaine Cansfield, Cambridge (GB); Miles Stuart Congreve, Cambridge (GB); Benjamin Gerald Tehan, Cambridge (GB); Barry John Teobald, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

(21) Appl. No.: 16/010,831

(22) Filed: Jun. 18, 2018

(65) Prior Publication Data
US 2018/0362507 A1    Dec. 20, 2018

(30) Foreign Application Priority Data
Jun. 16, 2017    (GB) .................................. 1709652.0

(51) Int. Cl.
| | | |
|---|---|---|
| *C07D 403/04* | (2006.01) | |
| *A61P 25/28* | (2006.01) | |
| *C07D 401/14* | (2006.01) | |
| *C07D 401/08* | (2006.01) | |
| *C07D 403/14* | (2006.01) | |
| *C07D 417/14* | (2006.01) | |
| *C07D 491/107* | (2006.01) | |
| *C07D 498/08* | (2006.01) | |
| *A61P 25/02* | (2006.01) | |
| *A61P 25/18* | (2006.01) | |
| *C07D 413/14* | (2006.01) | |
| *C07D 451/02* | (2006.01) | |
| *C07D 451/14* | (2006.01) | |

(52) U.S. Cl.
CPC ............ *C07D 403/04* (2013.01); *A61P 25/02* (2018.01); *A61P 25/18* (2018.01); *A61P 25/28* (2018.01); *C07D 401/08* (2013.01); *C07D 401/14* (2013.01); *C07D 403/14* (2013.01); *C07D 413/14* (2013.01); *C07D 417/14* (2013.01); *C07D 451/02* (2013.01); *C07D 451/14* (2013.01); *C07D 491/107* (2013.01); *C07D 498/08* (2013.01)

(58) Field of Classification Search
CPC ............................... C07D 403/04; A61P 25/28
See application file for complete search history.

(56) References Cited

U.S. PATENT DOCUMENTS

| 8,476,289 B2* | 7/2013 | Freyne ................. C07D 401/14 514/275 |
| 9,670,183 B2* | 6/2017 | Brown ................. C07D 401/14 |
| 9,957,257 B2* | 5/2018 | Nirogi ................. C07D 405/14 |

FOREIGN PATENT DOCUMENTS

| WO | 2004/014853 A1 | 2/2004 |
| WO | 2014/045031 A1 | 3/2014 |
| WO | 2017/077292 A1 | 5/2017 |

OTHER PUBLICATIONS

Search Report GB1709652.0, dated Mar. 14, 2018.

* cited by examiner

*Primary Examiner* — Golam M Shameem
(74) *Attorney, Agent, or Firm* — McCarter & English, LLP; Steven G. Davis; Mei Bai

(57) ABSTRACT

This invention relates to compounds that are agonists of the muscarinic $M_1$ and/or $M_4$ receptor and which are useful in the treatment of diseases mediated by the muscarinic $M_1$ and $M_4$ receptors. Also provided are pharmaceutical compositions containing the compounds and the therapeutic uses of the compounds. Compounds provided are of formula

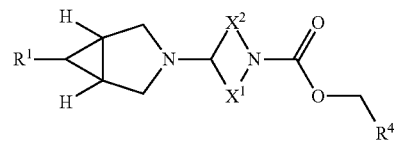

where $X^1$; $X^2$; $R^1$ and $R^4$ are as defined herein.

17 Claims, No Drawings

PHARMACEUTICAL COMPOUNDS

RELATED APPLICATION INFORMATION

This application claims priority from GB Application No.: 1709652.0, filed Jun. 16, 2017 in the United Kingdom. The entire contents of this applications are incorporated herein by reference in its entirety.

This invention relates to a class of novel 5,3 fused bicyclic compounds, their salts, pharmaceutical compositions containing them and their use in therapy of the human body. In particular, the invention is directed to a class of compounds, which are agonists of the muscarinic $M_1$ and/or $M_4$ receptors, and hence are useful in the treatment of Alzheimer's disease, schizophrenia, cognitive disorders and other diseases mediated by the muscarinic $M_1/M_4$ receptors, as well as the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which is also characterised by cognitive impairments, mAChR density is reduced in the pre-frontal cortex, hippocampus and caudate putamen of schizophrenic subjects (Dean et al., 2002 *Mol Psychiatry*). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (http://www.drugs.com/pro/donepezil.html; http://www.drugs.com/pro/rivastigmine.html).

Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidgenic and amyloidgenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 *Neuron*). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*). Muscarinic receptors have also been implicated in the neurobiology of addiction. The reinforcing effects of cocaine and other addictive substances are mediated by the mesolimbic dopamine system where behavioural and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore xanomeline has been demonstrated to block the effects of cocaine in these models.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 *Arch Neurol*). This compound was also assessed in a small Phase II study of schizophrenics and gave a significant reduction in positive and negative symptoms when compared to placebo control (Shekhar et al., 2008 *Am J Psych*). However, in all clinical studies xanomeline and other related mAChR agonists have displayed an unacceptable safety margin with respect to cholinergic side effects, including nausea, gastrointestinal pain, diarrhoea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 *Bioorg Med Chem Lett*; Johnson et al., 2010 *Bioorg Med Chem Lett*; Budzik et al., 2010 *ACS Med Chem Lett*). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

THE INVENTION

The present invention provides compounds having activity as muscarinic $M_1$ and/or $M_4$ receptor agonists. More particularly, the invention provides compounds that exhibit selectivity for the $M_1$ or $M_4$ receptor relative to the $M_2$ and $M_3$ receptor subtypes.

Accordingly, in a first embodiment (Embodiment 1.1), the invention provides a compound of the formula (1):

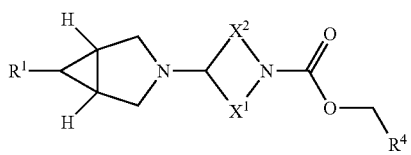

(1)

or a salt thereof, wherein:

$X^1$ and $X^2$ are saturated hydrocarbon groups which together contain a total of five to nine carbon atoms and zero or one oxygen atoms and which link together such that the moiety:

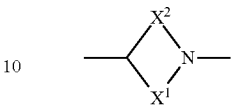

forms a monocyclic or bicyclic ring system optionally substituted with one or more fluorine atoms;

$R^1$ is selected from $OR^5$; $NR^5R^6$; $COR^5$; $COOR^5$; $CONR^5R^6$; $CONR^5OR^6$; $C(=NR^5)R^6$; $C(=NOR^5)R^6$; $OCOR^5$; $NR^7COR^5$; $NR^7CONR^5R^6$; $NR^7COOR^5$; $OCONR^5R^6$; $CH_2OR^5$; $CH_2NR^5R^6$; $CH_2COR^5$; $CH_2COOR^5$; $CH_2CONR^5R^6$; $CH_2CONR^5OR^6$; $CH_2C(=NR^5)R^6$; $CH_2C(=NOR^5)R^6$; $CH_2OCOR^5$; $CH_2NR^7COR^5$; $CH_2NR^7CONR^5R^6$; $CH_2NR^7COOR^5$; $CH_2OCONR^5R^6$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 4, 5- or 6-membered ring containing 0, 1, 2 or 3 heteroatoms selected from O, N and S and oxidized forms thereof;

$R^4$ is H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof; and $R^5$, $R^6$ and $R^7$ are the same or different and each is independently selected from hydrogen, a non-aromatic $C_{1-6}$ hydrocarbon group optionally substituted with one or more fluorine atoms or optionally substituted with a 4, 5- or 6-membered ring containing 0, 1, 2 or 3 heteroatoms selected from O, N and S and oxidized forms thereof, or $R^5$ and $R^6$ can be joined together to form an optionally substituted monocyclic or bicyclic ring containing 0, 1, 2 or 3 heteroatoms selected from O, N and S and oxidized forms thereof.

1.2 A compound according to Embodiment 1.1 wherein $R^1$ is $OR^5$; $NR^5R^6$; $COR^5$; $COOR^5$; $CONR^5R^6$; $C(=NR^5)R^6$; $CONR^5OR^6$; $C(=NOR^5)R^6$; $NR^7COR^5$; $CH_2OR^5$; $CH_2NR^5R^6$; $CH_2COR^5$; $CH_2COOR^5$; $CH_2CONR^5R^6$; $CH_2CONR^5OR^6$; $CH_2C(=NR^5)R^6$; $CH_2C(=NOR^5)R^6$; $CH_2OCOR^5$; $CH_2NR^7COR^5$; a $C_{1-6}$ non-aromatic hydrocarbon group which is optionally substituted with one to six fluorine atoms; and an optionally substituted 4-, 5- or 6-membered ring containing 0, 1, 2 or 3 heteroatoms selected from O, N and S and oxidized forms thereof.

1.3 A compound according to Embodiment 1.1 wherein $R^1$ is selected from $OR^5$; $NR^5R^6$; $COOR^5$; $CONR^5R^6$; $CONR^5OR^6$; $C(=NOR^5)R^6$; $CH_2NR^7COR^5$; a $C_{1-3}$ alkyl group which is optionally substituted with one to three fluorine atoms; and an optionally substituted 5- or 6-membered ring containing 1, or 2 heteroatoms selected from O, N and S and oxidized forms thereof.

1.4 A compound according to Embodiment 1.1 wherein $R^1$ is selected from $COOR^5$; $CONR^5R^6$; $CONR^5OR^6$; $C(=NOR^5)R^6$; and an optionally substituted 5-membered ring containing 1, or 2 heteroatoms selected from O, N and S and oxidized forms thereof.

1.5 A compound according to Embodiment 1.1 wherein $R^1$ is a $C_{1-6}$ non-aromatic hydrocarbon group containing 0, 1 or 2 carbon-carbon multiple bonds, wherein the hydrocarbon group is optionally substituted with one to six fluorine atoms and wherein one or two, but not all, carbon atoms of the hydrocarbon group may optionally be replaced by a heteroatom selected from O, N and S and oxidised forms thereof.

1.6 A compound according to Embodiment 1.1 wherein $R^1$ is $COOR^5$ or $CONR^5R^6CONR^5OR^6$.

1.7 A compound according to Embodiment 1.1 wherein $R^1$ is an optionally substituted 4, 5- or 6-membered ring containing 0, 1, 2 or 3 heteroatoms selected from O, N and S and oxidized forms thereof.

1.8 A compound according to Embodiment 1.1 wherein $R^1$ is $OR^5$ or $NR^5R^6$.

1.9 A compound according to Embodiment 1.1 wherein $R^1$ is $CH_2OR^5$, $CH_2NR^5R^6$ or $CH_2NR^7COR^5$.

1.10 A compound according to Embodiment 1.1 wherein $R^1$ is $C(=NR^5)R^6$ or $C(=NOR^5)R^6$;

1.11 A compound according to any one of Embodiments 1.1 to 1.10 wherein $R^1$ is selected from:

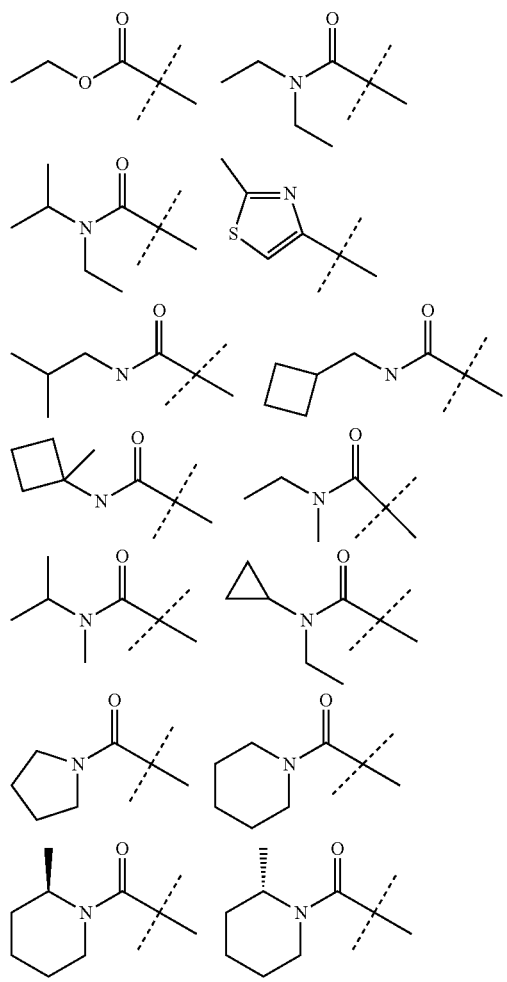

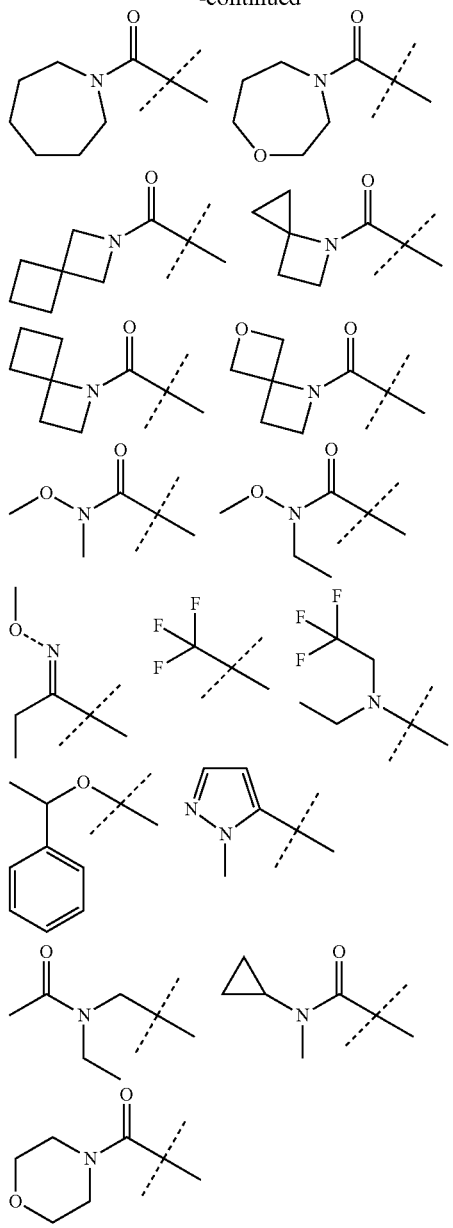

1.12 A compound according to any one of Embodiments 1.1 to 1.11 wherein $R^4$ is H or an acyclic $C_{1-4}$ hydrocarbon group optionally substituted with one or more fluorine atoms.

1.13 A compound according to Embodiment 1.12 wherein $R^4$ is H or an acyclic $C_{1-3}$ hydrocarbon group optionally substituted with one or more fluorine atoms.

1.14 A compound according to Embodiment 1.13 wherein $R^4$ is H or a $C_1 0.3$ alkyl group or a $C_{1-2}$ alkynyl group.

1.15 A compound according to Embodiment 1.14 wherein $R^4$ is selected from H, methyl, fluoromethyl, ethyl, ethynyl and 1-propynyl.

1.16 A compound according to Embodiment 1.15 wherein $R^4$ is methyl.

1.17 A compound according to Embodiment 1.15 wherein $R^4$ is H.

1.18 A compound according to any one of Embodiments 1.1 to 1.17 wherein the bicyclic ring system formed by the moiety:

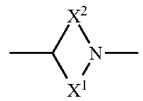

is selected from:
(a) piperidine;
(b) azepane;
(c) an azabicyclo-heptane, azabicyclo-octane or azabicyclo-nonane ring system having zero or one oxygen atoms;
(d) a 2-aza-spiro[3.3]heptane, 2-aza-spiro[3.4]octane or a 6-aza-spiro[3.4]octane ring system; and
(e) a cyclopentanopyrrolidine ring system.

1.19 A compound according to any one of Embodiments 1.1 to 1.18 wherein $X^1$ and $X^2$ together contain four to seven carbon atoms and zero or one oxygen atoms.

1.20 A compound according to any one of Embodiments 1.1 to 1.19 wherein the bicyclic ring system formed by the moiety:

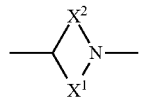

is a bridged bicyclic ring system.

1.21 A compound according to Embodiment 1.20 wherein the bridged bicyclic ring system is an azabicyclo-heptane, azabicyclo-octane or azabicyclo-nonane ring system having zero or one oxygen atoms.

1.22 A compound according to Embodiment 1.21 wherein the bridged bicyclic ring system is selected from an 2-azabicyclo[2.2.2]octane ring system, 3-aza-bicyclo[3.1.1]heptane ring system, 8-aza-bicyclo[3.2.1]octane ring system, a 9-aza-bicyclo[3.3.1]nonane ring system, a 9-aza-3-oxo-bicyclo[3.3.1]nonane ring system, a 3-aza-bicyclo[3.2.1]octane ring system and a 6-aza-bicyclo[3.2.1]octane ring system.

1.23 A compound according to any one of Embodiments 1.1 to 1.19 wherein the bicyclic ring system formed by the moiety:

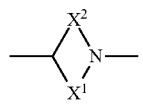

is a spirocyclic ring system.

1.24 A compound according to Embodiment 1.23 wherein the spirocyclic ring system is a 2-aza-spiro[3.3]heptane, 2-aza-spiro[3.4]octane or a 6-aza-spiro[3.4]octane ring system.

1.25 A compound according to any one of Embodiments 1.1 to 1.19 wherein the bicyclic ring system formed by the moiety:

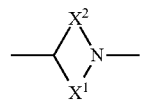

is a fused bicyclic ring system.

1.26 A compound according to Embodiment 1.25 wherein the fused bicyclic ring system is a cyclopentanopyrrolidine ring system.

1.27 A compound according to any one of Embodiments 1.1 to 1.26 wherein the bicyclic ring system formed by the moiety:

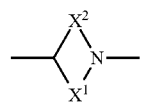

is selected from ring systems below:

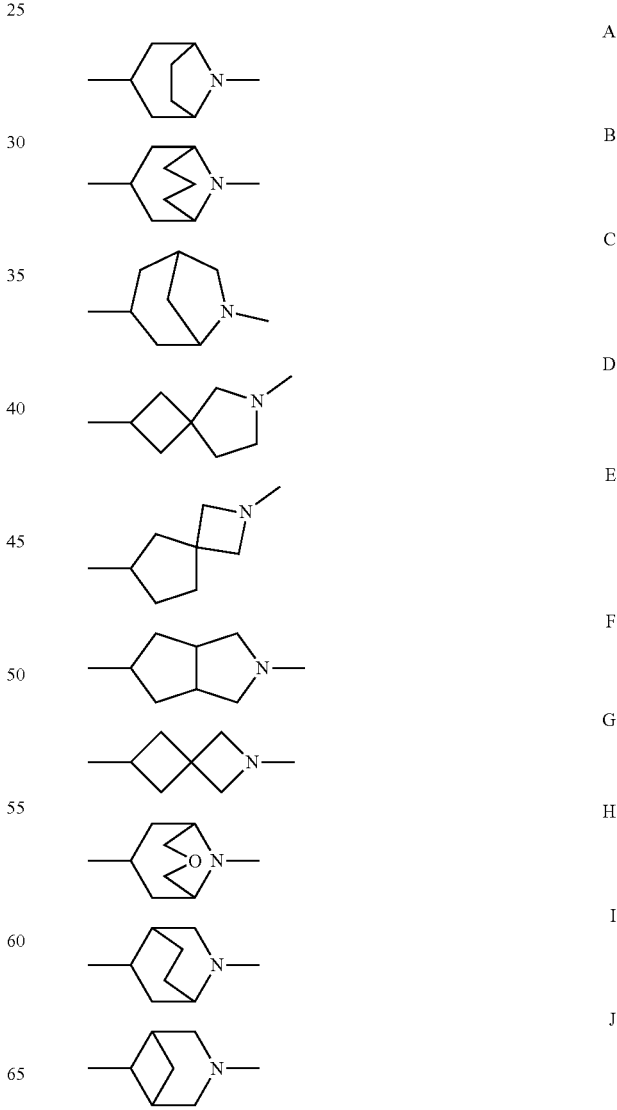

-continued

K 1.28 A compound according to Embodiment 1.1 having the formula (2):

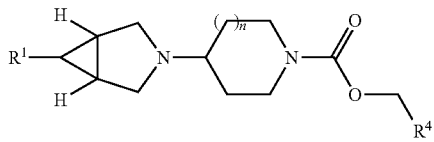

(2)

wherein:
n is 1 or 2; and
$R^1$ and $R^4$ are as defined in any one of Embodiments 1.1 to 1.17.

1.29 A compound according to Embodiment 1.1 having the formula (3):

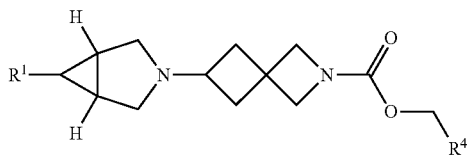

(3)

wherein:
$R^1$ and $R^4$ are as defined in any one of Embodiments 1.1 to 1.17.

1.30 A compound according to Embodiment 1.1 having the formula (4):

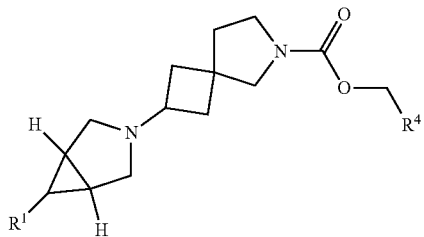

(4)

wherein:
$R^1$ and $R^4$ are as defined in any one of Embodiments 1.1 to 1.17.

1.31 A compound according to Embodiment 1.1 having the formula (5):

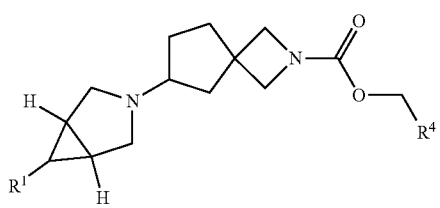

(5)

wherein:
$R^1$ and $R^4$ are as defined in any one of Embodiments 1.1 to 1.17.

1.32 A compound according to Embodiment 1.1 having the formula (6):

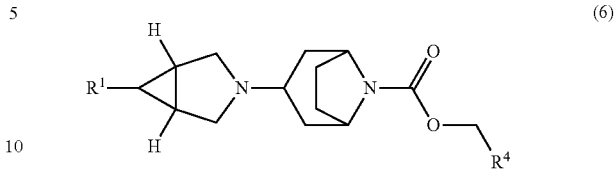

(6)

wherein:
$R^1$ and $R^4$ are as defined in any one of Embodiments 1.1 to 1.17.

1.33 A compound according to Embodiment 1.1 having the formula (7):

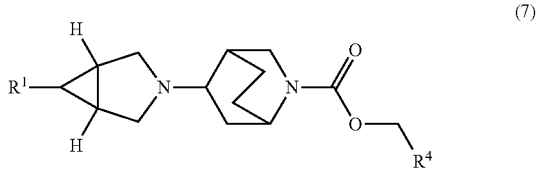

(7)

wherein:
$R^1$ and $R^4$ are as defined in any one of Embodiments 1.1 to 1.17.

1.34 A compound according to Embodiment 1.1 having the formula (8):

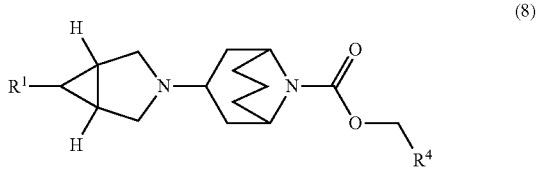

(8)

wherein:
$R^1$ and $R^4$ are as defined in any one of Embodiments 1.1 to 1.17.

1.35 A compound according to Embodiment 1.1 having the formula (9):

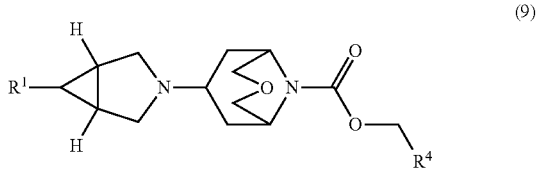

(9)

wherein:
$R^1$ and $R^4$ are as defined in any one of Embodiments 1.1 to 1.17.

1.36 A compound according to any one of Embodiments 1.1 to 1.35 wherein $R^5$ is selected from hydrogen, a non-aromatic $C_{1-6}$ hydrocarbon group optionally substituted with one or more fluorine atoms or optionally substituted with a 4, 5- or 6-membered ring containing 0, 1, 2 or 3 heteroatoms selected from O, N and S and oxidized forms thereof, or $R^5$ and $R^6$ can be joined together to form an optionally substituted monocyclic or bicyclic ring containing 0, 1, 2 or 3 heteroatoms selected from O, N and S and oxidized forms thereof.

1.37 A compound according to any one of Embodiments 1.1 to 1.36 wherein $R^6$ is selected from hydrogen, a non-aromatic $C_{1-6}$ hydrocarbon group optionally substituted with one or more fluorine atoms or optionally substituted with a 4-, 5- or 6-membered ring containing 0, 1, 2 or 3 heteroatoms selected from O, N and S and oxidized forms thereof, or $R^5$ and $R^6$ can be joined together to form an optionally substituted monocyclic or bicyclic ring containing 0, 1, 2 or 3 heteroatoms selected from O, N and S and oxidized forms thereof.

1.38 A compound according to any one of Embodiments 1.1 to 1.37 wherein $R^1$ is COOR$^5$ wherein $R^5$ is a non-aromatic $C_{1-6}$ hydrocarbon group or $R^1$ is CONR$^5$R$^6$ wherein $R^5$ is a non-aromatic $C_{1-6}$ hydrocarbon group and $R^6$ is selected from hydrogen and a non-aromatic $C_{1-6}$ hydrocarbon group, or $R^1$ is CONR$^5$R$^6$ and $R^5$ and $R^6$ are joined together to form an optionally substituted monocyclic or bicyclic ring containing. 0, 1, 2 or 3 heteroatoms selected from O, N and S and oxidized forms thereof, or $R^1$ is CONR$^5$OR$^6$ wherein $R^5$ is a non-aromatic $C_{1-6}$ hydrocarbon group and $R^6$ is a non-aromatic $C_{1-6}$ hydrocarbon group.

1.39 A compound according to any one of Embodiments 1.1 to 1.38 wherein $R^1$ is selected from NR$^5$R$^6$; CONR$^5$R$^6$; and CH$_2$NR$^5$R$^6$; and $R^5$ and $R^6$ are joined together to form an optionally substituted monocyclic or bicyclic ring containing. 0, 1, 2 or 3 heteroatoms selected from O, N and S and oxidized forms thereof.

1.40 A compound according to Embodiment 1.1 which is as defined in any one of Examples 1-1 to 12-1.

1.41 A compound according to any one of Embodiments 1.1 to 1.40 having a molecular weight of less than 550, for example less than 500, or less than 450.

1.42 A compound according to any one of Embodiments 1.1 to 1.41 which is in the form of a salt.

1.43 A compound according to Embodiment 1.42 wherein the salt is an acid addition salt.

1.44 A compound according to Embodiment 1.42 or Embodiment 1.43 wherein the salt is a pharmaceutically acceptable salt.

DEFINITIONS

In this application, the following definitions apply, unless indicated otherwise.

The term "treatment", in relation to the uses of the compounds of the formulas (1) to (9), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" (as in "$C_{1-5}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" and "cycloalkenyl" are used in their conventional sense (e.g. as defined in the IUPAC Gold Book) unless indicated otherwise.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^4$, $R^5$ and $R^6$ above, where stated, one or two but not all, carbon atoms of the non-aromatic hydrocarbon group may optionally be replaced by a heteroatom selected from O, N and S and oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a CH$_2$ group by oxygen (valency of two) will mean that the resulting molecule will contain two less hydrogen atoms and replacement of a carbon atom (valency of four) in a CH$_2$ group by nitrogen (valency of three) will mean that the resulting molecule will contain one less hydrogen atom.

Examples of a heteroatom replacements for carbon atoms include replacement of a carbon atom in a —CH$_2$—CH$_2$—CH$_2$— chain with oxygen or sulfur to give an ether —CH$_2$—O—CH$_2$— or thioether —CH$_2$—S—CH$_2$—, replacement of a carbon atom in a group CH$_2$—C≡C—H with nitrogen to give a nitrile (cyano) group CH$_2$—C≡N, replacement of a carbon atom in a group —CH$_2$—CH$_2$—CH$_2$— with C=O to give a ketone —CH$_2$—C(O)—CH$_2$—, replacement of a carbon atom in a group —CH$_2$—CH$_2$—CH$_2$— with S=O or SO$_2$ to give a sulfoxide —CH$_2$—S(O)—CH$_2$— or sulfone —CH$_2$—S(O)$_2$—CH$_2$—, replacement of a carbon atom in a —CH$_2$—CH$_2$—CH$_2$-chain with C(O)NH to give an amide —CH$_2$—CH$_2$—C(O)—NH—, replacement of a carbon atom in a —CH$_2$—CH$_2$—CH$_2$— chain with nitrogen to give an amine —CH$_2$—NH—CH$_2$—, and replacement of a carbon atom in a —CH$_2$—CH$_2$—CH$_2$— chain with C(O)O to give an ester (or carboxylic acid) —CH$_2$—CH$_2$—C(O)—O—. In each such replacement, at least one carbon atom of the hydrocarbon group must remain.

Salts

Many compounds of the formulas (1) to (9) can exist in the form of salts, for example acid addition salts or, in certain cases salts of organic and inorganic bases such as carboxylate, sulfonate and phosphate salts. All such salts are within the scope of this invention, and references to compounds of the formulas (1) to (9) include the salt forms of the compounds as defined in Embodiments 1.42 to 1.44.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.43) may be formed with a wide variety of acids, both inorganic and organic. Examples of acid addition salts falling within Embodiment 1.43 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) contain an amine function, these may form quaternary ammonium salts (Embodiment 1.72), for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci*., Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.73), the invention provides a geometric isomer of a compound according to any one of Embodiments 1.1 to 1.72.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.74) the invention provides a compound according to any one of Embodiments 1.1 to 1.73 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.75), the invention provides compositions containing a compound according to Embodiment 1.74 having one or more chiral centres, wherein at least 55% (e.g. at least 60%, 65%, 70%, 75%, 80%, 85%, 90% or 95%) of the compound of Embodiment 1.73 is present as a single optical isomer (e.g. enantiomer or diastereoisomer).

In one general embodiment (Embodiment 1.76), 99% or more (e.g. substantially all) of the total amount of the compound (or compound for use) of Embodiment 1.74 is present as a single optical isomer.

For example, in one embodiment (Embodiment 1.77) the compound is present as a single enantiomer.

In another embodiment (Embodiment 1.78), the compound is present as a single diastereoisomer.

The invention also provides mixtures of optical isomers, which may be racemic or non-racemic. Thus, the invention provides:

1.79 A compound according to Embodiment 1.74 which is in the form of a racemic mixture of optical isomers.

1.80 A compound according to Embodiment 1.74 which is in the form of a non-racemic mixture of optical isomers.

Isotopes

The compounds of the invention as defined in any one of Embodiments 1.1 to 1.80 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.81), the compound of any one of Embodiments 1.1 to 1.80 contains no radioactive isotopes. Such compounds are preferred for therapeutic use. In another embodiment (Embodiment 1.82), however, the compound of any one of Embodiments 1.1 to 1.80 may contain one or more radioisotopes. Compounds containing such radioisotopes may be useful in a diagnostic context.

Solvates

Compounds of the formula (1) as defined in any one of Embodiments 1.1 to 1.82 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.83 and 1.84, the invention provides:

1.83 A compound according to any one of Embodiments 1.1 to 1.82 in the form of a solvate.

1.84 A compound according to Embodiment 1.83 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.85), the invention provides a compound as defined in any one of Embodiments 1.1 to 1.83 in an anhydrous form (e.g. anhydrous crystalline form).

Crystalline and Amorphous Forms

The compounds of any one of Embodiments 1.1 to 1.83 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.86 A compound according to any one of Embodiments 1.1 to 1.85 in a crystalline form.

1.80 A compound according to any one of Embodiments 1.1 to 1.85 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.88 A compound according to any one of Embodiments 1.1 to 1.85 which is in an amorphous form.

Prodrugs

The compounds of the formula (1) as defined in any one of Embodiments 1.1 to 1.88 may be presented in the form of a pro-drug. By "prodrugs" is meant for example any compound that is converted in vivo into a biologically active compound of the formula (1), as defined in any one of Embodiments 1.1 to 1.88.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.89), the invention provides a pro-drug of a compound as defined in any one of Embodiments 1.1 to 1.82 wherein the compound contains a functional group which is convertible under physiological conditions to form a hydroxyl group or amino group.

Complexes and Clathrates

Also encompassed by formula (1) in Embodiments 1.1 to 1.89 are complexes (e.g. inclusion complexes or clathrates with compounds such as cyclodextrins, or complexes with metals) of the compounds of Embodiments 1.1 to 1.89.

Accordingly, in another embodiment (Embodiment 1.90), the invention provides a compound according to any one of Embodiments 1.1 to 1.89 in the form of a complex or clathrate.

Biological Activity and Therapeutic Uses

The compounds of the present invention have activity as muscarinic $M_1$ and/or $M_4$ receptor agonists. The muscarinic activity of the compounds can be determined using the Phospho-ERK1/2 assay described in Example A below.

A significant advantage of compounds of the invention is that they are highly selective for the $M_1$ and/or $M_4$ receptors relative to the $M_2$ and $M_3$ receptor subtypes. Compounds of the invention are neither agonists nor antagonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ and/or $M_4$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention have activity at both the $M_1$ and $M_4$ receptors, and some have activity at the $M_4$ receptor.

Accordingly, in Embodiments 2.1 to 2.15, the invention provides:

2.1 A compound according to any one of Embodiments 1.1 to 1.90 for use in medicine.

2.2 A compound according to any one of Embodiments 1.1 to 1.90 for use as a muscarinic $M_1$ and/or $M_4$ receptor agonist.

2.3 A compound according to any one of Embodiments 1.1 to 1.90 which is a muscarinic $M_1$ receptor agonist having a $pEC_{50}$ greater than 6.9 and an $E_{max}$ of at least 80 against the $M_1$ receptor in the assay of Example A herein or an assay substantially similar thereto.

2.4 A compound according to Embodiment 2.3 which is a muscarinic $M_1$ receptor agonist having a $pEC_{50}$ greater than 7.0.

2.5 A compound according to Embodiment 2.3 or Embodiment 2.4 having an $E_{max}$ of at least 90 against the $M_1$ receptor.

2.6 A compound according to any one of Embodiments 1.1 to 1.90 which is a muscarinic $M_1$ and $M_4$ receptor agonist having a $pEC_{50}$ in the range from 6.0 to 8.5 and an $E_{max}$ of at least 70 against the muscarinic $M_1$ and $M_4$ receptors in the assay of Example A herein or an assay substantially similar thereto.

2.7 A compound according to any one of Embodiments 1.1 to 1.90 which is a muscarinic $M_4$ receptor agonist having a $pEC_{50}$ greater than 7.0.

2.8 A compound according to Embodiment 2.6 or Embodiment 2.7 having an $E_{max}$ of at least 90 against the $M_4$ receptor.

2.9 A compound according to any one of Embodiments 1.1 to 1.90 which is a muscarinic $M_4$ receptor agonist having a $pEC_{50}$ in the range from 6.0 to 8.5 and an $E_{max}$ of at least 70 against the muscarinic $M_4$ receptor in the assay of Example A herein or an assay substantially similar thereto.

2.10 A compound according to any one of Embodiments 2.3 to 2.9 which is selective for the $M_1$ and $M_4$ receptor compared to the muscarinic $M_2$ and $M_3$ receptors.

2.11 A compound according to Embodiment 2.9 which is selective for the $M_4$ receptor compared to the muscarinic $M_2$ and $M_3$ receptors.

2.12 A compound according to any one of Embodiments 2.3 to 2.5 which is selective for the $M_1$ receptor compared to the muscarinic $M_2$, $M_3$ and $M_4$ receptors.

2.13 A compound according to any one of Embodiments 2.7 or 2.9 which is selective for the $M_4$ receptor compared to the muscarinic $M_1$, $M_2$ and $M_3$ receptors.

2.14 A compound according to any one of Embodiments 2.3 to 2.13 which has a $pEC_{50}$ of less than 5 and an $E_{max}$ of less than 50 against the muscarinic $M_2$ and $M_3$ receptor subtypes.

2.15 A compound according to Embodiment 2.14 which has a $pEC_{50}$ of less than 4.7 and/or an $E_{max}$ of less than 30 against the muscarinic $M_2$ and $M_3$ receptor subtypes.

2.16 A compound according to any one of Embodiments 1.1 to 1.90 and Embodiments 2.3 to 2.15 for use in the treatment of a disease or condition mediated by the muscarinic $M_1$ and/or $M_4$ receptors.

By virtue of their muscarinic $M_1$ and/or $M_4$ receptor agonist activity, compounds of the invention can be used in the treatment of Alzheimer's disease, schizophrenia and other psychotic disorders, cognitive disorders and other diseases mediated by the muscarinic $M_1$ and/or $M_4$ receptor, and can also be used in the treatment of various types of pain.

Accordingly, in Embodiments 2.17 to 2.38, the invention provides:

2.17 A compound according to any one of Embodiments 1.1 to 1.90 for use in the treatment of a cognitive disorder or psychotic disorder.

2.18 A compound for use in according to Embodiment 2.17 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as multi-infarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, *cannabis*, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and and schizo-affective disorder.

2.19 A compound according to any one of Embodiments 1.1 to 1.90 for use in the treatment of Alzheimer's disease.

2.20 A compound according to any one of Embodiments 1.1 to 1.90 for use in the treatment of Schizophrenia.

2.21 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.90.

2.22 A method according to Embodiment 2.21 wherein the cognitive disorder comprises, arises from or is associated with a condition as defined in Embodiment 2.18.

2.23 A method according to Embodiment 2.22 wherein the cognitive disorder arises from or is associated with Alzheimer's disease.

2.24 A method according to Embodiment 2.22 wherein the cognitive disorder is Schizophrenia.

2.25 The use of a compound according to any one of Embodiments 1.1 to 1.90 for the manufacture of a medicament for the treatment of a cognitive disorder.

2.26 The use according to Embodiment 2.25 wherein the cognitive disorder comprises, arises from or is associated with a condition as defined in Embodiment 2.18.

2.27 The use according to Embodiment 2.26 wherein the cognitive disorder arises from or is associated with Alzheimer's disease.

2.28 The use according to Embodiment 2.26 wherein the cognitive disorder is Schizophrenia.

2.29 A compound according to any one of Embodiments 1.1 to 1.90 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.30 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.90.

2.31 A compound according to any one of Embodiments 1.1 to 1.90 for the treatment of peripheral disorders such as reduction of intra ocular pressure in Glaucoma and treatment of dry eyes and dry mouth including Sjogren's Syndrome.

2.32 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.90.

2.33 The use of a compound according to any one of Embodiments 1.1 to 1.90 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.34 The use of a compound according to any one of Embodiments 1.1 to 1.90 for the use in the treatment of skin lesions for example due to pemphigus vulgaris, dermatitis herpetiformis, pemphigoid and other blistering skin conditions.

2.35 The use of a compound according to any one of Embodiments 1.1 to 1.90 for the use in treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhea.

2.36 The use of a compound according to any one of Embodiments 1.1 to 1.90 for the use in in the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

2.37 The use of a compound according to any one of Embodiments 1.1 to 1.90 for the treatment of addiction.

2.38 The use of a compound according to any one of Embodiments 1.1 to 1.90 for the treatment of movement disorders such as Parkinson's disease, ADHD, Huntingdon's disease, tourette's syndrome and other syndromes associated with dopaminergic dysfunction as an underlying pathogenetic factor driving disease.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.90, which process comprises:

(A) the reaction of a compound of the formula (10):

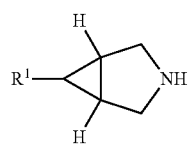

(10)

with a compound of the formula (11):

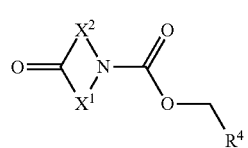

(11)

under reductive amination conditions; wherein $R^1$, $R^4$, $X^1$ and $X^2$ are as defined in any one of Embodiments 1.1 to 1.44; or B) the reaction of a compound of the formula (12):

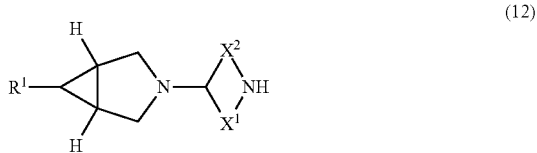

with a compound of the formula $Cl\text{—}C(\text{=}O)\text{—}O\text{—}CH_2\text{—}R^4$; wherein $R^1$, $R^4$, $X^1$ and $X^2$ are as defined in any one of Embodiments 1.1 to 1.44; or (C) when it is required to prepare a compound of formula (1) wherein $R^1$ comprises $CONR^5R^6$:

the reaction of a compound of the formula (13):

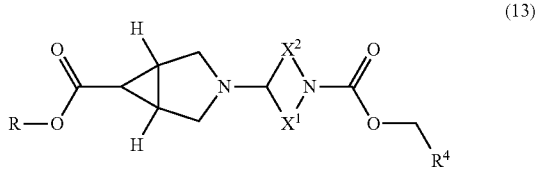

with an amine of the formula $R^5R^6NH$; wherein R represents a suitable group such as methyl- or ethyl- and $R^4$, $R^5$, $R^6$, $X^1$ and $X^2$ are as defined in any one of Embodiments 1.1 to 1.44; or (D) when it is required to prepare a compound of formula (1) wherein $R^1$ comprises $CONR^5R^6$:

the reaction of a compound of the formula (14):

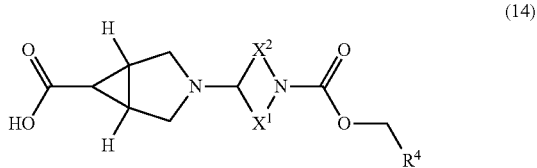

with an amine of the formula $R^5R^6NH$ under amide forming conditions; wherein $R^4$, $R^5$, $R^6$, $X^1$ and $X^2$ are as defined in any one of Embodiments 1.1 to 1.44; or E) when it is required to prepare a compound of formula (1) wherein $R^1$ comprises $C(\text{=}NR^5)R^6$:

the reaction of a compound of the formula (15):

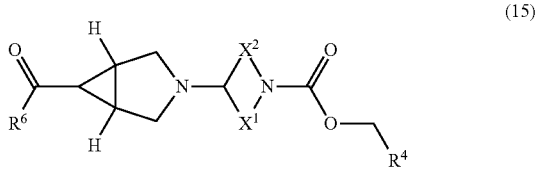

with an amine of the formula $R^5NH_2$; wherein $R^4$, $R^5$, $R^6$, $X^1$ and $X^2$ are as defined in any one of Embodiments 1.1 to 1.44;

and optionally:

(F) converting one compound of the formula (1) to another compound of the formula (1).

In process variant (A), the ketone (11) is reacted with the amine (10) under reductive amination conditions. The reductive amination reaction is typically carried out at ambient temperature to mild heating (e.g. at a temperature of about 20° C. to about 70° C.) using a borohydride reducing agent such as sodium triacetoxy-borohydride (STAB) in a solvent such as dichloromethane (DCM), dichloroethane (DCE), N,N-dimethylformamide (DMF) or methanol (MeOH) containing an acid such as acetic acid (AcOH) or trifluoroacetic acid (TFA), or sodium cyanoborohydride ($NaCNBH_3$) in combination with zinc chloride ($ZnCl_2$) in a solvent such as MeOH, or STAB in a solvent such as DCM or DCE containing an acid such as AcOH or TFA in combination with titanium tetraisopropoxide ($Ti(O^iPr)_4$). Optionally, the amine (10) may be present in the reaction as an acid salt such as a hydrogen chloride (HCl), hydrogen bromide (HBr) or a TFA salt, optionally in the presence of a tertiary base such as triethylamine (TEA) or N,N-diisopropylamine (DIPEA).

When it is required to prepare a compound of formula (1) wherein $R^1$ comprises $CONR^5R^6$, wherein $R^5$ and $R^6$ are as defined in any one of Embodiments 1.1 to 1.44, amines of the formula (10) can be prepared by the sequence of reactions shown in Scheme 1 below.

Scheme 1

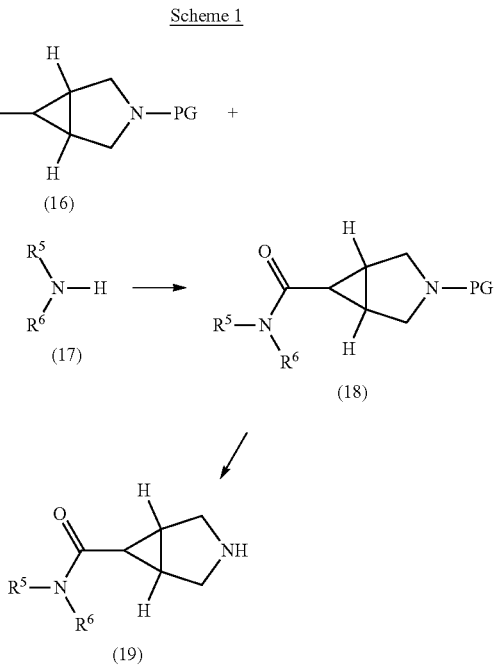

Thus, a protected amino ester (16), wherein R represents a suitable group such as methyl- or ethyl- and the protecting group PG represents a suitable protecting group such as tert-butyloxycarbonyl (BOC), is reacted with an amine (17), wherein $R^5$ and $R^6$ are as defined in any one of Embodiments 1.1 to 1.44 under conditions suitable to effect formation of protected amino amide (18). Typically, such conditions are reaction at a temperature between about 0° C. to about 110° C. in a solvent such as toluene in combination with a reagent such as trimethylaluminium ($Me_3Al$), optionally in the presence of a tertiary base such as TEA or DIPEA. It will be well known to the skilled person that other suitable conditions exist to effect formation of protected amino amide (18) from protected amino ester (16) and amine (17), such as reaction in the presence of isopropylmagnesium chloride ($^i$PrMgCl) in a suitable solvent, or direct heating, optionally in the presence of a suitable solvent. Once the protected amino amide (18) is formed, the protecting group PG can be removed using suitable conditions to form amine (19). For example, when the protecting group PG is BOC, then suitable conditions to effect its removal might be reaction with an acid such as HCl in a solvent such as 1,4-dioxane or diethyl ether ($Et_2O$), or TFA in a solvent such as DCM.

Alternatively, protected amino amide (18) can be prepared by the sequence of reactions shown in Scheme 2 below.

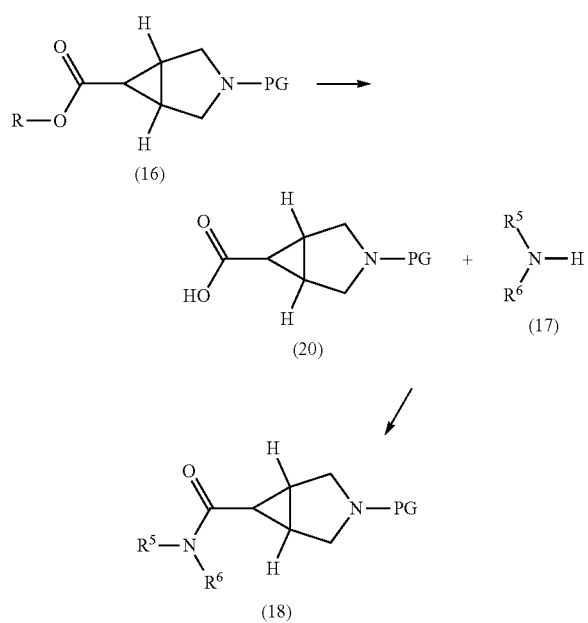

(1-cyano-2-ethoxy-2-oxoethylidenaminooxy)dimethyl-amino-morpholino-carbenium hexafluorophosphate (COMU) or 2,4,6-tripropyl-1,3,5,2,4,6-trioxatriphosphori-nane-2,4,6-trioxide (T3P), optionally in the presence of a tertiary base such as TEA or DIPEA, optionally in the presence of 1-hydroxybenzotriazole (HOBt), in a solvent such as DCM, THF or DMF, at a temperature between about 0° C. to about 100° C.

Alternatively, protected amino amide (18) can be prepared by the sequence of reactions shown in Scheme 3 below.

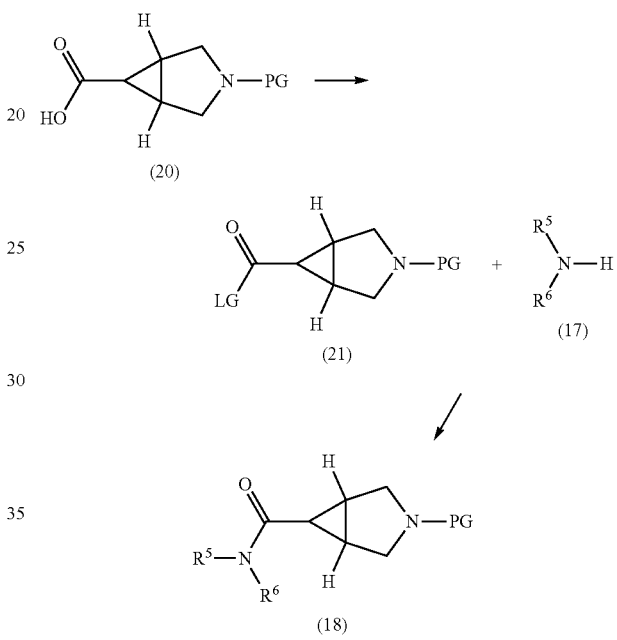

Thus, a protected amino ester (16), wherein R represents a suitable group such as methyl- or ethyl- and the protecting group PG represents a suitable protecting group such as BOC, is reacted under conditions suitable to effect hydrolysis of the ester to form protected amino acid (20). Typically, such conditions are reaction with a reagent such as lithium hydroxide (LiOH), sodium hydroxide (NaOH) or potassium hydroxide (KOH) in a solvent such as tetrahydrofuran (THF), MeOH, ethanol (EtOH), water ($H_2O$) or a combination of two or more of the aforementioned solvents, at a temperature of between about 0° C. to about 100° C. Once formed, the protected amino acid (20), is reacted with an amine (17), wherein $R^5$ and $R^6$ are as defined in any one of Embodiments 1.1 to 1.44, under conditions suitable to effect formation of protected amino amide (18). It will be well known to the skilled person that many suitable conditions exist in the art to effect formation of protected amino amide (18) from protected amino acid (20) and amine (17), for example reaction with an amide coupling reagent such as diisopropylcarbodiimide (DIC), ethyl-(N',N'-dimethyl-amino)propylcarbodiimide hydrochloride (EDC), (benzotri-azol-1-yloxy)tripyrrolidinophosphonium hexafluorophosphate (PyBOP), O-(7-azabenzotriazol-1-yl)-N,N,N',N'-tetramethyluronium hexafluorophosphate (HATU), Thus protected amino acid (20) can be reacted under conditions suitable to effect formation of protected intermediate (21), wherein LG represents a suitable leaving group such as chloride (Cl), 1-imidazolyl, or RO(C=O)O (wherein R represents a group such as ethyl- or isobutyl-). Typically, such conditions are reaction with a reagent such as oxalyl chloride or thionyl chloride (LG=Cl), 1,1'-carbo-nyldiimidazole (CDI) (LG=1-imidazolyl) or ethyl- or isobutyl-chloroformate (LG=RO(C=O)O), optionally in the presence of a tertiary base such as TEA or DIPEA, optionally in the presence of a catalyst such as DMF, in a suitable solvent such as DCM, THF or DMF. Once formed, the protected intermediate (21), is reacted with an amine (17), wherein $R^5$ and $R^6$ are as defined in any one of Embodiments 1.1 to 1.44 under conditions suitable to effect formation of protected amino amide (18). Typically, such conditions are reaction at a temperature between about 0° C. to about 100° C. in a solvent such as DCM, THF or DMF, optionally in the presence of a tertiary base such as TEA or DIPEA.

When it is required to prepare a compound of formula (1) wherein $R^1$ comprises an optionally substituted 5-membered heterocyclic ring, amines of the formula (10) can be prepared by a combination of the reactions shown in Scheme 4 below.

Scheme 4

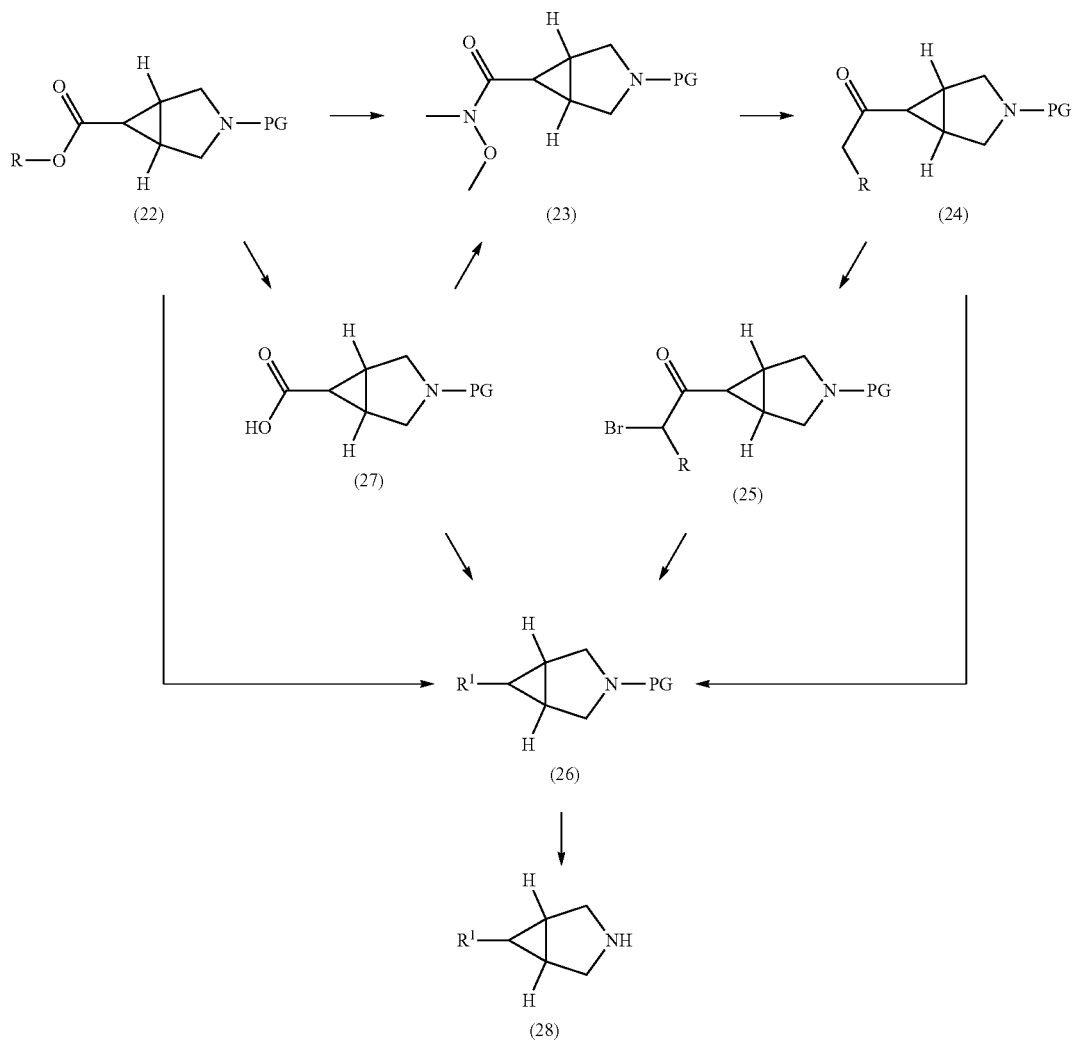

Thus, a protected amino ester (22), wherein R represents a suitable group such as methyl- or ethyl- and the protecting group PG represents a suitable protecting group such as BOC or benzyloxy carbonyl (CBZ), can be reacted under conditions suitable to effect formation of protected Weinreb amide (23) (e.g. reaction with N,O-dimethylhydroxylamine hydrochloride in the presence of a tertiary base such as TEA or DIPEA in a solvent such as toluene in combination with a reagent such as $Me_3Al$ at a temperature between about 0° C. to about 110° C.).

Alternatively, protected Weinreb amide (23) can be formed in two steps: protected amino ester (22) can be reacted under conditions suitable to effect hydrolysis of the ester to form protected amino acid (27) (e.g. reaction with a reagent such as LiOH, NaOH or KOH in a solvent such as THF, MeOH, EtOH, $H_2O$ or a combination of two or more of the aforementioned solvents, at a temperature between about 0° C. to about 100° C.). Once formed, the protected amino acid (27), can be reacted to effect formation of protected Weinreb amide (23) (e.g. reaction with N,O-dimethylhydroxylamine hydrochloride in the presence of a tertiary base such as TEA or DIPEA, in combination with an amide coupling reagent such as DIC, EDC, PyBOP, HATU, COMU or T3P, optionally in the presence of HOBt, in a solvent such as DCM, THF or DMF, at a temperature between about 0° C. to about 100° C.).

Once formed, the protected Weinreb amide (23) can be reacted with an organolithium or an organomagnesium halide (Grignard reagent) in a suitable solvent such as hexanes, toluene, THF or $Et_2O$, at a temperature between about −78° C. to about 50° C. to form a protected amino ketone (24), wherein R represents a functional group that is derived from the organolithium or organomagnesium halide.

Once formed, the protected amino ketone (24) can be reacted further using a combination of chemical transformations well described in the art to effect formation of protected amine (26), wherein $R^1$ comprises a suitable optionally substituted 5-membered heterocyclic ring. For example, the protected amino ketone (24) can be reacted with N,N-dimethylformamide dimethyl acetal in a solvent such as DMF at a temperature of about 20° C. to about 100° C., and then reacted further with methylhydrazine sulfate in a solvent such as DMF at a temperature of about 20° C. to about 100° C. to form protected amine (26), wherein $R^1$ comprises a 1-methyl-1H-pyrazol-5-yl group. Alternatively, the protected amino ketone (24) can be reacted with a brominating agent such as bromine, N-bromosuccinimide (NBS), or phenyltrimethylammonium tribromide in a suitable solvent such as MeOH, 1,4-dioxane, DCM or AcOH, optionally in the presence of an acid such as AcOH or in the presence of a base such as NaOH, to form protected amino bromide (25). Once formed, protected amino bromide (25) can be reacted further with thioacetamide in a solvent such as MeOH at a temperature of about 20° C. to about 65° C. to form protected amine (26), wherein $R^1$ comprises a 2-methyl-1,3-thiazol-4-yl group.

Alternatively, protected amino ester (22) or protected amino acid (27) can be reacted directly using a combination of chemical transformations well described in the art to effect formation of protected amine (26), wherein $R^1$ comprises a suitable optionally substituted 5-membered heterocyclic ring such as a 5-methyl-1,3,4-oxadiazol-2-yl group, a 5-amino-4H-1,2,4-triazol-3-yl group or a 1H-tetrazol-5-yl group.

Once the protected amine (26) is formed, the protecting group PG can be removed using suitable conditions to form amine (28), wherein $R^1$ comprises a suitable optionally substituted 5-membered heterocyclic ring as described above. For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ then suitable conditions to effect its removal might be reaction with hydrogen ($H_2$) in the presence of a palladium on carbon (Pd/C) catalyst in a solvent such as EtOH at a temperature of about 20° C. to about 80° C.

When it is required to prepare a compound of formula (1) wherein $R^1$ comprises $NR^5R^6$, wherein $R^5$ and $R^6$ are as defined in any one of Embodiments 1.1 to 1.44, amines of the formula (10) can be prepared by the sequence of reactions shown in Scheme 5 below.

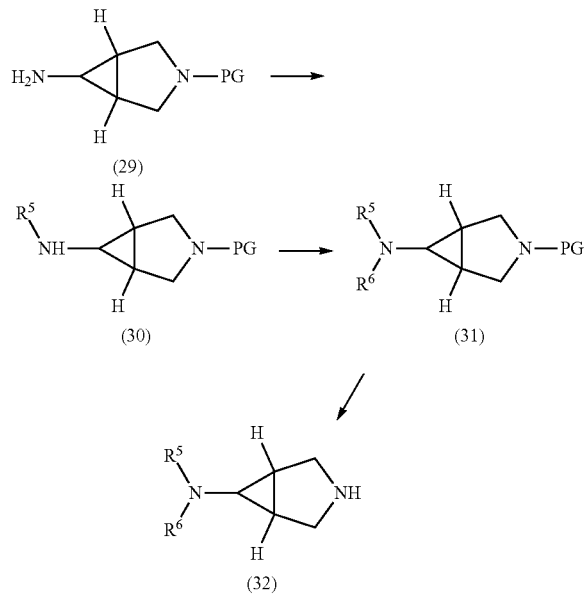

Thus, a mono protected diamine (29), wherein PG represents a suitable protecting group such as BOC or CBZ, is reacted under conditions suitable to effect formation of protected mono alkylated diamine (30), wherein $R^5$ is as defined in any one of Embodiments 1.1 to 1.44. Typically, such conditions might be a nucleophilic substitution reaction with a suitable electrophile such as an organo-halide (e.g. an organo-chloride, organo-bromide or organo-iodide) or an organo sulphonic acid ester (e.g. an organo tosylate, organo mesylate or organo triflate) at a temperature between about 0° C. to about 100° C. in a solvent such as DCM, THF, DMF or N-methylpyrrolidinone (NMP), optionally in the presence of a tertiary base such as TEA or DIPEA. Alternatively, formation of protected mono alkylated diamine (30) from mono protected diamine (29) might be conducted under reductive amination conditions. The reductive amination reaction is typically carried out with a suitable aldehyde or ketone at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or $NaCNBH_3$ in combination with $ZnCl_2$ in a solvent such as MeOH, or STAB in a solvent such as DCM or DCE containing an acid such as AcOH or TFA in combination with $Ti(O^iPr)_4$. Optionally, the mono protected diamine (29) may be present in the reaction as an acid salt such as an HCl, HBr or a TFA salt, optionally in the presence of a tertiary base such as TEA or DIPEA.

Once formed, the protected mono alkylated diamine (30), is reacted under conditions suitable to effect formation of protected dialkylated diamine (31), wherein $R^5$ and $R^6$ are as defined in any one of Embodiments 1.1 to 1.44. Typically, such conditions might be a nucleophilic substitution reaction with a suitable electrophile such as an organo-halide (e.g. an organo-chloride, organo-bromide or organo-iodide) or an organo sulphonic acid ester (e.g. an organo tosylate, organo mesylate or organo triflate) at a temperature between about 0° C. to about 100° C. in a solvent such as DCM, THF, DMF or NMP, optionally in the presence of a tertiary base such as TEA or DIPEA. Alternatively, formation of protected dialkylated diamine (31) from protected mono alkylated diamine (30) might be conducted under reductive amination conditions. The reductive amination reaction is typically carried out with a suitable aldehyde or ketone at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or $NaCNBH_3$ in combination with $ZnCl_2$ in a solvent such as MeOH, or STAB in a solvent such as DCM or DCE containing an acid such as AcOH or TFA in combination with $Ti(O^iPr)_4$. Optionally, the protected mono alkylated diamine (30) may be present in the reaction as an acid salt such as an HCl, HBr or a TFA salt, optionally in the presence of a tertiary base such as TEA or DIPEA.

Once the protected dialkylated diamine (31) is formed, the protecting group PG can be removed using suitable conditions to form amine (32). For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ then suitable conditions to effect its removal might be reaction with $H_2$ in the presence of a Pd/C catalyst in a solvent such as EtOH at a temperature of about 20° C. to about 80° C.

When it is required to prepare a compound of formula (1) wherein $R^1$ comprises $OR^5$, wherein $R^5$ is as defined in any one of Embodiments 1.1 to 1.44, amines of the formula (10) can be prepared by the sequence of reactions shown in Scheme 6 below. Thus, an N-protected amino alcohol (33), wherein PG represents a suitable protecting group such as BOC or CBZ, is reacted under conditions suitable to effect formation of N-protected ether (34), wherein $R^5$ is as defined in any one of Embodiments 1.1 to 1.44.

suitable conditions to form amine (35). For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ then suitable conditions to effect its removal might be reaction with $H_2$ in the presence of a Pd/C catalyst in a solvent such as EtOH at a temperature of about 20° C. to about 80° C.

When it is required to prepare a compound of formula (1) wherein $R^1$ comprises $CH_2NR^7COR^5$, wherein $R^5$ and $R^7$ are as defined in any one of Embodiments 1.1 to 1.44, amines of the formula (10) can be prepared by the sequence of reactions shown in Scheme 7 below. Thus, a protected amino ester (36), wherein R represents a suitable group such as methyl- or ethyl- and the protecting group PG represents a suitable protecting group such as BOC or CBZ, can be reacted under reducing conditions suitable to effect formation of N-protected amino alcohol (37). Typically, such conditions might be reaction with a borohydride

Scheme 6

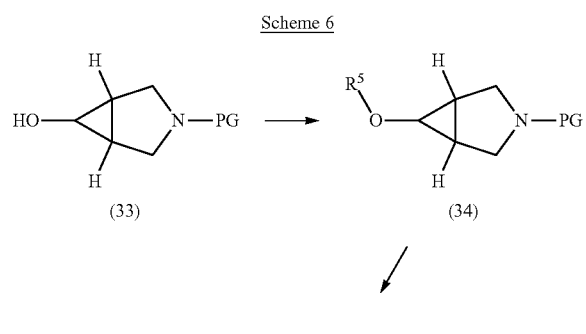

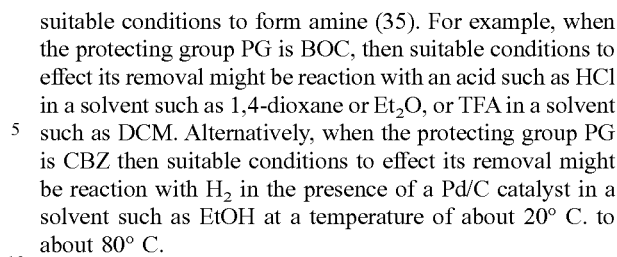

Scheme 7

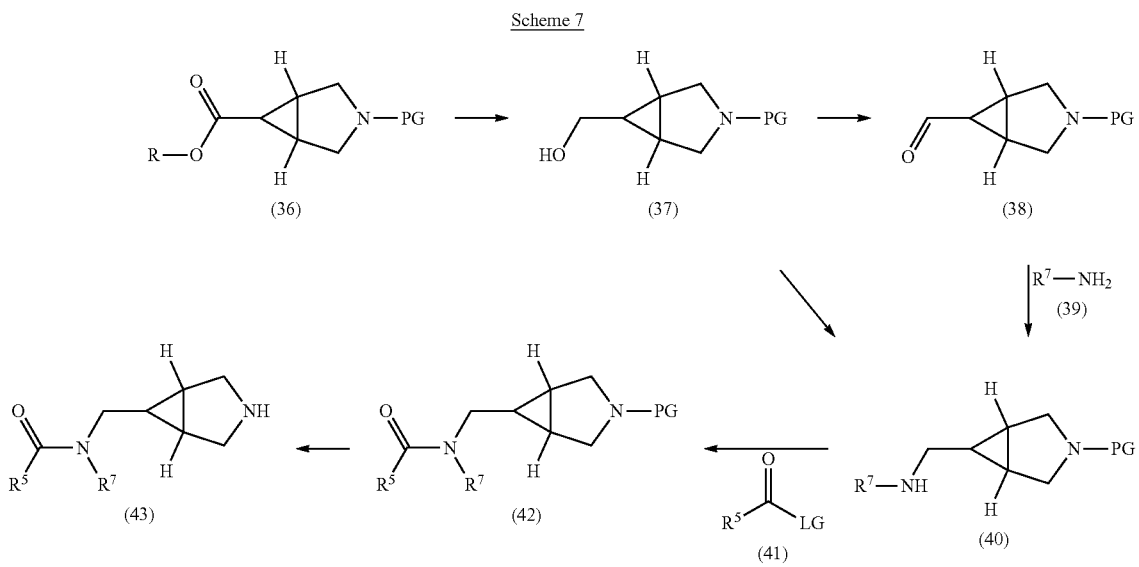

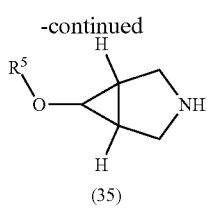

(35)

Typically, such conditions might be deprotonation of the alcohol moiety using a suitable base such as sodium hydride (NaH), sodium bis(trimethylsilyl)amide (NaHMDS), potassium bis(trimethylsilyl)amide (KHMDS) or potassium tert-butoxide ($K^tOBu$), followed by a nucleophilic substitution reaction with a suitable electrophile such as an organo-halide (e.g. an organo-chloride, organo-bromide or organo-iodide) or an organo sulphonic acid ester (e.g. an organo tosylate, organo mesylate or organo triflate) at a temperature between about 0° C. to about 100° C. in a solvent such as THF, DMF or NMP. Once the N-protected ether (34) is formed, the protecting group PG can be removed using reducing agent such as lithium borohydide ($LiBH_4$) or an aluminium hydride reagent such as lithium aluminium hydride (LAH), in a solvent such as $Et_2O$ or THF, at a temperature of about −20° C. to about 50° C. Once formed, N-protected amino alcohol (37) can be reacted under oxidising conditions suitable to effect formation of N-protected amino aldehyde (38). It will be well known to the skilled person that many suitable conditions exist in the art to effect formation of N-protected amino aldehyde (38) from N-protected amino alcohol (37), for example reaction with dimethyl sulphoxide (DMSO) in combination with oxalyl chloride in the presence of a tertiary base such as TEA in a solvent such as DCM at a temperature of about −78° C. to about 20° C. (Swern oxidation conditions), or reaction with Dess-Martin periodinane in a solvent such as DCM at a temperature of about 0° C. to about 20° C. (Dess-Martin oxidation conditions), or reaction with a chromium reagent such as pyridinium dichromate (PDC) or pyridinium chlorochromate (PCC) in a solvent such as DCM at a temperature of about 0° C. to about 40° C.

Once formed, N-protected amino aldehyde (38) is reacted with an amine (39), wherein $R^7$ is as defined in any one of Embodiments 1.1 to 1.44, under reductive amination conditions to form mono alkylated diamine (40). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or NaCNBH$_3$ in combination with ZnCl$_2$ in a solvent such as MeOH, or STAB in a solvent such as DCM or DCE containing an acid such as AcOH or TFA in combination with Ti(O$^i$Pr)$_4$. Optionally, the amine (39) may be present in the reaction as an acid salt such as an HCl, HBr or a TFA salt, optionally in the presence of a tertiary base such as TEA or DIPEA. Alternatively, it will be well known to the skilled person that many suitable conditions exist in the art to effect formation of mono alkylated diamine (40) from N-protected amino alcohol (37), without first forming N-protected amino aldehyde (38). For example the alcohol moiety in N-protected amino alcohol (37) can be converted into a suitable leaving group such as a halogen (e.g. a chloride, bromide or iodide) or a sulphonic acid ester (e.g. a tosylate, mesylate or triflate) and then reacted further with amine (39) under conditions suitable to effect a nucleophilic substitution reaction. Once formed, mono alkylated diamine (40) can be reacted with acylating agent (41), wherein R$^5$ is as defined in any one of Embodiments 1.1 to 1.44 and LG represents an OH group or a suitable leaving group such as Cl, 1-imidazolyl, or RO(C=O)O (wherein R represents a group such as ethyl- or isobutyl-), to form N-protected amide (42). For example, when LG represents an OH group, then mono alkylated diamine (40) can be reacted with acylating agent (41) using suitable amide coupling conditions (e.g. using a reagent such as DIC, EDC, PyBOP, HATU, COMU or T3P, optionally in the presence of a tertiary base such as TEA or DIPEA, optionally in the presence of HOBt, in a solvent such as DCM, THF or DMF, at a temperature between about 0° C. to about 100° C.). Alternatively, when LG represents a leaving group such as Cl, 1-imidazolyl, or RO(C=O)O (wherein R represents a group such as ethyl- or isobutyl-), then mono alkylated diamine (40) can be reacted with acylating agent (41) at a temperature between about 0° C. to about 100° C. in a solvent such as DCM, THF or DMF, optionally in the presence of a tertiary base such as TEA or DIPEA. Once the N-protected amide (42) is formed, the protecting group PG can be removed using suitable conditions to form amine (43). For example, when the protecting group PG is BOC, then suitable conditions to effect its removal might be reaction with an acid such as HCl in a solvent such as 1,4-dioxane or Et$_2$O, or TFA in a solvent such as DCM. Alternatively, when the protecting group PG is CBZ then suitable conditions to effect its removal might be reaction with H$_2$ in the presence of a Pd/C catalyst in a solvent such as EtOH at a temperature of about 20° C. to about 80° C.

Ketones of the formula (11) can be prepared by the sequence of reactions shown in Scheme 8 below. Thus, a protected amino ketone (44), wherein X$^1$ and X$^2$ are as defined in any one of Embodiments 1.1 to 1.44 and PG represents a suitable protecting group such as BOC or CBZ, can be deprotected to give amino ketone (45). For example, when the protecting group PG is BOC, then suitable conditions to effect its removal might be reaction with an acid such as HCl in a solvent such as 1,4-dioxane or Et$_2$O, or TFA in a solvent such as DCM. Alternatively, when the protecting group PG is CBZ then suitable conditions to effect its removal might be reaction with H$_2$ in the presence of a palladium on carbon (Pd/C) catalyst in a solvent such as EtOH at a temperature of about 20° C. to about 80° C. Once formed, amino ketone (45) can be reacted with chloroformate (46), wherein R$^4$ is as defined in any Scheme 8 one of Embodiments 1.1 to 1.44, under suitable conditions to form ketone (11). Typically, such conditions are reaction at a temperature between about 0° C. to about 50° C. in a solvent such as DCM, THF or DMF, optionally in the presence of a tertiary base such as TEA or DIPEA.

In process variant (B), the compound of formula (12) is typically reacted with a compound of formula Cl—C(=O)—O—CH$_2$—R$^4$, wherein R$^4$ is as defined in any one of Embodiments 1.1 to 1.44, at a temperature between about 0° C. to about 50° C. in a solvent such as DCM, THF or DMF, optionally in the presence of a tertiary base such as TEA or DIPEA.

Compounds of formula (12) can be prepared by the sequence of reactions shown in Scheme 9 below. Thus, a compound of formula (10), wherein R$^1$ is as defined in any one of Scheme 9

Embodiments 1.1 to 1.44, is reacted with a compound of formula (47), wherein X¹ and X² are as defined in any one of Embodiments 1.1 to 1.44 and PG represents a suitable protecting group such as BOC or CBZ, under reductive amination conditions to form a compound of formula (48).

The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or NaCNBH₃ in combination with ZnCl₂ in a solvent such as MeOH, or STAB in a solvent such as DCM or DCE containing an acid such as AcOH or TFA in combination with Ti(O$^i$Pr)₄. Optionally, compound (10) may be present in the reaction as an acid salt such as an HCl, HBr or a TFA salt, optionally in the presence of a tertiary base such as TEA or DIPEA. Once formed, the protecting group PG can be removed from a compound of formula (48) to form a compound of formula (12). For example, when the protecting group PG is BOC, then suitable conditions to effect its removal might be reaction with an acid such as HCl in a solvent such as 1,4-dioxane or Et₂O, or TFA in a solvent such as DCM. Alternatively, when the protecting group PG is CBZ then suitable conditions to effect its removal might be reaction with H₂ in the presence of a Pd/C catalyst in a solvent such as EtOH at a temperature of about 20° C. to about 80° C.

In process variant (C), the compound of formula (13) is typically reacted with an amine of the formula R⁵R⁶NH; wherein R⁵ and R⁶ are as defined in any one of Embodiments 1.1 to 1.44, at a temperature between about 0° C. to about 110° C. in a solvent such as toluene in combination with a reagent such as Me₃Al, optionally in the presence of a tertiary base such as TEA or DIPEA. It will be well known to the skilled person that other suitable conditions exist to effect the same transformation, such as reaction in the presence of $^i$PrMgCl in a suitable solvent, or direct heating, optionally in the presence of a suitable solvent.

Compounds of formula (13) can be prepared by the reaction shown in Scheme 10 below.

Thus, a compound of formula (11) is reacted with an amine of formula (49), wherein R represents a suitable group such as methyl- or ethyl-, under reductive amination conditions to form a compound of formula (13). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or NaCNBH₃ in combination with ZnCl₂ in a solvent such as MeOH, or STAB in a solvent such as DCM or DCE containing an acid such as AcOH or TFA in combination with Ti(O$^i$Pr)₄. Optionally, compound (49) may be present in the reaction as an acid salt such as an HCl, HBr or a TFA salt, optionally in the presence of a tertiary base such as TEA or DIPEA.

In process variant (D), the compound of formula (14) is typically reacted with an amine of the formula R⁵R⁶NH; wherein R⁵ and R⁶ are as defined in any one of Embodiments 1.1 to 1.44, using suitable amide coupling conditions. It will be well known to the skilled person that many suitable conditions exist in the art to effect formation of an amide from the compound of formula (14) and an amine of the formula R⁵R⁶NH, for example using a reagent such as DIC, EDC, PyBOP, HATU, COMU or T3P, optionally in the presence of a tertiary base such as TEA or DIPEA, optionally in the presence of HOBt, in a solvent such as DCM, THF or DMF, at a temperature between about 0° C. to about 100° C. Alternatively, the compound of formula (14) can be reacted with an amine of the formula R⁵R⁶NH using the sequence of reactions shown in Scheme 11 below.

Scheme 11

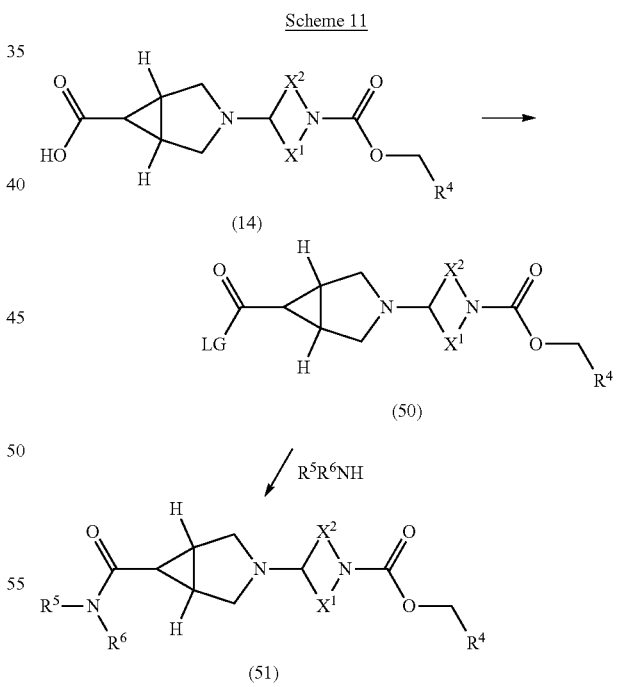

Thus a compound of formula (14) can be reacted under conditions suitable to effect formation of intermediate (50), wherein LG represents a suitable leaving group such as Cl, 1-imidazolyl, or RO(C=O)O (wherein R represents a group such as ethyl- or isobutyl-). Typically, such conditions are reaction with a reagent such as oxalyl chloride or thionyl chloride (LG=Cl), CDI (LG=1-imidazolyl) or ethyl- or Scheme 10

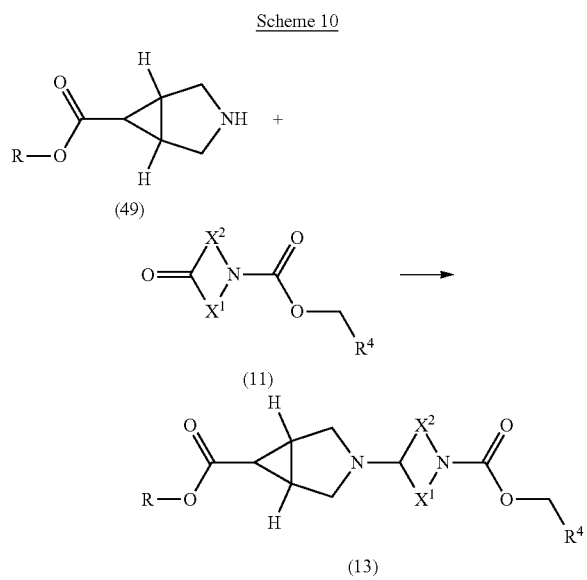

isobutyl-chloroformate (LG=RO(C=O)O), optionally in the presence of a tertiary base such as TEA or DIPEA, optionally in the presence of a catalyst such as DMF, in a suitable solvent such as DCM, THF or DMF. Once formed, the intermediate (50) is reacted with an amine of the formula $R^5R^6NH$, wherein $R^5$ and $R^6$ are as defined in any one of Embodiments 1.1 to 1.44 under conditions suitable to effect formation of a compound of formula (51). Typically, such conditions are reaction at a temperature between about 0° C. to about 100° C. in a solvent such as DCM, THF or DMF, optionally in the presence of a tertiary base such as TEA or DIPEA.

Compounds of formula (14) can be prepared by the reaction shown in Scheme 12 below.

Scheme 12

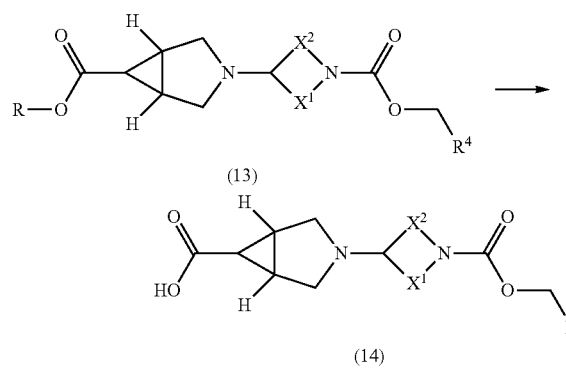

(13)

(14)

Thus a compound of formula (13), wherein R represents a suitable group such as methyl- or ethyl- and $R^4$, $X^1$ and $X^2$ are as defined in any one of Embodiments 1.1 to 1.44, can be reacted under conditions suitable to effect hydrolysis of the ester to form a compound of formula (14). For example, reaction with a reagent such as LiOH, NaOH or KOH in a solvent such as THF, MeOH, EtOH, $H_2O$ or a combination of two or more of the aforementioned solvents, at a temperature between about 0° C. to about 100° C.

In process variant (E), the compound of formula (15) is typically reacted with an amine of formula $R^5NH_2$, wherein $R^5$ is as defined in any one of Embodiments 1.1 to 1.44, under conditions suitable to effect imine formation. It will be well known to the skilled person that many suitable conditions exist in the art to effect formation of an imine from the compound of formula (15) and an amine of the formula $R^5NH_2$. For example vigorous heating under reflux conditions in a solvent such as benzene or toluene, optionally in the presence of a catalyst such as para-toluenesulphonic acid or TFA; in a solvent such as MeOH or EtOH, at a temperature between about 25° C. and reflux temperature, optionally in the presence of a catalyst such as AcOH or sodium acetate; or in a solvent such as THF or DCM at a temperature between about 25° C. and reflux temperature, optionally in the presence of a desiccant such as anhydrous magnesium sulphate or 4 A molecular sieves. Optionally, the amine of formula $R^5NH_2$ may be present in the reaction as an acid salt such as an HCl, HBr or a TFA salt, optionally in the presence of a tertiary base such as TEA or DIPEA.

Compounds of formula (15) can be prepared by the reactions shown in Scheme 13 below.

Scheme 13

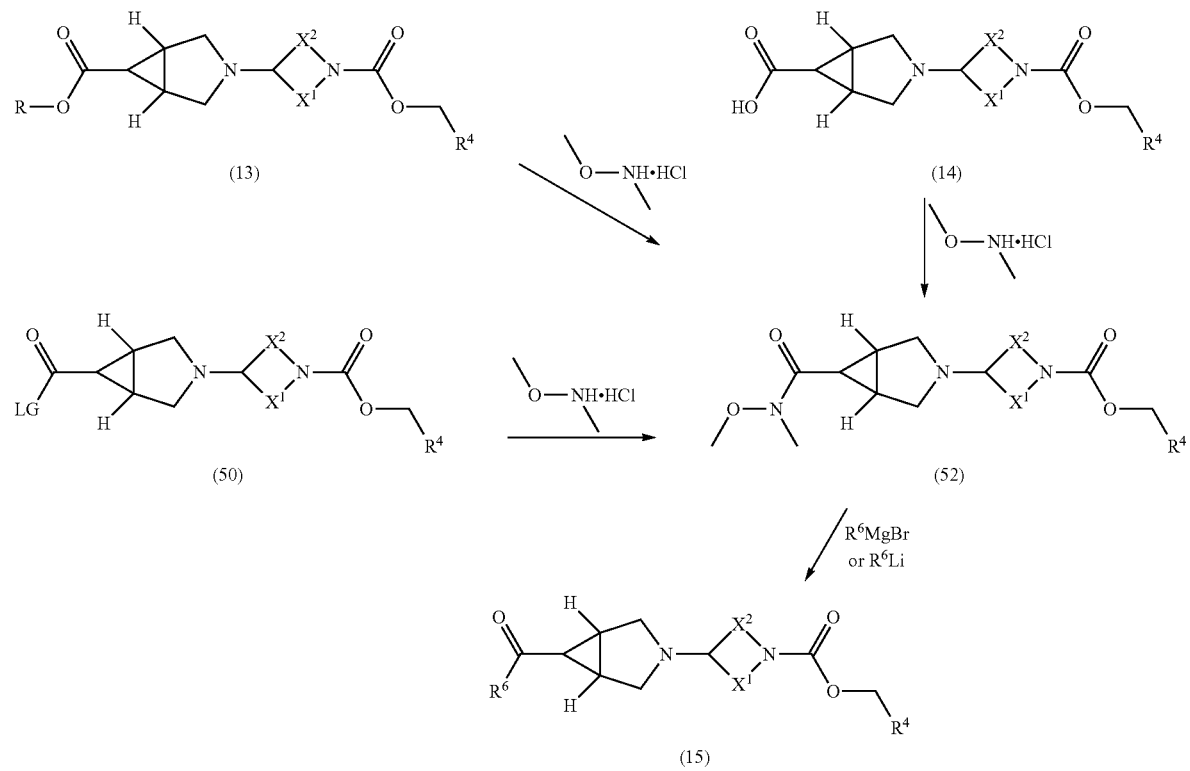

Thus a compound of formula (13), wherein R represents a suitable group such as methyl- or ethyl- and $R^4$, $X^1$ and $X^2$ are as defined in any one of Embodiments 1.1 to 1.44, can be reacted with N,O-dimethylhydroxylamine hydrochloride at a temperature between about 0° C. to about 110° C. in a solvent such as toluene in combination with a reagent such as $Me_3Al$, in the presence of a tertiary base such as TEA or DIPEA, to form a compound of formula (52). It will be well known to the skilled person that other suitable conditions exist to effect the same transformation, such as reaction in the presence of $^iPrMgCl$ in a suitable solvent, in the presence of a tertiary base such as TEA or DIPEA, or direct heating, optionally in the presence of a suitable solvent, in the presence of a tertiary base such as TEA or DIPEA. Alternatively, a compound of formula (14), wherein $R^4$, $X^1$ and $X^2$ are as defined in any one of Embodiments 1.1 to 1.44, can be reacted with N,O-dimethylhydroxylamine hydrochloride using suitable amide coupling conditions. It will be well known to the skilled person that many suitable conditions exist in the art to effect formation of a compound of formula (52) from the compound of formula (14) and N,O-dimethylhydroxylamine hydrochloride, for example using a reagent such as DIC, EDC, PyBOP, HATU, COMU or T3P, in the presence of a tertiary base such as TEA or DIPEA, optionally in the presence of HOBt, in a solvent such as DCM, THF or DMF, at a temperature between about 0° C. to about 100° C. Alternatively, a compound of formula (50), wherein LG represents a suitable leaving group such as Cl, 1-imidazolyl, or RO(C=O)O (wherein R represents a group such as ethyl- or isobutyl-) and $R^4$, $X^1$ and $X^2$ are as defined in any one of Embodiments 1.1 to 1.44, can be reacted with N,O-dimethylhydroxylamine hydrochloride at a temperature between about 0° C. to about 100° C. in a solvent such as DCM, THF or DMF, in the presence of a tertiary base such as TEA or DIPEA. Once formed, the compound of formula (52) can be reacted with a Grignard reagent of the formula $R^6MgBr$ or an organolithium reagent of the formula $R^6Li$, wherein and $R^6$ is as defined in any one of Embodiments 1.1 to 1.44 under conditions suitable to effect formation of a compound of formula (15). Typically, such conditions are reaction at a temperature between about −78° C. to about 25° C. in a solvent such as THF or $Et_2O$.

In process variant (F), one compound of the formula (1) can be converted into another compound of the formula (1) by methods well known to the skilled person. Examples of synthetic procedures for converting one functional group into another functional group are set out in standard texts such as *March's Advanced Organic Chemistry: Reactions, Mechanisms, and Structure,* 7th Edition, Michael B. Smith, John Wiley, 2013, (ISBN: 978-0-470-46259-1), *Organic Syntheses,* Online Edition, www.orgsyn.org, (ISSN 2333-3553) and *Fiesers' Reagents for Organic Synthesis,* Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Greene's Protective Groups in Organic Synthesis,* Fifth Edition, Editor: Peter G. M. Wuts, John Wiley, 2014, (ISBN: 9781118057483).

Compounds made by the foregoing methods may be isolated and purified by any of a variety of methods well known to those skilled in the art and examples of such methods include recrystallisation and chromatographic techniques such as column chromatography (e.g. flash chromatography), HPLC and SFC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.90 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g. solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/ bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 12-1

The compounds of Examples 1-1 to 12-1 shown in Table 1 below have been prepared. Their NMR and LCMS properties and the methods used to prepare them are set out in Table 3. The starting materials for each of the Examples are listed in Table 2.

TABLE 1

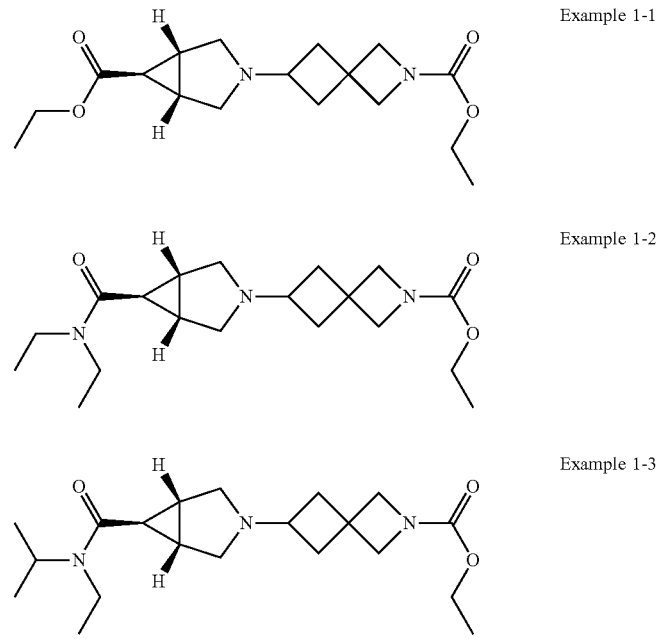

Example 1-1

Example 1-2

Example 1-3

TABLE 1-continued
| | |
|---|---|
| 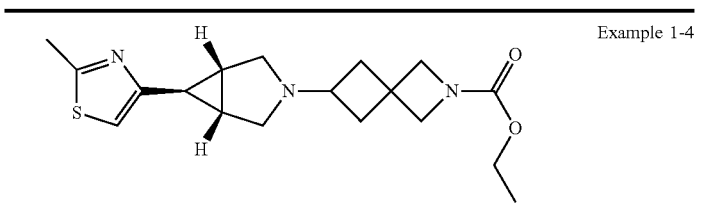 | Example 1-4 |
| 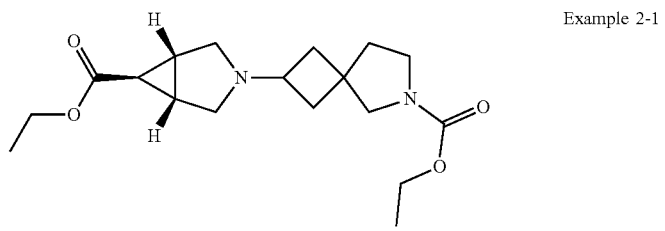 | Example 2-1 |
| 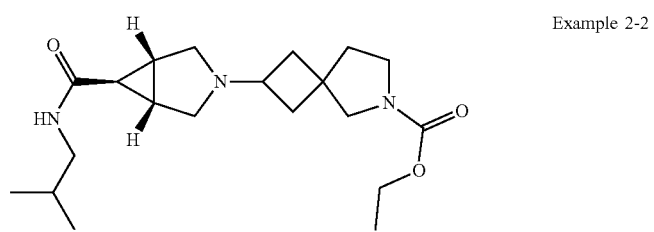 | Example 2-2 |
| 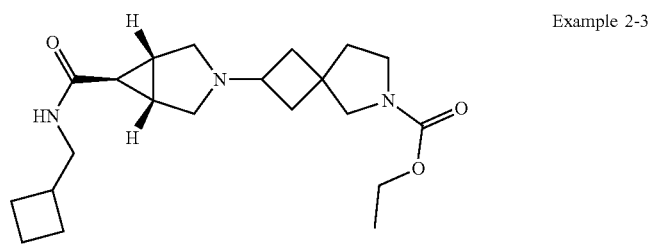 | Example 2-3 |
| 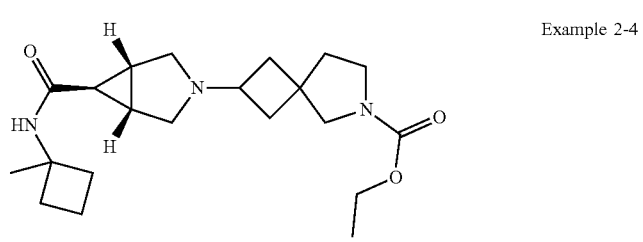 | Example 2-4 |
| 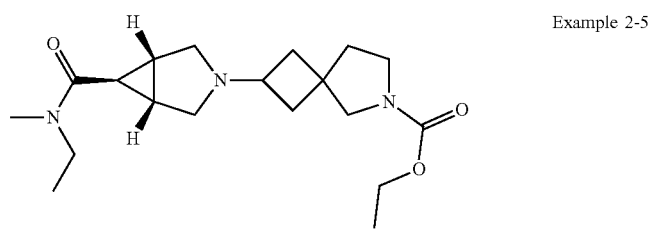 | Example 2-5 |
| 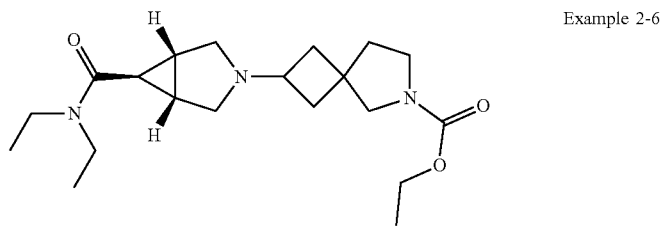 | Example 2-6 |

TABLE 1-continued
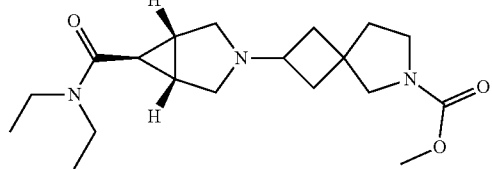
Example 2-7
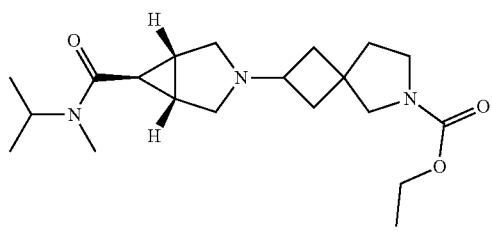 [SMILES: CCOC(=O)N1CCC2(CC(N3C[C@@H]4[C@H](C3)[C@H]4C(=O)N(C)C(C)C)C2)C1]
Example 2-8
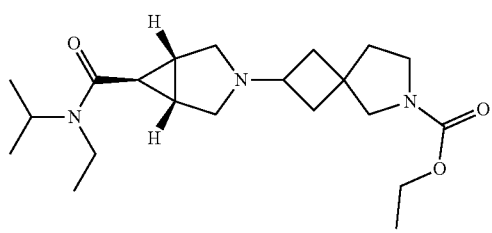 [SMILES: CCOC(=O)N1CCC2(CC(N3C[C@@H]4[C@H](C3)[C@H]4C(=O)N(CC)C(C)C)C2)C1]
Example 2-9
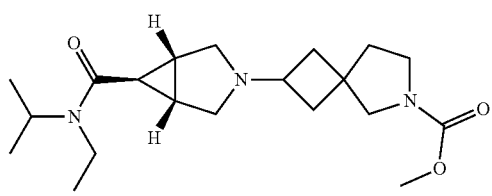 [SMILES: CCN(C(=O)[C@H]1[C@@H]2CN(C3CC4(CCN(C(=O)OC)C4)C3)C[C@@H]21)C(C)C]
Example 2-10
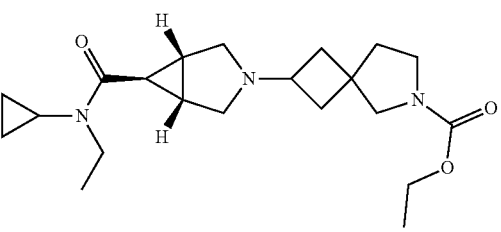 [SMILES: CCOC(=O)N1CCC2(CC(N3C[C@@H]4[C@H](C3)[C@H]4C(=O)N(CC)C3CC3)C2)C1]
Example 2-11
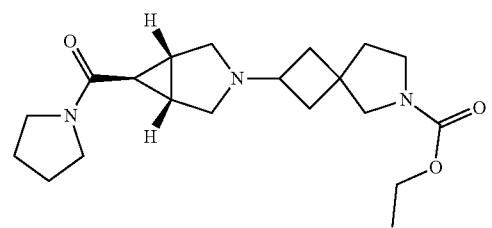 [SMILES: CCOC(=O)N1CCC2(CC(N3C[C@@H]4[C@H](C3)[C@H]4C(=O)N3CCCC3)C2)C1]
Example 2-12
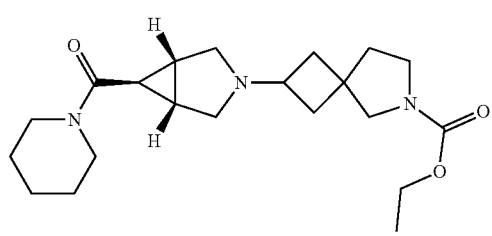 [SMILES: CCOC(=O)N1CCC2(CC(N3C[C@@H]4[C@H](C3)[C@H]4C(=O)N3CCCCC3)C2)C1]
Example 2-13

TABLE 1-continued
| | |
|---|---|
| 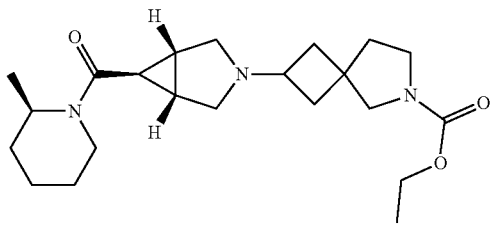 [SMILES: CCOC(=O)N1CCC2(CC(N3C[C@@H]4[C@H](C3)[C@H]4C(=O)N3CCCC[C@H]3C)C2)C1] | Example 2-14 |
| 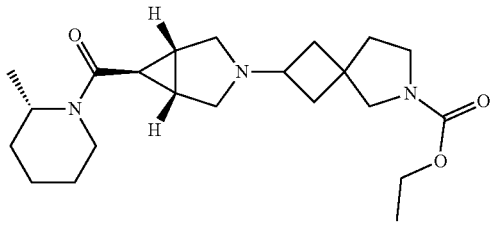 [SMILES: CCOC(=O)N1CCC2(CC(N3C[C@@H]4[C@H](C3)[C@H]4C(=O)N3CCCC[C@@H]3C)C2)C1] | Example 2-15 |
| 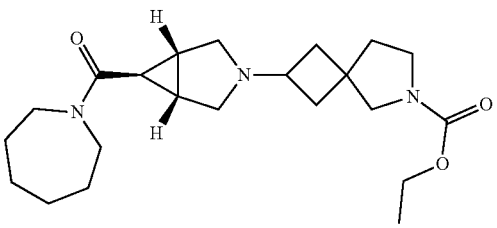 [SMILES: CCOC(=O)N1CCC2(CC(N3C[C@@H]4[C@H](C3)[C@H]4C(=O)N3CCCCCC3)C2)C1] | Example 2-16 |
| 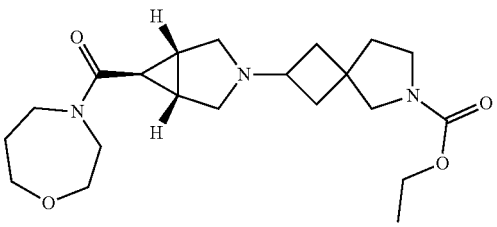 [SMILES: CCOC(=O)N1CCC2(CC(N3C[C@@H]4[C@H](C3)[C@H]4C(=O)N3CCCOCC3)C2)C1] | Example 2-17 |
| 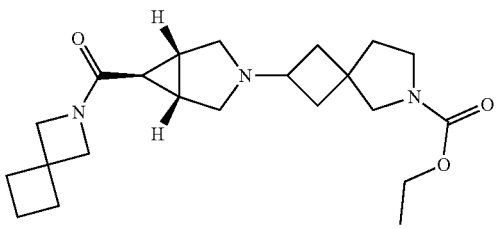 [SMILES: CCOC(=O)N1CCC2(CC(N3C[C@@H]4[C@H](C3)[C@H]4C(=O)N3CC4(CCC4)C3)C2)C1] | Example 2-18 |
| 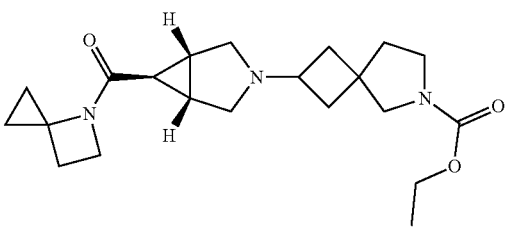 [SMILES: CCOC(=O)N1CCC2(CC(N3C[C@@H]4[C@H](C3)[C@H]4C(=O)N3CCC34CC4)C2)C1] | Example 2-19 |
| 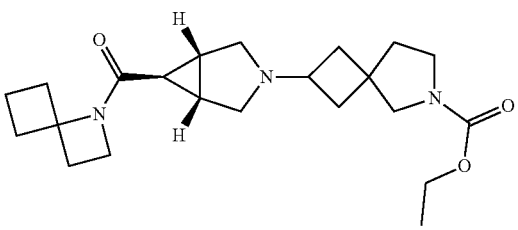 [SMILES: CCOC(=O)N1CCC2(CC(N3C[C@@H]4[C@H](C3)[C@H]4C(=O)N3CCC34CCC4)C2)C1] | Example 2-20 |

TABLE 1-continued
| | |
|---|---|
| 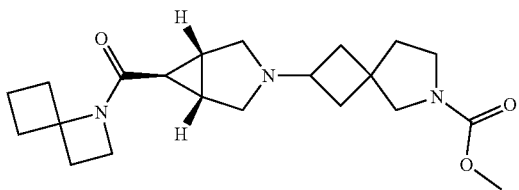 [SMILES: COC(=O)N1CCC2(CC(N3C[C@@H]4[C@H](C3)[C@H]4C(=O)N3CCC34CCC4)C2)C1] | Example 2-21 |
| 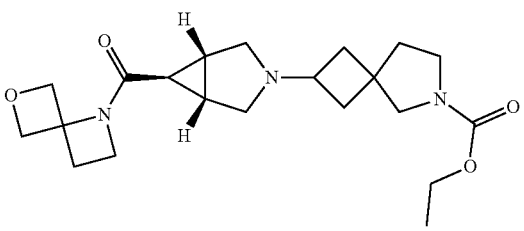 [SMILES: CCOC(=O)N1CCC2(CC(N3C[C@@H]4[C@H](C3)[C@H]4C(=O)N3CCC34COC4)C2)C1] | Example 2-22 |
| 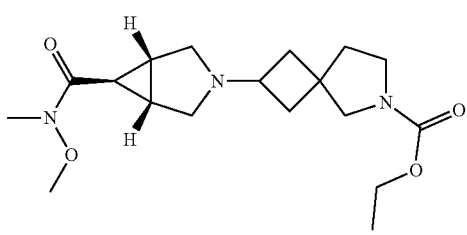 [SMILES: CCOC(=O)N1CCC2(CC(N3C[C@@H]4[C@H](C3)[C@H]4C(=O)N(C)OC)C2)C1] | Example 2-23 |
| 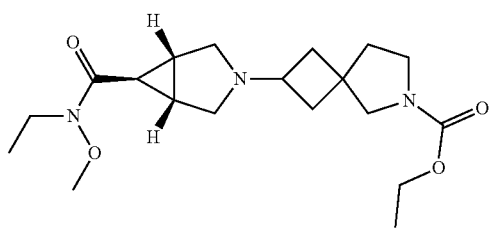 | Example 2-24 |
| 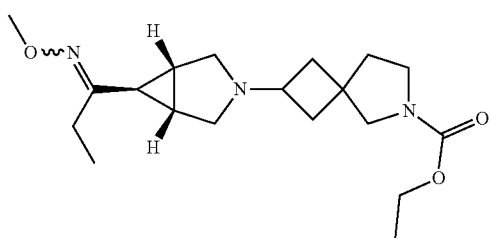 [SMILES: CCOC(=O)N1CCC2(CC(N3C[C@@H]4[C@H](C3)[C@H]4C(CC)=NOC)C2)C1] | Example 2-25 |
| 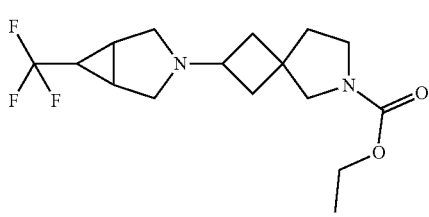 [SMILES: CCOC(=O)N1CCC2(CC(N3CC4C(C3)C4C(F)(F)F)C2)C1] | Example 2-26 |
| 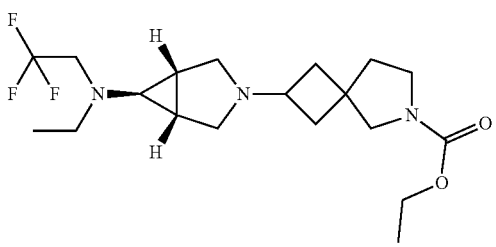 [SMILES: CCOC(=O)N1CCC2(CC(N3C[C@@H]4[C@H](C3)[C@H]4N(CC)CC(F)(F)F)C2)C1] | Example 2-27 |

TABLE 1-continued
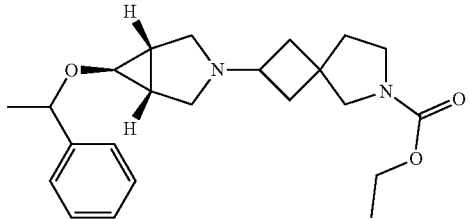 [SMILES: CCOC(=O)N1CCC2(CC(N3C[C@@H]4[C@H](C3)[C@H]4OC(C)c3ccccc3)C2)C1]
Example 2-28
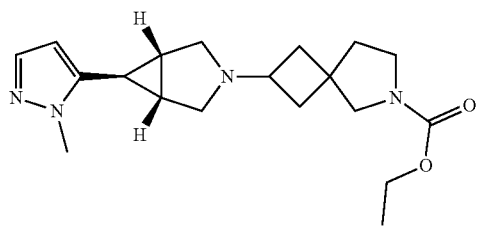 [SMILES: CCOC(=O)N1CCC2(CC(N3C[C@@H]4[C@H](C3)[C@H]4c3ccnn3C)C2)C1]
Example 2-29
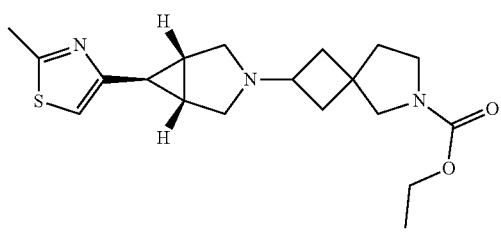 [SMILES: CCOC(=O)N1CCC2(CC(N3C[C@@H]4[C@H](C3)[C@H]4c3csc(C)n3)C2)C1]
Example 2-30
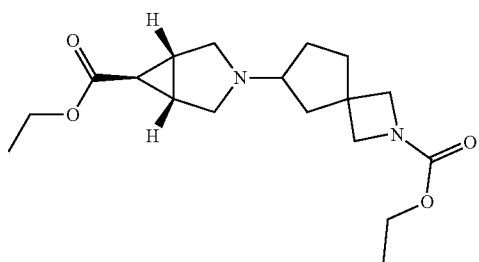 [SMILES: CCOC(=O)[C@H]1[C@@H]2CN(C3CCC4(C3)CN(C(=O)OCC)C4)C[C@@H]21]
Example 3-1
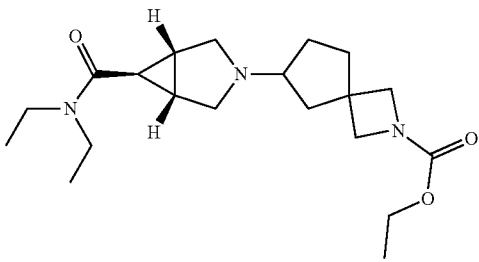 [SMILES: CCOC(=O)N1CC2(CCC(N3C[C@@H]4[C@H](C3)[C@H]4C(=O)N(CC)CC)C2)C1]
Example 3-2
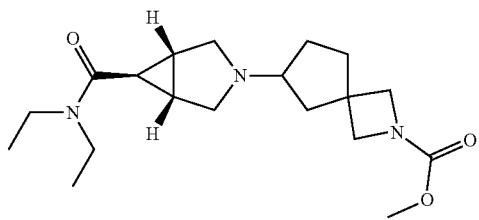 [SMILES: CCN(CC)C(=O)[C@H]1[C@@H]2CN(C3CCC4(C3)CN(C(=O)OC)C4)C[C@@H]21]
Example 3-3

TABLE 1-continued
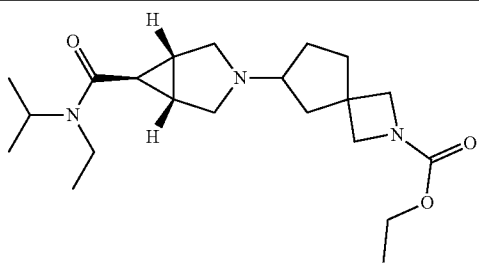 Example 3-4
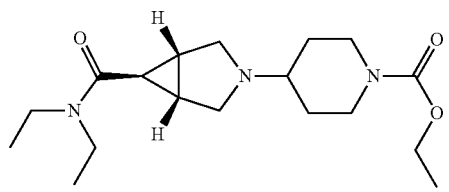 [SMILES: CCOC(=O)N1CCC(N2C[C@@H]3[C@H](C2)[C@H]3C(=O)N(CC)CC)CC1] Example 4-1
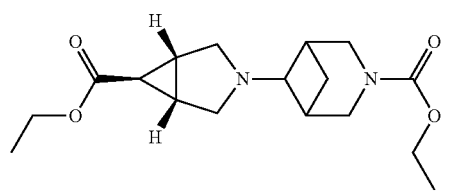 [SMILES: CCOC(=O)[C@H]1[C@@H]2CN(C3C4CC3CN(C(=O)OCC)C4)C[C@@H]21] Example 5-1
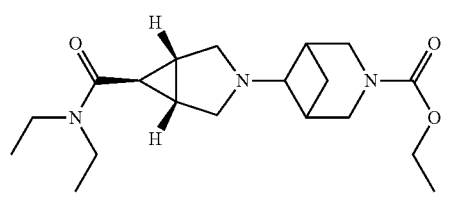 [SMILES: CCOC(=O)N1CC2CC(C1)C2N1C[C@@H]2[C@H](C1)[C@H]2C(=O)N(CC)CC] Example 5-2
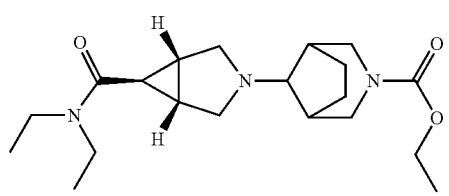 [SMILES: CCOC(=O)N1CC2CCC(C1)C2N1C[C@@H]2[C@H](C1)[C@H]2C(=O)N(CC)CC] Example 6-1
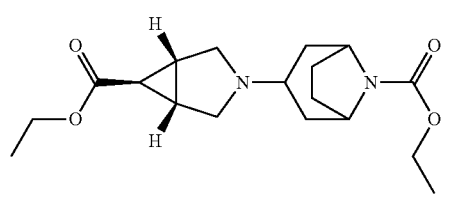 [SMILES: CCOC(=O)[C@H]1[C@@H]2CN(C3CC4CCC(C3)N4C(=O)OCC)C[C@@H]21] Example 7-1
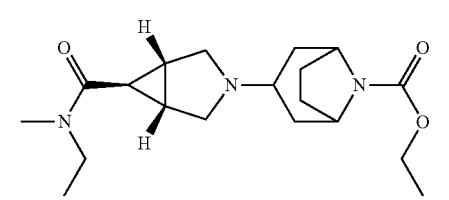 [SMILES: CCOC(=O)N1C2CCC1CC(N1C[C@@H]3[C@H](C1)[C@H]3C(=O)N(C)CC)C2] Example 7-2
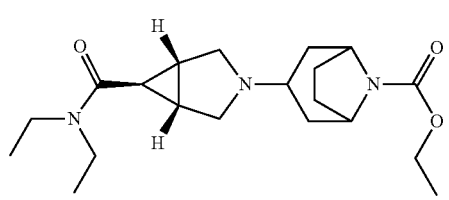 [SMILES: CCOC(=O)N1C2CCC1CC(N1C[C@@H]3[C@H](C1)[C@H]3C(=O)N(CC)CC)C2] Example 7-3

TABLE 1-continued
| | |
|---|---|
| 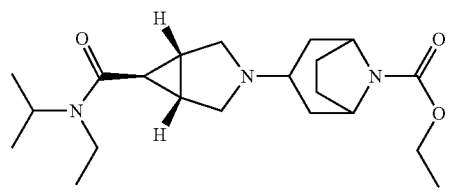 [SMILES: CCOC(=O)N1C2CCC1CC(N1C[C@@H]3[C@H](C1)[C@H]3C(=O)N(CC)C(C)C)C2] | Example 7-4 |
| 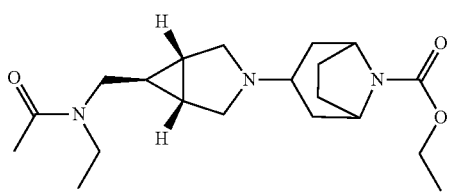 [SMILES: CCOC(=O)N1C2CCC1CC(N1C[C@@H]3[C@@H](CN(CC)C(C)=O)[C@@H]3C1)C2] | Example 7-5 |
| 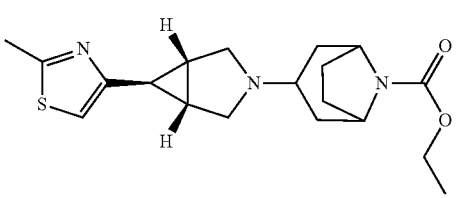 [SMILES: CCOC(=O)N1C2CCC1CC(N1C[C@@H]3[C@H](C1)[C@H]3c1csc(C)n1)C2] | Example 7-6 |
| 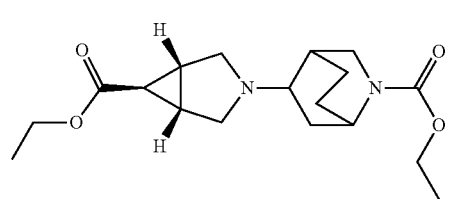 [SMILES: CCOC(=O)[C@H]1[C@@H]2CN(C3CC4CCC3CN4C(=O)OCC)C[C@@H]21] | Example 8-1 |
| 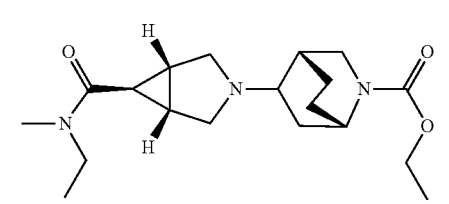 [SMILES: CCOC(=O)N1C[C@@H]2CC[C@H]1CC2N1C[C@@H]2[C@H](C1)[C@H]2C(=O)N(C)CC] | Example 8-2 |
| 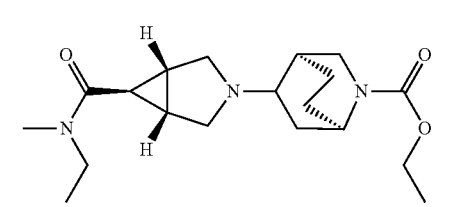 [SMILES: CCOC(=O)N1C[C@H]2CC[C@@H]1CC2N1C[C@@H]2[C@H](C1)[C@H]2C(=O)N(C)CC] | Example 8-3 |
| 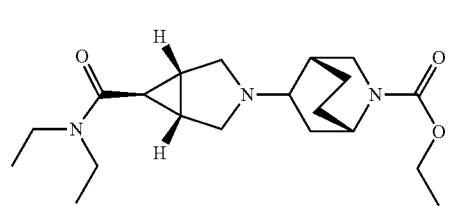 [SMILES: CCOC(=O)N1C[C@@H]2CC[C@H]1CC2N1C[C@@H]2[C@H](C1)[C@H]2C(=O)N(CC)CC] | Example 8-4 |
| 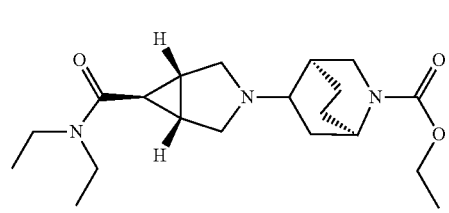 [SMILES: CCOC(=O)N1C[C@H]2CC[C@@H]1CC2N1C[C@@H]2[C@H](C1)[C@H]2C(=O)N(CC)CC] | Example 8-5 |

TABLE 1-continued
| | |
|---|---|
| 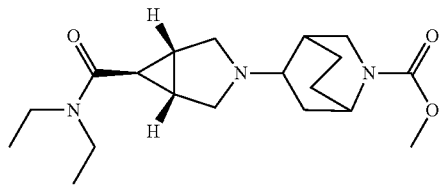 [SMILES: CCN(CC)C(=O)[C@H]1[C@@H]2CN(C3CC4CCC3CN4C(=O)OC)C[C@@H]21] | Example 8-6 |
| 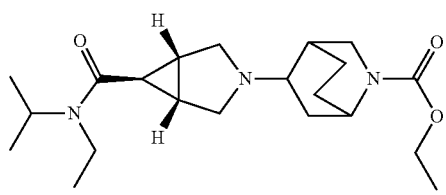 [SMILES: CCOC(=O)N1CC2CCC1CC2N1C[C@@H]2[C@H](C1)[C@H]2C(=O)N(CC)C(C)C] | Example 8-7 |
| 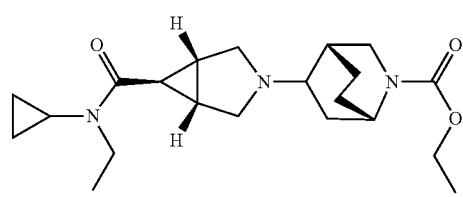 [SMILES: CCOC(=O)N1C[C@@H]2CC[C@H]1CC2N1C[C@@H]2[C@H](C1)[C@H]2C(=O)N(CC)C1CC1] | Example 8-8 |
| 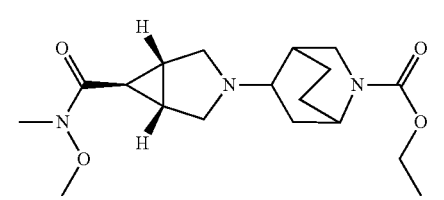 [SMILES: CCOC(=O)N1CC2CCC1CC2N1C[C@@H]2[C@H](C1)[C@H]2C(=O)N(C)OC] | Example 8-9 |
| 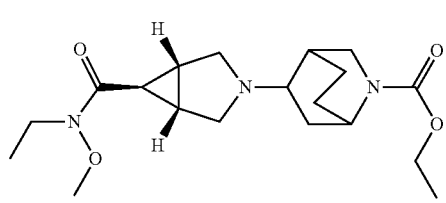 [SMILES: CCOC(=O)N1CC2CCC1CC2N1C[C@@H]2[C@H](C1)[C@H]2C(=O)N(CC)OC] | Example 8-10 |
| 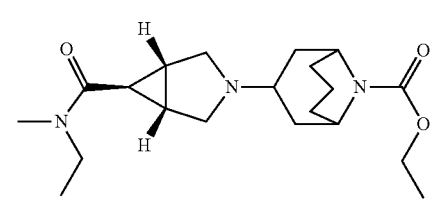 [SMILES: CCOC(=O)N1C2CCCC1CC(N1C[C@@H]3[C@H](C1)[C@H]3C(=O)N(C)CC)C2] | Example 9-1 |
| 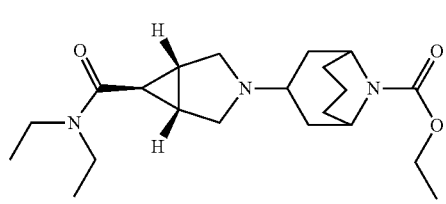 [SMILES: CCOC(=O)N1C2CCCC1CC(N1C[C@@H]3[C@H](C1)[C@H]3C(=O)N(CC)CC)C2] | Example 9-2 |
| 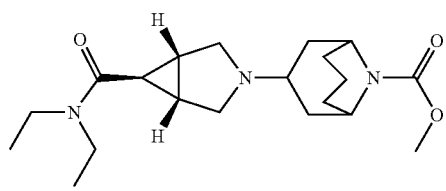 [SMILES: CCN(CC)C(=O)[C@H]1[C@@H]2CN(C3CC4CCCC(C3)N4C(=O)OC)C[C@@H]21] | Example 9-3 |

TABLE 1-continued
| | |
|---|---|
| 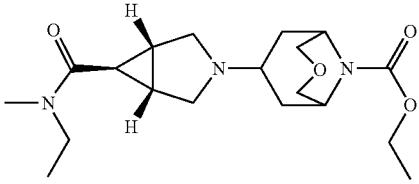 [SMILES: CCOC(=O)N1C2COCC1CC(N1C[C@@H]3[C@H](C1)[C@H]3C(=O)N(C)CC)C2] | Example 10-1 |
| 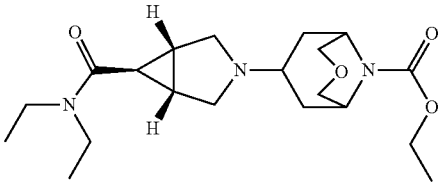 [SMILES: CCOC(=O)N1C2COCC1CC(N1C[C@@H]3[C@H](C1)[C@H]3C(=O)N(CC)CC)C2] | Example 10-2 |
| 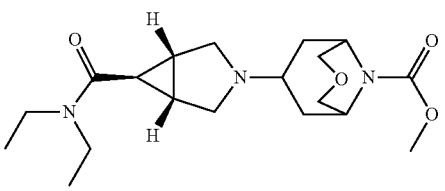 [SMILES: CCN(CC)C(=O)[C@H]1[C@@H]2CN(C3CC4COCC(C3)N4C(=O)OC)C[C@@H]21] | Example 10-3 |
| 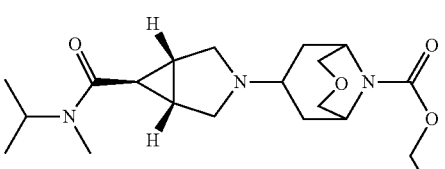 | Example 10-4 |
| 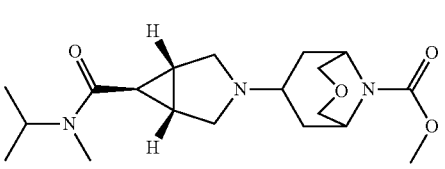 [SMILES: COC(=O)N1C2COCC1CC(N1C[C@@H]3[C@H](C1)[C@H]3C(=O)N(C)C(C)C)C2] | Example 10-5 |
| 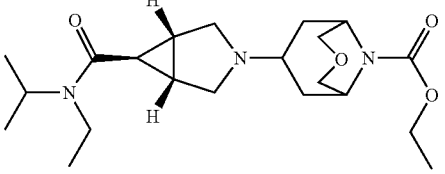 | Example 10-6 |
| 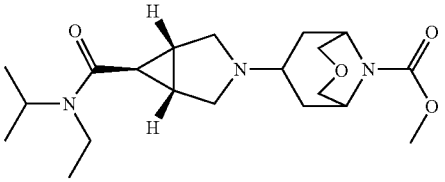 [SMILES: CCN(C(=O)[C@H]1[C@@H]2CN(C3CC4COCC(C3)N4C(=O)OC)C[C@@H]21)C(C)C] | Example 10-7 |
| 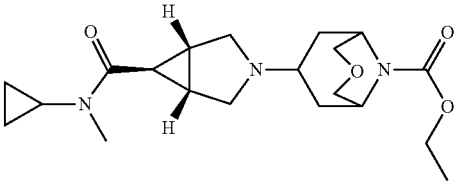 [SMILES: CCOC(=O)N1C2COCC1CC(N1C[C@@H]3[C@H](C1)[C@H]3C(=O)N(C)C1CC1)C2] | Example 10-8 |

TABLE 1-continued
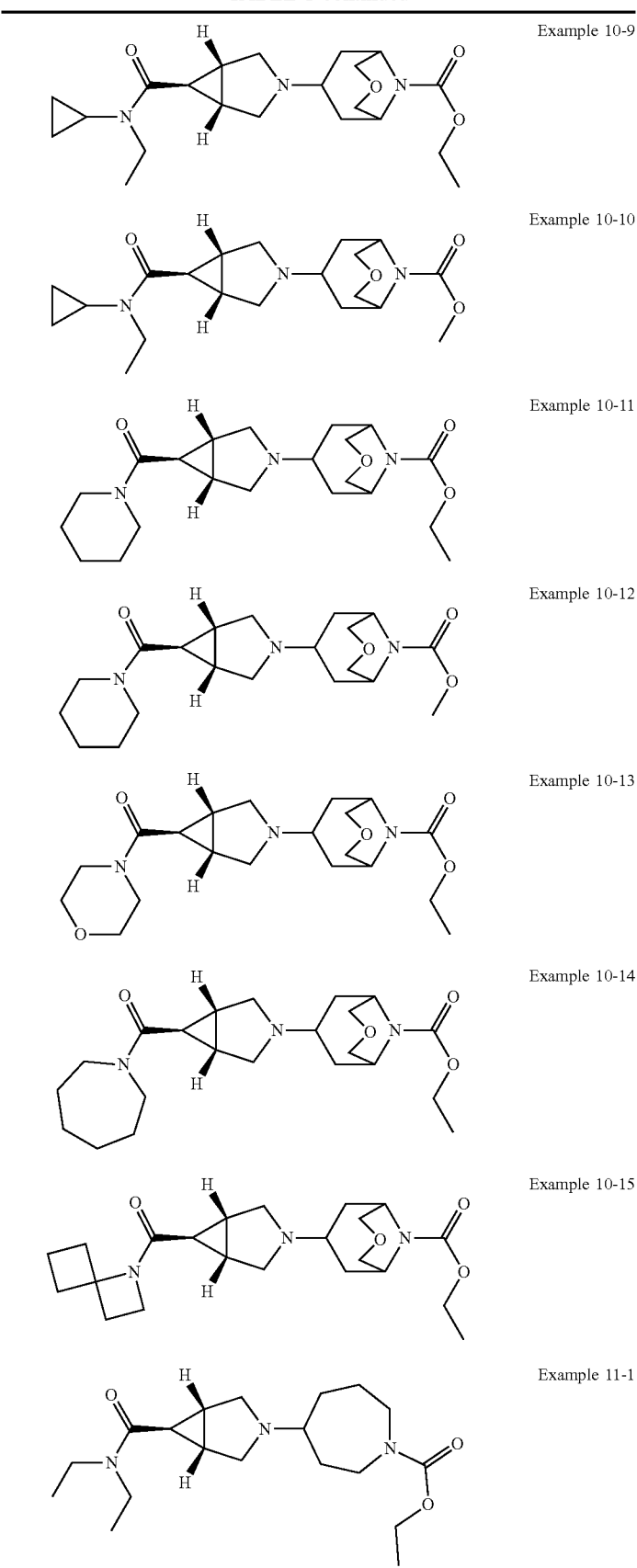
Example 10-9
Example 10-10
Example 10-11
Example 10-12
Example 10-13
Example 10-14
Example 10-15
Example 11-1

TABLE 1-continued

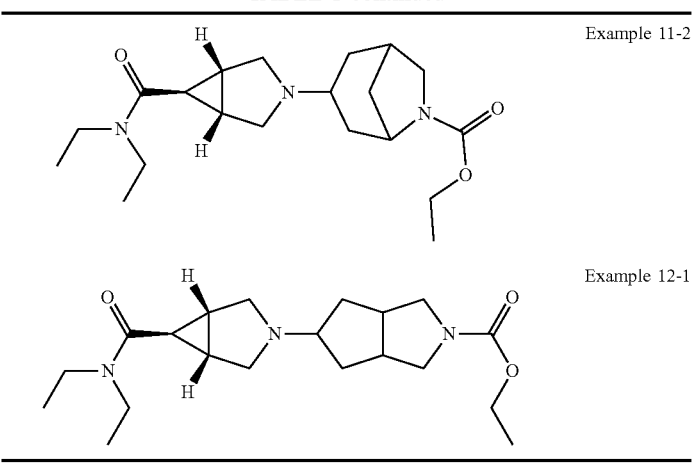

Example 11-2

Example 12-1

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions unless otherwise stated. TLC for monitoring reactions refers to TLC run using the specified mobile phase and the Silica gel F254 as a stationary phase from Merck. Microwave-mediated reactions were performed in Biotage Initiator or CEM Discover microwave reactors.

LCMS Analysis

LCMS analysis of compounds was performed under electrospray conditions using the instruments and methods given in the tables below:

LCMS Instrument Details

| System | Instrument Name | LC Detector | Mass Detector |
|---|---|---|---|
| 1 | Waters 2695 | Photo Diode Array | ZQ-2000 Detector |
| 2 | Waters Acquity H Class | Photo Diode Array | SQ Detector |
| 3 | Shimadzu Nexera | Photo Diode Array | LCMS-2020 |
| 4 | Agilent 1290 RRLC | Photo Diode Array | Agilent 6120 |
| 5 | Hewlett Packard HP 1100 | G1315A DAD | Micromass ZQ |
| 6 | Agilent 1260 Infinity LC | Photo Diode Array | Agilent 6120B |

LCMS Method Details

| Method Name | Solvent System | Column | Gradient | UV Range | Mass Range | Column Temp. ° C. | Flow Rate ml/min |
|---|---|---|---|---|---|---|---|
| A | (A) 5 mM ammonium acetate + 0.1% formic acid in water (B) 0.1% formic acid in acetonitrile | BEH C18 2.1 × 50 mm, 1.7 μm or equivalent | 95:5 at 0.01 min up to 0.40 min, 65:35 at 0.80 min, 45:55 at 1.20 min, 0:100 at 2.50 min up to 3.30 min, 95:5 at 3.31 min up to 4.00 min | 200-400 nm | 100-1200 amu | Ambient | 0.55 |
| B | (A) 20 mM ammonium acetate in water (B) methanol | X-Bridge C18 4.6 × 150 mm, 5 μm or equivalent | 90:10 at 0.01 min, 10:90 at 5.00 min, 0:100 at 7.00 min up to 11.00 min, 90:10 at 11.01 min up to 12.00 min | 200-400 nm | 60-1000 amu | Ambient | 1.00 |
| C | (A) 0.1% ammonia in water (B) 0.1% ammonia in acetonitrile | X-Bridge C18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |
| D | (A) 5 mM ammonium acetate + 0.1% formic acid in water (B) 0.1% formic acid in acetonitrile | BEH C18 2.1 × 50 mm, 1.7 μm or equivalent | 95:5 at 0.01 min up to 0.40 min, 60:40 at 0.60 min, 40:60 at 1.20 min, 0:100 at 2.30 min up to 3.00 min, 95:5 at 3.01 min up to 3.50 min | 200-400 nm | 100-1200 amu | Ambient | 0.55 |
| E | (A) 5 mM ammonium bicarbonate in water (B) acetonitrile | X-Bridge C18 4.6 × 50 mm, 3.5 μm or equivalent | 95:5 at 0.01 min, 10:90 at 5.0 min & 5:95 at 5.80 min till 7.20 min, 95:5 at 7.21 min up to 10.0 min | 200-400 nm | 60-1000 amu | Ambient | 1.00 |

LCMS Method Details

| Method Name | Solvent System | Column | Gradient | UV Range | Mass Range | Column Temp. ° C. | Flow Rate ml/min |
|---|---|---|---|---|---|---|---|
| F | (A) 2.5 L water + 2.5 mL 28% ammonia solution in water (B) 2.5 L acetonitrile + 135 mL water + 2.5 mL 28% ammonia solution in water | Gemini-NX C-18, 2.0 × 30 mm, 3 μm | 98:2 at 0.00 min up to 0.10 min, 5:95 at 2.50 min up to 3.50 min | 230-400 nm | 130-800 amu | 45 | 1.50 |
| G | (A) 2.5 L water + 2.5 mL 28% ammonia solution in water B) 2.5 L acetonitrile + 135 mL water + 2.5 mL 28% ammonia solution in water | Gemini-NX C-18, 2.0 × 30 mm, 3 μm | 98:2 at 0.00 min up to 0.10 min, 5:95 at 8.40 min up to 10.00 min | 230-400 nm | 130-800 amu | 45 | 1.50 |
| H | (A) 2.5 L water + 2.5 mL 28% ammonia solution in water (B) 2.5 L acetonitrile + 130 mL water + 2.5 mL 28% ammonia solution in water | Gemini-NX C-18, 2.0 × 30 mm, 3 μm | 95:5 at 0.00 min, 5:95 at 2.00 min up to 2.50 min, 95:5 at 2.60 min up to 3.0 min | 190-400 nm | 150-800 amu | 40 | 1.50 |
| I | (A) 2.5 L water + 2.5 mL 28% ammonia solution in water (B) 2.5 L acetonitrile + 130 mL water + 2.5 mL 28% ammonia solution in water | Gemini-NX C-18, 2.0 × 30 mm, 3 μm | 98:2 at 0.00 min up to 0.10 min, 5:95 at 8.40 min up to 10.00 min | 190-400 nm | 150-800 amu | 40 | 1.50 |

LCMS data in the experimental section and Tables 2 and 3 are given in the format: (Instrument system, Method): Mass ion, retention time, UV detection wavelength.

Compound Purification

Final purification of compounds was performed by preparative reversed phase HPLC, chiral HPLC or chiral SFC using the instruments and methods detailed below where data is given in the following format: Purification technique: [phase (column description, column length×internal diameter, particle size), solvent flow-rate, gradient—given as % of mobile phase B in mobile phase A (over time), mobile phase (A), mobile phase (B)].

Preparative HPLC Purification:

Shimadzu LC-20AP binary system with SPD-20A UV detector

Gilson semi preparative HPLC system with 321 pump, GX-271 liquid handler and Gilson 171 DAD controlled with Gilson Trilution software Chiral HPLC Purification:

Shimadzu LC-20Aβ binary system with SPD-20A UV detector

Chiral SFC Purification:

WatersSFC 200

Sepiatec 100

Berger Multigram 2

Purification Method A

Prep HPLC: [Reversed Phase (X-BRIDGE C-18, 150×19 mm, 5 μm), 15 mL/min, gradient 5%-30% (over 30 min), 30% (over 5 min), 100% (over 2 min), 100%-5% (over 3 min), mobile phase (A): 0.1% ammonia in water, (B): 100% acetonitrile].

Purification Method B

Prep HPLC: [Reversed Phase (X-BRIDGE C-18, 250×19 mm, 5 μm), 17 mL/min, gradient 30%-50% (over 12 min), 100% (over 2 min), 100%-30% (over 2 min), mobile phase (A): 0.1% ammonia in water, (B): 100% acetonitrile].

Purification Method C

Prep HPLC: [Reversed Phase (Gemini C-18, 250×21.2 mm, 5 μm), 15 mL/min, gradient 40%-50% (over 17 min), 100% (over 2 min), 100%-40% (over 3 min), mobile phase (A): 0.1% ammonia in water, (B): 100% acetonitrile].

Purification Method D

Prep HPLC: [Reversed Phase (X-BRIDGE C-18, 250×19 mm, 5 μm), 17 mL/min, gradient 35%-60% (over 12 min), 100% (over 2 min), 100%-35% (over 2 min), mobile phase (A): 0.1% ammonia in water, (B): 100% acetonitrile].

Purification Method E

Prep HPLC: [Reversed Phase (X-BRIDGE C-18, 150×19 mm, 5 μm), 15 mL/min, gradient 35%-56% (over 12 min), 100% (over 1 min), 100%-35% (over 3 min), mobile phase (A): 0.1% ammonia in water, (B): 100% acetonitrile].

Purification Method F

Prep HPLC: [Reversed Phase (X-BRIDGE C-18, 150×19 mm, 5 μm), 14 mL/min, gradient 27% (over 30 min), 100% (over 3 min), 100%-27% (over 3 min), mobile phase (A): 0.1% ammonia in water, (B): 100% acetonitrile].

Purification Method G

Prep HPLC: [Reversed Phase (X-BRIDGE C-18, 150×19 mm, 5 μm), 17 mL/min, gradient 2%-30% (over 30 min), 30% (over 5 min), 95% (over 3 min), 95%-2% (over 2 min), mobile phase (A): 0.1% ammonia in water, (B): 100% acetonitrile].

Purification Method H

Prep HPLC: [Reversed Phase (X-BRIDGE C-18, 150×19 mm, 5 μm), 10 mL/min, gradient 5% (over 5 min), 5%-30% (over 5 min), 30% (over 23 min), 100% (over 3 min), 100%-5% (over 4 min), mobile phase (A): 0.1% ammonia in water, (B): 100% acetonitrile].

Purification Method I

Prep HPLC: [Reversed Phase (X SELECT PHENYL HEXYL, 250×19 mm, 5 μm), 16 mL/min, gradient 5%-34% (over 40 min), 34% (over 2 min), 100% (over 1 min), 100%-5% (over 3 min), mobile phase (A): 5 mM ammonium bicarbonate in water+0.05% ammonia in water, (B) 100% acetonitrile].

Purification Method J

SFC: [(CHIRALPAK AD-H, 250×21 mm, 5 μm), 75 mL/min, Isochratic (A:B) 85:15 (over 6 min), mobile phase (A): 100% liquid $CO_2$, (B): 0.1% diethylamine in isopropanol:methanol (50:50)].

Purification Method K

Prep HPLC: [Reversed Phase (YMC ACTUS TRIART C-18, 250×20 mm, 5 μm), 15 mL/min, gradient 25%-58% (over 18 min), 100% (over 2 min), 100%-25% (over 2 min), mobile phase (A): 10 mM ammonium bicarbonate in water, (B): 100% acetonitrile].

Purification Method L

Prep HPLC: [Reversed Phase (X SELECT PHENYL HEXYL, 250×19 mm, 5 μm), 15 mL/min, gradient 20%-30% (over 10 min), 30% (over 13 min), 100% (over 3 min), 100%-20% (over 4 min), mobile phase (A): 0.1% ammonia in water, (B) 100% acetonitrile].

Purification Method M

Chiral HPLC: [Normal Phase (CHIRALPAK AD-H, 250× 21 mm, 5 μm), 10 mL/min, Isochratic (A:B) 85:15 (over 25 min), mobile phase (A): 0.3% diethylamine in hexane, (B): 0.3% diethylamine in isopropanol:methanol (70:30)].

Purification Method N

Prep HPLC: [Reversed Phase (X-BRIDGE C-18, 250×19 mm, 5 μm), 16 mL/min, gradient 15%-40% (over 32 min), 100% (over 3 min), 100-15% (over 5 min), mobile phase (A): 0.05% ammonia in water, (B): 100% acetonitrile].

Purification Method O

Chiral HPLC: [Normal Phase (CHIRALPAK AD-H, 250× 21 mm, 5 μm), 18 mL/min, Isochratic (A:B) 85:15 (over 15 min), mobile phase (A): 0.1% diethylamine in hexane, (B): 0.1% diethylamine in isopropanol].

Purification Method P

Prep HPLC: [Reversed Phase (GEMINI C-18, 250×21.2 mm, 5 μm), 16 mL/min, gradient 35%-60% (over 18 min), 100% (over 2 min), 100%-35% (over 2 min), mobile phase (A): 10 mM ammonium bicarbonate in water, (B): 100% acetonitrile].

Purification Method Q

SFC: [(CHIRALPAK AD-H, 250×21 mm, 5 μm), 80 mL/min, Isochratic (A:B) 85:15 (over 5 min), mobile phase (A): 100% liquid $CO_2$, (B): 0.1% TFA in isopropanol].

Purification Method R

Prep HPLC: [Reversed Phase (X-BRIDGE C-18, 250×19 mm, 5 μm), 14 mL/min, gradient 50% (over 18 min), 100% (over 3 min), 100%-50% (over 4 min), mobile phase (A): 0.1% ammonia in water, (B): acetonitrile:methanol (50:50)].

Purification Method S

SFC: [(CHIRALPAK AD-H, 250×21 mm, 5 μm), 80 mL/min, Isochratic (A:B) 80:20 (over 5 min), mobile phase (A): 100% liquid $CO_2$, (B): 0.1% TFA in isopropanol].

Purification Method T

Prep HPLC: [Reversed Phase (YMC ACTUS TRIART C-18, 250×20 mm, 5 μm), 15 mL/min, gradient 45%-60% (over 20 min), 100% (over 3 min), 100%-45% (over 2 min), mobile phase (A): 0.1% ammonia in water, (B): 100% acetonitrile].

Purification Method U

Prep HPLC: [Reversed Phase (X SELECT PHENYL HEXYL, 250×19 mm, 5 μm), 15 mL/min, gradient 5% (over 5 min), 5%-24% (over 3 min), 24% (over 34 min), 100% (over 3 min), 100%-5% (over 3 min), mobile phase (A): 0.1% ammonia in water, (B) 100% acetonitrile].

Purification Method V

Prep HPLC: [Reversed Phase (X SELECT PHENYL HEXYL, 250×19 mm, 5 μm), 15 mL/min, gradient 5% (over 5 min), 5%-30% (over 3 min), 30%-35% (over 37 min), 100% (over 2 min), 100%-5% (over 3 min), mobile phase (A): 0.1% ammonia in water, (B) 100% acetonitrile].

Purification Method W

Prep HPLC: [Reversed Phase (X SELECT PHENYL HEXYL, 250×19 mm, 5 μm), 16 mL/min, gradient 40%-55% (over 10 min), 100% (over 2 min), 100%-40% (over 2 min), mobile phase (A): 10 mM ammonium bicarbonate in water, (B) 100% acetonitrile].

Purification Method X

SFC: [(CHIRALPAK AD-H, 250×21 mm, 5 μm), 50 mL/min, Isochratic (A:B) 80:20 (over 5 min), mobile phase (A): 100% liquid $CO_2$, (B): 0.1% TFA in isopropanol].

Purification Method Y

Prep HPLC: [Reversed Phase (X-BRIDGE C-18, 250×19 mm, 5 μm), 15 mL/min, gradient 30%-50% (over 20 min), 100% (over 2 min), 100%-30% (over 2 min), mobile phase (A): 10 mM ammonium bicarbonate in water, (B): 100% acetonitrile].

Purification Method Z

Prep HPLC: [Reversed Phase (X SELECT PHENYL HEXYL, 150×19 mm, 5 μm), 15 mL/min, gradient 15%-65% (over 16 min), 100% (over 2 min), 100%-15% (over 2 min), mobile phase (A): 10 mM ammonium bicarbonate in water, (B) 100% acetonitrile].

Purification Method AA

SFC: [(CHIRALPAK AD-H, 250×21 mm, 5 μm), 70 mL/min, Isochratic (A:B) 85:15 (over 10 min), mobile phase (A): 100% liquid $CO_2$, (B): isopropanol].

Purification Method AB

Prep HPLC: [Reversed Phase (X SELECT PHENYL HEXYL, 250×19 mm, 5 μm), 17 mL/min, gradient 10%-30% (over 40 min), 30% (over 3 min), 100% (over 2 min), 100%-10% (over 2 min), mobile phase (A): 5 mM ammonium bicarbonate in water+0.05% ammonia in water, (B) 100% acetonitrile].

Purification Method AC

Prep HPLC: [Reversed Phase (GEMINI C-18, 250×21.2 mm, 5 μm), 16 mL/min, gradient 45%-80% (over 12 min), 100% (over 2 min), 100%-45% (over 2 min), mobile phase (A): 0.1% ammonia in water, (B): 100% acetonitrile].

Purification Method AD

Prep HPLC: [Reversed Phase (X SELECT PHENYL HEXYL, 250×19 mm, 5 μm), 15 mL/min, gradient 15%-45% (over 28 min), 100% (over 2 min), 100%-15% (over 2 min), mobile phase (A): 5 mM ammonium bicarbonate in water+0.05% ammonia in water, (B) 100% acetonitrile].

Purification Method AE

SFC: [(CHIRALCEL AD-H, 250×21 mm, 5 μm), 70 mL/min, Isochratic (A:B) 85:15 (over 12 min), mobile phase (A): 100% liquid $CO_2$, (B): 0.1% diethylamine in isopropanol:methanol (50:50)].

Purification Method AF

Prep HPLC: [Reversed Phase (X-BRIDGE C-18, 250×19 mm, 5 μm), 16 mL/min, gradient 38%-45% (over 16 min), 100% (over 2 min), 100%-38% (over 4 min), mobile phase (A): 0.1% ammonia in water, (B): 100% acetonitrile].

Purification Method AG

SFC: [(CHIRALPAK AD-H, 250×21 mm, 5 μm), 60 mL/min, Isochratic (A:B) 80:20 (over 6 min), mobile phase (A): 100% liquid $CO_2$, (B): 0.1% ammonia in isopropanol].

Purification Method AH

Prep HPLC: [Reversed Phase (X SELECT PHENYL HEXYL, 250×19 mm, 5 μm), 15 mL/min, gradient 22% (over 30 min), 100% (over 2 min), 100%-22% (over 3 min), mobile phase (A): 5 mM ammonium bicarbonate in water, (B) 100% acetonitrile].

Purification Method AI

Prep HPLC: [Reversed Phase (X-BRIDGE C-18, 250×19 mm, 5 μm), 12 mL/min, gradient 27% (over 35 min), 100% (over 2 min), 100%-27% (over 3 min), mobile phase (A): 0.1% ammonia in water, (B): 100% acetonitrile].

Purification Method AJ

Prep HPLC: [Reversed Phase (X-BRIDGE C-18, 250×19 mm, 5 μm), 11 mL/min, gradient 33% (over 25 min), 100% (over 2 min), 100%-33% (over 3 min), mobile phase (A): 10 mM ammonium bicarbonate in water, (B): 100% acetonitrile].

Purification Method AK

Prep HPLC: [Reversed Phase (X-BRIDGE C-18, 250×19 mm, 5 μm), 18 mL/min, gradient 35% (over 85 min), 100% (over 2 min), 100%-35% (over 8 min), mobile phase (A): 0.1% ammonia in water, (B): 100% acetonitrile].

Purification Method AL

Prep HPLC: [Reversed Phase (X SELECT PHENYL HEXYL, 250×19 mm, 5 μm), 15 mL/min, gradient 40% (over 25 min), 100% (over 2 min), 100%-40% (over 3 min), mobile phase (A): 0.02% ammonia in water, (B) 100% acetonitrile].

Purification Method AM

Prep HPLC: [Reversed Phase (YMC ACTUS TRIART C-18, 250×20 mm, 5 μm), 15 mL/min, gradient 60%-92% (over 16 min), 100% (over 2 min), 100%-60% (over 4 min), mobile phase (A): 0.1% ammonia in water, (B): 100% acetonitrile].

Purification Method AN

Prep HPLC: [Reversed Phase (X SELECT PHENYL HEXYL, 250×19 mm, 5 μm), 16 mL/min, gradient 10%-50% (over 10 min), 50% (over 15 min), 100% (over 2 min), 100%-10% (over 3 min), mobile phase (A): 5 mM ammonium bicarbonate in water, (B) 100% acetonitrile].

Purification Method AO

Prep HPLC: [Reversed Phase (X-BRIDGE C-18, 150×19 mm, 5 μm), 15 mL/min, gradient 30% (over 27.5 min), 100% (over 2.5 min), 100%-30% (over 4 min), mobile phase (A): 0.1% ammonia in water, (B): 100% acetonitrile].

Purification Method Aβ

Prep HPLC: [Reversed Phase (X SELECT PHENYL HEXYL, 250×19 mm, 5 μm), 16 mL/min, gradient 15% (over 2 min), 15%-35% (over 8 min), 35% (over 18 min), 100% (over 3 min), 100%-15% (over 4 min), mobile phase (A): 10 mM ammonium bicarbonate in water, (B) 100% acetonitrile].

Purification Method AQ

Prep HPLC: [Reversed Phase (YMC ACTUS TRIART C-18, 250×20 mm, 5 μm), 17 mL/min, gradient 20%-55% (over 20 min), 100% (over 2 min), 100%-20% (over 3 min), mobile phase (A): 0.1% ammonia in water, (B): 100% acetonitrile].

Purification Method AR

Prep HPLC: [Reversed Phase (X-BRIDGE C-18, 250×19 mm, 5 μm), 15 mL/min, gradient 60%-70% (over 15 min), 100% (over 2 min), 100%-60% (over 3 min), mobile phase (A): 0.1% ammonia in water, (B): acetonitrile:methanol (50:50)].

Purification Method AS

SFC: [(CHIRALPAK IC, 250×21 mm, 5 μm), 70 mL/min, Isochratic (A:B) 70:30 (over 15 min), mobile phase (A): 100% liquid $CO_2$, (B): 0.3% diethylamine in methanol].

Purification Method AT

Prep HPLC: [Reversed Phase (X SELECT PHENYL HEXYL, 150×19 mm, 5 μm), 15 mL/min, gradient 35%-40% (over 15 min), 100% (over 3 min), 100%-35% (over 2 min), mobile phase (A): 10 mM ammonium bicarbonate in water+0.1% ammonia in water, (B) 100% acetonitrile].

Purification Method AU

Prep HPLC: [Reversed Phase (X-BRIDGE C-18, 250×19 mm, 5 μm), 15 mL/min, gradient 20%-35% (over 20 min), 100% (over 2 min), 100%-20% (over 2 min), mobile phase (A): 5 mM ammonium bicarbonate in water+0.1% ammonia in water, (B): 100% acetonitrile].

Purification Method AV

SFC: [(CHIRALPAK IB, 250×20 mm, 5 μm), 70 mL/min, Isochratic (A:B) 85:15 (over 5 min), mobile phase (A): 100% liquid $CO_2$, (B): 0.1% diethylamine in isopropanol:methanol (50:50)].

Purification Method AW

Prep HPLC: [Reversed Phase (YMC ACTUS TRIART C-18, 150×20 mm, 5 μm), 15 mL/min, gradient 50% (over 17 min), 100% (over 2 min), 100%-50% (over 4 min), mobile phase (A): 5 mM ammonium bicarbonate in water+0.1% ammonia in water, (B): 100% acetonitrile].

Purification Method AX

SFC: [(CHIRALPAK IC, 250×21 mm, 5 μm), 70 mL/min, Isochratic (A:B) 88:12 (over 11 min), mobile phase (A): 100% liquid $CO_2$, (B): 0.1% diethylamine in isopropanol:methanol (50:50)].

Purification Method AY

Prep HPLC: [Reversed Phase (X SELECT PHENYL HEXYL, 250×19 mm, 5 μm), 15 mL/min, gradient 20%-70% (over 20 min), 100% (over 2 min), 100%-20% (over 3 min), mobile phase (A): 5 mM ammonium bicarbonate in water+0.1% ammonia in water, (B) 100% acetonitrile].

Purification Method AZ

SFC: [(CHIRALPAK AD-H, 250×21 mm, 5 μm), 70 mL/min, Isochratic (A:B) 85:15 (over 4.5 min), mobile phase (A): 100% liquid $CO_2$, (B): 0.1% diethylamine in methanol].

Purification Method BA

Prep HPLC: [Reversed Phase (X SELECT PHENYL HEXYL, 150×19 mm, 5 μm), 15 mL/min, gradient 22%-45% (over 40 min), 100% (over 2 min), 100%-22% (over 3 min), mobile phase (A): 0.02% ammonia in water, (B) 100% acetonitrile].

Purification Method BB

Prep HPLC: [Reversed Phase (Gemini-NX C-18, 100×30 mm, 5 μm), 30 mL/min, gradient 20%-50% (over 8.7 min), 50% (over 0.5 min), 50%-100% (over 0.2 min), 100% (over 1 min), 100%-20% (over 0.2 min), 20% (over 0.9 min), mobile phase (A): 2.5 L of water+5 mL of 28% ammonia solution in water, (B): 100% acetonitrile].

Purification Method BC

Prep HPLC: [Reversed Phase (X SELECT PHENYL HEXYL, 250×19 mm, 5 μm), 15 mL/min, gradient 30%-50% (over 27 min), 50%-100% (over 2 min), 100% (over 1 min), 100%-30% (over 1 min), mobile phase (A): 0.02% ammonia in water, (B) 100% acetonitrile].

Purification Method BD

Prep HPLC: [Reversed Phase (X SELECT PHENYL HEXYL, 250×19 mm, 5 μm), 15 mL/min, gradient 30%-35% (over 28 min), 35%-55% (over 7 min), 100% (over 2 min), 100%-30% (over 2 min), mobile phase (A): 0.02% ammonia in water, (B) 100% acetonitrile].

Purification Method BE

Prep HPLC: [Reversed Phase (X SELECT PHENYL HEXYL, 250×19 mm, 5 μm), 15 mL/min, gradient 15%-65% (over 18 min), 100% (over 2 min), 100%-15% (over 3 min), mobile phase (A): 5 mM ammonium bicarbonate in water+0.1% ammonia in water, (B) 100% acetonitrile].

Purification Method BF
Prep HPLC: [Reversed Phase (X SELECT PHENYL HEXYL, 250×19 mm, 5 μm), 15 mL/min, gradient 43% (over 14 min), 43%-70% (over 1 min), 70% (over 7 min), 100% (over 1 min), 100%-43% (over 2 min), mobile phase (A): 10 mM ammonium bicarbonate in water, (B) 100% acetonitrile].

Purification Method BG
Prep HPLC: [Reversed Phase (X-BRIDGE C-18, 150×19 mm, 5 μm), 15 mL/min, gradient 40%-55% (over 16 min), 55% (over 2 min), 100% (over 3 min), 100%-40% (over 3 min), mobile phase (A): 0.1% ammonia in water, (B): 100% acetonitrile].

Purification Method BH
Prep HPLC: [Reversed Phase (Gemini-NX C-18, 100×30 mm, 5 μm), 30 mL/min, gradient 30%-50% (over 8.7 min), 50% (over 0.5 min), 50%-100% (over 0.2 min), 100% (over 1 min), 100%-30% (over 0.2 min), 30% (over 0.9 min), mobile phase (A): 2.5 L of water+5 mL of 28% ammonia solution in water, (B): 100% acetonitrile].

Purification Method BI
SFC: [(CHIRALPAK AS-H, 250×20 mm, 5 μm), 50 mL/min, Isochratic (A:B) 80:20, mobile phase (A): 100% liquid $CO_2$, (B): 0.1% ammonia in ethanol].

Purification Method BJ
Prep HPLC: [Reversed Phase (Gemini-NX C-18, 100×30 mm, 5 μm), 30 mL/min, gradient 40%-60% (over 8.7 min), 60% (over 0.5 min), 60%-100% (over 0.2 min), 100% (over 1 min), 100%-40% (over 0.2 min), 40% (over 0.9 min), mobile phase (A): 2.5 L of water+5 mL of 28% ammonia solution in water, (B): 100% acetonitrile].

Purification Method BK
SFC: [(LUX C4, 250×21.2 mm, 5 μm), 50 mL/min, Isochratic (A:B) 70:30, mobile phase (A): 100% liquid $CO_2$, (B): 0.1% ammonia in methanol].

Purification Method BL
Prep HPLC: [Reversed Phase (X-BRIDGE C-18, 250×19 mm, 5 μm), 15 mL/min, gradient 25%-60% (over 15 min), 100% (over 3 min), 100%-25% (over 2 min) mobile phase (A): 10 mM ammonium bicarbonate in water, (B): 100% acetonitrile].

Purification Method BM
SFC: [(CHIRALPAK AD-H, 250×21 mm, 5 μm), 70 mL/min, Isochratic (A:B) 80:20 (over 15 min), mobile phase (A): 100% liquid $CO_2$, (B): isopropanol:acetonitrile (50:50)].

Purification Method BN
Prep HPLC: [Reversed Phase (X SELECT PHENYL HEXYL, 250×19 mm, 5 μm), 15 mL/min, gradient 35%-50% (over 17 min), 100% (over 2 min), 100%-35% (over 2 min), mobile phase (A): 0.1% ammonia in water, (B) 100% acetonitrile].

Purification Method BO
Prep HPLC: [Reversed Phase (Gemini-NX C-18, 100×30 mm, 5 μm), 30 mL/min, gradient 50%-70% (over 8.7 min), 70% (over 0.5 min), 70%-100% (over 0.2 min), 100% (over 1 min), 100%-50% (over 0.2 min), 50% (over 0.9 min), mobile phase (A): 2.5 L of water+5 mL of 28% ammonia solution in water, (B): 100% acetonitrile].

Purification Method BP
Prep HPLC: [Reversed Phase (X-BRIDGE C-18, 250×19 mm, 5 μm), 12 mL/min, gradient 55% (over 28 min), 100% (over 2 min), 100%-55% (over 5 min), mobile phase (A): 10 mM ammonium bicarbonate in water, (B): 100% acetonitrile].

Purification Method BQ
Prep HPLC: [Reversed Phase (X-BRIDGE C-18, 250×19 mm, 5 μm), 15 mL/min, gradient 20%-45% (over 40 min), 100% (over 3 min), 100%-20% (over 3 min), mobile phase (A): 10 mM ammonium bicarbonate in water, (B): 100% acetonitrile].

Purification Method BR
Prep HPLC: [Reversed Phase (X-BRIDGE C-8, 250×19 mm, 5 μm), 15 mL/min, gradient 10%-30% (over 10 min), 30% (over 22 min), 100% (over 2 min), 100%-10% (over 3 min), mobile phase (A): 5 mM ammonium bicarbonate in water+0.1% ammonia in water, (B): 100% acetonitrile].

Purification Method BS
Prep HPLC: [Reversed Phase (X SELECT PHENYL HEXYL, 250×19 mm, 5 μm), 16 mL/min, gradient 20%-50% (over 20 min), 50% (over 12 min), 100% (over 2 min), 100%-20% (over 3 min), mobile phase (A): 5 mM ammonium bicarbonate in water, (B) acetonitrile:methanol (50:50)].

Purification Method BT Chiral HPLC: [Normal Phase (CHIRALPAK IC, 250×21 mm, 5 μm), 18 mL/min, Isochratic (A:B) 75:25 (over 38 min), mobile phase (A): 0.1% diethylamine in hexane, (B): 0.1% diethylamine in isopropanol:methanol (50:50)].

Purification Method BU
Prep HPLC: [Reversed Phase (X-BRIDGE C-8, 250×19 mm, 5 μm), 17 mL/min, gradient 30% (over 22 min), 100% (over 2 min), 100%-30% (over 3 min), mobile phase (A): 5 mM ammonium bicarbonate in water+0.05% ammonia in water, (B): 100% acetonitrile].

Purification Method BV
Prep HPLC: [Reversed Phase (X SELECT PHENYL HEXYL, 250×19 mm, 5 μm), 15 mL/min, gradient 15%-40% (over 10 min), 40% (over 3 min), 100% (over 2 min), 100%-15% (over 3 min), mobile phase (A): 5 mM ammonium bicarbonate in water, (B) 100% acetonitrile].

Purification Method BW
SFC: [(CHIRALCEL OX-H, 250×21 mm, 5 μm), 70 mL/min, Isochratic (A:B) 80:20 (over 13 min), mobile phase (A): 100% liquid $CO_2$, (B): 0.1% diethylamine in isopropanol methanol (50:50)].

Purification Method BX
Prep HPLC: [Reversed Phase (X SELECT PHENYL HEXYL, 250×19 mm, 5 μm), 15 mL/min, gradient 15%-40% (over 18 min), 100% (over 2 min), 100%-15% (over 4 min), mobile phase (A): 5 mM ammonium bicarbonate in water, (B) 100% acetonitrile].

Purification Method BY
SFC: [(CHIRALPAK IC, 250×21 mm, 5 μm), 70 mL/min, Isochratic (A:B) 70:30 (over 10 min), mobile phase (A): 100% liquid $CO_2$, (B): 0.3% diethylamine in isopropanol:acetonitrile (60:40)].

Purification Method BZ
Prep HPLC: [Reversed Phase (X SELECT PHENYL HEXYL, 250×19 mm, 5 μm), 15 mL/min, gradient 20%-35% (over 18 min), 100% (over 2 min), 100%-20% (over 3 min), mobile phase (A): 5 mM ammonium bicarbonate in water+0.1% ammonia in water, (B) 100% acetonitrile].

Purification Method CA
SFC: [(CHIRALCEL OX-H, 250×21 mm, 5 μm), 75 mL/min, Isochratic (A:B) 85:15 (over 20 min), mobile phase (A): 100% liquid $CO_2$, (B): 0.1% diethylamine in isopropanol methanol (50:50)].

Purification Method CB
Prep HPLC: [Reversed Phase (X SELECT PHENYL HEXYL, 250×19 mm, 5 μm), 15 mL/min, gradient 25-35% (over 20 min), 100% (over 2 min), 100%-25% (over 1 min), mobile phase (A): 5 mM ammonium bicarbonate in water+0.1% ammonia in water, (B) 100% acetonitrile].

Purification Method CC

SFC: [(CHIRALPAK IB, 250×20 mm, 5 µm), 70 mL/min, Isochratic (A:B) 87:13 (over 5 min), mobile phase (A): 100% liquid $CO_2$, (B): 0.1% diethylamine in isopropanol:methanol (50:50)].

Purification Method CD

Prep HPLC: [Reversed Phase (X SELECT PHENYL HEXYL, 250×19 mm, 5 µm), 16 mL/min, gradient 5%-40% (over 20 min), 100% (over 2 min), 100%-5% (over 3 min), mobile phase (A): 5 mM ammonium bicarbonate in water+0.1% ammonia in water, (B) 100% acetonitrile].

Purification Method CE

SFC: [(CHIRALPAK IB, 250×20 mm, 5 µm), 70 mL/min, Isochratic (A:B) 85:15 (over 6 min), mobile phase (A): 100% liquid $CO_2$, (B): 0.1% diethylamine in methanol].

Purification Method CF

SFC: [(CHIRALPAK IC, 250×21 mm, 5 µm), 70 mL/min, Isochratic (A:B) 75:25 (over 21 min), mobile phase (A): 100% liquid $CO_2$, (B): 0.1% diethylamine in isopropanol].

Purification Method CG

Prep HPLC: [Reversed Phase (X SELECT PHENYL HEXYL, 250×19 mm, 5 µm), 16 mL/min, gradient 5%-37% (over 27 min), 37% (over 2 min), 100% (over 2 min), 100%-5% (over 4 min), mobile phase (A): 5 mM ammonium bicarbonate in water+0.1% ammonia in water, (B) 100% acetonitrile].

Purification Method CH

SFC: [(CHIRALPAK IB, 250×20 mm, 5 µm), 80 mL/min, Isochratic (A:B) 85:15 (over 5 min), mobile phase (A): 100% liquid $CO_2$, (B): 0.1% diethylamine in isopropanol:methanol (50:50)].

Purification Method CI

Prep HPLC: [Reversed Phase (X SELECT PHENYL HEXYL, 250×19 mm, 5 µm), 15 mL/min, gradient 0%-55% (over 20 min), 100% (over 2 min), 100%-0% (over 3 min), mobile phase (A): 5 mM ammonium bicarbonate in water+0.1% ammonia in water, (B) 100% acetonitrile].

Purification Method CJ

SFC: [(CHIRALPAK IB, 250×20 mm, 5 µm), 50 mL/min, Isochratic (A:B) 85:15 (over 6 min), mobile phase (A): 100% liquid $CO_2$, (B): 0.1% diethylamine in methanol].

Purification Method CK

Prep HPLC: [Reversed Phase (X-BRIDGE C-18, 150×19 mm, 5 µm), 15 mL/min, gradient 22% (over 60 min), 100% (over 5 min), 100%-22% (over 4 min), mobile phase (A): 5 mM ammonium bicarbonate in water+0.05% ammonia in water, (B): 100% acetonitrile].

Purification Method CL

Prep HPLC: [Reversed Phase (X SELECT PHENYL HEXYL, 250×19 mm, 5 µm), 15 mL/min, gradient 10-40% (over 20 min), 40% (over 2 min), 100% (over 2 min), 100-10% (over 3 min), mobile phase (A): 5 mM ammonium bicarbonate in water+0.1% ammonia in water, (B) 100% acetonitrile].

Purification Method CM

SFC: [(CHIRALPAK IB, 250×20 mm, 5 µm), 70 mL/min, Isochratic (A:B) 88:12 (over 10 min), mobile phase (A): 100% liquid $CO_2$, (B): 0.1% diethylamine in methanol].

Purification Method CN

Prep HPLC: [Reversed Phase (X-BRIDGE C-8, 250×19 mm, 5 µm), 16 mL/min, gradient 15%-16.5% (over 15 min), 16.5% (over 13 min), 100% (over 4 min), 100%-15% (over 5 min), mobile phase (A): 5 mM ammonium bicarbonate in water, (B): 100% acetonitrile].

Purification Method CO

SFC: [(CHIRALCEL OX-H, 250×21 mm, 5 µm), 80 mL/min, Isochratic (A:B) 75:25 (over 13 min), mobile phase (A): 100% liquid $CO_2$, (B): 0.1% diethylamine in methanol].

Purification Method CP

Prep HPLC: [Reversed Phase (X-BRIDGE C-18, 250×19 mm, 5 µm), 15 mL/min, gradient 5%-25% (over 29 min), 25% (over 9 min), 100% (over 3 min), 100%-5% (over 4 min), mobile phase (A): 5 mM ammonium bicarbonate in water+0.05% ammonia in water, (B): 100% acetonitrile].

Purification Method CQ

SFC: [(CHIRALPAK IB, 250×20 mm, 5 µm), 70 mL/min, Isochratic (A:B) 75:25 (over 14 min), mobile phase (A): 100% liquid $CO_2$, (B): 0.1% diethylamine in isopropanol:methanol (50:50)].

Purification Method CR

Prep HPLC: [Reversed Phase (X SELECT PHENYL HEXYL, 250×19 mm, 5 µm), 15 mL/min, gradient 0%-33% (over 26 min), 100% (over 2 min), 100%-0% (over 2 min), mobile phase (A): 5 mM ammonium bicarbonate in water+0.1% ammonia in water, (B): 100% acetonitrile].

Purification Method CS

SFC: [(CHIRALPAK IB, 250×20 mm, 5 µm), 70 mL/min, Isochratic (A:B) 87:13 (over 8 min), mobile phase (A): 100% liquid $CO_2$, (B): 0.1% diethylamine in isopropanol:methanol (50:50)].

Purification Method CT

Prep HPLC: [Reversed Phase (X-BRIDGE C-8, 250×19 mm, 5 µm), 16 mL/min, gradient 13%-40% (over 32 min), 100% (over 2 min), 100%-13% (over 2 min), mobile phase (A): 5 mM ammonium bicarbonate in water+0.05% ammonia in water, (B): 100% acetonitrile].

Purification Method CU

Prep HPLC: [Reversed Phase (X SELECT PHENYL HEXYL, 250×19 mm, 5 µm), 17 mL/min, gradient 5%-23% (over 40 min), 23% (over 30 min), 100% (over 3 min), 100%-5% (over 4 min), mobile phase (A): 5 mM ammonium bicarbonate in water+0.05% ammonia in water, (B) 100% acetonitrile].

Purification Method CV

Prep HPLC: [Reversed Phase (X-BRIDGE C-8, 250×19 mm, 5 µm), 15 mL/min, gradient 20%-45% (over 18 min), 45% (over 2 min), 100% (over 2 min), 100%-20% (over 5 min), mobile phase (A): 5 mM ammonium bicarbonate in water+0.1% ammonia in water, (B): 100% acetonitrile].

Purification Method CW

SFC: [(CHIRALPAK IB, 250×20 mm, 5 µm), 70 mL/min, Isochratic (A:B) 70:30 (over 20 min), mobile phase (A): 100% liquid $CO_2$, (B): 0.1% diethylamine in methanol].

Purification Method CX

Prep HPLC: [Reversed Phase (X SELECT PHENYL HEXYL, 250×19 mm, 5 µm), 16 mL/min, gradient 5%-37% (over 27 min), 37% (over 2 min), 100% (over 2 min), 100%-5% (over 4 min), mobile phase (A): 5 mM ammonium bicarbonate in water+0.1% ammonia in water, (B): 100% acetonitrile].

Purification Method CY

Prep HPLC: [Reversed Phase (X-BRIDGE C-8, 250×19 mm, 5 µm), 11 mL/min, gradient 5%-65% (over 25 min), 65% (over 5 min), 100% (over 2 min), 100%-5% (over 3 min), mobile phase (A): 5 mM ammonium bicarbonate in water+0.1% ammonia in water, (B): 100% acetonitrile].

Purification Method CZ

Prep HPLC: [Reversed Phase (X-BRIDGE C-8, 250×19 mm, 5 µm), 15 mL/min, gradient 30%-45% (over 16 min), 100% (over 2 min), 100%-30% (over 5 min), mobile phase (A): 5 mM ammonium bicarbonate in water+0.1% ammonia in water, (B): 100% acetonitrile].

Abbreviations
aq.=aqueous
conc.=concentrated
DCM=dichloromethane
DIPEA=diisopropylethylamine
DMF=dimethylformamide
DMSO=dimethylsulfoxide
ES(I)=electro spray ionisation
EtOAc=ethyl acetate
h=hour(s)
H$_2$O=water
HATU=1-[bis(dimethylamino)methylene]-1H-1,2,3-triazolo[4,5-b]pyridinium 3-oxid hexafluorophosphate
HCl=hydrogen chloride, hydrochloric acid
HPLC=high performance liquid chromatography
LC=liquid chromatography
MeOH=Methanol
min(s)=minute(s)
MS=mass spectrometry
nm=nano meter(s)
NMR=nuclear magnetic resonance
SFC=supercritical fluid chromatography
STAB=sodium triacetoxyborohydride
TEA=triethylamine
TFA=trifluoroacetic acid
THF=tetrahydrofuran
TLC=thin layer chromatography Prefixes n-, s-, i-, t- and tert- have their usual meanings: normal, secondary, iso, and tertiary.

Synthesis of Intermediates

Route 1

Procedure for the Preparation of Intermediate 46, methyl 6-oxo-2-azaspiro[3.4]octane-2-carboxylate

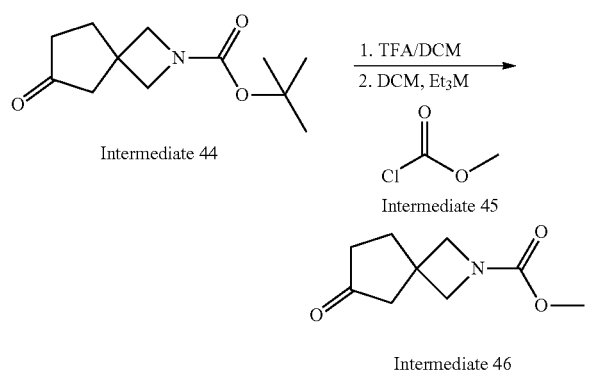

tert-Butyl 6-oxo-2-azaspiro [3.4] octane-2-carboxylate, (Intermediate 44) (120 mg, 0.533 mmol) was dissolved in DCM (2 mL) at 0° C. and TFA (1 mL) was added. The reaction mixture was allowed to warm to room temperature and was stirred for 2 h, then concentrated in-vacuo. The residue was dried by co-evaporation from diethyl ether (3×10 mL) to give 2-azaspiro[3.4]octan-6-one trifluoroacetic acid salt (120 mg, 100%) as a gum.

LCMS (System 1, Method E): m/z 125 (M+H)$^+$ (ES$^+$), at 0.60 min, 202 nm.

2-Azaspiro[3.4]octan-6-one trifluoroacetic acid salt (60 mg, 0.251 mmol) was dissolved in DCM (5 mL) and triethylamine (0.2 mL, 1.25 mmol) was added at 0° C. Methyl chloroformate, (Intermediate 45) (94 mg, 0.37 mmol) was added at 0° C. and the reaction mixture was allowed to warm to room temperature and was stirred for 2 h. The mixture was concentrated in-vacuo and the residue was partitioned between H$_2$O (25 mL) and EtOAc (25 mL). The aqueous layer was further extracted with EtOAc (2×10 mL) and the combined organic layers were dried (Na$_2$SO$_4$) and the solvent was removed in-vacuo to give methyl 6-oxo-2-azaspiro[3.4]octane-2-carboxylate, (Intermediate 46) (30 mg, 34%) as an oil.

The data for Intermediate 46 are in Table 2.

Route 2

Procedure for the Preparation of Intermediate 53, ethyl 5-oxo-2-azabicyclo[2.2.2]octane-2-carboxylate

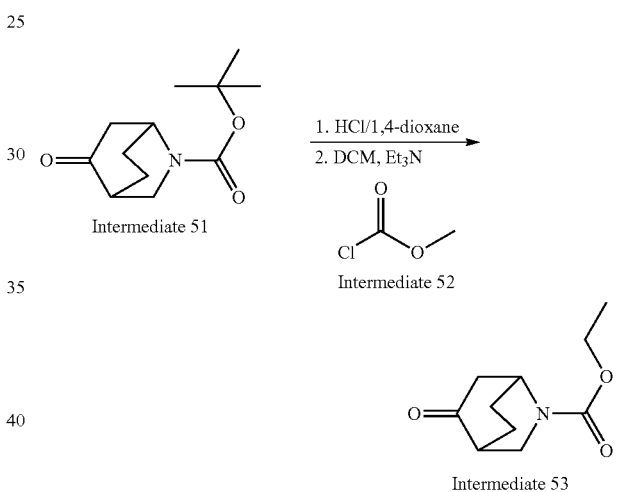

tert-Butyl 5-oxo-2-azabicyclo[2.2.2]octane-2-carboxylate, (Intermediate 51) (120 mg, 0.53 mmol) was stirred in HCl solution in 1,4-dioxane (4 M, 0.5 mL) for 1 h at room temperature. The mixture was concentrated in-vacuo and triturated with diethyl ether (2×2 mL) to give 2-azabicyclo[2.2.2]octan-5-one hydrochloride salt (80 mg, 93%) as a solid.

LCMS (System 2, Method A): m/z 126 (M+H)$^+$ (ESI +ve), at 2.01 min, 250 nm.

2-Azabicyclo[2.2.2]octan-5-one hydrochloride salt (80 mg, 0.49 mmol) and triethylamine (0.2 mL, 1.48 mmol) were dissolved in DCM (4 mL) and ethyl chloroformate, (Intermediate 52) (0.07 mL, 0.74 mmol) was added at 0° C. The mixture was stirred at room temperature for 2 h and then partitioned between cold H$_2$O (15 mL) and EtOAc (15 mL). The aqueous layer was further extracted with EtOAc (2×15 mL), and the combined organic layers were dried (Na$_2$SO$_4$) and the solvent was removed in-vacuo to give ethyl 5-oxo-2-azabicyclo[2.2.2]octane-2-carboxylate, (Intermediate 53) (90 mg, 96%) as a gum.

The data for Intermediate 53 are in Table 2.

General Synthetic Procedures

Route A

Typical Procedure for the Preparation of Amines as Exemplified by the Preparation of Example 1-1, ethyl 6-[(1R,5S,6r)-6-(ethoxycarbonyl)-3-azabicyclo[3.1.0]hex-3-yl]-2-azaspiro[3.3]heptane-2-carboxylate

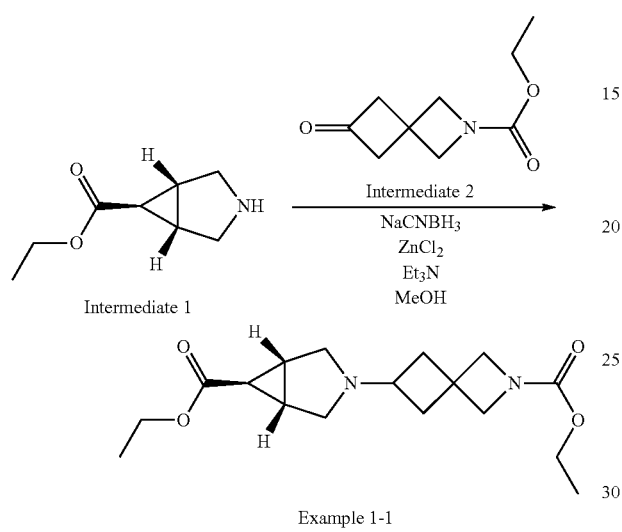

Example 1-1

Ethyl (1R,5S,6r)-3-azabicyclo[3.1.0]hexane-6-carboxylate, (Intermediate 1) (0.12 g, 0.62 mmol), ethyl 6-oxo-2-azaspiro[3.3]heptane-2-carboxylate, (Intermediate 2) (0.14 g, 0.82 mmol), triethylamine (0.082 g, 0.82 mmol) and zinc chloride (4.2 mg, 0.031 mmol) were dissolved in methanol (15 mL) under a nitrogen atmosphere. The resulting mixture was stirred for 3 h at 50-60° C. and then NaCNBH$_3$ (0.052 g, 0.82 mmol) was added portion-wise at 0-10° C. The reaction mixture was stirred for 2 h at room temperature, then partitioned between H$_2$O (15 mL) and EtOAc (25 mL). The aqueous layer was further extracted with EtOAc (2×25 mL), the combined organic layers were dried (Na$_2$SO$_4$) and the solvent was removed in-vacuo. The residue was purified using purification method A to give ethyl 6-[(1R,5S,6r)-6-(ethoxycarbonyl)-3-azabicyclo[3.1.0]hex-3-yl]-2-azaspiro[3.3]heptane-2-carboxylate, Example 1-1 (40 mg, 20%) as a gum.

The data for Example 1-1 are in Table 3.

Route B

Typical Procedure for the Preparation of Amines as Exemplified by the Preparation of Example 1-2, ethyl 6-[(1R,5S,6r)-6-(diethylcarbamoyl)-3-azabicyclo[3.1.0]hex-3-yl]-2-azaspiro[3.3]heptane-2-carboxylate

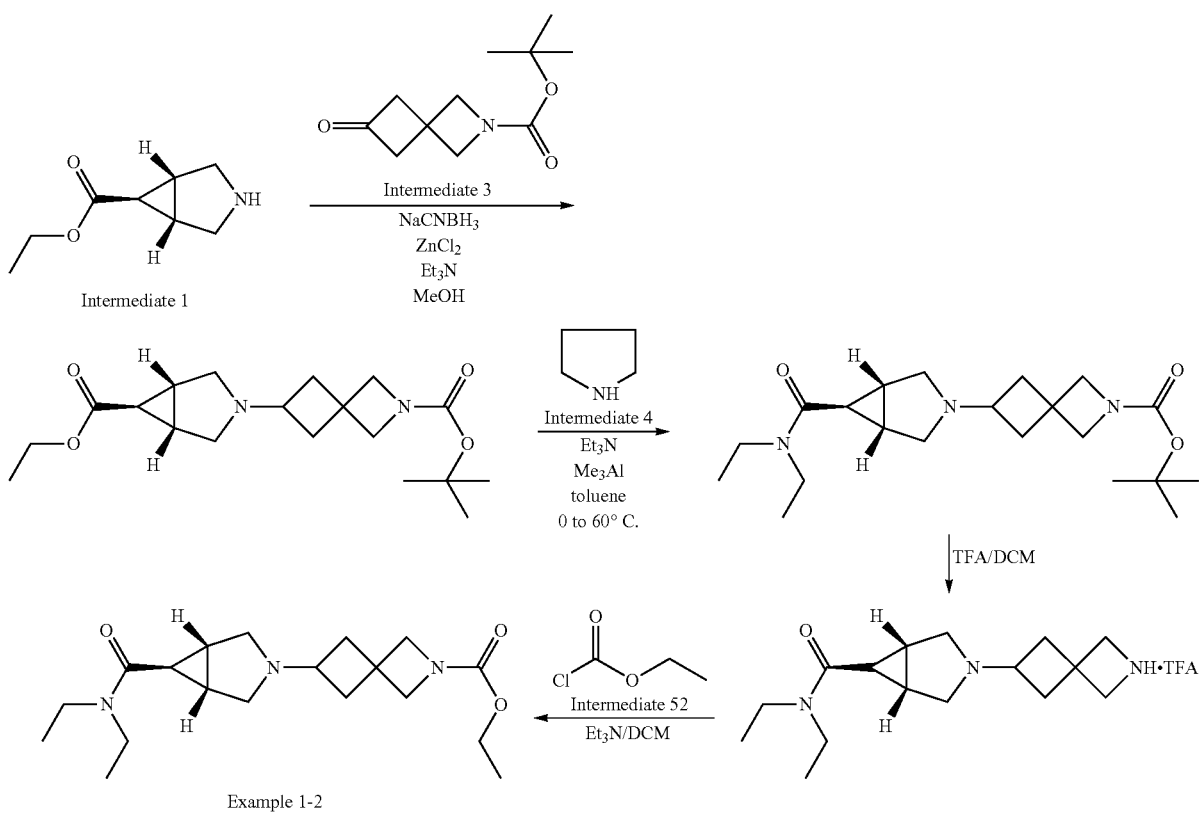

Example 1-2

Ethyl (1R,5S,6r)-3-azabicyclo[3.1.0]hexane-6-carboxylate, (Intermediate 1) (100 mg, 0.52 mmol), TEA (0.36 mL, 2.61 mmol), tert-butyl 6-oxo-2-azaspiro[3.3]heptane-2-carboxylate, (Intermediate 3) (117 mg, 0.52 mmol) and ZnCl$_2$ solution in diethyl ether (1 M, 0.02 mL, 0.02 mmol) were dissolved in MeOH (10 mL) under nitrogen and stirred for 4 h at 60° C. NaCNBH$_3$ (98 mg, 1.57 mmol) was then added portion-wise at 0° C. and the resulting reaction mixture was stirred for 12 h at room temperature. The reaction mixture was partitioned between H$_2$O (30 mL) and 10% MeOH in DCM (50 mL), and the aqueous layer was further extracted with 10% MeOH in DCM (2×50 mL). The combined organic layers were dried (Na$_2$SO$_4$), the solvent was removed in-vacuo and the crude product was purified by column chromatography (Neutral Alumina, 0-2% methanol in DCM) to give tert-butyl 6-[(1R,5S,6r)-6-(ethoxycarbonyl)-3-azabicyclo[3.1.0]hexan-3-yl]-2-azaspiro[3.3]heptane-2-carboxylate (92 mg, 50%) as a gum. LCMS (System 1, Method C): m/z 351 (M+H)+(ESI +ve), at 5.21 min, 202 nm.

tert-Butyl 6-[(1R,5S,6r)-6-(ethoxycarbonyl)-3-azabicyclo[3.1.0]hexan-3-yl]-2-azaspiro[3.3]heptane-2-carboxylate (92 mg, 0.26 mmol), TEA (0.07 mL, 0.53 mmol) and diethylamine, (Intermediate 4) (0.081 mL, 0.79 mmol) were dissolved in toluene (10 mL) at 0° C. under nitrogen and the mixture was stirred for 20 min at room temperature. Trimethylaluminium solution in toluene (2 M, 0.39 mL, 0.79 mmol) was added at 0° C. and the reaction mixture was then heated at 60° C. for 16 h. The reaction mixture was partitioned between ice-cold water (50 mL) and 10% MeOH in DCM (100 mL), and the aqueous layer was further extracted with 10% MeOH in DCM (2×100 mL). The combined organic layers were washed with ammonium chloride solution, dried (Na$_2$SO$_4$) and the solvent was removed in-vacuo to give crude tert-butyl 6-[(1R,5S,6r)-6-(diethylcarbamoyl)-3-azabicyclo[3.1.0]hexan-3-yl]-2-azaspiro[3.3]heptane-2-carboxylate (108 mg, >100%) as a gum.

LCMS (System 1, Method C): m/z 378 (M+H)+ (ESI +ve), at 4.44 min, 210 nm.

tert-Butyl 6-[(1R,5S,6r)-6-(diethylcarbamoyl)-3-azabicyclo[3.1.0]hexan-3-yl]-2-azaspiro[3.3]heptane-2-carboxylate (108 mg, 0.29 mmol) was dissolved in DCM (10 mL) and trifluoroacetic acid (0.22 mL, 2.86 mmol) was added at 0° C. The resulting reaction mixture was stirred at 25° C. for 16 h. The solvents were removed in-vacuo and the residue was purified by triturating with diethyl ether (3×30 mL) to give (1R,5S,6r)-3-(2-azaspiro[3.3]heptan-6-yl)-N, N-diethyl-3-azabicyclo[3.1.0]hexane-6-carboxamide trifluoroacetic acid salt (110 mg, 95%) as a gum.

LCMS (System 1, Method C): m/z 278 (M+H)+ (ESI +ve), at 0.30 min, 202 nm.

(1R,5S,6r)-3-(2-azaspiro[3.3]heptan-6-yl)-N, N-diethyl-3-azabicyclo[3.1.0]hexane-6-carboxamide trifluoroacetic acid salt (79 mg, 0.29 mmol) and TEA (0.12 mL, 0.86 mmol) were dissolved in DCM (10 mL). Ethyl chloroformate, (Intermediate 52) (0.04 mL, 0.43 mmol) was added at 0° C. and the reaction mixture was stirred at room temperature for 16 h. The reaction mixture was partitioned between ammonium chloride solution (50 mL) and 10% MeOH in DCM (100 mL) and the aqueous layer was further extracted with 10% MeOH in DCM (2×100 mL). The combined organic layers were dried (Na$_2$SO$_4$) and the solvent was removed in-vacuo. The crude product was purified using purification method B to give ethyl 6-[(1R,5S,6r)-6-(diethylcarbamoyl)-3-azabicyclo[3.1.0]hex-3-yl]-2-azaspiro[3.3]heptane-2-carboxylate, Example 1-2 (13 mg, 9%) as a gum.

The data for Example 1-2 are in Table 3.

Route C

Typical Procedure for the Preparation of Amines as Exemplified by the Preparation of Example 1-3, ethyl 6-{(1R,5S,6r)-6-[ethyl(propan-2-yl)carbamoyl]-3-azabicyclo[3.1.0]hex-3-yl}-2-azaspiro[3.3]heptane-2-carboxylate

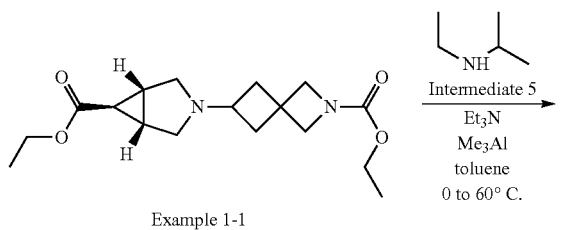

Example 1-1

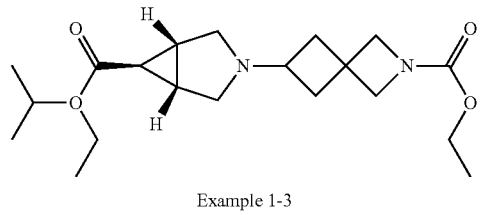

Example 1-3

Ethyl 6-[(1R,5S,6r)-6-(ethoxycarbonyl)-3-azabicyclo[3.1.0]hex-3-yl]-2-azaspiro[3.3]heptane-2-carboxylate, Example 1-1 (45 mg, 0.14 mmol), TEA (0.03 mL, 0.28 mmol) and N-ethylisopropylamine, (Intermediate 5) (0.05 mL, 0.42 mmol) were dissolved in toluene (10 mL) at 0° C. under nitrogen and the resulting mixture was stirred for 20 min at room temperature. Trimethylaluminium solution in toluene (2 M, 0.35 mL, 0.70 mmol) was added at 0° C. and the reaction mixture was heated at 60° C. for 16 h. The reaction mixture was partitioned between ice-cold water (25 mL) and 10% MeOH in DCM (50 mL) and the aqueous layer was further extracted with 10% MeOH in DCM (2×50 mL). The combined organic layers were washed with ammonium chloride solution, dried (Na$_2$SO$_4$) and the solvent was removed in-vacuo. The crude product was purified using purification method C to give ethyl 6-{(1R,5S,6r)-6-[ethyl(propan-2-yl)carbamoyl]-3-azabicyclo[3.1.0]hex-3-yl}-2-azaspiro[3.3]heptane-2-carboxylate, Example 1-3 (2 mg, 1%) as a gum.

The data for Example 1-3 are in Table 3.

Route D

Typical Procedure for the Preparation of Amines as Exemplified by the Preparation of Example 1-4, ethyl 6-[(1R,5S,6r)-6-(2-methyl-1,3-thiazol-4-yl)-3-azabicyclo[3.1.0]hex-3-yl]-2-azaspiro[3.3]heptane-2-carboxylate

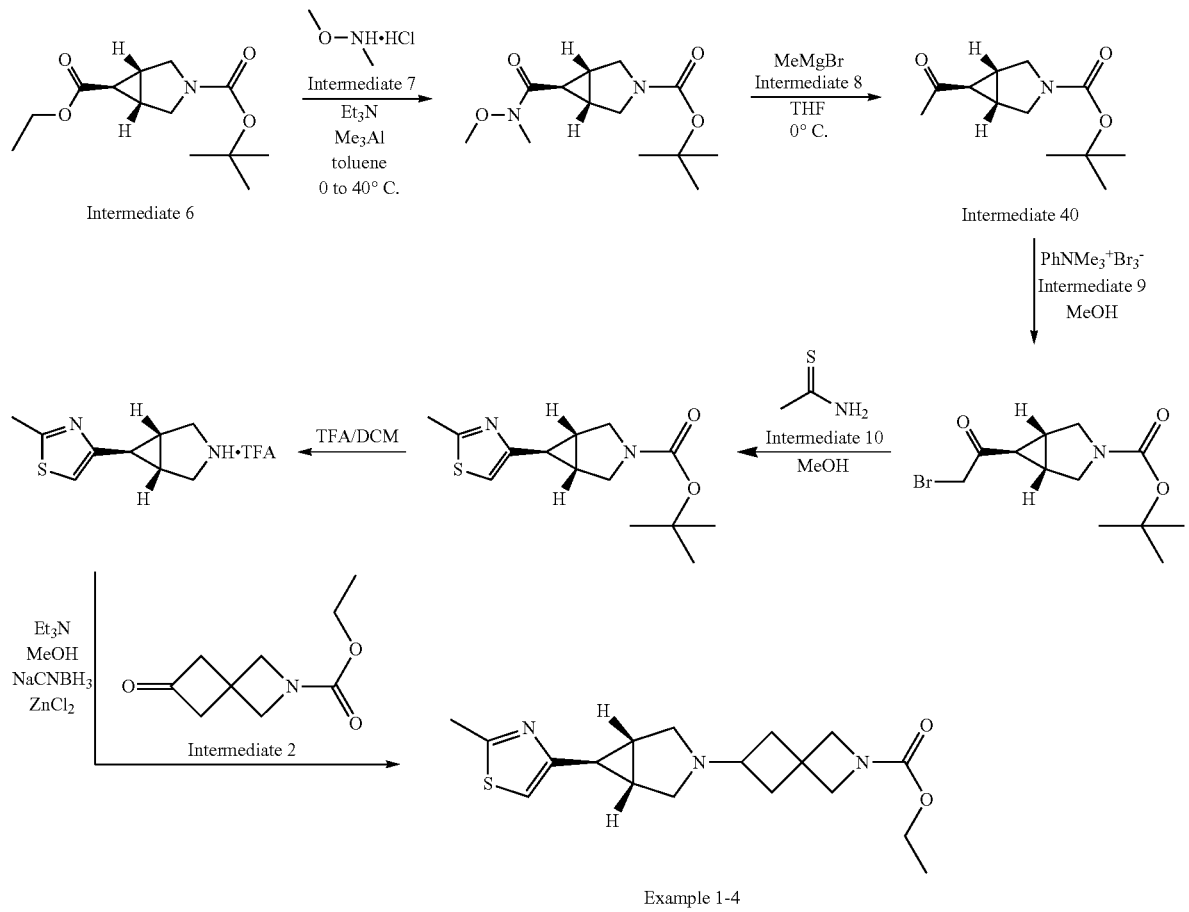

Example 1-4

3-tert-Butyl 6-ethyl (1R,5S,6r)-3-azabicyclo[3.1.0]hexane-3,6-dicarboxylate, (Intermediate 6) (400 mg, 1.57 mmol) was dissolved in toluene (10 mL). N,O-Dimethylhydroxylamine hydrochloride, (Intermediate 7) (183 mg, 1.88 mmol) and triethylamine (0.7 mL, 4.71 mmol) were added and the resulting mixture was stirred at 25° C. for 30 min. Trimethylaluminium solution in toluene (2 M, 3.1 mL, 6.27 mmol) was added dropwise at 0° C., and the reaction mixture was stirred at 40° C. for 2 h. The solvents were removed in-vacuo, the residue was partitioned between $H_2O$ (120 mL) and EtOAc (100 mL) and the aqueous layer was further extracted with EtOAc (2×100 mL). The combined organic layers were dried ($Na_2SO_4$), the solvent was removed in-vacuo and the residue was purified by column chromatography (Normal basic activated alumina, 0.5-1.0% MeOH in DCM) to give tert-butyl (1R,5S,6r)-6-[methoxy(methyl)carbamoyl]-3-azabicyclo[3.1.0]hexane-3-carboxylate (260 mg, 61%) as a gum.

LCMS (System 1, Method C): m/z 271 (M+H)$^+$ (ESI +ve), at 3.82 min, 215 nm.

tert-Butyl (1R,5S,6r)-6-[methoxy(methyl)carbamoyl]-3-azabicyclo[3.1.0]hexane-3-carboxylate (260 mg, 0.96 mmol) was dissolved in THF (5 mL) and the solution was cooled down to 0° C. Methylmagnesium bromide solution in diethyl ether, (Intermediate 8) (3 M, 1.0 mL, 2.88 mmol) was added dropwise and the resulting reaction mixture was stirred at 0° C. for 1 h. The solvents were then removed in-vacuo, and the residue was partitioned between $H_2O$ (100 mL) and EtOAc (80 mL). The aqueous layer was further extracted with EtOAc (2×80 mL), and the combined organic layers were dried ($Na_2SO_4$), and the solvents were removed in-vacuo to give crude tert-butyl (1R,5S,6r)-6-acetyl-3-azabicyclo[3.1.0]hexane-3-carboxylate, (Intermediate 40) (190 mg, 88%) as a gum. The crude product was used in the next step without further purification.

LCMS (System 1, Method C): m/z 170 (M+H-56)$^+$ (ESI +ve), at 4.00 min, 202 nm.

tert-Butyl (1R,5S,6r)-6-acetyl-3-azabicyclo[3.1.0]hexane-3-carboxylate (50 mg, 0.22 mmol) was dissolved in MeOH (3 mL). Phenyltrimethylammonium tribromide (Intermediate 9) (83 mg, 0.22 mmol) was added and the resulting reaction mixture was stirred at 25° C. for 7 h and then concentrated in-vacuo to give crude tert-butyl (1R,5S,6r)-6-(bromoacetyl)-3-azabicyclo[3.1.0]hexane-3-carboxylate (65 mg, 97%) as a gum. The crude product was used in the next step without further workup or purification due to its instability.

LCMS (System 2, Method A): m/z 289/291 (M+H-16)$^+$ (ESI +ve), at 2.30 min, 202 nm.

tert-Butyl (1R,5S,6r)-6-(bromoacetyl)-3-azabicyclo[3.1.0]hexane-3-carboxylate (65 mg, 0.21 mmol) was dissolved in MeOH (3 mL), thioacetamide, (Intermediate 10) (32 mg, 0.43 mmol) was added and the resulting mixture was stirred at 25° C. for 2 h. The solvents were removed in-vacuo and the residue was partitioned between H$_2$O (40 mL) and EtOAc (30 mL). The aqueous layer was further extracted with EtOAc (2×30 mL), the combined organic layers were dried (Na$_2$SO$_4$) and the solvents were removed in-vacuo. The residue was purified by column chromatography (Normal neutral activated alumina, 15-20% EtOAc in hexane) to give tert-butyl (1R,5S,6r)-6-(2-methyl-1,3-thiazol-4-yl)-3-azabicyclo[3.1.0]hexane-3-carboxylate (21 mg, 34%) as a gum.

LCMS (System 1, Method C): m/z 281 (M+H)$^+$ (ESI +ve), at 4.78 min, 251 nm.

tert-Butyl (1R,5S,6r)-6-(2-methyl-1,3-thiazol-4-yl)-3-azabicyclo[3.1.0]hexane-3-carboxylate (20 mg, 0.07 mmol) was dissolved in DCM (1 mL) and trifluoroacetic acid (0.3 mL) was added dropwise. The resulting reaction mixture was stirred at 25° C. for 5 h and then the solvents were removed in-vacuo. The residue was purified by triturating with pentane (3×0.5 mL) to give (1R,5S,6r)-6-(2-methyl-1,3-thiazol-4-yl)-3-azabicyclo[3.1.0]hexane trifluoroacetic acid salt (12 mg, 92%) as a solid.

LCMS (System 1, Method C): m/z 181 (M+H)$^+$ (ESI +ve), at 3.03 min, 220 nm.

(1R,5S,6r)-6-(2-Methyl-1,3-thiazol-4-yl)-3-azabicyclo[3.1.0]hexane trifluoroacetic acid salt (12 mg, 0.07 mmol), ethyl 6-oxo-2-azaspiro[3.3]heptane-2-carboxylate, (Intermediate 2) (14 mg, 0.07 mmol), triethylamine (0.03 mL, 0.22 mmol) and ZnCl$_2$ (1 mg, 0.01 mmol) were dissolved in MeOH (2 mL) and the resulting mixture was stirred at 65° C. for 5 h. The mixture was cooled to 0° C. and NaBH$_3$CN (13 mg, 0.22 mmol) was added portion-wise. The resulting reaction mixture was stirred at 25° C. for 17 h and then the solvents were removed in-vacuo. The residue was partitioned between H$_2$O (30 mL) and EtOAc (20 mL) and the aqueous layer was further extracted with EtOAc (2×20 mL). The combined organic layers were dried (Na$_2$SO$_4$) and the solvent was removed in-vacuo. The residue was purified using purification method D to give ethyl 6-[(1R,5S,6r)-6-(2-methyl-1,3-thiazol-4-yl)-3-azabicyclo[3.1.0]hex-3-yl]-2-azaspiro[3.3]heptane-2-carboxylate, Example 1-4 (4 mg, 17%) as a gum.

The data for Example 1-4 are in Table 3.

Route E

Typical Procedure for the Preparation of Amines as Exemplified by the Preparation of Example 2-19, ethyl 2-[(1R,5S,6r)-6-(4-azaspiro[2.3]hex-4-ylcarbonyl)-3-azabicyclo[3.1.0]hex-3-yl]-6-azaspiro[3.4]octane-6-carboxylate

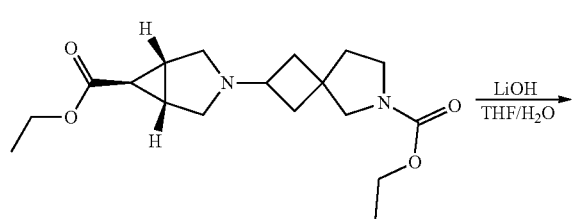

Example 2-1

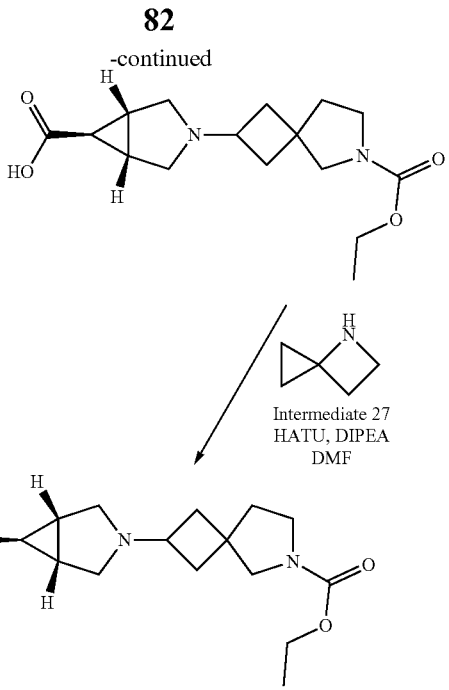

Example 2-19

Ethyl 2-[(1R,5S,6r)-6-(ethoxycarbonyl)-3-azabicyclo[3.1.0]hex-3-yl]-6-azaspiro[3.4]octane-6-carboxylate, Example 2-1 (150 mg, 0.45 mmol) was dissolved in THF (2 mL) and a solution of LiOH (32 mg, 1.34 mmol) in water (2 mL) was added at −20° C. The resulting mixture was stirred at room temperature for 5 h. The reaction mixture was then acidified by the addition of conc. aq. HCl and the solvents were removed in-vacuo to give (1R,5S,6r)-3-[6-(ethoxycarbonyl)-6-azaspiro[3.4]oct-2-yl]-3-azabicyclo[3.1.0]hexane-6-carboxylic acid (115 mg, 84%) as a solid.

LCMS (System 2, Method D): m/z 309 (M+H)$^+$ (ESI +ve), at 1.35 min, 202 nm.

(1R,5S,6r)-3-[6-(Ethoxycarbonyl)-6-azaspiro[3.4]oct-2-yl]-3-azabicyclo[3.1.0]hexane-6-carboxylic acid (115 mg, 0.37 mmol) and HATU (212 mg, 0.56 mmol) were dissolved in DMF at 0° C. and DIPEA (0.19 mL, 1.12 mmol) was added. The resulting mixture was stirred at 0° C. for 1 h, then 4-azaspiro[2.3]hexane, (Intermediate 27) (35.0 mg, 0.41 mmol) was added at 0° C. and the resulting mixture was stirred at room temperature for 3 h. The reaction mixture was partitioned between cold H$_2$O (20 mL) and EtOAc (10 mL), and the aqueous layer was further extracted with EtOAc (2×10 mL). The combined organic layers were dried (Na$_2$SO$_4$) and the solvent was removed in-vacuo to give the crude product, which was purified using purification method AD followed by purification method AE to give ethyl 2-[(1R,5S,6r)-6-(4-azaspiro[2.3]hex-4-ylcarbonyl)-3-azabicyclo[3.1.0]hex-3-yl]-6-azaspiro[3.4]octane-6-carboxylate, Example 2-19 Isomer 1 (18 mg, 12%) as a gum and ethyl 2-[(1R,5S,6r)-6-(4-azaspiro[2.3]hex-4-ylcarbonyl)-3-azabicyclo[3.1.0]hex-3-yl]-6-azaspiro[3.4]octane-6-carboxylate, Example 2-19 Isomer 2 (18 mg, 12%) as a gum.

The data for Example 2-19 Isomer 1 and Isomer 2 are in Table 3.

Route F

Typical Procedure for the Preparation of Amines as Exemplified by the Preparation of Example 2-25, ethyl 2-[(1R,5S,6r)-6-(N-methoxypropanimidoyl)-3-azabicyclo[3.1.0]hexan-3-yl]-6-azaspiro[3.4]octane-6-carboxylate

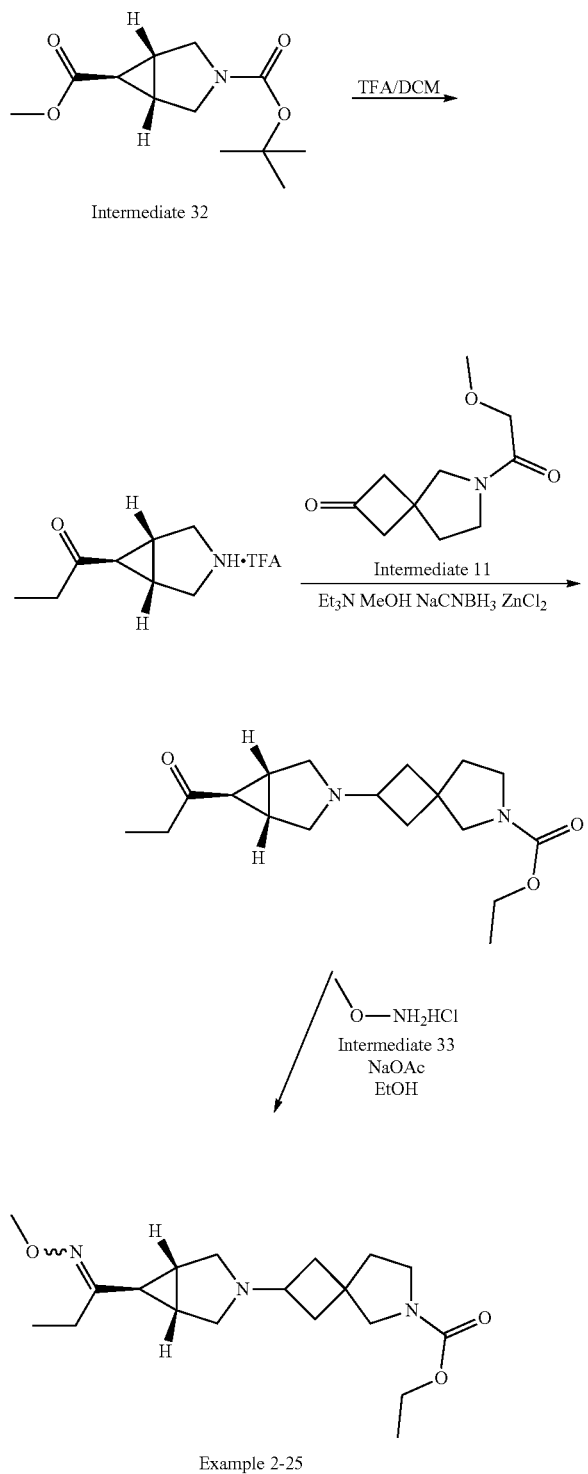

Intermediate 32

Intermediate 11
Et₃N MeOH NaCNBH₃ ZnCl₂

Intermediate 33
NaOAc
EtOH

Example 2-25 tert-Butyl (1R,5S,6r)-6-propanoyl-3-azabicyclo[3.1.0]hexane-3-carboxylate, (Intermediate 32) (160 mg, 0.67 mmol) was dissolved in DCM (3 mL) and trifluoroacetic acid (1 mL) was added dropwise. The resulting reaction mixture was stirred at 25° C. for 5 h. The solvents were removed in-vacuo, and the residue was purified by triturating with pentane (3×1 mL) to give 1-[(1R,5S,6r)-3-azabicyclo[3.1.0]hex-6-yl]propan-1-one trifluoroacetic acid salt (80 mg, 99%) as a gum.

LCMS (System 1, Method C): m/z 140 (M+H)⁺ (ESI +ve), at 2.76 min, 202 nm.

1-[(1R,5S,6r)-3-azabicyclo[3.1.0]hex-6-yl]propan-1-one trifluoroacetic acid salt (80 mg, 0.57 mmol), ethyl 2-oxo-6-azaspiro[3.4]octane-6-carboxylate, (Intermediate 11) (124 mg, 0.63 mmol), triethylamine (0.1 mL, 1.72 mmol) and ZnCl₂ (7 mg, 0.06 mmol) were dissolved in MeOH (10 mL) and the resulting mixture was stirred at 65° C. for 5 h. The mixture was then cooled to 0° C. and NaBH₃CN (109 mg, 0.57 mmol) was added portion-wise. The reaction mixture was stirred at 25° C. for 17 h, then the solvents were removed in-vacuo. The residue was partitioned between H₂O (100 mL) and EtOAc (80 mL), and the aqueous layer was further extracted with EtOAc (2×80 mL). The combined organic layers were dried (Na₂SO₄), the solvent was removed in-vacuo, and the residue was purified by column chromatography (Normal neutral activated alumina, 50% EtOAc in hexane) to give ethyl 2-[(1R,5S,6r)-6-propanoyl-3-azabicyclo[3.1.0]hexan-3-yl]-6-azaspiro[3.4]octane-6-carboxylate (130 mg, 75%) as a gum.

LCMS (System 1, Method C): m/z 321 (M+H)⁺ (ESI +ve), at 4.23 min, 220 nm.

Ethyl 2-[(1R,5S,6r)-6-propanoyl-3-azabicyclo[3.1.0]hexan-3-yl]-6-azaspiro[3.4]octane-6-carboxylate (100 mg, 0.31 mmol) and sodium acetate (77 mg, 0.94 mmol) were dissolved in ethanol (5 mL) and the resulting mixture was stirred at 25° C. for 30 min. O-Methylhydroxylamine hydrochloride, (Intermediate 33) (52 mg, 0.63 mmol) was added and the reaction mixture was stirred at 25° C. for 17 h. The solvents were removed in-vacuo, and the residue was partitioned between H₂O (80 mL) and EtOAc (60 mL). The aqueous layer was further extracted with EtOAc (2×60 mL), the combined organic layers were dried (Na₂SO₄) and the solvent was removed in-vacuo. The residue was purified using purification method AK to give ethyl 2-[(1R,5S,6r)-6-(N-methoxypropanimidoyl)-3-azabicyclo[3.1.0]hexan-3-yl]-6-azaspiro[3.4]octane-6-carboxylate, Example 2-25 Isomer 1 (7 mg, 6%), ethyl 2-[(1R,5S,6r)-6-(N-methoxypropanimidoyl)-3-azabicyclo[3.1.0]hexan-3-yl]-6-azaspiro[3.4]octane-6-carboxylate, Example 2-25 Isomer 2 (9 mg, 8%), ethyl 2-[(1R,5S,6r)-6-(N-methoxypropanimidoyl)-3-azabicyclo[3.1.0]hexan-3-yl]-6-azaspiro[3.4]octane-6-carboxylate, Example 2-25 Isomer 3 (18 mg, 17%) and ethyl 2-[(1R,5S,6r)-6-(N-methoxypropanimidoyl)-3-azabicyclo[3.1.0]hexan-3-yl]-6-azaspiro[3.4]octane-6-carboxylate, Example 2-25 Isomer 4 (17 mg, 16%), all as gums.

The data for Example 2-25 Isomer 2 and Isomer 4 are in Table 3.

Route G

Typical Procedure for the Preparation of Amines as Exemplified by the Preparation of Example 2-27, ethyl 2-{(1R,5S,6s)-6-[ethyl(2,2,2-trifluoroethyl)amino]-3-azabicyclo[3.1.0]hexan-3-yl}-6-azaspiro[3.4]octane-6-carboxylate

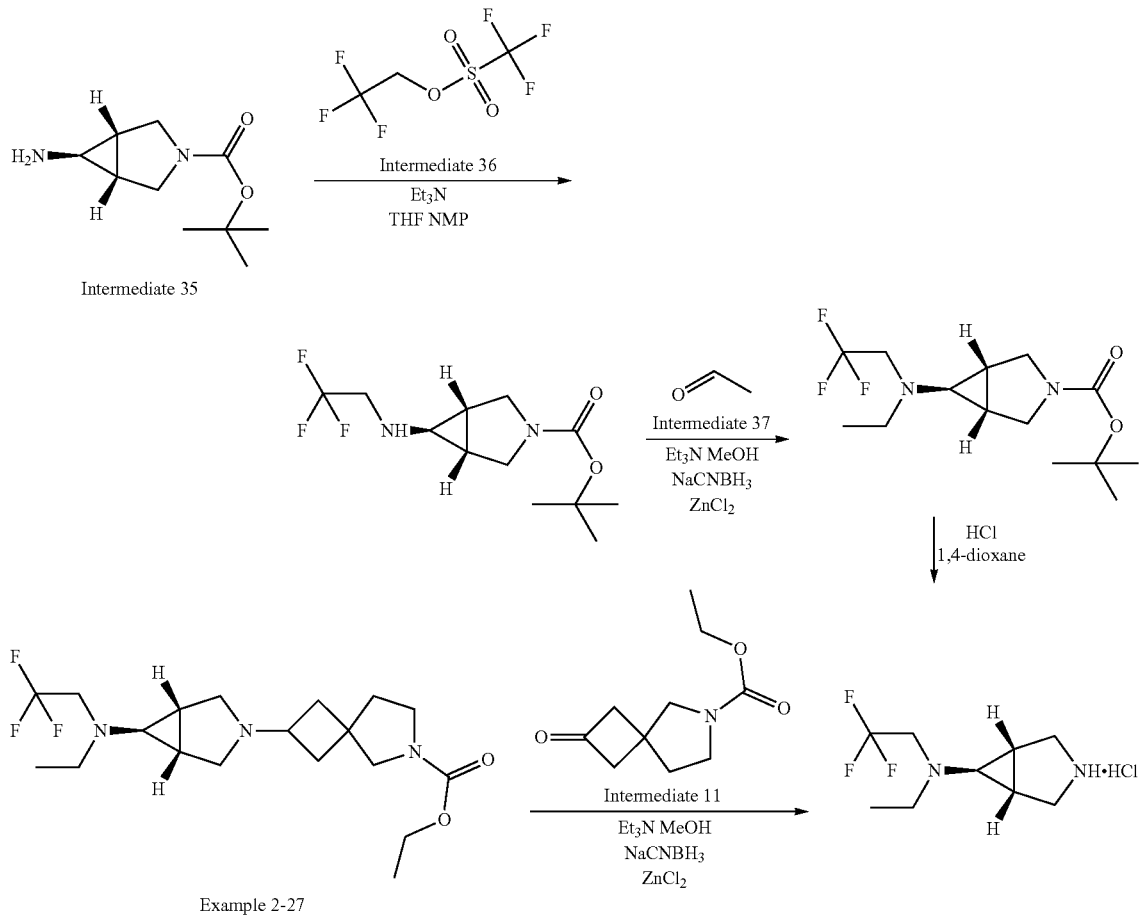

Example 2-27 tert-Butyl (1R,5S,6s)-6-amino-3-azabicyclo[3.1.0]hexane-3-carboxylate, (Intermediate 35) (100 mg, 0.51 mmol) was dissolved in THF (5 mL) and N-methyl-2-pyrrolidinone (150 mg, 1.52 mmol) and triethylamine (0.3 mL, 2.02 mmol) were added. The resulting mixture was stirred at 70° C. for 1 h, then 2,2,2-trifluoroethyl trifluoromethanesulfonate, (Intermediate 36) (129 mg, 0.56 mmol) was added at 25° C. The resulting reaction mixture was stirred at 80° C. for 18 h, then the solvents were removed in-vacuo. The residue was partitioned between H₂O (80 mL) and EtOAc (60 mL), and the aqueous layer was further extracted with EtOAc (2×60 mL). The combined organic layers were dried (Na₂SO₄), the solvents were removed in-vacuo and residue was purified by column chromatography (Normal neutral activated alumina, 2-5% MeOH in DCM) to give tert-butyl (1R,5S,6s)-6-[(2,2,2-trifluoroethyl)amino]-3-azabicyclo[3.1.0]hexane-3-carboxylate (118 mg, 84%) as a gum.

LCMS (System 1, Method C): m/z 225 (M+H-56)⁺ (ESI +ve), at 4.61 min, 202 nm.

tert-Butyl (1R,5S,6s)-6-[(2,2,2-trifluoroethyl)amino]-3-azabicyclo[3.1.0]hexane-3-carboxylate (118 mg, 0.43 mmol) was dissolved in methanol (5 mL) and acetaldehyde, (Intermediate 37) (38 mg, 0.86 mmol), triethylamine (0.2 mL, 1.29 mmol) and ZnCl₂ (6 mg, 0.43 mmol) were added. The resulting mixture was stirred at 40° C. for 7 h, then NaBH₃CN (81 mg, 1.29 mmol) was added portion-wise. The reaction mixture was stirred at 25° C. for 17 h, then the solvents were removed in-vacuo. The residue was partitioned between H₂O (100 mL) and EtOAc (80 mL), and the aqueous layer was further extracted with EtOAc (2×80 mL). The combined organic layers were dried (Na2SO4), the solvent was removed in-vacuo and the residue was purified by column chromatography (Normal basic activated alumina, 0.5-1.0% MeOH in DCM) to give tert-butyl (1R,5S,6s)-6-[ethyl(2,2,2-trifluoroethyl)amino]-3-azabicyclo[3.1.0]hexane-3-carboxylate (125 mg, 96%) as a gum.

LCMS (System 1, Method C): m/z 309 (M+H)⁺ (ESI +ve), at 5.58 min, 202 nm.

tert-Butyl (1R,5S,6s)-6-[ethyl(2,2,2-trifluoroethyl)amino]-3-azabicyclo[3.1.0]hexane-3-carboxylate (125 mg, 0.41 mmol) was dissolved in 1,4-dioxane (5 mL) and HCl solution in 1,4-dioxane (4 M, 3 mL) was added dropwise.

The resulting mixture was stirred at 25° C. for 5 h, then the solvents were removed in-vacuo. The residue was purified by triturating with diethyl ether (3×3 mL) to give (1R,5S,6s)-N-ethyl-N-(2,2,2-trifluoroethyl)-3-azabicyclo[3.1.0]hexan-6-amine hydrochloride salt (100 mg, 100%) as a solid.

LCMS (System 2, Method A): m/z 209 (M+H)⁺ (ESI +ve), at 1.42 min, 202 nm.

(1R,5S,6s)-N-ethyl-N-(2,2,2-trifluoroethyl)-3-azabicyclo[3.1.0]hexan-6-amine hydrochloride salt (100 mg, 0.48 mmol), ethyl 2-oxo-6-azaspiro[3.4]octane-6-carboxylate, (Intermediate 11) (95 mg, 0.48 mmol), triethylamine (0.2 mL, 1.44 mmol) and ZnCl₂ (7 mg, 0.05 mmol) were dissolved in MeOH (10 mL) and the resulting mixture was stirred at 70° C. for 8 h. The mixture was cooled to 0° C. and NaBH3CN (91 mg, 1.44 mmol) was added portion-wise. The reaction mixture was stirred at 25° C. for 17 h, then the solvents were removed in-vacuo, The residue was partitioned between H₂O (100 mL) and EtOAc (80 mL), and the aqueous layer was further extracted with EtOAc (2×80 mL). The combined organic layers were dried (Na₂SO₄), the solvent was removed in-vacuo, and the residue was purified using purification method AM to give ethyl 2-{(1R,5S,6s)-6-[ethyl(2,2,2-trifluoroethyl)amino]-3-azabicyclo[3.1.0]hexan-3-yl}-6-azaspiro[3.4]octane-6-carboxylate, Example 2-27 (53 mg, 33%) as a gum.

The data for Example 2-27 are in Table 3.
Route H

Typical Procedure for the Preparation of Amines as Exemplified by the Preparation of Example 2-28, ethyl 2-[(1R,5S,6s)-6-(1-phenylethoxy)-3-azabicyclo[3.1.0]hex-3-yl]-6-azaspiro[3.4]octane-6-carboxylate the solvents were removed in-vacuo. The residue was partitioned between H₂O (80 mL) and EtOAc (60 mL), and the aqueous layer was further extracted with EtOAc (2×60 mL). The combined organic layers were dried (Na₂SO₄), the solvent was removed in-vacuo and the residue was purified by triturating with pentane give tert-butyl (1R,5S,6s)-6-hydroxy-3-azabicyclo[3.1.0]hexane-3-carboxylate (180 mg, 81%) as a liquid.

LCMS (System 1, Method C): m/z 144 (M+H-56)⁺ (ESI +ve), at 3.40 min, 210 nm.

tert-butyl (1R,5S,6s)-6-hydroxy-3-azabicyclo[3.1.0]hexane-3-carboxylate (180 mg, 0.90 mmol) was dissolved in DMF (8 mL), cooled to 0° C. and NaH (60% in paraffin oil, 108 mg, 2.71 mmol) was added. The mixture was stirred at 0° C. for 20 min, then (1-bromoethyl)benzene, (Intermediate 39) (250 mg, 1.36 mmol) was added dropwise at 0° C. The resulting reaction mixture was stirred at 25° C. for 5 h, then the solvents were removed in-vacuo. The residue was partitioned between H₂O (100 mL) and EtOAc (60 mL), and the aqueous layer was further extracted with EtOAc (2×60 mL). The combined organic layers were dried (Na₂SO₄), and the solvents were removed in-vacuo to give tert-butyl (1R,5S,6s)-6-(1-phenylethoxy)-3-azabicyclo[3.1.0]hexane-3-carboxylate (250 mg, 91%) as a liquid.

LCMS (System 1, Method C): m/z 248 (M+H-56)⁺ (ESI +ve), at 5.70 min, 210 nm.

tert-Butyl (1R,5S,6s)-6-(1-phenylethoxy)-3-azabicyclo[3.1.0]hexane-3-carboxylate (250 mg, 0.83 mmol) was dissolved in DCM (10 mL) and cooled to 0° C. Trifluoroacetic acid (2 mL) was added dropwise and the resulting reaction mixture was stirred at 25° C. for 6 h. The solvents were

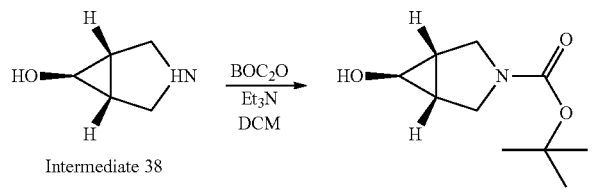

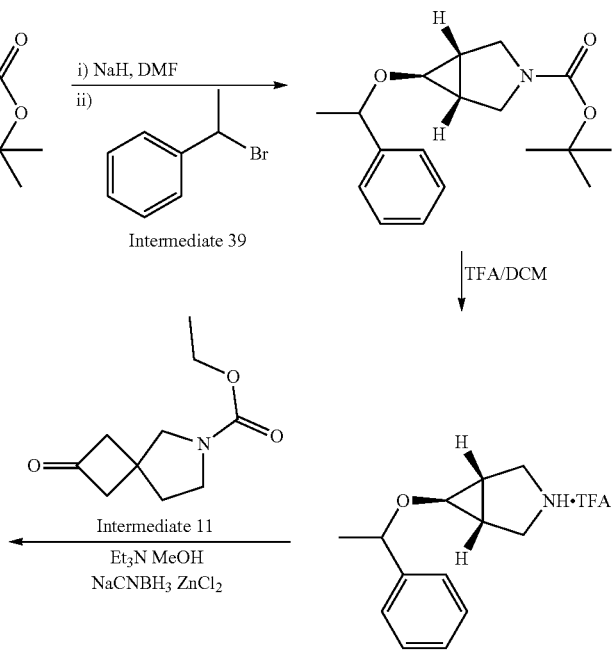

Example 2-28

(1R,5S,6s)-3-Azabicyclo[3.1.0]hexan-6-ol, (Intermediate 38) (110 mg, 1.11 mmol) was dissolved in DCM (10 mL) and triethylamine (0.5 mL, 3.30 mmol) was added. The mixture was stirred at 0° C. for 20 min, then di-tert-butyl dicarbonate (362 mg, 1.66 mmol) was added at 0° C. The resulting reaction mixture was stirred at 25° C. for 2 h, then removed in-vacuo, and the residue was purified by triturating with pentane (3×1 mL) to give (1R,5S,6s)-6-(1-phenylethoxy)-3-azabicyclo[3.1.0]hexane trifluoroacetic acid salt (160 mg, 96%) as a gum.

LCMS (System 1, Method C): m/z 204 (M+H)⁺ (ESI +ve), at 3.97 min, 210 nm.

(1R,5S,6s)-6-(1-Phenylethoxy)-3-azabicyclo[3.1.0]hexane trifluoroacetic acid salt (150 mg, 0.74 mmol), ethyl 2-oxo-6-azaspiro[3.4]octane-6-carboxylate, (Intermediate 11) (145 mg, 0.74 mmol), triethylamine (0.3 mL, 2.21 mmol) and ZnCl$_2$ (10 mg, 0.07 mmol) were dissolved in MeOH (10 mL) and the resulting mixture was stirred at 65° C. for 7 h. The mixture was cooled to 0° C. and NaBH3CN (139 mg, 2.21 mmol) was added portion-wise. The reaction mixture was stirred at 25° C. for 17 h, the the solvents were removed in-vacuo. The residue was partitioned between H$_2$O (100 mL) and EtOAc (80 mL), and the aqueous layer was further extracted with EtOAc (2×80 mL). The combined organic layers were dried (Na$_2$SO$_4$), the solvent was removed in-vacuo, and the residue was purified using purification method AN to give ethyl 2-[(1R,5S,6s)-6-(1-phenylethoxy)-3-azabicyclo[3.1.0]hex-3-yl]-6-azaspiro[3.4]octane-6-carboxylate, Example 2-28 Isomer 1 (8 mg, 3%) as a gum and ethyl 2-[(1R,5S,6s)-6-(1-phenylethoxy)-3-azabicyclo[3.1.0]hex-3-yl]-6-azaspiro[3.4]octane-6-carboxylate, Example 2-28 Isomer 2 (7 mg, 3%) as a gum.

The data for Example 2-28 Isomer 1 and Isomer 2 are in Table 3.

Route I

Typical Procedure for the Preparation of Amines as Exemplified by the Preparation of Example 2-29, ethyl 2-[(1R,5S,6r)-6-(1-methyl-1H-pyrazol-5-yl)-3-azabicyclo[3.1.0]hex-3-yl]-6-azaspiro[3.4]octane-6-carboxylate

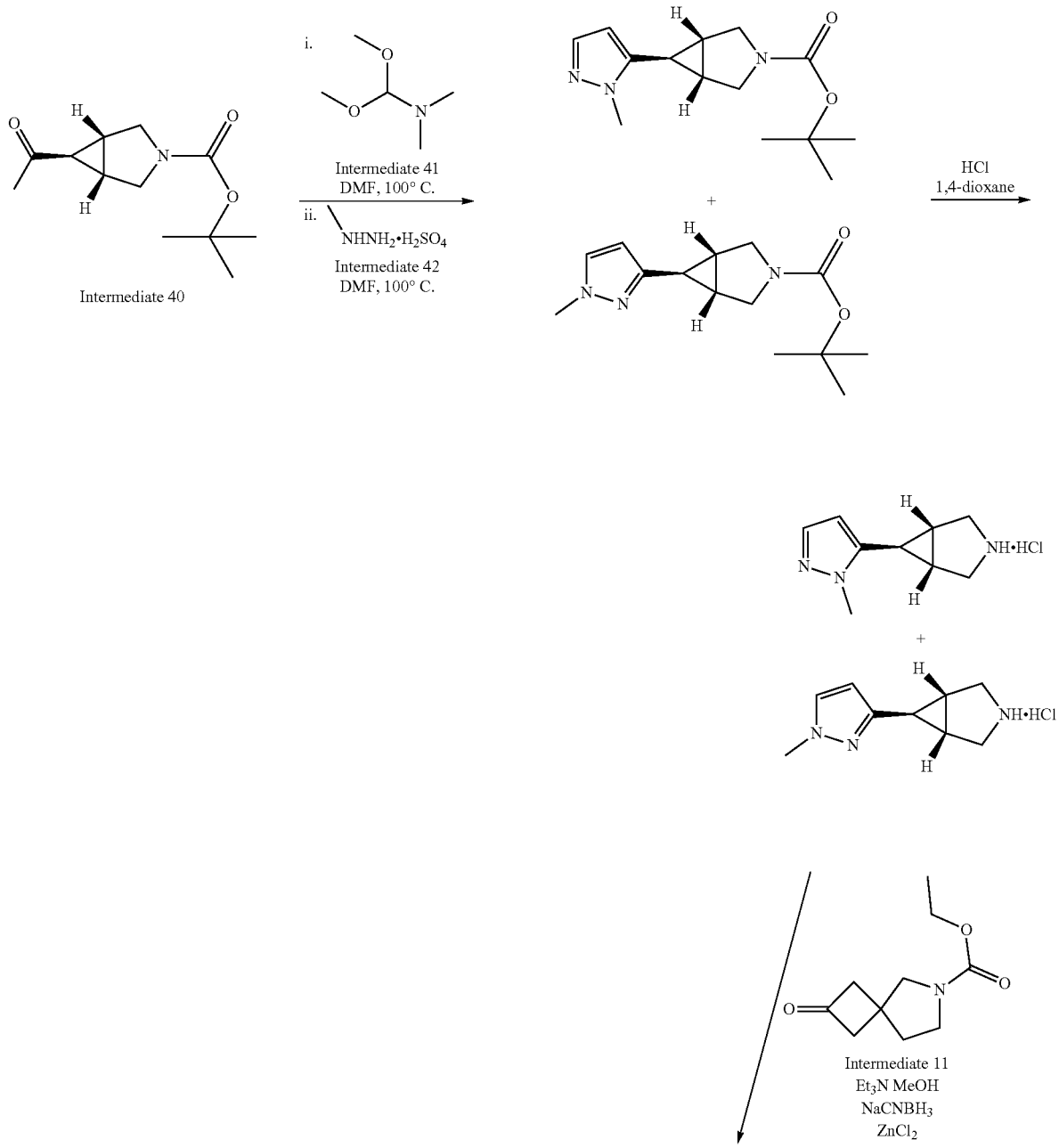

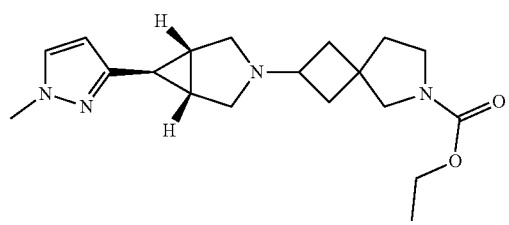 + 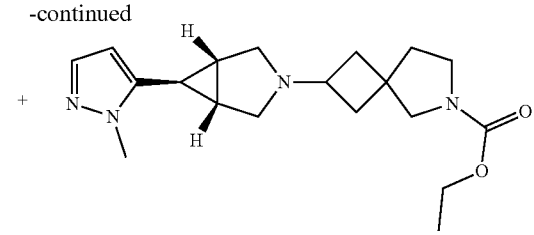

Example 2-29
Isomers 1 and 2 tert-Butyl (1R,5S,6r)-6-acetyl-3-azabicyclo[3.1.0]hexane-3-carboxylate, (Intermediate 40) (200 mg, 0.89 mmol) was dissolved in DMF (10 mL) and N,N-dimethylformamide dimethyl acetal, (Intermediate 41) (211 mg, 1.78 mmol) was added. The resulting mixture was stirred at 100° C. for 24 h, then methylhydrazine sulfate, (Intermediate 42) (269 mg, 1.86 mmol) was added at 25° C., and the mixture was stirred at 100° C. for 30 h. The solvents were removed in-vacuo, and the residue was partitioned between H₂O (150 mL) and EtOAc (100 mL). The aqueous layer was further extracted with EtOAc (2×100 mL), the combined organic layers were dried (Na₂SO₄), and the solvents were removed in-vacuo. The residue was purified by column chromatography (Normal basic activated alumina, 1-3% MeOH in DCM) to give a mixture of tert-butyl (1R,5S,6r)-6-(1-methyl-1H-pyrazol-5-yl)-3-azabicyclo[3.1.0]hexane-3-carboxylate and tert-butyl (1R,5S,6r)-6-(1-methyl-1H-pyrazol-3-yl)-3-azabicyclo[3.1.0]hexane-3-carboxylate (170 mg, 73%) as a liquid.

LCMS (System 1, Method C): m/z 264 (M+H)⁺ (ESI +ve), at 4.10 min, 202 nm.

A mixture of tert-butyl (1R,5S,6r)-6-(1-methyl-1H-pyrazol-5-yl)-3-azabicyclo[3.1.0]hexane-3-carboxylate and tert-butyl (1R,5S,6r)-6-(1-methyl-1H-pyrazol-3-yl)-3-azabicyclo[3.1.0]hexane-3-carboxylate (170 mg, 0.65 mmol) was dissolved in 1,4-dioxane (5 mL) and HCl solution in 1,4-dioxane (4 M, 3 mL) was added dropwise. The resulting mixture was stirred at 25° C. for 16 h, then the solvents were removed in-vacuo. The residue was purified by triturating with diethyl ether (3×5 mL) to give a mixture of (1R,5S,6r)-6-(1-methyl-1H-pyrazol-5-yl)-3-azabicyclo[3.1.0]hexane hydrochloride salt and (1R,5S,6r)-6-(1-methyl-1H-pyrazol-3-yl)-3-azabicyclo[3.1.0]hexane hydrochloride salt (120 mg, 93%) as a gum.

LCMS (System 1, Method C): m/z 164 (M+H)⁺ (ESI +ve), at 2.53 min, 221 nm.

A mixture of (1R,5S,6r)-6-(1-methyl-1H-pyrazol-5-yl)-3-azabicyclo[3.1.0]hexane hydrochloride salt and (1R,5S,6r)-6-(1-methyl-1H-pyrazol-3-yl)-3-azabicyclo[3.1.0]hexane hydrochloride salt (120 mg, 0.74 mmol), ethyl 2-oxo-6-azaspiro[3.4]octane-6-carboxylate, (Intermediate 11) (160 mg, 0.81 mmol), triethylamine (0.3 mL, 2.20 mmol) and ZnCl₂ (10 mg, 0.07 mmol) were dissolved in MeOH (10 mL) and stirred together at 65° C. for 8 h. The mixture was then cooled to 0° C., NaBH₃CN (140 mg, 2.20 mmol) was added portion-wise, and the resulting mixture was stirred at 25° C. for 17 h. The solvents were removed in-vacuo, and the residue was partitioned between H₂O (100 mL) and EtOAc (80 mL). The aqueous layer was further extracted with EtOAc (2×80 mL), the combined organic layers were dried (Na₂SO₄), and the solvent was removed in-vacuo. The residue was purified using purification method AO to give ethyl 2-[(1R,5S,6r)-6-(1-methyl-1H-pyrazol-5-yl)-3-azabicyclo[3.1.0]hex-3-yl]-6-azaspiro[3.4]octane-6-carboxylate, Example 2-29 Isomer 1 (9 mg, 4%), ethyl 2-[(1R,5S,6r)-6-(1-methyl-1H-pyrazol-3-yl)-3-azabicyclo[3.1.0]hex-3-yl]-6-azaspiro[3.4]octane-6-carboxylate Isomer 1 (8 mg, 3%), ethyl 2-[(1R,5S,6r)-6-(1-methyl-1H-pyrazol-5-yl)-3-azabicyclo[3.1.0]hex-3-yl]-6-azaspiro[3.4]octane-6-carboxylate, Example 2-29 Isomer 2 (6 mg, 2%) and ethyl 2-[(1R,5S,6r)-6-(1-methyl-1H-pyrazol-3-yl)-3-azabicyclo[3.1.0]hex-3-yl]-6-azaspiro[3.4]octane-6-carboxylate Isomer 2 (8 mg, 3%), all as gums.

The data for Example 2-29 Isomer 2 are in Table 3.

Route J

Typical Procedure for the Preparation of Amines as Exemplified by the Preparation of Example 3-3, methyl 6-[(1R,5S,6r)-6-(diethylcarbamoyl)-3-azabicyclo[3.1.0]hex-3-yl]-2-azaspiro[3.4]octane-2-carboxylate

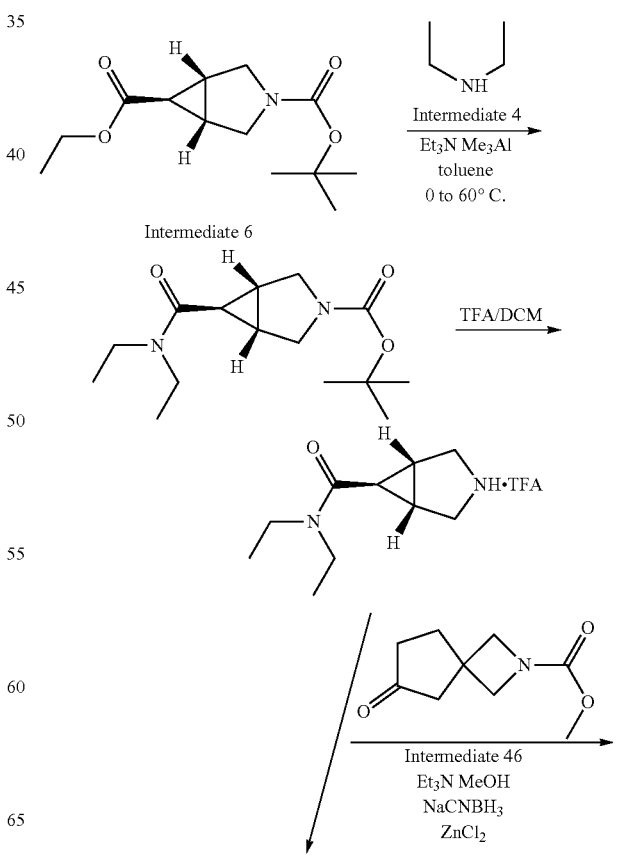

93

-continued

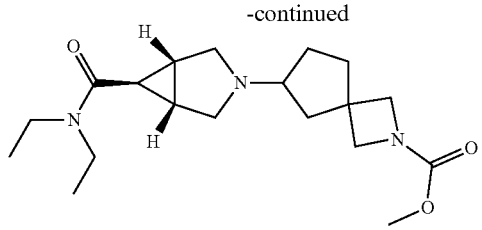

Exampe 3-3

3-tert-Butyl 6-ethyl (1R,5S,6r)-3-azabicyclo[3.1.0]hexane-3,6-dicarboxylate, (Intermediate 6) (200 mg, 0.78 mmol) and TEA (0.31 mL, 2.35 mmol) were dissolved in toluene and cooled to 0° C. Diethylamine, (Intermediate 4) (0.16 mL, 1.57 mmol) was added, followed by trimethylaluminium solution in toluene (2 M, 0.8 mL, 1.57 mmol). The reaction mixture was heated at 60° C. for 5 h, then diluted with water (150 mL) and extracted with EtOAc (3×60 mL). The combined organic layers were dried (Na$_2$SO$_4$) and concentrated in-vacuo to give the crude product, which was purified by column chromatography (Normal neutral activated alumina, 0-30% EtOAc in hexane) to give tert-butyl (1R,5S,6r)-6-(diethylcarbamoyl)-3-azabicyclo[3.1.0]hexane-3-carboxylate (130 mg, 59%) as a gum.

LCMS (System 1, Method C): m/z 283 (M+H)$^+$ (ESI +ve), at 4.22 min, 210 nm.

tert-Butyl (1R,5S,6r)-6-(diethylcarbamoyl)-3-azabicyclo[3.1.0]hexane-3-carboxylate (125 mg, 0.44 mmol) was dissolved in dichloromethane (5 mL) and cooled to 0° C. TFA (2.5 mL) was added and the resulting mixture was allowed to stir at room temperature for 3 h. The mixture was then diluted with toluene (2.5 mL) and concentrated in-vacuo to give the crude (1R,5S,6r)-N,N-diethyl-3-azabicyclo[3.1.0]hexane-6-carboxamide trifluoroacetic acid salt (125 mg, 100%) as a gum, which was used in the next step without further purification.

LCMS (System 1, Method C): m/z 183 (M+H)$^+$ (ESI +ve), at 2.60 min, 215 nm.

(1R,5S,6r)-N,N-Diethyl-3-azabicyclo[3.1.0]hexane-6-carboxamide trifluoroacetic acid salt (125 mg, 0.68 mmol), methyl 6-oxo-2-azaspiro[3.4]octane-2-carboxylate, (Intermediate 46) (125 mg, 1.31 mmol) and TEA (0.47 mL, 3.41 mmol) were dissolved in methanol (10 mL). The mixture was degassed for 30 min under nitrogen, ZnCl$_2$ solution in diethyl ether (1 M, 0.03 mL, 0.03 mmol) was added, and the mixture was stirred at 60° C. for 3 h. The mixture was cooled to 0° C. and NaCNBH$_3$ (129 mg, 2.04 mmol) was added portion-wise. The reaction mixture was then stirred at room temperature for 5 h, diluted with water (150 mL) and extracted with EtOAc (3×60 mL). The combined organic layers were dried (Na$_2$SO$_4$) and concentrated in-vacuo. The residue was purified using purification method AS to give methyl 6-[(1R,5S,6r)-6-(diethylcarbamoyl)-3-azabicyclo[3.1.0]hex-3-yl]-2-azaspiro[3.4]octane-2-carboxylate, Example 3-3 Isomer 1 (20 mg, 8%) as a gum and methyl 6-[(1R,5S,6r)-6-(diethylcarbamoyl)-3-azabicyclo[3.1.0]hex-3-yl]-2-azaspiro[3.4]octane-2-carboxylate, Example 3-3 Isomer 2 (18 mg, 8%) as a gum.

The data for Example 3-3 Isomer 1 and Isomer 2 are in Table 3.

Route J

Typical Procedure for the Preparation of Amines as Exemplified by the Preparation of Example 7-5, ethyl 3-[(1R,5S,6r)-6-{[acetyl(ethyl)amino]methyl}-3-azabicyclo[3.1.0]hex-3-yl]-8-azabicyclo[3.2.1]octane-8-carboxylate

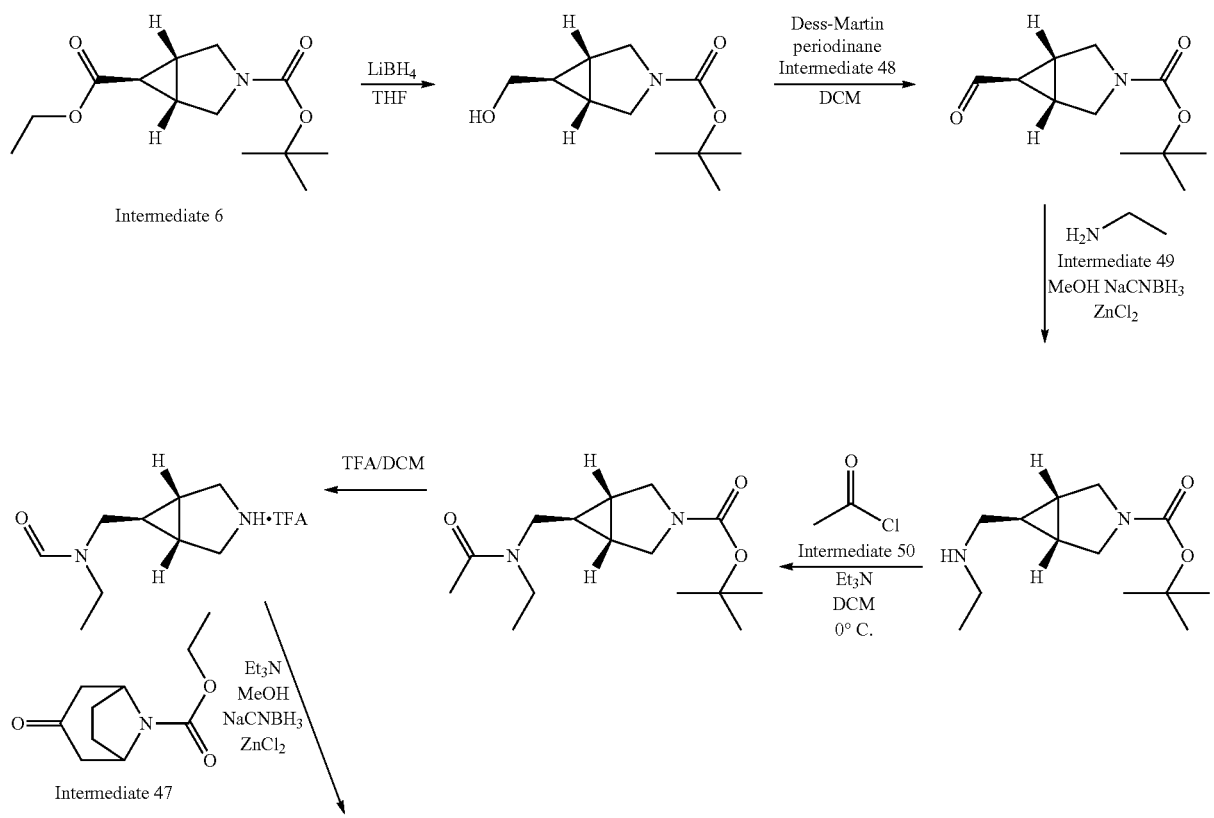

-continued

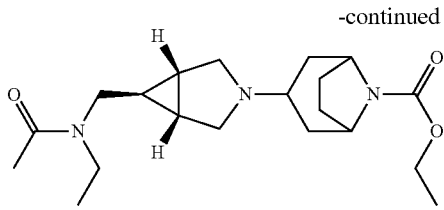

Example 7-5

3-tert-Butyl 6-ethyl (1R,5S,6r)-3-azabicyclo[3.1.0]hexane-3,6-dicarboxylate, (Intermediate 6) (650 mg, 2.55 mmol) was dissolved in THF (10 mL) and cooled to 0° C. LiBH$_4$ solution in THF (3 M, 3.4 mL, 10.2 mmol) was added and the mixture was stirred at room temperature for 16 h. The mixture was diluted with water (150 mL) and extracted with EtOAc (3×60 mL). The combined organic layers were dried (Na$_2$SO$_4$), concentrated in-vacuo and the residue was purified by column chromatography (Normal phase, neutral silica gel, 60-120 mesh, 0-30% EtOAc in hexane) to give tert-butyl (1R,5S,6r)-6-(hydroxymethyl)-3-azabicyclo[3.1.0]hexane-3-carboxylate (400 mg, 74%) as a liquid.

LCMS (System 1, Method C): m/z 214 (M+H)$^+$ (ESI +ve), at 3.37 min, 210 nm.

tert-Butyl (1R,5S,6r)-6-(hydroxymethyl)-3-azabicyclo[3.1.0]hexane-3-carboxylate (230 mg, 1.08 mmol) was dissolved in dichloromethane (10 mL) and cooled to 0° C. Dess-Martin periodinane, (Intermediate 48) (503 mg, 1.19 mmol) was added portion-wise and the reaction mixture was stirred at room temperature for 6 h. The reaction mixture was quenched with a saturated aqueous solution of NaHCO$_3$, then diluted with water (100 mL) and extracted with EtOAc (3×40 mL). The combined organic layers were dried (Na$_2$SO$_4$) and concentrated in-vacuo to give the crude tert-butyl (1R,5S,6r)-6-formyl-3-azabicyclo[3.1.0]hexane-3-carboxylate (240 mg, 100%) as a liquid, which was used in the next step without further purification.

LCMS (System 1, Method C): m/z 156 (M+H-56)$^+$ (ESI +ve), at 3.97 min, 210 nm.

tert-Butyl (1R,5S,6r)-6-formyl-3-azabicyclo[3.1.0]hexane-3-carboxylate (230 mg, 1.10 mmol) was dissolved in methanol (10 mL). Ethylamine solution in THF, (Intermediate 49) (2 M, 2.7 mL, 5.45 mmol) was added, followed by ZnCl$_2$ solution in diethyl ether (1 M, 0.05 mL, 0.05 mmol). The resulting mixture was stirred at 60° C. for 6 h, then cooled to 0° C. and NaCNBH$_3$ (202 mg, 2.13 mmol) was added. The mixture was stirred at room temperature for 16 h, then concentrated in-vacuo. The residue was diluted with water (160 mL) and extracted with EtOAc (3×50 mL). The combined organic layers were dried (Na$_2$SO$_4$) and concentrated in-vacuo to give the crude tert-butyl (1R,5S,6r)-6-[(ethylamino)methyl]-3-azabicyclo[3.1.0]hexane-3-carboxylate (200 mg, 77%) as a liquid, which was used in the next step without further purification.

LCMS (System 1, Method E): m/z 241 (M+H)$^+$ (ESI +ve), at 3.78 min, 210 nm.

tert-Butyl (1R,5S,6r)-6-[(ethylamino)methyl]-3-azabicyclo[3.1.0]hexane-3-carboxylate (20 mg, 0.83 mmol) was dissolved in dichloromethane (10 mL) and cooled to 0° C. TEA (0.3 mL, 2.49 mmol) was added, followed by acetyl chloride, (Intermediate 50) (130 mg, 1.66 mmol). The reaction mixture was stirred at 0° C. for 2 h, then diluted with water (150 mL) and extracted with EtOAc (3×40 mL). The combined organic layers were dried (Na$_2$SO$_4$) and concentrated in-vacuo. The residue was purified by column chromatography (Normal phase, neutral alumina, 0-2% MeOH in DCM) to give tert-butyl (1R,5S,6r)-6-{[acetyl(ethyl)amino]methyl}-3-azabicyclo[3.1.0]hexane-3-carboxylate (130 mg, 55%) as a liquid.

LCMS (System 1, Method E): m/z 227 (M+H-56)$^+$ (ESI +ve), at 4.18 min, 202 nm.

tert-Butyl (1R,5S,6r)-6-{[acetyl(ethyl)amino]methyl}-3-azabicyclo[3.1.0]hexane-3-carboxylate (120 mg, 0.43 mmol) was dissolved in dichloromethane (5 mL) and cooled to 0° C. TFA (2.5 mL) was added and the reaction mixture was stirred at room temperature for 2 h. The mixture was diluted with toluene (2.5 mL) and concentrated in-vacuo to give the crude N-[(1R,5S,6r)-3-azabicyclo[3.1.0]hex-6-ylmethyl]-N-ethylacetamide trifluoroacetic acid salt (120 mg, 100%) as a gum, which was used in the next step without further purification.

LCMS (System 1, Method E): m/z 183 (M+H)$^+$ (ESI +ve), at 2.31 min, 202 nm.

N-[(1R,5S,6r)-3-azabicyclo[3.1.0]hex-6-ylmethyl]-N-ethylacetamide trifluoroacetic acid salt (103 mg, 0.57 mmol) and TEA (0.4 mL, 2.83 mmol) were dissolved in MeOH (5 mL). Ethyl 3-oxo-8-azabicyclo[3.2.1]octane-8-carboxylate, (Intermediate 47) (122 mg, 0.62 mmol) was added, followed by ZnCl$_2$ solution in diethyl ether (1 M, 0.3 mL, 0.28 mmol). The resulting mixture was stirred at 60° C. for 5 h, then cooled to 0° C. and NaCNBH$_3$ (105 mg, 1.69 mmol) was added. The mixture was stirred at 60° C. for 12 h, then diluted with water (150 mL) and extracted with EtOAc (3×40 mL). The combined organic layers were dried (Na$_2$SO$_4$) and concentrated in-vacuo and the residue was purified using purification method BE to give ethyl 3-[(1R,5S,6r)-6-{[acetyl(ethyl)amino]methyl}-3-azabicyclo[3.1.0]hex-3-yl]-8-azabicyclo[3.2.1]octane-8-carboxylate, Example 4-5 Isomer 1 (52 mg, 25%) as a gum and ethyl 3-[(1R,5S,6r)-6-{[acetyl(ethyl)amino]methyl}-3-azabicyclo[3.1.0]hex-3-yl]-8-azabicyclo[3.2.1]octane-8-carboxylate, Example 4-5 Isomer 2 (21 mg, 10%) as a gum.

The data for Example 4-5 Isomer 2 are in Table 3.

TABLE 2

| | | | | |
|---|---|---|---|---|
| | | Intermediates | | |
| Intermediate Number | Name | Synthetic Route | Intermediates Used | Data |
| 1 | Ethyl (1R,5S,6r)-3-azabicyclo[3.1.0]hexane-6-carboxylate | — | — | Commercially available, CAS: 174456-77-0 |

TABLE 2-continued

Intermediates

| Intermediate Number | Name | Synthetic Route | Intermediates Used | Data |
|---|---|---|---|---|
| 2 | Ethyl 6-oxo-2-azaspiro[3.3]heptane-2-carboxylate | — | — | See WO2016147011 |
| 3 | tert-Butyl 6-oxo-2-azaspiro[3.3]heptane-2-carboxylate | — | — | Commercially available, CAS: 1181816-12-5 |
| 4 | Diethylamine | — | — | Commercially available, CAS: 109-89-7 |
| 5 | N-Ethylisopropylamine | — | — | Commercially available, CAS: 19961-27-4 |
| 6 | 3-tert-Butyl 6-ethyl (1R,5S,6r)-3-azabicyclo[3.1.0]hexane-3,6-dicarboxylate | — | — | Commercially available, CAS: 134575-37-4 |
| 7 | N,O-Dimethylhydroxylamine hydrochloride | — | — | Commercially available, CAS: 6638-79-5 |
| 8 | Methylmagnesium bromide | — | — | Commercially available, CAS: 75-16-1 |
| 9 | Phenyltrimethylammonium tribromide | — | — | Commercially available, CAS: 4207-56-1 |
| 10 | Thioacetamide | — | — | Commercially available, CAS: 62-55-5 |
| 11 | Ethyl 2-oxo-6-azaspiro[3.4]octane-6-carboxylate | — | — | See WO2015118342 |
| 12 | Isobutylamine | — | — | Commercially available, CAS: 78-81-9 |
| 13 | Cyclobutylmethylamine hydrochloride | — | — | Commercially available, CAS: 5454-82-0 |
| 14 | 1-Methylcyclobutylamine | — | — | Commercially available, CAS: 40571-47-9 |
| 15 | N-Methylethylamine | — | — | Commercially available, CAS: 624-78-2 |
| 16 | Methyl 2-oxo-6-azaspiro[3.4]octane-6-carboxylate | — | — | See WO2015118342 |
| 17 | Methyl 2-[(1R,5S,6r)-6-(ethoxycarbonyl)-3-azabicyclo[3.1.0]hex-3-yl]-6-azaspiro[3.4]octane-6-carboxylate | A | 1 and 16 | LCMS (System 1, Method C): m/z 323 (M + H)$^+$ (ES$^+$), at 4.33 min, 202 nm |
| 18 | N-Methylpropan-2-amine | — | — | Commercially available, CAS: 4747-21-1 |
| 19 | N-Ethylcyclopropanamine | — | — | Commercially available, CAS: 26389-72-0 |
| 20 | Pyrrolidine | — | — | Commercially available, CAS: 123-75-1 |
| 21 | Piperidine | — | — | Commercially available, CAS: 98-77-1 |
| 22 | (2R)-2-Methylpiperidine | — | — | Commercially available, CAS: 1722-95-8 |
| 23 | (2S)-2-Methylpiperidine | — | — | Commercially available, CAS: 3197-42-0 |
| 24 | Azepane | — | — | Commercially available, CAS: 111-49-9 |
| 25 | 1,4-Oxazepane | — | — | Commercially available, CAS: 5638-60-8 |
| 26 | 2-Azaspiro[3.3]heptane hydrochloride | — | — | Commercially available, CAS: 1420271-08-4 |
| 27 | 4-Azaspiro[2.3]hexane | — | — | Commercially available, CAS: 125441-13-6 |
| 28 | 1-Azaspiro[3.3]heptane hydrochloride | — | — | Commercially available, CAS: 1986337-29-4 |
| 29 | 6-Oxa-1-azaspiro[3.3]heptane hemioxalate | — | — | Commercially available, CAS: 1380571-72-1 |
| 30 | N-Methoxyethanamine | — | — | Commercially available, CAS: 1195657-97-6 |
| 31 | Ethylmagnesium bromide | — | — | Commercially available, CAS: 925-90-6 |
| 32 | tert-Butyl (1R,5S,6r)-6-propanoyl-3-azabicyclo[3.1.0]hexane-3-carboxylate | D (first two steps) | 6, 7 and 31 | LCMS (System 2, Method A): m/z 184 (M + H-56)$^+$ (ES$^+$), at 2.16 min, 202 nm |
| 33 | O-Methylhydroxylamine hydrochloride | — | — | Commercially available, CAS: 593-56-6 |
| 34 | 6-(Trifluoromethyl)-3-azabicyclo[3.1.0]hexane hydrochloride | — | — | Commercially available, CAS: 1311314-49-4 |
| 35 | tert-Butyl (1R,5S,6s)-6-amino-3-azabicyclo[3.1.0]hexane-3-carboxylate | — | — | Commercially available, CAS: 273206-92-1 |

TABLE 2-continued

Intermediates

| Intermediate Number | Name | Synthetic Route | Intermediates Used | Data |
|---|---|---|---|---|
| 36 | 2,2,2-Trifluoroethyl trifluoromethanesulfonate | — | — | Commercially available, CAS: 6226-25-1 |
| 37 | Acetaldehyde | — | — | Commercially available, CAS: 75-07-0 |
| 38 | (1R,5S,6s)-3-Azabicyclo[3.1.0]hexan-6-ol | — | — | Commercially available, CAS: 1524707-84-3 |
| 39 | (1-Bromoethyl)benzene | — | — | Commercially available, CAS: 585-71-7 |
| 40 | tert-Butyl (1R,5S,6r)-6-acetyl-3-azabicyclo[3.1.0]hexane-3-carboxylate | D (first two steps) | 6, 7 and 8 | LCMS (System 1, Method C): m/z 170 (M + H-56)$^+$ (ESI + ve), at 4.00 min, 202 nm |
| 41 | N,N-Dimethylformamide dimethyl acetal | — | — | Commercially available, CAS: 4637-24-5 |
| 42 | Methylhydrazine sulfate | — | — | Commercially available, CAS: 302-15-8 |
| 43 | Ethyl 6-oxo-2-azaspiro[3.4]octane-2-carboxylate | — | — | See WO2016147011 |
| 44 | tert-Butyl 6-oxo-2-azaspiro [3.4] octane-2-carboxylate | — | — | Commercially available, CAS: 1363382-39-1 |
| 45 | Methyl chloroformate | — | — | Commercially available, CAS: 79-22-1 |
| 46 | Methyl 6-oxo-2-azaspiro[3.4]octane-2-carboxylate | 1 | 44 and 45 | LCMS (System 1, Method E): m/z 184 (M + H)$^+$ (ES$^+$), at 2.47 min, 202 nm |
| 47 | Ethyl 3-oxo-8-azabicyclo[3.2.1]octane-8-carboxylate | — | — | Commercially available, CAS: 32499-64-2 |
| 48 | Dess-Martin periodinane | — | — | Commercially available, CAS: 87413-09-0 |
| 49 | Ethylamine | — | — | Commercially available, CAS: 75-04-7 |
| 50 | Acetyl chloride | — | — | Commercially available, CAS: 75-36-5 |
| 51 | tert-Butyl 5-oxo-2-azabicyclo[2.2.2]octane-2-carboxylate | — | — | Commercially available, CAS: 617714-22-4 |
| 52 | Ethyl chloroformate | — | — | Commercially available, CAS: 541-41-3 |
| 53 | Ethyl 5-oxo-2-azabicyclo[2.2.2]octane-2-carboxylate | 2 | 51 and 52 | LCMS (System 2, Method A): m/z 198 (M + H)$^+$ (ES$^+$), at 1.64 min, 229 nm |
| 54 | tert-Butyl (1S,4S)-5-oxo-2-azabicyclo[2.2.2]octane-2-carboxylate | — | — | Commercially available, CAS: 1932043-29-2 |
| 55 | Ethyl (1S,4S)-5-oxo-2-azabicyclo[2.2.2]octane-2-carboxylate | 2 | 54 and 52 | LCMS (System 6, Method H): m/z 198 (M + H)$^+$ (ES$^+$), at 0.83 min, 230-400 nm |
| 56 | Ethyl (1S,4S)-5-[(1R,5S,6r)-6-(ethoxycarbonyl)-3-azabicyclo[3.1.0]hexan-3-yl]-2-azabicyclo[2.2.2]octane-2-carboxylate | A | 1 and 55 | LCMS (System 5, Method F): m/z 337 (M + H)$^+$ (ES$^+$), at 2.34 min, 230-400 nm |
| 57 | tert-Butyl (1R,4R)-5-oxo-2-azabicyclo[2.2.2]octane-2-carboxylate | — | — | Commercially available, CAS: 1818843-13-8 |
| 58 | Ethyl (1R,4R)-5-oxo-2-azabicyclo[2.2.2]octane-2-carboxylate | 2 | 57 and 52 | LCMS (System 6, Method H): m/z 198 (M + H)$^+$ (ES$^+$), at 0.83 min, 190-400 nm |
| 59 | Ethyl (1R,4R)-5-[(1R,5S,6r)-6-(ethoxycarbonyl)-3-azabicyclo[3.1.0]hex-3-yl]-2-azabicyclo[2.2.2]octane-2-carboxylate | A | 1 and 58 | LCMS (System 6, Method H): m/z 337 (M + H)$^+$ (ES$^+$), at 1.55 min, 190-400 nm |
| 60 | Methyl 5-oxo-2-azabicyclo[2.2.2]octane-2-carboxylate | 1 | 51 and 45 | LCMS (System 2, Method D): m/z 184 (M + H)$^+$ (ES$^+$), at 1.39 min, 202 nm |
| 61 | Methyl 5-[(1R,5S,6r)-6-(ethoxycarbonyl)-3-azabicyclo[3.1.0]hex-3-yl]-2-azabicyclo[2.2.2]octane-2-carboxylate | A | 1 and 60 | LCMS (System 1, Method C): m/z 323 (M + H)+ (ES), at 4.88 min, 220 nm |
| 62 | tert-Butyl 3-oxo-9-azabicyclo[3.3.1]nonane-9-carboxylate | — | — | Commercially available, CAS: 512822-27-4 |
| 63 | Ethyl 3-oxo-9-azabicyclo[3.3.1]nonane-9-carboxylate | 1 | 62 and 52 | LCMS (System 1, Method C): m/z 212 (M + H)$^+$ (ES$^+$), at 3.51 min, 202 nm |
| 64 | Ethyl 3-[(1R,5S,6r)-6-(ethoxycarbonyl)-3-azabicyclo[3.1.0]hexan-3-yl]-9-azabicyclo[3.3.1]nonane-9-carboxylate | A | 1 and 63 | LCMS (System 1, Method E): m/z 351 (M + H)$^+$ (ES$^+$), at 5.30 and 5.39 min, 202 nm |

TABLE 2-continued

Intermediates

| Intermediate Number | Name | Synthetic Route | Intermediates Used | Data |
|---|---|---|---|---|
| 65 | Methyl 3-oxo-9-azabicyclo[3.3.1]nonane-9-carboxylate | 2 | 62 and 45 | LCMS (System 1, Method E): m/z 198 (M + H)+ (ES+), at 3.34 min, 215 nm |
| 66 | Methyl 3-[(1R,5S,6r)-6-(ethoxycarbonyl)-3-azabicyclo[3.1.0]hexan-3-yl]-9-azabicyclo[3.3.1]nonane-9-carboxylate | A | 1 and 65 | LCMS (System 1, Method E): m/z 337 (M + H)+ (ES+), at 4.99 and 5.03 min, 202 nm |
| 67 | tert-Butyl 7-oxo-3-oxa-9-azabicyclo[3.3.1]nonane-9-carboxylate | — | — | Commercially available, CAS: 280761-97-9 |
| 68 | Ethyl 7-oxo-3-oxa-9-azabicyclo[3.3.1]nonane-9-carboxylate | 1 | 67 and 52 | LCMS (System 2, Method A): m/z 214 (M + H)+ (ES+), at 1.53 min, 202 nm |
| 69 | Ethyl 7-[(1R,5S,6r)-6-(ethoxycarbonyl)-3-azabicyclo[3.1.0]hexan-3-yl]-3-oxa-9-azabicyclo[3.3.1]nonane-9-carboxylate | A | 1 and 68 | LCMS (System 1, Method C): m/z 353 (M + H)+ (ES+), at 4.10 min, 202 nm |
| 70 | Methyl 7-oxo-3-oxa-9-azabicyclo[3.3.1]nonane-9-carboxylate | 1 | 67 and 45 | LCMS (System 2, Method D): m/z 200 (M + H)+ (ES+), at 1.28 min, 222 nm |
| 71 | Methyl 7-[(1R,5S,6r)-6-(ethoxycarbonyl)-3-azabicyclo[3.1.0]hexan-3-yl]-3-oxa-9-azabicyclo[3.3.1]nonane-9-carboxylate | A | 1 and 70 | LCMS (System 1, Method C): m/z 339 (M + H)+ (ES+), at 3.75 min, 202 nm |
| 72 | Ethyl 4-oxopiperidine-1-carboxylate | — | — | Commercially available, CAS: 29976-53-2 |
| 73 | Ethyl (1R,5S,6r)-3-[1-(ethoxycarbonyl)piperidin-4-yl]-3-azabicyclo[3.1.0]hexane-6-carboxylate | A | 1 and 72 | LCMS (System 3, Method E): m/z 311 (M + H)+ (ES+), at 3.92 min, 202 nm |
| 74 | tert-Butyl 6-oxo-3-azabicyclo[3.1.1]heptane-3-carboxylate | — | — | Commercially 1251013-26-9 CAS: 1251013-26-9 |
| 75 | Ethyl 6-oxo-3-azabicyclo[3.1.1]heptane-3-carboxylate | 1 | 74 and 52 | LCMS (System 4, Method m/z 184 (M + H)+ (ES+), at 4.12 min, 202 nm |
| 76 | tert-Butyl 8-oxo-3-azabicyclo[3.2.1]octane-3-carboxylate | — | — | Commercially available, CAS: 637301-19-0 |
| 77 | Ethyl 8-oxo-3-azabicyclo[3.2.1]octane-3-carboxylate | 1 | 76 and 52 | LCMS (System 2, Method D): m/z 198 (M + H)+ (ES+), at 1.48 min, 202 nm |
| 78 | Ethyl 8-[(1R,5S,6r)-6-(ethoxycarbonyl)-3-azabicyclo[3.1.0]hexan-3-yl]-3-azabicyclo[3.2.1]octane-3-carboxylate | A | 1 and 77 | LCMS (System 3, Method E): m/z 337 (M + H)+ (ES+), at 5.07 min, 202 nm |
| 79 | N-Methylcyclopropanamine | — | — | Commercially available, CAS: 5163-20-2 |
| 80 | Morpholine | — | — | Commercially available, CAS: 110-91-8 |
| 81 | Ethyl 4-oxoazepane-1-carboxylate | — | — | Commercially available, CAS: 56515-89-0 |
| 82 | Ethyl (1R,5S,6r)-3-(1-(ethoxycarbonyl)azepan-4-yl)-3-azabicyclo[3.1.0]hexane-6-carboxylate | A | 1 and 81 | LCMS (System 3, Method E): m/z 325 (M + H)+ (ES+), at 4.18 min, 202 nm |
| 83 | tert-Butyl 3-oxo-6-azabicyclo[3.2.1]octane-6-carboxylate | — | — | Commercially available, CAS: 359779-74-1 |
| 84 | Ethyl 3-oxo-6-azabicyclo[3.2.1]octane-6-carboxylate | 1 | 83 and 52 | LCMS (System 4, Method B): m/z 198 (M + H)+ (ES+), at 4.39 min, 202 nm |
| 85 | Ethyl 3-[(1R,5S,6r)-6-(ethoxycarbonyl)-3-azabicyclo[3.1.0]hexan-3-yl]-6-azabicyclo[3.2.1]octane-6-carboxylate | A | 1 and 84 | LCMS (System 3, Method m/z 337 (M + H)+ (ES+), at 3.83 and 4.71 min, 202 nm |
| 86 | tert-Butyl 5-oxohexahydrocyclopenta[c]pyrrole-2(1H)-carboxylate | — | — | Commercially available, CAS: 148404-28-8 |
| 87 | Ethyl 5-oxohexahydrocyclopenta[c]pyrrole-2(1H)-carboxylate | 1 | 86 and 52 | $^1$H NMR (400 MHz, DMSO-$d_6$) δ: 1.19 (t, J = 7.25 Hz, 3 H), 2.05-2.16 (m, 2 H), 2.36-2.47 (m, 2 H), 2.84-2.96 (m, 2 H), 3.12-3.21 (m, 2 H), 3.53-3.63 (m, 2 H), 4.02-4.08 (m, 2 H). |

TABLE 2-continued

Intermediates

| Intermediate Number | Name | Synthetic Route | Intermediates Used | Data |
|---|---|---|---|---|
| 88 | ethyl 5-((1R,5S)-6-(ethoxycarbonyl)-3-azabicyclo[3.1.0]hexan-3-yl)hexahydrocyclopenta[c]pyrrole-2(1H)-carboxylate | A | 1 and 87 | LCMS (System 3, Method E): m/z 337 (M + H)+ (ES+), at 4.09 min, 202 nm |

TABLE 3

| Ex. No. | Name | Synthetic Method and Intermediates Used | Purification Method | $^1$H NMR | LC-MS System and Method | LCMS data |
|---|---|---|---|---|---|---|
| 1-1 | Ethyl 6-[(1R,5S,6r)-6-(ethoxycarbonyl)-3-azabicyclo[3.1.0]hex-3-yl]-2-azaspiro[3.3]heptane-2-carboxylate | A 1 and 2 | A | (400 MHz, DMSO-d$_6$) δ: 1.09-1.22 (m, 6H), 1.79 (s, 1 H), 1.86-1.90 (m, 2 H), 1.90-1.99 (m. 2 H), 2.12-2.21 (m, 2 H), 2.24 (d, J = 8.6 Hz, 2 H), 2.81-2.84 (m, 1 H), 2.92 (d, J = 9.0 Hz, 2 H), 3.73-3.83 (m, 2 H), 3.83-3.91 (m, 2 H), 3.93-4.07 (m, 4 H). | 1 C | m/z 323 (M + H)+ (ES+), at 4.36 min, 202 nm |
| 1-2 | Ethyl 6-[(1R,5S,6r)-6-(ethoxycarbonyl)-3-azabicyclo[3.1.0]hex-3-yl]-2-azaspiro[3.3]heptane-2-carboxylate | B 1, 3, 4 and 52 | B | (400 MHz, METHANOL-d$_4$) δ: 1.09 (t, J = 7.0 Hz, 3 H), 1.16-1.32 (m, 6 H), 1.86-1.90 (m, 2 H), 2.02-2.15 (m, 2 H), 2.18-2.23 (m, 1 H), 2.24-2.34 (m, 2 H), 2.42 (d, J = 9.2 Hz, 2 H), 2.94 (quin, J = 7.7 Hz, 1 H), 3.02 (d, J = 9.2 Hz, 2 H), 3.36 (q, J = 7.2 Hz, 2 H), 3.53 (q, J = 7.0 Hz, 2 H), 3.84-3.91 (m, 2 H), 3.95-4.01 (m, 2 H), 4.06 (q, J = 7.0 Hz, 2 H). | 4 C | m/z 350 (M + H)+ (ES+), at 3.46 min, 210 nm |
| 1-3 | Ethyl 6-{(1R,5S,6r)-6-[ethyl(propan-2-yl)carbamoyl]-3-azabicyclo[3.1.0]hex-3-yl}-2-azaspiro[3.3]heptane-2-carboxylate | C Example 1-1 and 5 | C | (400 MHz, METHANOL-d$_4$) δ: 1.07-1.17 (m, 3 H), 1.22 (t, J = 7.2 Hz), 3 H), 1.25-1.32 (m, 6 H), 1.89-1.95 (m, 2 H), 2.02-2.14 (m, 2 H), 2.16-2.21 (m, 0.7 H), 2.23-2.34 (m, 2.3 H), 2.37-2.48 (m, 2 H), 2.88-2.98 (m, 1 H), 2.99-3.08 (m, 2 H), 3.22-3.29 (m, 1 H), 3.41-3.51 (m, 1 H), 3.83-3.91 (m, 2 H), 3.92-4.01 (m, 2 H), 4.06 (q, J = 7.09 Hz, 2 H), 4.41-4.49 (m, 0.3 H), 4.57-4.69 (m, 0.7 H). | 1 C | m/z 364 (M + H)+ (ES+), at 4.07 min, 202 nm |
| 1-4 | Ethyl 6-[(1R,5S,6r)-6-(2-methyl-1,3-thiazol-4-yl)-3-azabicyclo[3.1.0]hex-3-yl]-2-azaspiro[3.3]heptane-2-carboxylate | D 6, 7, 8, 9, 10 and 2 | D | (400 MHz, METHANOL-d$_4$) δ: 1.22 (t, J = 7.0 Hz, 3 H), 1.80-1.87 (m, 2 H), 2.04-2.15 (m, 2 H), 2.22-2.37 (m, 4 H), 2.43 (d, J = 8.9 Hz, 2 H), 2.63 (s, 3 H), 2.93 (quin, J = 7.6 Hz, 1 H), 3.07 (d, J = 9.2 Hz, 2 H), 3.85-3.91 (m, 2 H), 3.93-4.01 (m, 2 H), 4.06 (q, J = 7.0 Hz, 2 H). | 4 C | m/z 348 (M + H)+ (ES+), at 4.08 min, 210 nm |
| 2-1 | Mixture of isomers: ethyl 2-[(1R,5S,6r)-6-(ethoxycarbonyl)-3-azabicyclo[3.1.0]hex-3-yl]-6-azaspiro[3.4]octane-6-carboxylate | A 1 and 11 | E | (400 MHz, DMSO-d$_6$) δ: 1.17 (dt, J = 7.0, 3.5 Hz, 6 H), 1.73-2.03 (m, 8 H), 2.24-2.27 (m, 2 H), 2.88-3.02 (m, 3 H), 3.10-3.30 (m, 5 H), 3.95-4.08 (m, 4 H). | 1 C | m/z 337 (M + H)+ (ES+), at 4.65 min, 202 nm |
| 2-2 | Isomer 1: ethyl 2-{(1R,5S,6r)-6-[(2-methylpropyl)carbamoyl]-3-azabicyclo[3.1.0]hex-3-yl}-6-azaspiro[3.4]octane-6-carboxylate | C Example 2-1 and 12 | F | (400 MHz, METHANOL-d$_4$) δ: 0.92 (d, J = 6.6 Hz, 6 H), 1.14-1.36 (m, 4 H), 1.72-1.81 (m, 1 H), 1.83-1.97 (m, 7 H), 2.08 (t, J = 9.0 Hz, 2 H), 2.44 (d, J = 9.0 Hz, 2 H), 2.87-3.13 (m, 4 H), 3.35-3.43 (m, 4 H), 4.12 (q, J = 7.1 Hz). One exchangeable proton not observed. | 1 C | m/z 364 (M + H)+ (ES+), at 3.91 min, 202 nm |
| 2-2 | Isomer 2: ethyl 2-{(1R,5S,6r)-6-[(2-methylpropyl)carbamoyl]-3-azabicyclo[3.1.0]hex-3-yl}-6-azaspiro[3.4]octane-6-carboxylate | C Example 2-1 and 12 | F | (400 MHz, METHANOL-d$_4$) δ: 0.93 (d, J = 6.4 Hz, 6 H), 1.23-1.35 (m, 4 H), 1.70-1.84 (m, 1 H), 1.84-2.02 (m, 8 H), 2.02-2.15 (m, 2 H), 2.34-2.51 (m, 2 H), 2.93-3.10 (m, 4 H), 3.38-3.45 (m, 3 H), 4.06-4.17 (m, 2 H). One exchangeable proton not observed. | 1 C | m/z 364 (M + H)+ (ES+), at 3.96 min, 202 nm |
| 2-3 | Isomer 1: ethyl 2-{(1R,5S,6r)-6-[(cyclobutyl-methyl)carbamoyl]-3-azabicyclo[3.1.0]hex-3-yl}-6-azaspiro[3.4]octane-6-carboxylate | C Example 2-1 and 13 | G | (400 MHz, METHANOL-d$_4$) δ: 1.27 (t, J = 6.8 Hz, 3 H), 1.63-1.79 (m, 2 H), 1.80-1.99 (m, 9 H), 1.99-2.19 (m, 4 H), 2.35-2.57 (m, 3 H), 2.93-3.13 (m, 4 H), 3.19 (d, J = 7.1 Hz, 2 H), 3.36-3.46 (m, 3 H), 4.12 (q, J = 6.9 Hz, 2 H). One exchangeable proton not observed. | 1 C | m/z 376 (M + H)+ (ES+), at 4.02 min, 202 nm |
| 2-3 | Isomer 2: ethyl 2-{(1R,5S,6r)-6-[(cyclobutyl-methyl)carbamoyl]-3-azabicyclo[3.1.0]hex-3-yl}-6-azaspiro[3.4]octane-6-carboxylate | C Example 2-1 and 13 | G | (400 MHz, METHANOL-d$_4$) δ: 1.27 (t, J = 7.0 Hz, 3 H), 1.63-1.80 (m, 2 H), 1.80-2.00 (m, 9 H), 2.00-2.14 (m, 4 H), 2.33-2.56 (m, 3 H), 2.95-3.16 (m, 4 H), 3.20 (d, J = 7.1 Hz, 2H), 3.36-3.46 (m, 3 H), 4.11 (q, J = 7.0 Hz, 2 H). One exchangeable proton not observed. | 1 C | m/z 376 (M + H)+ (ES+), at 4.04 min, 202 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 2-4 | Isomer 1: ethyl 2-{(1R,5S,6r)-6-[(1-methyl-cyclobutyl)carbamoyl]-3-azabicyclo[3.1.0]hex-3-yl}-6-azaspiro[3.4]octane-6-carboxylate | C Example 2-1 and 14 | H | (400 MHz, METHANOL-$d_4$) δ: 1.21-.33 (m, 3 H), 1.43 (s, 3 H), 1.80-2.11 (m, 14 H), 2.19-2.36 (m, 2 H), 2.42 (d, J = 9.2 Hz, 2 H), 2.86-3.15 (m, 3 H), 3.36 (d, J -5.8 Hz, 3 H), 4.12 (q, J = 7.0 Hz, 2 H). One exchangeable proton not observed. | 1 C | m/z 376 (M + H)⁺ (ES⁺), at 3.96 min, 202 nm |
| 2-4 | Isomer 2: ethyl 2-{(1R,5S,6r)-6-[(1-methyl-cyclobutyl)carbamoyl]-3-azabicyclo[3.1.0]hex-3-yl}-6-azaspiro[3.4]octane-6-carboxylate | C Example 2-1 and 14 | H | (400 MHz, METHANOL-$d_4$) δ: 1.27 (t, J = 7.0 Hz, 3 H), 1.43 (s, 3 H), 1.72-1.97 (m, 10 H), 1.97-2.18 (m, 4 H), 2.22-2.35 (m, 2 H), 2.35-2.52 (m, 2 H), 2.94-3.13 (m, 3 H), 3.35-3.47 (m, 3 H), 4.11 (q, J = 7.0 Hz, 2 H). One exchangeable proton not observed. | 1 C | m/z 376 (M + H)⁺ (ES⁺), at 4.00 min, 202 nm |
| 2-5 | Isomer 1: ethyl 2-{(1R,5S,6r)-6-[ethyl(methyl)carbamoyl]-3-azabicyclo[3.1.0]hex-3-yl}-6-azaspiro[3.4]octane-6-carboxylate | C Example 2-1 and 15 | I then J | (400 MHz, METHANOL-$d_4$) δ: 1.10 (t, J = 7.3 Hz, 1 H), 1.18-1.41 (m, 5 H), 1.74-2.02 (m, 7 H), 2.02-2.19 (m, 2 H), 2.27-2.29 (m, 1 H), 2.45 (t, J = 7.3 Hz, 2 H), 2.93 (s, 2 H), 3.06 (d, J = 9.8 Hz, 3 H), 3.19 (s, 1 H), 3.35-3.51 (m, 4 H), 3.59 (q, J = 7.3 Hz, 1 H), 4.12 (q, J = 7.1 Hz, 2 H). | 3 E | m/z 350 (M + H)⁺ (ES⁺), at 3.08 min, 215 nm |
| 2-5 | Isomer 2: ethyl 2-{(1R,5S,6r)-6-[ethyl(methyl)carbamoyl]-3-azabicyclo[3.1.0]hex-3-yl}-6-azaspiro[3.4]octane-6-carboxylate | C Example 2-1 and 15 | I then J | (400 MHz, METHANOL-$d_4$) δ: 1.10 (t, J = 7.0 Hz, 1 H), 1.26 (t, J = 7.3 Hz, 5 H), 1.78-2.02 (m, 7 H), 2.02-2.15 (m, 2 H), 2.27-2.29 (m, 1 H), 2.37-2.55 (m, 2 H), 2.93 (s, 1 H), 3.00-3.14 (m, 3 H), 3.19 (s, 1 H), 3.24-3.30 (m, 2 H), 3.35-3.48 (m, 3 H), 3.59 (q, J = 6.7 Hz, 1 H), 4.11 (q, J = 6.7 Hz, 2 H). | 3 E | m/z 350 (M + H)⁺ (ES⁺), at 3.12 min, 215 nm |
| 2-6 | Isomer 1: ethyl 2-[(1R,5S,6r)-6-(diethylcarbamoyl)-3-azabicyclo[3.1.0]hex-3-yl]-6-azaspiro[3.4]octane-6-carboxylate | C Example 2-1 and 4 | K | (400 MHz, METHANOL-$d_4$) δ: 1.12 (t, J = 7.1 Hz, 3 H), 1.22-1.42 (m, 8 H), 1.87-2.03 (m, 2 H), 2.17-2.33 (m, 5 H), 2.34-2.47 (m, 2 H), 3.35-3.47 (m, 6 H), 3.52-3.61 (m, 2 H), 3.80 (d, J = 11.7 Hz, 2 H), 3.85-3.96 (m, 1 H), 4.13 (q, J = 7.1 Hz, 2 H). | 4 C | m/z 364 (M + H)⁺ (ES⁺), at 3.63 min, 202 nm |
| 2-6 | Isomer 2: ethyl 2-[(1R,5S,6r)-6-(diethylcarbamoyl)-3-azabicyclo[3.1.0]hex-3-yl]-6-azaspiro[3.4]octane-6-carboxylate | C Example 2-1 and 4 | K | (400 MHz, DMSO-$d_6$) δ: 0.31 (t, J = 7.1 Hz, 3 H), 0.41-0.57 (m, 8 H), 1.11-1.26 (m, 2 H), 1.35-1.78 (m, 7 H), 2.55-2.68 (m, 6 H), 2.70-2.85 (m, 2 H), 3.00 (d, J = 11.5 Hz, 2 H), 3.04-3.18 (m, 1 H), 3.31 (q, J = 6.8 Hz, 2 H). | 4 C | m/z 364 (M + H)⁺ (ES⁺), at 3.67 min, 202 nm |
| 2-7 | Isomer 1: methyl 2-[(1R,5S,6r)-6-(diethylcarbamoyl)-3-azabicyclo[3.1.0]hex-3-yl]-6-azaspiro[3.4]octane-6-carboxylate | C 17 and 4 | L then M | (400 MHz, METHANOL-$d_4$) δ: 1.11 (t, J = 7.1 Hz, 3 H), 1.28 (t, J = 7.1 Hz, 6 H), 1.93 (d, J = 8.8 Hz, 2 H), 2.03-2.25 (m, 6 H), 2.32-2.43 (m, 1 H), 2.78-2.95 (m, 2 H), 3.35-3.43 (m, 6 H), 3.57 (q, J = 6.8 Hz, 2 H), 3.70 (s, 3 H). | 1 C | m/z 350 (M + H)⁺ (ES⁺), at 3.67 min, 210 nm |
| 2-7 | Isomer 2: methyl 2-[(1R,5S,6r)-6-(diethylcarbamoyl)-3-azabicyclo[3.1.0]hex-3-yl]-6-azaspiro[3.4]octane-6-carboxylate | C 17 and 4 | L then M | (400 MHz, METHANOL-$d_4$) δ: 1.11 (t, J = 6.8 Hz, 3 H), 1.28 (t, J = 7.1 Hz, 3 H), 1.91-2.04 (m, 6 H), 2.05-2.14 (m, 2 H), 2.23-2.29 (m, 1 H), 2.55 (d, J = 9.3 Hz, 2 H), 3.08-3.20 (m, 3 H), 3.29 (s, 2 H), 3.35-3.43 (m, 4 H), 3.56 (q, J = 7.0 Hz, 2 H), 3.68 (s, 3 H). | 1 C | m/z 350 (M + H)⁺ (ES⁺), at 3.66 min, 210 nm |
| 2-8 | Isomer 1: ethyl 2-{(1R,5S,6r)-6-[methyl(propan-2-yl)carbamoyl]-3-azabicyclo[3.1.0]hex-3-yl}-6-azaspiro[3.4]octane-6-carboxylate | C Example 2-1 and 18 | N then O | (400 MHz, METHANOL-$d_4$) δ: 1.07-1.14 (m, 3 H), 1.21-1.30 (m, 6 H), 1.82-1.97 (m, 6 H), 2.04-2.12 (m, 2 H), 2.21-2.25 (m, 0.5 H), 2.29-2.34 (m, 0.5 H), 2.40-2.48 (m, 2 H), 2.74-2.79 (m, 1 H), 2.99-3.08 (m, 4 H), 3.32-3.39 (m, 4 H), 3.53-3.59 (m, 0.5 H), 3.65-3.71 (m, 0.5 H), 4.05-4.15 (m, 2 H), 4.45-4.53 (m, 0.5 H), 4.68-4.77 (m, 0.5 H). | 3 E | m/z 364 (M + H)⁺ (ES⁺), at 3.32 min, 202 nm |
| 2-8 | Isomer 2: ethyl 2-{(1R,5S,6r)-6-[methyl(propan-2-yl)carbamoyl]-3-azabicyclo[3.1.0]hex-3-yl}-6-azaspiro[3.4]octane-6-carboxylate | C Example 2-1 and 18 | N then O | (400 MHz, METHANOL-$d_4$) δ: 1.06-1.14 (m, 3 H), 1.21-1.29 (m, 6 H), 1.88-1.99 (m, 6 H), 2.01-2.10 (m, 2 H), 2.21-2.26 (m, 0.5 H), 2.29-2.33 (m, 0.5 H), 2.40-2.47 (m, 2 H), 2.75-2.79 (m, 1 H), 2.99-3.10 (m, 4 H), 3.24-3.28 (m, 2 H), 3.34-3.42 (m, 2 H), 3.53-3.59 (m, 0.5 H), 3.65-3.71 (m, 0.5 H), 4.04-4.14 (m, 2 H), 4.45-4.55 (m, 0.5 H), 4.68-4.76 (m, 0.5 H). | 3 E | m/z 364 (M + H)⁺ (ES⁺), at 3.20 min, 202 nm |
| 2-9 | Isomer 1: ethyl 2-{(1R,5S,6r)-6-[ethyl(propan-2-yl)carbamoyl]-3-azabicyclo[3.1.0]hex-3-yl}-6-azaspiro[3.4]octane-6-carboxylate | C Example 2-1 and 5 | P then Q | (400 MHz, METHANOL-$d_4$) δ: 1.10-1.18 (m, 4 H), 1.25-1.39 (m, 10 H), 1.85-1.99 (m, 6 H), 2.02-2.14 (m, 2 H), 2.21-2.33 (m, 1 H), 2.39-2.53 (m, 2 H), 3.06 (d, J = 9.3 Hz, 3 H), 3.21-3.99 (m, 1 H), 3.36-3.39 (m, 2 H), 3.48 (q, J = 6.8 Hz, 1 H), 4.12 (q, J = 6.8 Hz), 2 H), 4.42-4.70 (m, 1H). | 1 C | m/z 378 (M + H)⁺ (ES⁺), at 4.23 min, 215 nm |
| 2-9 | Isomer 2: ethyl 2-{(1R,5S,6r)-6-[ethyl(propan-2-yl)carbamoyl]-3-azabicyclo[3.1.0]hex-3-yl}-6-azaspiro[3.4]octane-6-carboxylate | C Example 2-1 and 5 | P then Q | (400 MHz, METHANOL-$d_4$) δ: 1.08-1.17 (m, 4 H), 1.20-1.35 (m, 10 H), 1.94 (q, J = 7.3 Hz, 2 H), 1.98-2.09 (m, 4 H), 2.09-2.16 (m, 2 H), 2.19 (m, 1 H), 2.61-2.75 (m, 2 H), 3.16-3.25 (m, 3 H), 3.34-3.42 (m, 3 H), 3.46 (q, J = 6.8 Hz, 2 H), 4.09 (q, J = 6.8 Hz, 2 H), 4.42-4.66 (m, 1 H). | 1 C | m/z 378.0 (M + H)⁺ (ES⁺), at 4.24 min, 215 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 2-10 | Isomer 1: methyl 2-{(1R,5S,6r)-6-[ethyl(propan-2-yl)carbamoyl]-3-azabicyclo[3.1.0]hex-3-yl}-6-azaspiro[3.4]octane-6-carboxylate | C 17 and 5 | R then S | (400 MHz, METHANOL-d₄) δ: 1.09-1.22 (m, 5 H), 1.22-1.38 (m, 8 H), 1.93 (d, J = 6.8 Hz, 2 H), 2.22-2.41 (m, 7 H), 3.03-3.08 (m, 1 H), 3.40-3.51 (m, 4 H), 3.69 (s, 3 H), 3.83 (d, J = 11.7 Hz, 2 H), 4.37-4.64 (m, 1 H). | 1 C | m/z 364 (M + H)⁺ (ES⁺), at 3.97 min, 210 nm |
| 2-10 | Isomer 2: methyl 2-{(1R,5S,6r)-6-[ethyl(propan-2-yl)carbamoyl]-3-azabicyclo[3.1.0]hex-3-yl}-6-azaspiro[3.4]octane-6-carboxylate | C 17 and 5 | R then S | (400 MHz, METHANOL-d₄) δ: 1.06-1.22 (m, 5 H), 1.22-1.43 (m, 8 H), 1.91-2.07 (m, 2 H), 2.19-2.35 (m, 3 H), 2.36 (d, J = 7.8 Hz, 4 H), 3.01-3.08 (m, 1 H), 3.40-3.50 (m, 3 H), 3.68 (s, 3 H), 3.84 (d, J = 11.2 Hz, 3 H), 4.33-4.66 (m, 1 H). | 1 C | m/z 364 (M + H)⁺ (ES⁺), at 4.00 min, 210 nm |
| 2-11 | Mixture of isomers: ethyl 2-{(1R,5S,6r)-6-[cyclopropyl(ethyl)carbamoyl]-3-azabicyclo[3.1.0]hex-3-yl}-6-azaspiro[3.4]octane-6-carboxylate | C Example 2-1 and 19 | T | (400 MHz, METHANOL-d₄) δ: 0.99-1.07 (m, 2 H), 1.13 (t, J = 7.1 Hz, 3 H), 1.21-1.34 (m, 4 H), 1.84-2.01 (m, 6 H), 2.03-2.16 (m, 2 H), 2.50 (t, J = 7.6 Hz, 2 H), 2.66-2.71 (m, 1 H), 2.80-2.95 (m, 1 H), 3.04-3.17 (m, 3 H), 3.25-3.31 (m, 1 H), 3.36-3.47 (m, 6 H), 4.06-4.18 (m, 2 H). | 1 C | m/z 376 (M + H)⁺ (ES⁺), at 4.22 min, 202 nm |
| 2-12 | Isomer 1: ethyl 2-[(1R,5S,6r)-6-(pyrrolidin-1-ylcarbonyl)-3-azabicyclo[3.1.0]hex-3-yl]-6-azaspiro[3.4]octane-6-carboxylate | C Example 2-1 and 20 | U | (400 MHz, DMSO-d₆) δ: 1.17 (t, J = 6.7 Hz, 3 H), 1.66-1.84 (m, 8 H), 1.84-2.03 (m, 5 H), 2.23-2.37 (m, 2 H), 2.91 (d, J = 8.9 Hz, 2 H), 2.98-3.06 (m, 1 H), 3.17-3.29 (m, 6 H), 3.53 (t, J = 6.7 Hz, 2 H), 4.00 (q, J = 7.0 Hz, 2 H). | 1 C | m/z 362 (M + H)⁺ (ES⁺), at 3.66 min, 202 nm |
| 2-12 | Isomer 2: ethyl 2-[(1R,5S,6r)-6-(pyrrolidin-1-ylcarbonyl)-3-azabicyclo[3.1.0]hex-3-yl]-6-azaspiro[3.4]octane-6-carboxylate | C Example 2-1 and 20 | U | (400 MHz, DMSO-d₆) δ: 1.16 (t, J = 7.0 Hz, 3 H), 1.68-1.97 (m, 13 H), 2.19-2.38 (m, 2 H), 2.90 (d, J = 8.9 Hz, 2 H), 2.99-3.06 (m, 1 H), 3.16 (d, J = 10.4 Hz, 2 H), 3.20-3.30 (m, 4 H), 3.53 (t, J = 6.7 Hz, 2 H), 3.99 (q, J = 6.4 Hz, 2 H). | 1 C | m/z 362 (M + H)⁺ (ES⁺), at 3.70 min, 202 nm |
| 2-13 | Isomer 1: ethyl 2-[(1R,5S,6r)-6-(piperidin-1-ylcarbonyl)-3-azabicyclo[3.1.0]hex-3-yl]-6-azaspiro[3.4]octane-6-carboxylate | C Example 2-1 and 21 | V | (400 MHz, DMSO-d₆) δ: 1.17 (t, J = 6.8 Hz, 3 H), 1.32-1.45 (m, 2 H), 1.48-2.54 (m, 2 H), 1.58 (d, J = 4.6 Hz, 2 H), 1.70-1.87 (m, 6 H), 1.87-2.01 (m, 2 H), 2.03-2.07 (m, 1 H), 2.28 (d, J = 8.6 Hz, 2 H), 2.90 (d, J = 9.0 Hz, 2 H), 2.94-3.09 (m, 1 H), 3.15-3.28 (m, 4 H), 3.38-3.46 (m, 2 H), 3.46-3.58 (m, 2 H), 4.00 (q, J = 7.0 Hz, 2 H). | 1 C | m/z 376 (M + H)⁺ (ES⁺), at 4.05 min, 202 nm |
| 2-13 | Isomer 2: ethyl 2-[(1R,5S,6r)-6-(piperidin-1-ylcarbonyl)-3-azabicyclo[3.1.0]hex-3-yl]-6-azaspiro[3.4]octane-6-carboxylate | C Example 2-1 and 21 | V | (400 MHz, DMSO-d₆) δ: 1.16 (t, J = 7.0 Hz, 3 H), 1.34-1.46 (m, 2 H), 1.47-1.55 (m, 2 H), 1.55-1.65 (m, 2 H), 1.70-1.97 (m, 9 H), 2.05 (s, 1 H), 2.28 (d, J = 8.3 Hz, 2 H), 2.90 (d, J = 8.8 Hz, 2 H), 2.97-3.07(m, 1 H), 3.16 (d, J = 8.8 Hz, 2 H), 3.26 (q, J = 6.9 Hz, 2 H), 3.37-3.44 (m, 2 H), 3.47-3.59 (m, 2 H), 3.99 (q, J = 6.8 Hz, 2 H). | 1 C | m/z 376 (M + H)⁺ (ES⁺), at 4.07 min, 202 nm |
| 2-14 | Isomer 1: ethyl 2-[(1R,5S,6r)-6-{[(2R)-2-methylpiperidin-1-yl]carbonyl}-3-azabicyclo[3.1.0]hex-3-yl]-6-azaspiro[3.4]octane-6-carboxylate | C Example 2-1 and 22 | W and X | (400 MHz, METHANOL-d₄) δ: 1.09-1.21 (m. 1 H), 1.22-1.38 (m, 8 H), 1.38-1.52 (m, 2 H), 1.52-1.81 (m, 5 H), 1.81-2.01 (m, 5 H), 2.01-2.16 (m, 2 H), 2.23-2.33 (m, 1 H), 2.45 (d, J = 6.8 Hz, 1.5 H), 2.73-2.79 (m, 0.5 H), 3.05 (d, J = 9.3 Hz, 1 H), 3.16-3.29 (m, 1 H), 3.35-3.40 (m., 3 H), 4.12 (q, 6.8 Hz, 2 H), 4.33-4.79 (m, 1 H). | 1 C | m/z 390 (M + H)⁺ (ES⁺), at 4.35 min, 205 nm |
| 2-14 | Isomer 2: ethyl 2-[(1R,5S,6r)-6-{[(2R)-2-methylpiperidin-1-yl]carbonyl}-3-azabicyclo[3.1.0]hex-3-yl]-6-azaspiro[3.4]octane-6-carboxylate | C Example 2-1 and 22 | W and X | (400 MHz, METHANOL-d₄) δ: 0.87-0.99 (m, 1 H), 1.13-1.21 (m, 1 H), 1.22-1.40 (m, 4 H), 1.56-1.81 (m, 4 H), 1.86-2.01 (m, 4 H), 2.02-2.12 (m, 2 H), 2.24-2.33 (m, 1 H), 2.39-2.51 (m, 2 H), 2.70-2.83 (m, 1 H), 3.00-3.11 (m, 2 H), 3.22-3.31 (m, 2 H), 3.35-3.44 (m, 2 H), 4.05-4.18 (m, 3 H), 4.30-4.41 (m, 1 H), 4.53-4.64 (m, 1 H), 4.74-4.84 (m, 1 H). | 1 C | m/z 390 (M + H)⁺ (ES⁺), at 4.33 min, 205 nm |
| 2-15 | Mixture of isomers: ethyl 2-[(1R,5S,6r)-6-{[(2R)-2-methylpiperidin-1-yl]carbonyl}-3-azabicyclo[3.1.0]hex-3-yl]-6-azaspiro[3.4]octane-6-carboxylate | C Example 2-1 and 23 | Y | (400 MHz, METHANOL-d₄) δ: 1.07-1.21 (m, 2 H), 1.21-1.47 (m, 7 H), 1.47-1.74 (m, 6 H), 1.79-2.02 (m, 6 H), 2.02-2.17 (m, 2 H), 2.28 (d, J = 15.7 Hz, 1 H), 2.45 (d, J = 7.8 Hz, 1.5 H), 2.73-2.46 (m, 0.5 H), 3.00-3.12 (m, 2 H), 3.28 (m, 1 H), 3.35-3.49 (m, 3 H), 4.06-4.16 (m, 2 H), 4.33-4.82 (m, 1H). | 1 C | m/z 390 (M + H)⁺ (ES⁺), at 4.36 min, 202 nm |
| 2-16 | Isomer 1: ethyl 2-[(1R,5S,6r)-6-(azepan-1-ylcarbonyl)-3-azabicyclo[3.1.0]hex-3-yl]-6-azaspiro[3.4]octane-6-carboxylate | C Example 2-1 and 24 | Z and AA | (400 MHz, METHANOL-d₄) δ: 1.23-1.42 (m, 5 H), 1.51-1.77 (m, 6 H), 1.77-1.99 (m, 7 H), 2.02-2.15 (m, 2 H), 2.29-2.30 (m, 1 H), 2.47 (d, J = 9.3 Hz, 2 H), 3.06 (d, J = 9.8 Hz, 3 H), 3.35-3.41 (m, 3 H), 3.52 (t, J = 6.1 Hz, 2 H), 3.70 (t, J = 6.1 Hz, 2 H), 4.12 (q, J = 6.8 Hz, 2 H). | 1 C | m/z 390 (M + H)⁺ (ES⁺), at 4.27 min, 215 nm |

TABLE 3-continued

| Ex. No. | Name | Synthetic Method and Intermediates Used | Purification Method | $^1$H NMR | LC-MS System and Method | LCMS data |
|---|---|---|---|---|---|---|
| 2-16 | Isomer 2: ethyl 2-[(1R,5S,6r)-6-(azepan-1-ylcarbonyl)-3-azabicyclo[3.1.0]hex-3-yl]-6-azaspiro[3.4]octane-6-carboxylate | C Example 2-1 and 24 | Z and AA | (400 MHz, METHANOL-d$_4$) δ: 1.26 (t, J = 7.1 Hz, 3 H), 1.29-1.39 (m, 2 H), 1.52-1.77 (m, 5 H), 1.83 (quin, J = 5.9 Hz, 2 H), 1.89-2.02 (m, 5 H), 2.02-2.14 (m, 2 H), 2.29-2.30 (m, 1 H), 2.46 (d, J = 9.3 Hz, 2 H), 2.98-3.14 (m, 3 H), 3.28 (d, J = 3.4 Hz, 2 H), 3.36-3.45 (m, 2 H), 3.52 (t, J = 6.1 Hz, 2 H), 3.70 (t, J = 6.1 Hz, 2 H), 4.11 (q, J = 6.8 Hz, 2 H). | 1 C | m/z 390 (M + H)$^+$ (ES$^+$), at 4.30 min, 215 nm |
| 2-17 | Isomer 1: ethyl 2-[(1R,5S,6r)-6-(1,4-oxazepan-4-ylcarbonyl)-3-azabicyclo[3.1.0]hex-3-yl]-6-azaspiro[3.4]octane-6-carboxylate | C Example 2-1 and 25 | AB | (400 MHz, METHANOL-d$_4$) δ: 1.26 (t, J = 7.3 Hz, 3 H), 1.83-1.90 (m, 1 H), 1.90-2.04 (m, 7 H), 2.04-2.12 (m, 2 H), 2.25-2.51 (m, 1 H), 2.41-2.52 (m, 2 H), 3.01-3.15 (m, 3 H), 3.28 (m, 2 H), 3.36-3.43 (m, 2 H), 3.66 (t, J = 6.1 Hz, 2 H), 3.69-3.81 (m, 3 H), 3.81-3.91 (m, 3 H), 4.11 (q, J = 6.9 Hz, 2 H). | 3 E | m/z 392 (M + H)$^+$ (ES$^+$), at 3.10 min, 202 nm |
| 2-17 | Isomer 2: ethyl 2-[(1R,5S,6r)-6-(1,4-oxazepan-4-ylcarbonyl)-3-azabicyclo[3.1.0]hex-3-yl]-6-azaspiro[3.4]octane-6-carboxylate | C Example 2-1 and 25 | AB | (400 MHz, METHANOL-d$_4$) δ: 1.23-1.32 (m, 3 H), 1.82-2.04 (m, 8 H), 2.10 (t, J = 9.2 Hz, 2 H), 2.26-(m, 1 H), 2.47 (d, J = 9.2 Hz, 2 H), 3.06 (dd, J = 9.8, 3.7 Hz, 3 H), 3.35-3.42 (m, 4 H), 3.66 (t, J = 6.1 Hz, 2 H), 3.69-3.81 (m, 3 H), 3.81-3.89 (m, 3 H), 4.12 (q, J = 6.7 Hz, 2 H). | 3 E | m/z 392 (M + H)$^+$ (ES$^+$), at 3.14 min, 202 nm |
| 2-18 | Mixture of isomers: ethyl 2-[(1R,5S,6r)-6-(2-azaspiro[3.3]hept-2-ylcarbonyl)-3-azabicyclo[3.1.0]hex-3-yl]-6-azaspiro[3.4]octane-6-carboxylate | C Example 2-1 and 26 | AC | (400 MHz, METHANOL-d$_4$) δ: 1.26 (t, J = 6.3 Hz, 3 H), 1.79-1.99 (m, 9 H), 1.99-2.13 (m, 2 H), 2.13-2.32 (m, 4 H), 2.41 (d, J = 9.0 Hz, 2 H), 2.96-3.07 (m, 3 H), 3.26 (d, J= 2.8 Hz, 1 H), 3.33-3.43 (m, 3 H), 3.91 (s, 2 H), 4.10 (qd, J = 7.1, 2.8 Hz, 2 H), 4.25 (s, 2 H). | 1 C | m/z 388 (M + H)$^+$ (ES$^+$), at 4.20 min, 210 nm |
| 2-19 | Isomer 2: ethyl 2-[(1R,5S,6r)-6-(2-azaspiro[2.3]hex-4-ylcarbonyl)-3-azabicyclo[3.1.0]hex-3-yl]-6-azaspiro[3.4]octane-6-carboxylate | C Example 2-1 and 27 | AD then AE | (400 MHz, METHANOL-d$_4$) δ: 0.53-0.61 (m, 2 H), 1.21-1.29 (m, 3 H), 1.50-1.58 (m, 2 H), 1.80-1.88 (m, 2 H), 1.88-2.00 (m, 4 H), 2.01-2.10 (m, 2 H), 2.37-2.45 (m, 2 H), 2.44-2.53 (m, 2 H), 2.96-3.09 (m, 2 H), 3.23-3.28 (m, 2 H), 3.34-3.44 (m, 4 H), 3.89-3.96 (m, 0.5 H), 4.04-4.15 (m, 2 H), 4.27-4.35 (m, 1.5 H). | 2 D | m/z 374 (M + H)$^+$ (ES$^+$), at 1.67 min, 220 nm |
| 2-20 | Mixture of isomers: ethyl 2-[(1R,5S,6r)-6-(1-azaspiro[3.3]hept-1-ylcarbonyl)-3-azabicyclo[3.1.0]hex-3-yl]-6-azaspiro[3.4]octane-6-carboxylate | C Example 2-1 and 28 | AF | (400 MHz, METHANOL-d$_4$) δ: 1.19-1.30 (m, 3 H), 1.62-2.10 (m, 12 H), 2.17-2.33 (m, 1 H), 2.33-2.52 (m, 4 H), 2.81 (q, J = 10.3 Hz, 1 H), 2.87-2.98 (m, 1 H), 2.98-3.16 (m, 3 H), 3.23-3.27 (m, 1 H), 3.33-3.42 (m, 3 H), 3.77 (t, J = 7.7 Hz, 1 H), 4.03-4.18 (m, 3 H). | 1 C | m/z 388 (M + H)$^+$ (ES$^+$), at 4.28 min, 202 nm |
| 2-21 | Isomer 1: ethyl 2-[(1R,5S,6r)-6-(1-azaspiro[3.3]hept-1-ylcarbonyl)-3-azabicyclo[3.1.0]hex-3-yl]-6-azaspiro[3.4]octane-6-carboxylate | C 17 and 28 | AG | (400 MHz, METHANOL-d$_4$) δ: 1.24-1.37 (m, 5 H), 1.56-1.78 (m, 1 H), 1.80-1.94 (m, 4 H), 1.94-2.19 (m, 4 H), 2.19-2.37 (m, 1 H), 2.37-2.54 (m, 3 H), 2.76-2.99 (m, 2 H), 3.00-3.17 (m, 2 H), 3.36-3.41 (m, 4 H), 3.69 (s, 3 H), 3.74-3.84 (m, 1 H), 4.14 (t, J = 7.6 Hz, 1 H). | 1 C | m/z 374 (M + H)$^+$ (ES$^+$), at 3.95 min, 202 nm |
| 2-21 | Isomer 2: ethyl 2-[(1R,5S,6r)-6-(1-azaspiro[3.3]hept-1-ylcarbonyl)-3-azabicyclo[3.1.0]hex-3-yl]-6-azaspiro[3.4]octane-6-carboxylate | C 17 and 28 | AG | (400 MHz, METHANOL-d$_4$) δ: 1.23-1.37 (m, 4 H), 1.58-1.77 (m, 1 H), 1.77-2.14 (m, 9 H), 2.24-2.36 (m, 1 H), 2.36-2.54 (m, 3 H), 2.76-2.88 (m, 1 H), 2.88-2.99 (m, 1 H), 2.99-3.18 (m, 2 H), 3.27 (s, 1 H), 3.35-3.44 (m, 3 H), 3.68 (s, 3 H), s, 3 H), 3.75-3.86 (m, 1 H), 4.14 (t, J = 7.6 Hz, 1 H). | 1 C | m/z 374 (M + H)$^+$ (ES$^+$), at 3.95 min, 202 nm |
| 2-22 | Isomer 2: ethyl 2-[(1R,5S,6r)-6-(6-oxa-1-azaspiro[3.3]hept-1-ylcarbonyl)-3-azabicyclo[3.1.0]hex-3-yl]-6-azaspiro[3.4]octane-6-carboxylate | C Example 2-1 and 29 | AH | (400 MHz, METHANOL-d$_4$) δ: 1.24 (t, J = 7.1 Hz, 3 H), 1.82-1.99 (m, 6 H), 1.99-2.11 (m, 2 H), 2.36-2.52 (m, 2 H), 2.52-2.62 (m, 2 H), 2.92-3.11 (m, 3 H), 3.23-3.27 (m, 2 H), 3.37 (q, J = 6.2 Hz, 2 H), 3.73 (t, J = 7.6 Hz, 1 H), 4.10 (quin, J = 6.8 Hz, 4 H), 4.62 (d, J = 6.8 Hz, 2 H), 5.14 (d, J = 7.8 Hz, 1 H), 5.32 (d, J = 7.3 Hz, 1 H). | 1 C | m/z 390 (M + H)$^+$ (ES$^+$), at 3.38 min, 210 nm |
| 2-23 | Isomer 2: ethyl 2-{(1R,5S,6r)-6-[methoxy(methyl)carbamoyl]-3-azabicyclo[3.1.0]hex-3-yl}-6-azaspiro[3.4]octane-6-carboxylate | C Example 2-1 and 7 | AI | (400 MHz, METHANOL-d$_4$) δ: 1.26 (t, J = 7.1 Hz, 3 H), 1.88-2.01 (m, 6 H), 2.01-2.11 (m, 2 H), 2.46 (d, J = 9.3 Hz, 2 H), 2.56-2.68 (m, 1 H), 3.02-3.10 (m, 3 H), 3.16-3.24 (m, 2 H), 3.25-3.29 (m, 3 H), 3.36-3.44 (m, 2 H), 3.80 (s, 3 H), 4.11 (q, J = 6.8 Hz, 2 H). | 1 C | m/z 352 (M + H)$^+$ (ES$^+$), at 3.77 min, 202 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 2-24 | Isomer 1: ethyl 2-{(1R,5S,6r)-6-[ethyl(methoxy)carbamoyl]-3-azabicyclo[3.1.0]hex-3-yl}-6-azaspiro[3.4]octane-6-carboxylate | C Example 2-1 and 30 | AJ | (400 MHz, METHANOL-$d_4$) δ: 1.18 (t, J = 6.8 Hz, 3 H), 1.27 (td, J = 7.0, 3.2 Hz, 3 H), 1.82-2.01 (m, 6 H), 2.04-2.15 (m, 2 H), 2.47 (d, J = 9.3 Hz, 2 H), 2.54-2.56 (m, 1 H), 3.07 (d, J = 9.8 Hz, 3 H), 3.38 (d, J = 5.9 Hz, 4 H), 3.62-3.74 (m, 2 H), 3.79 (s, 3 H), 4.12 (q, J = 6.8 Hz, 2 H). | 1 C | m/z 366 $(M + H)^+$ $(ES^+)$, at 4.06 min, 202 nm |
| 2-24 | Isomer 2: ethyl 2-{(1R,5S,6r)-6-[ethyl(methoxy)carbamoyl]-3-azabicyclo[3.1.0]hex-3-yl}-6-azaspiro[3.4]octane-6-carboxylate | C Example 2-1 and 30 | AJ | (400 MHz, METHANOL-$d_4$) δ: 1.18 (t, J = 6.6 Hz, 3 H), 1.26 (t, J = 7.1 Hz, 3 H), 1.88-2.01 (m, 6 H), 2.02-2.13 (m, 2 H), 2.47 (d, J = 9.3 Hz, 2 H), 2.53-2.67 (m, 1 H), 3.0.3-3.10 (m, 3 H), 3.25-3.29 (m, 2 H), 3.39 (q, J = 6.7 Hz, 2 H), 3.61-3.73 (m, 2 H), 3.79 (s, 3 H), 4.11 (q, J = 6.8 Hz, 2 H). | 1 C | m/z 366 $(M + H)^+$ $(ES^+)$, at 4.12 min, 202 nm |
| 2-25 | Isomer 2: ethyl 2-[(1R,5S,6r)-6-[N-methoxypropanimidoyl)-3-azabicyclo[3.1.0]hexan-3-yl]-6-azaspiro[3.4]octane-6-carboxylate | F 32, 11 and 33 | AK | (400 MHz, METHANOL-$d_4$) δ: 1.06 (t, J = 7.5 Hz, 3 H), 1.27 (t, J = 7.0 Hz, 3 H), 1.81-2.02 (m, 7 H), 2.02-2.15 (m, 2 H), 2.46 (d, J = 9.0 Hz, 2 H), 2.55 (t, J =3.4 Hz, 1 H), 3.06 (d, J = 9.3 Hz, 3 H), 3.28 (d, J = 3.7 Hz, 2 H), 3.35-3.47 (m, 3 H), 3.81 (s, 3 H), 4.11 (q, J = 7.0 Hz, 2 H). | 1 C | m/z 350 $(M + H)^+$ $(ES^+)$, at 5.09 min, 202 nm |
| 2-25 | Isomer 4: ethyl 2-[(1R,5S,6r)-6-[N-methoxypropanimidoyl)-3-azabicyclo[3.1.0]hexan-3-yl]-6-azaspiro[3.4]octane-6-carboxylate | F 32, 11 and 33 | AK | (400 MHz, METHANOL-$d_4$) δ: 1.08 (t, J = 7.6 Hz, 3 H), 1.27 (t, J = 7.1 Hz, 3 H), 1.77-1.84 (m., 3 H), 1.89-2.03 (m, 4 H), 2.03-2.14 (m, 2 H), 2.28 (q, J = 7.6 Hz, 2 H), 2.46 (d, J = 9.3 Hz, 2 H), 3.01-3.14 (m, 3 H), 3.28 (d, J = 2.9 Hz, 2 H), 3.39 (q, J = 6.6 Hz, 2 H), 3.74 (s, 3 H), 4.11 (q, J = 7.1 Hz, 2 H). | 1 C | m/z 350 $(M + H)^+$ $(ES^+)$, at 5.24 min, 202 nm |
| 2-26 | Mixture of isomers: ethyl 2-[6-(trifluoromethyl)-3-azabicyclo[3.1.0]hex-3-yl]-6-azaspiro[3.4]octane-6-carboxylate | A 34 and 11 | AL | (400 MHz, METHANOL-$d_4$) δ: 1.16 (t, J = 7.0 Hz, 3 H), 1.70-1.88 (m, 6 H), 1.88-2.03 (m, 3 H), 2.16-2.30 (m, 2 H), 2.85-3.05 (m, 3 H), 3.09-3.30 (m, 4 H), 3.91-4.10 (m, 2 H). | 1 C | m/z 333 $(M + H)^+$ $(ES^+)$, at 5.20 min, 202 nm |
| 2-27 | Mixture of isomers: ethyl 2-{(1R,5S,6r)-6-[ethyl(2,2,2-(trifluoromethyl)amino]-3-azabicyclo[3.1.0]hexan-3-yl}-6-azaspiro[3.4]octane-6-carboxylate | G 35, 36, 37 and 11 | AM | (400 MHz, DMSO-$d_4$) δ: 1.01 (t, J = 7.0 Hz, 3 H), 1.16 (t, J = 7.0 Hz, 3 H), 1.46 (s, 2 H), 1.65-1.85 (m, 4 H), 1.85-1.99 (m, 2 H), 2.09-2.30 (m, 3 H), 2.71 (q, J = 7.2 Hz, 2 H), 2.79-2.97 (m, 3 H), 3.14 (d, J = 8.9 Hz, 1 H), 3.17-3.32 (m, 5 H), 3.92-4.07 (m, 2 H). | 1 C | m/z 390 $(M + H)^+$ $(ES^+)$, at 5.58 min, 202 nm |
| 2-28 | Isomer 1: ethyl 2-[(1R,5S,6s)-6-(1-phenylethoxy)-3-azabicyclo[3.1.0]hex-3-yl]-6-azaspiro[3.4]octane-6-carboxylate | H 38, 39 and 11 | AN | (400 MHz, METHANOL-$d_4$) δ: 1.25 (t, J = 6.8 Hz, 3 H), 1.39 (d, J = 5.9 Hz, 3 H), 1.50-1.61 (m, 1 H), 1.61-1.70 (m, 1 H), 1.70-2.17 (m, 7 H), 2.25-2.35 (m, 1 H), 2.35-2.48 (m, 1 H), 2.65-2.95 (m, 3 H), 3.20-3.30 (m, 3 H), 3.35-3.51 (m, 1 H), 4.10 (q, J = 6.7 Hz, 2 H), 4.53 (q, J = 6.4 Hz, 1 H), 7.11-7.33 (m, 1 H), 7.33-7.49 (m, 4 H). | 1 C | m/z 385 $(M + H)^+$ $(ES^+)$, at 5.67 min, 215 nm |
| 2-28 | Isomer 2: ethyl 2-[(1R,5S,6s)-6-(1-phenylethoxy)-3-azabicyclo[3.1.0]hex-3-yl]-6-azaspiro[3.4]octane-6-carboxylate | H 38, 39 and 11 | AN | (400 MHz, METHANOL-$d_4$) δ: 1.25 (t, J = 7.1 Hz, 3 H), 1.39 (d, J = 6.4 Hz, 3 H), 1.50-1.62 (m, 1 H), 1.62-1.71 (m, 1 H), 1.74-1.92 (m, 4 H), 1.92-2.02 (m, 2 H), 2.26-2.48 (m, 2 H), 2.71-2.96 (m, 3 H), 3.20 (s, 2 H), 3.23-3.27 (m, 1 H), 3.35-3.43 (m, 2 H), 4.09 (q, J = 6.8 Hz, 2 H), 4.53 (q, J = 6.5 Hz, 1 H), 7.20-7.42 (m, 5 H). | 1 C | m/z 385 $(M + H)^+$ $(ES^+)$, at 5.69 min, 215 nm |
| 2-29 | Isomer 2: ethyl 2-[(1R,5S,6r)-6-(1-methyl-1H-pyrazol-5-yl)-3-azabicyclo[3.1.0]hex-3-yl]-6-azaspiro[3.4]octane-6-carboxylate | I 40, 41, 42 and 11 | AO | (400 MHz, METHANOL-$d_4$) δ: 1.21-1.28 (m, 2 H), 1.86-2.01 (m, 4 H), 2.01-2.09 (m, 2 H), 2.19-2.26 (m, 1 H), 2.40-2.50 (m, 2 H), 3.01-3.11 (m, 3 H), 3.25-3.28 (m, 2 H), 3.34-3.41 (m, 2 H), 3.78 (s, 3 H), 4.06-4.13 (m, 2 H), 5.91-5.97 (m, 1 H), 7.34-7.43 (m, 1 H). | 1 C | m/z 345 $(M + H)^+$ $(ES^+)$, at 4.10 min, 226 nm |
| 2-30 | Isomer 1: ethyl 2-[(1R,5S,6r)-6-(2-methyl-1,3-thiazol-4-yl)-3-azabicyclo[3.1.0]hex-3-yl]-6-azaspiro[3.4]octane-6-carboxylate | D 6, 7, 8, 9, 10 and 11 | AP | (400 MHz, METHANOL-$d_4$) δ: 1.25-1.32 (m, 3 H), 1.82-2.02 (m, 6 H), 2.03-2.15 (m, 2 H), 2.29-2.43 (m, 1 H), 2.47 (d, J = 8.8 Hz, 2 H), 2.65 (s, 3 H), 2.98-3.19 (m, 3 H), 3.35-3.41 (m, 4 H), 4.13 (q, J = 7.1 Hz, 2 H), 6.89 (s, 1 H). | 1 C | m/z 362 $(M + H)^+$ $(ES^+)$, at 4.60 min, 254 nm |
| 2-30 | Isomer 2: ethyl 2-[(1R,5S,6r)-6-(2-methyl-1,3-thiazol-4-yl)-3-azabicyclo[3.1.0]hex-3-yl]-6-azaspiro[3.4]octane-6-carboxylate | D 6, 7, 8, 9, 10 and 11 | AP | (400 MHz, METHANOL-$d_4$) δ: 1.24-1.31 (m, 3 H), 1.84-1.91 (m, 2 H), 1.90-2.03 (m, 4 H), 2.03-2.14 (m, 2 H), 2.32-2.42 (m, 1 H), 2.48 (d, J = 8.8 Hz, 2 H), 2.65 (s, 3 H), 3.02-3.19 (m, 3 H), 3.25-3.29 (m, 2 H), 3.36-3.34 (m, 2 H), 4.12 (q, J = 7.1 Hz, 2 H), 6.89 (s, 1 H). | 1 C | m/z 362 $(M + H)^+$ $(ES^+)$, at 4.61 min, 254 nm |
| 3-1 | Mixture of isomers: ethyl 6-[(1R,5S,6r)-6-(ethoxycarbonyl)-3-azabicyclo[3.1.0]hex-3-yl]-2-azaspiro[3.4]octane-2-carboxylate | A 1 and 43 | AQ | (400 MHz, DMSO-$d_6$) δ: 1.09-1.23 (m, 6 H), 1.32-1.54 (m, 1 H), 1.60-1.80 (m, 4 H), 1.80-2.03 (m, 5 H), 2.26 (t, J = 8.7 Hz, 2 H), 2.53-2.68 (m, 3 H), 3.00 (t, J = 8.4 Hz, 2 H), 3.34 (s, 1 H), 4.00 (dq, J = 18.5, 7.1 Hz, 4 H). | 1 C | m/z 337 $(M + H)^+$ $(ES^+)$, at 4.62 min, 202 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 3-2 | Mixture of isomers: ethyl 6-[(1R,5S,6r)-6-(diethylcarbamoyl)-3-azabicyclo[3.1.0]hex-3-yl]-2-azaspiro[3.4]octane-2-carboxylate | C Example 3-1 and 4 | AR | (400 MHz, METHANOL-d₄) δ: 1.11 (t, J = 7.1 Hz, 3 H), 1.18-1.35 (m, 6 H), 1.47-1.65 (m, 1 H), 1.75 (dd, J = 12.8, 8.4 Hz, 1 H), 1.81-2.03 (m, 5 H), 2.08 (dd, J = 12.7, 6.6 Hz, 1 H), 2.23 (t, J = 2.7 Hz, 1 H), 2.56 (m, 2 H), 2.68 (quin, J = 7.3 Hz, 1 H), 3.15 (dd, J = 9.5, 2.44-1.7 Hz, 2 H), 3.38 (q, J = 7.1 Hz, 2 H), 3.55 (q, J = 7.1 Hz, 2 H), 3.71-3.99 (m, 4 H), 4.09 (q, J = 7.1 Hz, 2 H). | 4 C | m/z 364 (M + H)⁺ (ES⁺), at 3.66 min, 210 nm |
| 3-3 | Isomer 1: methyl 6-[(1R,5S,6r)-6-(diethylcarbamoyl)-3-azabicyclo[3.1.0]hex-3-yl]-2-azaspiro[3.4]octane-2-carboxylate | J 6, 4 and 46 | AS | (400 MHz, METHANOL-d₄) δ: 1.11 (t, J = 7.1 Hz, 3 H), 1.27 (t, J = 7.1 Hz, 3 H), 1.47-1.63 (m, 1 H), 1.67-2.02 (m, 5H), 2.02-2.13 (m, 1 H), 2.08 (dd, J = 13.0, 6.6 Hz, 1 H), 2.19-2.27 (m, 1 H), 2.42-2.55 (m, 2 H), 2.58-2.75 (m, 1 H), 3.14 (d, J = 9.8 Hz, 2 H), 3.36-3.42 (m, 2 H), 3.48-3.60 (m, 2 H), 3.65 (s, 3 H), 3.75-3.99 (m, 4 H). | 1 C | m/z 350 (M + H)⁺ (ES⁺), at 3.68 min, 210 nm |
| 3-3 | Isomer 2: methyl 6-[(1R,5S,6r)-6-(diethylcarbamoyl)-3-azabicyclo[3.1.0]hex-3-yl]-2-azaspiro[3.4]octane-2-carboxylate | J 6, 4 and 46 | AS | (400 MHz, METHANOL-d₄) δ: 1.11 (t, J = 7.1 Hz, 3 H), 1.27 (t, J = 7.1 Hz, 3 H), 1.45-1.63 (m, 1 H), 1.74 (dd, J = 13.0, 8.6 Hz, 1 H), 1.82-2.02 (m, 5 H), 2.07 (dd, J = 13.0, 6.6 Hz, 1 H), 2.23 (t, J = 2.7 Hz, 1 H), 2.40-2.56 (m, 2 H), 2.68 (quin, J = 7.3 Hz, 1 H), 3.14 (d, J = 9.3 Hz, 2 H), 3.38 (q, J = 6.8 Hz, 2 H), 3.55 (q, J = 6.8 Hz, 2 H), 3.65 (s, 3 H), 3.74-3.97 (m, 4 H). | 1 C | m/z 350 (M + H)⁺ (ES⁺), at 3.70 min, 210 nm |
| 3-4 | Mixture of isomers: ethyl 6-{(1R,5S,6r)-6-[ethyl(propan-2-yl)carbamoyl]-3-azabicyclo[3.1.0]hex-3-yl}-2-azaspiro[3.4]octane-2-carboxylate | C Example 3-1 and 5 | AT | (400 MHz, DMSO-d₆) δ: 1.05-1.16 (m, 5 H), 1.17-1.32 (m, 8 H), 1.46-1.61 (m, 1 H), 1.73 (dt, J = 12.7, 8.3 Hz, 1 H), 1.79-1.90 (m, 2 H), 1.90-1.99 (m, 3 H), 2.00-2.10 (m, 1 H), 2.14-2.29 (m, 1 H), 2.39-2.53 (m, 2 H), 2.55-2.73 (m, 1 H), 3.12 (d, J = 9.5 Hz, 2 H), 3.45 (q, J = 7.0 Hz, 1 H), 3.74-3.92 (m, 4 H), 4.07 (q, J = 7.2 Hz, 2 H), 4.37-4.69 (m, 1 H). | 1 C | m/z 378 (M + H)⁺ (ES⁺), at 4.28 min, 202 nm |
| 4-1 | Ethyl 4-[(1R,5S,6r)-6-diethylcarbamoyl]-3-azabicyclo[3.1.0]hexan-3-yl]piperidine-1-carboxylate | C 73 and 4 | AU then AV | (400 MHz, DMSO-d₆) δ: 1.05-1.13 (m, 3 H), 1.25 (s, 6 H), 1.29-1.42 (m, 2 H), 1.82-1.91 (m, 2 H), 1.91-1.97 (m, 2 H), 2.17-2.21 (m, 1 H), 2.25-2.35 (m, 1 H), 2.50-2.57 (m, 2 H), 2.79-2.96 (m, 2 H), 3.14-3.21 (m, 2 H), 3.32-3.41 (m, 2 H), 3.47-3.57 (m, 2 H), 3.99-4.07 (m, 2 H), 4.07-4.14 (m, 2 H). | 3 E | m/z 338 (M + H)⁺ (ES⁺), at 3.24 min, 202 nm |
| 5-1 | Isomer 1: ethyl 6-[(1R,5S,6r)-6-(ethoxycarbonyl)-3-azabicyclo[3.1.0]hexan-3-yl]-3-azabicyclo[3.1.1]heptane-3-carboxylate | A 1 and 75 | AW then AX | (400 MHz, DMSO-d₆) δ: 1.19-1.26 (m, 3 H), 1.26-1.33 (m, 3 H), 1.35-1.40 (m, 1 H), 1.43-1.49 (m, 2 H), 1.82-1.91 (m, 2 H), 1.91-1.98 (m, 2 H), 2.26-2.33 (m, 2 H), 2.34-2.45 (m, 2 H), 2.57-2.63 (m, 1 H), 3.00-3.07 (m, 1 H), 3.38-3.55 (m, 3 H), 4.04-4.23 (m, 3 H). | 3 E | m/z 323 (M + H)⁺ (ES⁺), at 4.65 min, 220 nm |
| 5-1 | Isomer 2: ethyl 6-[(1R,5S,6r)-6-(ethoxycarbonyl)-3-azabicyclo[3.1.0]hexan-3-yl]-3-azabicyclo[3.1.1]heptane-3-carboxylate | A 1 and 75 | AW then AX | (400 MHz, DMSO-d₆) δ: 1.21-1.31 (m, 5 H), 1.33-1.40 (m, 2 H), 1.96-2.05 (m, 3 H), 2.23-2.33 (m, 4 H), 2.36-2.40 (m, 1 H), 2.46-2.54 (m, 1 H), 3.19-3.25 (m, 2 H), 3.42-3.54 (m, 2 H), 3.65 (s, 3 H), 4.06-4.18 (m, 3 H). | 3 E | m/z 323 (M + H)⁺ (ES⁺), at 4.69 min, 220 nm |
| 5-2 | Isomer 1: ethyl 6-[(1R,5S,6r)-6-(diethylcarbamoyl)-3-azabicyclo[3.1.0]hexan-3-yl]-3-azabicyclo[3.1.1]heptane-3-carboxylate | C Example 5-1 and 4 | CY | (400 MHz, METHANOL-d₄) δ: 1.03-1.16 (m, 3 H), 1.22-1.34 (m, 6 H), 1.34-1.44 (m, 1 H), 1.90-2.02 (m, 2 H), 2.21-2.24 (m, 6 H), 2.48-2.59 (m, 1 H), 3.20-3.27 (m, 2 H), 3.35-3.42 (m, 2 H), 3.43-3.61 (m, 4 H), 3.62-3.75 (m, 2 H), 4.08-4.23 (m, 2 H). | 3 E | m/z 350 (M + H)⁺ (ES⁺), at 3.86 min, 202 nm |
| 6-1 | Isomer 2: ethyl 8-[(1R,5S,6r)-6-(diethylcarbamoyl)-3-azabicyclo[3.1.0]hexan-3-yl]-3-azabicyclo[3.1.1]heptane-3-carboxylate | C 78 and 4 | AY then AZ | (400 MHz, METHANOL-d₄) δ: 1.04-1.14 (m, 3 H), 1.24 (s, 6 H), 1.28-1.33 (m, 1 H), 1.34-1.43 (m, 1 H), 1.73-1.81 (m, 2 H), 1.87-1.95 (m, 2 H), 1.99-2.06 (m, 1 H), 2.13-2.24 (m, 2 H), 2.34-2.41 (m, 2 H), 2.82-2.98 (m, 2 H), 3.07-3.16 (m, 2 H), 3.33-3.40 (m, 2 H), 3.45-3.55 (m, 2 H), 3.78-3.88 (m, 2 H), 4.06-4.15 (m, 2 H). | 3 E | m/z 364 (M + H)⁺ (ES⁺), at 4.19 min, 202 nm |
| 7-1 | Isomer 2: ethyl 3-[(1R,5S,6r)-6-(ethoxycarbonyl)-3-azabicyclo[3.1.0]hex-3-yl]-8-azabicyclo[3.2.1]octane-8-carboxylate | A 1 and 47 | BA | (400 MHz, DMSO-d₆) δ: 1.13-1.21 (m, 6 H), 1.59-1.89 (m, 9 H), 1.89-1.99 (m, 2 H), 2.14-2.21 (m, 2 H), 2.35-2.46 (m, 1 H), 3.15-3.29 (m, 2 H), 3.95-4.07 (m, 6 H). | 1 C | m/z 337 (M + H)⁺ (ES⁺), at 5.28 min, 202 nm |
| 7-2 | Isomer 1: ethyl 3-{(1R,5S,6r)-6-[ethyl(methyl)carbamoyl]-3-azabicyclo[3.1.0]hex-3-yl}-8-azabicyclo[3.2.1]octane-8-carboxylate | E Example 7-1 and 15 | BB | (400 MHz, DMSO-d₆) δ: 0.94 (t, J = 7.0 Hz, 1 H), 1.09 (t, J = 7.2 Hz, 2 H), 1.15 (t, J = 7.0 Hz, 3 H), 1.19-1.44 (m, 2 H), 1.57-1.74 (m, 6 H), 1.74-1.88 (m, 2 H), 1.91 (t, J = 2.9 Hz, 1 H), 2.23-2.33 (m, 2 H), 2.50-2.59 (m, 1 H), 2.75 (s, 2 H), 2.92 (dd, J = 9.0, 4.7 Hz, 2 H), 3.00 (s, 1 H), 3.24 (q, J = 7.0 Hz, 1 H), 3.39 (q, J = 7.0 Hz, 1 H), 3.96-4.05 (m, 2 H), 4.05-4.13 (m, 1 H). | 5 G | m/z 350 (M + H)⁺ (ES⁺), at 3.41 min, 230-400 nm |
| 7-2 | Isomer 2: ethyl 3-{(1R,5S,6r)-6-[ethyl(methyl)carbamoyl]-3-azabicyclo[3.1.0]hex-3-yl}-8-azabicyclo[3.2.1]octane-8-carboxylate | E Example 7-1 and 15 | BB | (400 MHz, DMSO-d₆) δ: 0.95 (t, J = 7.0 Hz, 2 H), 1.03-1.20 (m, 4 H), 1.56-1.89 (m, 10 H), 2.13 (d, J = 8.2 Hz, 2 H), 2.36-2.45 (m, 1 H), 2.77 (s, 2 H), 2.83-2.94 (m, 1 H), 3.01 (s, 1 H), 3.22 (d, J = 9.0 Hz, 2 H), 3.26 (d, J = 7.4 Hz, 1 H), 3.38-3.47 (m, 1 H), 3.90-4.14 (m, 4 H). | 5 G | m/z 350 (M + H)⁺ (ES⁺), at 4.10 min, 230-400 nm |

TABLE 3-continued

| Ex. No. | Name | Synthetic Method and Intermediates Used | Purification Method | $^1$H NMR | LC-MS System and Method | LCMS data |
|---|---|---|---|---|---|---|
| 7-3 | Isomer 1: ethyl 3-[(1R,5S,6r)-6-(diethylcarbamoyl)-3-azabicyclo[3.1.0]hex-3-yl]-8-azabicyclo[3.2.1]octane-8-carboxylate | C Example 7-1 and 4 | BC | (400 MHz, METHANOL-d$_4$) δ: 1.10 (t, J = 7.1 Hz, 3 H), 1.19-1.36 (m, 6 H), 1.55 (q, J = 12.6 Hz, 2 H), 1.67-1.81 (m, 2 H), 1.81-1.90 (m, 2 H), 1.90-2.09 (m, 4 H), 2.21 (t, J = 2.7 Hz, 1 H), 2.51 (d, J = 9.3 Hz, 2 H), 2.66 (tt, J = 11.1, 5.4 Hz, 1 H), 3.12 (d, J = 8.6 Hz, 2 H), 3.35-3.44 (m, 2 H), 3.53 (q, J = 7.1 Hz, 2 H), 4.14 (q, J = 7.1 Hz, 2 H), 4.22-4.32 (m, 2 H). | 1 C | m/z 364 (M + H)$^+$ (ES$^+$), at 3.94 min, 202 nm |
| 7-3 | Isomer 2: ethyl 3-[(1R,5S,6r)-6-(diethylcarbamoyl)-3-azabicyclo[3.1.0]hex-3-yl]-8-azabicyclo[3.2.1]octane-8-carboxylate | C Example 7-1 and 4 | BC | (400 MHz, METHANOL-d$_4$) δ: 1.12 (t, J = 7.1 Hz, 3 H), 1.27 (t, J = 7.2 Hz, 6 H), 1.82-2.11 (m, 11 H), 2.28 (d, J = 8.8 Hz, 2 H), 2.49-2.59 (m, 1 H), 3.35-3.47 (m, 4 H), 3.53 (q, J = 7.1 Hz, 2 H), 4.05-4.35 (m, 4 H). | 1 C | m/z 364 (M + H)$^+$ (ES$^+$), at 4.66 min, 202 nm |
| 7-4 | Isomer 1: ethyl 3-{(1R,5S,6r)-6-[ethyl(propan-2-yl)carbamoyl]-3-azabicyclo[3.1.0]hex-3-yl}-8-azabicyclo[3.2.1]octane-8-carboxylate | C Example 7-1 and 5 | BD | (400 MHz, METHANOL-d$_4$) δ: 1.05-1.18 (m, 3 H), 1.23-1.34 (m, 9 H), 1.45-1.64 (m, 2 H), 1.74 (d, J = 6.3 Hz, 2 H), 1.79-1.88 (m, 2 H), 1.88-2.07 (m, 4 H), 2.11-2.32 (m, 1 H), 2.39-2.56 (m, 2 H), 2.56-2.72 (m, 1 H), 3.10 (d, J = 9.0 Hz, 2 H), 3.21-3.28 (m, 1 H), 3.44 (q, J = 7.0 Hz, 1 H), 4.13 (q, J = 7.0 Hz, 2 H), 4.20-4.30 (m, 2 H), 4.37-4.71 (m, 1 H). | 1 C | m/z 378 (M + H)$^+$ (ES$^+$), at 4.30 min, 210 nm |
| 7-4 | Isomer 2: ethyl 3-{(1R,5S,6r)-6-[ethyl(propan-2-yl)carbamoyl]-3-azabicyclo[3.1.0]hex-3-yl}-8-azabicyclo[3.2.1]octane-8-carboxylate | C Example 7-1 and 5 | BD | (400 MHz, METHANOL-d$_4$) δ: 1.10-1.18 (m, 5 H), 1.23-1.36 (m, 7 H), 1.80-2.10 (m, 11 H), 2.28 (d, J = 8.8 Hz, 2 H), 2.45-2.58 (m, J = 4.8 Hz, 1 H), 3.30-3.40 (m, 2 H), 3.45 (q, J = 7.0 Hz, 2 H), 4.06-4.24 (m, 4 H), 4.28-4.78 (m, 1 H). | 1 C | m/z 378 (M + H)$^+$ (ES$^+$), at 4.99 min, 212 nm |
| 7-5 | Isomer 2: ethyl 3-[(1R,5S,6r)-6-{[acetyl(ethyl)amino]methyl}-3-azabicyclo[3.1.0]hex-3-yl]-8-azabicyclo[3.2.1]octane-8-carboxylate | J 6, 48, 49, 50 and 47 | BE | (400 MHz, METHANOL-d$_4$) δ: 1.13-1.29 (m, 6 H), 1.45 (d, J = 13.6 Hz, 2 H), 1.82-2.00 (m, 9 H), 2.10 (s, 1 H), 2.13 (s, 2 H), 2.19 (dd, J = 13.6, 8.7 Hz, 1 H), 2.32-2.49 (m, 1 H), 3.21-3.31 (m, 4 H), 3.41-3.55 (m, 2 H), 4.06-4.22 (m, 4 H). | 1 E | m/z 364 (M + H)$^+$ (ES$^+$), at 4.17 min, 202 nm |
| 7-6 | Isomer 2: ethyl 3-[(1R,5S,6r)-6-(2-methyl-1,3-thiazol-4-yl)-3-azabicyclo[3.1.0]hex-3-yl]-8-azabicyclo[3.2.1]octane-8-carboxylate | D 6, 7, 8, 9, 10 and 47 | BF | (400 MHz, METHANOL-d$_4$) δ: 1.25 (t, J = 7.0 Hz, 3 H), 1.74-2.01 (m, 8 H), 2.02-2.17 (m, 2 H), 2.24 (t, J = 3.0 Hz, 1 H), 2.28 (d, J = 8.5 Hz, 2 H), 2.42-2.54 (m, 1 H), 2.63 (s, 3 H), 3.40 (d, J = 8.8 Hz, 2 H), 3.99-4.24 (m, 4 H), 6.84 (s, 1 H). | 1 C | m/z 362 (M + H)$^+$ (ES$^+$), at 5.56 min, 202 nm |
| 8-1 | Mixture of isomers: ethyl 3-[(1R,5S,6r)-6-(ethoxycarbonyl)-3-azabicyclo[3.1.0]hex-3-yl]-2-azabicyclo[2.2.2]octane-2-carboxylate | A 1 and 53 | BG | (400 MHz, DMSO-d$_6$) δ: 1.08-1.22 (m, 6 H), 1.29-1.41 (m, 1 H), 1.41-1.52 (m, 1 H), 1.52-1.71 (m, 2 H), 1.71-1.99 (m, 5 H), 2.15-2.35 (m, 3 H), 3.02-3.26 (m, 4 H), 3.37-3.44 (m, 1 H), 3.70-3.89 (m, 1 H), 3.93-4.10 (m, 4 H). | 1 C | m/z 337 (M + H)$^+$ (ES$^+$), at 5.23 min, 202 nm |
| 8-2 | Isomer 1: ethyl (1S,4S)-5-{(1R,5S,6r)-6-[ethyl(methyl)carbamoyl]-3-azabicyclo[3.1.0]hex-3-yl}-2-azabicyclo[2.2.2]octane-2-carboxylate | E 56 and 15 | BH | (400 MHz, DMSO-d$_6$) δ: 0.95 (t, J = 7.0 Hz, 1 H), 0.99-1.18 (m, 5 H), 1.36 (d, J = 12.1 Hz, 2 H), 1.49-1.65 (m, 2 H), 1.70-1.91 (m, 4 H), 1.95-2.04 (m, 1 H), 2.14-2.24 (m, 2 H), 2.24-2.35 (m, 1 H), 2.76 (s, 1.5 H), 2.82-2.89 (m, 1 H), 2.90-2.98 (m, 1 H), 3.02 (s, 1.5 H), 3.09-3.29 (m, 3 H), 3.39-3.51 (m, 2 H), 3.80 (d, J = 13.7 Hz, 1 H), 3.98 (q, J = 7.0 Hz, 2 H). | 5 G | m/z 350 (M + H)$^+$ (ES$^+$), at 3.79 min, 230-400 nm |
| 8-2 | Isomer 2: ethyl (1S,4S)-5-{(1R,5S,6r)-6-[ethyl(methyl)carbamoyl]-3-azabicyclo[3.1.0]hex-3-yl}-2-azabicyclo[2.2.2]octane-2-carboxylate | E 56 and 15 | BH | (400 MHz, DMSO-d$_6$) δ: 0.94 (t, J = 7.0 Hz, 1 H), 1.03-1.18 (m, 5 H), 1.41-1.52 (m, 2 H), 1.52-1.68 (m, 2 H), 1.71-1.87 (m, 4 H), 1.93-2.02 (m, 1 H), 2.13-2.22 (m, 2 H), 2.23-2.29 (m, 1 H), 2.76 (s, 1 H), 2.79-2.89 (m, 2 H), 3.02 (s, 2 H), 3.06-3.16 (m, 1 H), 3.20-3.28 (m, 2 H), 3.37-3.46 (m, 2 H), 3.74-3.86 (m, 1 H), 3.98 (q, J = 7.0 Hz, 2 H). | 5 G | m/z 350 (M + H)$^+$ (ES$^+$), at 3.81 min, 230-400 nm |
| 8-3 | Isomer 1: ethyl (1S,4R)-5-{(1R,5S,6r)-6-[ethyl(methyl)carbamoyl]-3-azabicyclo[3.1.0]hexan-3-yl}-2-azabicyclo[2.2.2]octane-2-carboxylate | E 59 and 15 | BI | (400 MHz, CHLOROFORM-d) δ: 1.04-1.14 (m, 1 H), 1.17-1.32 (m, 5 H), 1.43-1.73 (m, 4 H), 1.74-1.89 (m, 2 H), 1.89-2.01 (m, 2 H), 2.04-2.13 (m, 1 H), 2.21-2.36 (m, 2 H), 2.92 (d, J = 1.56 Hz, 3 H), 3.00-3.09 (m, 1 H), 3.11 (s, 1 H), 3.13-3.28 (m, 2 H), 3.36-3.45 (m, 1 H), 3.46-3.60 (m, 2 H), 3.92-3.97 (m, 1 H), 4.03-4.08 (m, 1 H), 4.09-4.19 (m, 2 H). | 5 G | m/z 350 (M + H)$^+$ (ES$^+$), at 3.87 min, 230-400 nm |
| 8-4 | Isomer 1: ethyl (1S,4S)-5-[(1R,5S,6r)-6-(diethylcarbamoyl)-3-azabicyclo[3.1.0]hexan-3-yl]-2-azabicyclo[2.2.2]octane-2-carboxylate | E 56 and 4 | BJ then BK | (400 MHz, CHLOROFORM-d) δ: 1.08 (t, J = 7.0 Hz, 3 H), 1.17-1.28 (m, 6 H), 1.41-1.70 (m, 4 H), 1.73-1.87 (m, 2 H), 1.87-1.99 (m, 3 H), 2.03 (d, J = 9.8 Hz, 1 H), 2.21-2.33 (m, 3 H), 3.02 (dd, J = 14.8, 9.0 Hz), 1 H), 3.11-3.21 (m, 2 H), 3.35 (q, J = 6.8 Hz, 2 H), 3.39-3.48 (m, 2 H), 3.48-3.57 (m, 1 H), 3.89-4.05 (m, 1 H), 4.11 (q, J = 7.0 Hz, 2 H). | 5 G | m/z 364 (M + H)$^+$ (ES$^+$), at 4.09 min, 230-400 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 8-4 | Isomer 2: ethyl (1S,4S)-5-[(1R,5S,6r)-6-(diethylcarbamoyl)-3-azabicyclo[3.1.0]hexan-3-yl]-2-azabicyclo[2.2.2]octane-2-carboxylate | E 56 and 4 | BJ then BK | (400 MHz, CHLOROFORM-d) δ: 1.08 (t, J = 7.0 Hz, 3 H), 1.17-1.29 (m, 6 H), 1.34-1.48 (m, 2 H), 1.55-1.67 (m, 1 H), 1.67-1.79 (m, 1 H), 1.79-1.90 (m, 2 H), 1.90-2.07 (m, 4 H), 2.22-2.37 (m, 3 H), 2.99 (d, J = 9.0 Hz, 1 H), 3.15 (t, J = 8.2 Hz, 1 H), 3.25-3.32 (m, 1 H), 3.36 (q, J = 6.8 Hz, 3 H), 3.40-3.50 (m, 2 H), 3.85-4.03 (m, 1 H), 4.10 (q, J = 7.0 Hz, 2 H). | 5 G | m/z 364 (M + H)⁺ (ES⁺), at 4.11 min, 230-400 nm |
| 8-5 | Isomer 1: ethyl (1R,4R)-5-[(1R,5S,6r)-6-(diethylcarbamoyl)-3-azabicyclo[3.1.0]hexan-3-yl]-2-azabicyclo[2.2.2]octane-2-carboxylate | E 59 and 4 | BI | (400 MHz, CHLOROFORM-d) δ: 1.06-1.14 (m, 3 H), 1.19-1.31 (m, 7 H), 1.43-1.62 (m, 3 H), 1.78-1.89 (m, 2 H), 1.90-2.01 (m, 2 H), 2.02-2.09 (m, 1 H), 2.23-2.35 (m, 3 H), 3.00-3.09 (m, 1 H), 3.14-3.26 (m, 2 H), 3.33-3.41 (m, 2 H), 3.41-3.50 (m, 2 H), 3.50-3.59 (m, 1 H), 3.92-3.96 (m, 1 H), 4.02-4.08 (m, 1 H), 4.08-4.19 (m, 2 H). | 5 G | m/z 364 (M + H)⁺ (ES⁺), at 4.19 min, 230-400 nm |
| 8-5 | Isomer 2: ethyl (1R,4R)-5-[(1R,5S,6r)-6-(diethylcarbamoyl)-3-azabicyclo[3.1.0]hexan-3-yl]-2-azabicyclo[2.2.2]octane-2-carboxylate | E 59 and 4 | BI | (400 MHz, CHLOROFORM-d) δ: 1.11 (t, J = 7.22 Hz, 3 H), 1.25 (q, J = 7.16 Hz, 6 H), 1.36-1.47 (m, 2 H), 1.69-1.80 (m, 1 H), 1.82-1.93 (m, 2 H), 1.94-2.09 (m, 4 H), 2.27-2.32 (m, 2 H), 2.33-2.40 (m, 1 H), 2.98-3.04 (m, 1 H), 3.15-3.21 (m, 1 H), 3.27-3.34 (m, 1 H), 3.35-3.42 (m, 3 H), 3.42-3.52 (m, 2 H), 3.89-3.94 (m, 1 H), 4.00-4.06 (m, 1 H), 4.13 (q, J = 7.16 Hz, 2 H). | 5 G | m/z 364 (M + H)⁺ (ES⁺), at 4.18 min, 230-400 nm |
| 8-6 | Isomer 1: methyl 5-[(1R,5S,6r)-6-(diethylcarbamoyl)-3-azabicyclo[3.1.0]hex-3-yl]-2-azabicyclo[2.2.2]octane-2-carboxylate | C 61 and 4 | BL then BM | (400 MHz, METHANOL-$d_4$) δ: 1.11 (t, J = 7.1 Hz, 3 H), 1.22-1.37 (m, 6 H), 1.48-1.78 (m, 4 H), 1.90-2.03 (m, 4 H), 2.23 (t, J = 2.4 Hz, 1 H), 2.37-2.51 (m, 2 H), 3.11-3.25 (m, 1 H), 3.25-2.30 (m, 1 H), 3.36-3.43 (m, 3 H), 3.49-3.63 (m, 2 H), 3.65-3.72 (m, 3 H), 3.91-4.00 (m, 1 H). | 4 C | m/z 350 (M + H)⁺ (ES⁺), at 3.72 min, 202 nm |
| 8-6 | Isomer 2: methyl 5-[(1R,5S,6r)-6-(diethylcarbamoyl)-3-azabicyclo[3.1.0]hex-3-yl]-2-azabicyclo[2.2.2]octane-2-carboxylate | C 61 and 4 | BL then BM | (400 MHz, METHANOL-$d_4$) δ: 1.11 (t, J = 7.1 Hz, 3 H), 1.23-1.39 (m, 6 H), 1.57-1.77 (m, 4 H), 1.89-2.02 (m, 4 H), 2.19-2.55 (m, 1 H), 2.31-2.48 (m, 3 H), 3.09-3.19 (m, 1 H), 3.21-3.30 (m, 1 H), 3.38 (q, J = 7.3 Hz, 2 H), 3.51-3.62 (m, 2 H), 3.66-3.71 (m, 3 H), 3.92-4.01 (m, 1 H). | 4 C | m/z 350 (M + H)⁺ (ES⁺), at 3.69 min, 210 nm |
| 8-7 | Mixture of isomers: ethyl 5-{(1R,5S,6r)-6-[ethyl(propan-2-yl)carbamoyl]-3-azabicyclo[3.1.0]hex-3-yl}-2-azabicyclo[2.2.2]octane-2-carboxylate | C Example 8-1 and 5 | BN | (400 MHz, METHANOL-$d_4$) δ: 1.10-1.18 (m, 5 H), 1.24-1.32 (m, 7 H), 1.43-1.54 (m, 1 H), 1.57-1.85 (m, 3 H), 1.88-2.08 (m, 5 H), 2.18-2.28 (m, 1 H), 2.31-2.244 (m, 3 H), 3.06-3.20 (m, 1 H), 3.22-3.26 (m, 1 H), 3.34-3.39 (m, 2 H), 3.41-3.52 (m, 1 H), 3.92-4.00 (m, 1 H), 4.08-4.18 (m, 2 H), 4.40-4.71 (m, 1 H). | 1 C | m/z 378 (M + H)⁺ (ES⁺), at 4.71 min, 210 nm |
| 8-8 | Mixture of isomers: ethyl (1S,4S)-5-{(1R,5S,6r)-6-[cyclopropyl(ethyl)carbamoyl]-3-azabicyclo[3.1.0]hex-3-yl}-2-azabicyclo[2.2.2]octane-2-carboxylate | E 56 and 19 | BO | (400 MHz, CHLOROFORM-d) δ: 0.69-0.81 (m, 2 H), 0.81-0.94 (m, 2 H), 1.08 (t, J = 7.0 Hz, 3 H), 1.18-1.25 (m, 3 H), 1.31-2.19 (m, 10 H), 2.19-2.29 (m, 3 H), 2.48-2.56 (m, 1 H), 2.67-2.78 (m, 1 H), 2.93-3.06 (m, 1 H), 3.10-3.21 (m, 1 H), 3.23-3.38 (m, 2 H), 3.39-3.54 (m, 1 H), 3.83-4.02 (m, 1 H), 4.08 (q, J = 7.0 Hz, 2 H). | 5 G | m/z 376 (M + H)⁺ (ES⁺), at 4.40 min, 230-400 nm |
| 8-9 | Isomer 1: ethyl 5-{(1R,5S,6r)-6-[methoxy(methyl)carbamoyl]-3-azabicyclo[3.1.0]hexan-3-yl}-2-azabicyclo[2.2.2]octane-2-carboxylate | C Example 8-1 and 7 | BP | (400 MHz, METHANOL-$d_4$) δ: 1.26 (q, J = 7.0 Hz, 3 H), 1.40-1.59 (m, 2 H), 1.73 (t, J = 12.0 Hz, 2 H), 1.87-1.99 (m, 4 H), 1.99-2.13 (m, 1 H), 2.27-2.46 (m, 3 H), 2.49-2.63 (m, 1 H), 3.11 (dd, J = 9.3, 3.4 Hz, 1 H), 3.16-3.25 (m, 3 H), 3.28 (dd, J = 9.3, 3.4 Hz, 2 H), 3.35-3.46 (m, 1 H), 3.78 (s, 3 H), 3.91-3.70 (m, 1 H), 4.12 (q, J = 6.8 Hz, 2 H). | 1 C | m/z 352 (M + H)⁺ (ES⁺), at 4.12 min, 210 nm |
| 8-10 | Isomer 1: ethyl 5-{(1R,5S,6r)-6-[ethyl(methoxy)carbamoyl]-3-azabicyclo[3.1.0]hex-3-yl}-2-azabicyclo[2.2.2]octane-2-carboxylate | C Example 8-1 and 30 | BQ | (400 MHz, METHANOL-$d_4$) δ: 1.18 (t, J = 6.8 Hz, 3 H), 1.26 (q, J = 7.3 Hz, 3 H), 1.41-1.59 (m, 2 H), 1.63-1.85 (m, 2 H), 1.88-2.10 (m, 5 H), 2.29-2.45 (m, 3 H), 2.46-2.62 (m, 1 H), 3.11 (dd, J = 9.0, 3.2 Hz, 1 H), 3.29 (dd, J = 9.3, 2.9 Hz, 1 H), 3.35-3.48 (m, 2 H), 3.62-3.73 (m, 2 H), 3.78 (s, 3 H), 3.87-3.99 (m, 1 H), 4.12 (q, J = 6.8 Hz, 2 H). | 1 C | m/z 366 (M + H)⁺ (ES⁺), at 4.44 min, 202 nm |
| 8-10 | Isomer 2: ethyl 5-{(1R,5S,6r)-6-[ethyl(methoxy)carbamoyl]-3-azabicyclo[3.1.0]hex-3-yl}-2-azabicyclo[2.2.2]octane-2-carboxylate | C Example 8-1 and 30 | BQ | (400 MHz, METHANOL-$d_4$) δ: 1.18 (t, J = 6.4 Hz, 3 H), 1.28 (q, J = 7.3 Hz, 3 H), 1.52-1.68 (m, 3 H), 1.72 (d, J = 3.4 Hz, 1 H), 1.75-1.84 (m, 1 H), 1.89-2.00 (m, 3 H), 2.29-2.43 (m, 3 H), 2.47-2.63 (m, 1 H), 3.14 (dd, J = 9.3, 5.4 Hz, 1 H), 3.17-3.24 (m, 1 H), 3.27 (dd, J = 9.3, 3.9 Hz, 2 H), 3.53-3.63 (m, 1 H), 3.67 (q, J = 7.8 Hz, 2 H), 3.77 (s, 3 H), 3.91-4.02 (m, 1 H), 4.13 (q, J = 7.2 Hz, 2 H). | 1 C | m/z 366 (M + H)⁺ (ES⁺), at 4.53 min, 202 nm |
| 9-1 | Isomer 1: ethyl 3-{(1R,5S,6r)-6-[ethyl(methyl)carbamoyl]-3-azabicyclo[3.1.0]hex-3-yl}-9-azabicyclo[3.3.1]nonane-9-carboxylate | C 64 and 15 | BR | (400 MHz, METHANOL-$d_4$) δ: 1.10 (t, J = 7.2 Hz, 1 H), 1.19-1.38 (m, 7 H), 1.43-1.68 (m, 5 H), 1.91-1.97 (m, 2 H), 1.97-2.13 (m, 2 H), 2.27 (t, J = 7.6 Hz, 3 H), 2.52 (d, J = 8.5 Hz, 2 H), 2.92 (s, 2 H), 3.13-3.26 (m, 3 H), 3.41 (q, J = 7.2 Hz, 1 H), 3.58 (q, J = 7.0 Hz, 1 H), 4.13 (q, J = 7.0 Hz, 2 H), 4.40-4.51 (m, 2 H). | 1 E | m/z 364 (M + H)⁺ (ES⁺), at 3.74 min, 202 nm |
| 9-1 | Isomer 2: ethyl 3-{(1R,5S,6r)-6-[ethyl(methyl)carbamoyl]-3-azabicyclo[3.1.0]hex-3-yl}-9-azabicyclo[3.3.1]nonane-9-carboxylate | C 64 and 15 | BR | (400 MHz, METHANOL-$d_4$) δ: 1.09 (t, J = 7.2 Hz, 1 H), 1.16-1.34 (m, 5 H), 1.53-1.80 (m, 7 H), 1.88-2.04 (m, 5 H), 2.20-2.31 (m, 1 H), 2.43-2.64 (m, 2 H), 2.92 (s, 2 H), 2.98-3.12 (m, 1 H), 3.12-3.21 (m, 3 H), 3.40 (q, J = 7.2 Hz, 1 H), 3.57 (q, J = 7.0 Hz, 1 H), 4.14 (q, J = 7.0 Hz, 2 H), 4.29-4.40 (m, 2 H). | 1 E | m/z 364 (M + H)⁺ (ES⁺), at 3.75 min, 202 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 9-2 | Isomer 1: ethyl 3-[(1R,5S,6r)-6-(diethylcarbamoyl)-3-azabicyclo[3.1.0]hex-3-yl]-9-azabicyclo[3.3.1]nonane-9-carboxylate | C 64 and 4 | BS then BT | (400 MHz, METHANOL-$d_4$) δ: 1.10 (t, J = 7.2 Hz, 3 H), 1.19-1.37 (m, 6 H), 1.55-1.85 (m, 7 H), 1.87-2.02 (m, 4 H), 2.18-2.27 (m, 1 H), 2.53 (d, J = 9.5 Hz, 2 H), 2.62-2.66 (m, 1 H), 2.99-3.13 (m, 1 H), 3.16 (dd, J = 9.5 Hz, 4.8 Hz, 2 H), 3.35-3.44 (m, 2 H), 3.46-3.60 (m, 2 H), 4.14 (q, J = 7.0 Hz, 2 H), 4.28-4.42 (m, 2 H). | 1 C | m/z 378 (M + H)⁺ (ES⁺), at 4.15 min, 202 nm |
| 9-2 | Isomer 2: ethyl 3-[(1R,5S,6r)-6-(diethylcarbamoyl)-3-azabicyclo[3.1.0]hex-3-yl]-9-azabicyclo[3.3.1]nonane-9-carboxylate | C 64 and 4 | BS then BT | (400 MHz, METHANOL-$d_4$) δ: 1.11 (t, J = 7.2 Hz, 3 H), 1.22-1.37 (m, 9 H), 1.45-1.66 (m, 4 H), 1.92-1.96 (m, 2 H), 1.98-2.12 (m, 2 H), 2.23 (t, J = 2.9 Hz, 1 H), 2.24-2.36 (m, 2 H), 2.53 (d, J = 9.2 Hz, 2 H), 3.18 (d, J = 9.5 Hz, 2 H), 3.36-3.45 (m, 2 H), 3.55 (q, J = 7.3 Hz, 2 H), 4.12 (q, J = 7.0 Hz, 2 H), 4.39-4.58 (m, 2 H). | 1 C | m/z 378 (M + H)⁺ (ES⁺), at 4.07 min, 202 nm |
| 9-3 | Isomer 1: methyl 3-[(1R,5S,6r)-6-(diethylcarbamoyl)-3-azabicyclo[3.1.0]hex-3-yl]-9-azabicyclo[3.3.1]nonane-9-carboxylate | C 66 and 4 | BU | (400 MHz, METHANOL-$d_4$) δ: 1.10 (t, J = 7.0 Hz, 3 H), 1.25 (t, J = 7.2 Hz, 3 H), 1.57-1.85 (m, 6 H), 1.88-2.03 (m, 4 H), 2.06 (s, 2 H), 2.21 (t, J = 2.6 Hz, 1 H), 2.53 (d, J = 9.2 Hz, 2 H), 3.06 (tt, J = 11.4, 5.5 Hz, 1 H), 3.12-3.20 (m, 2 H), 3.36-3.42 (m, 2 H), 3.53 (q, J = 7.0 Hz, 2 H), 3.70 (s, 3 H), 4.27-4.39 (m, 2 H). | 1 E | m/z 364 (M + H)⁺ (ES⁺), at 3.72 min, 202 nm |
| 9-3 | Isomer 2: methyl 3-[(1R,5S,6r)-6-(diethylcarbamoyl)-3-azabicyclo[3.1.0]hex-3-yl]-9-azabicyclo[3.3.1]nonane-9-carboxylate | C 66 and 4 | BU | (400 MHz, METHANOL-$d_4$) δ: 1.11 (t, J = 7.0 Hz, 3 H), 1.22-1.38 (m, 5 H), 1.45-1.75 (m, 5 H), 1.90-2.01 (m, 3 H), 2.01-2.13 (m, 2 H), 2.18-2.37 (m, 2 H), 2.53 (d, J = 9.5 Hz, 2 H), 3.13-3.24 (m, 2 H), 3.36-3.43 (m, 3 H), 3.49-3.60 (m, 2 H), 3.64-3.76 (m, 2 H), 4.30-4.51 (m, 2 H). | 1 E | m/z 364 (M + H)⁺ (ES⁺), at 3.74 min, 202 nm |
| 10-1 | Isomer 1: ethyl 7-{(1R,5S,6r)-6-[ethyl(methyl)carbamoyl]-3-azabicyclo[3.1.0]hex-3-yl}-3-oxa-9-azabicyclo[3.3.1]nonane-9-carboxylate | C 69 and 15 | BV then BW | (400 MHz, METHANOL-$d_4$) δ: 1.10 (t, J = 7.3 Hz, 1 H), 1.23-1.33 (m, 5 H), 1.57 (t, J = 11.9 Hz, 2 H), 1.91-1.95 (m, 2 H), 2.01 (tt, J = 11.8, 5.3 Hz, 1 H), 2.28 (d, J = 8.5 Hz, 1 H), 2.31-2.41 (m, 2 H), 2.51 (d, J = 9.2 Hz, 2 H), 2.92 (s, 2 H), 3.14-3.20 (m, 3 H), 3.37-3.44 (m, 1 H), 3.48-3.66 (m, 5 H), 4.12-4.28 (m, 4 H). | 1 E | m/z 366 (M + H)⁺ (ES⁺), at 3.20 min, 202 nm |
| 10-1 | Isomer 2: ethyl 7-{(1R,5S,6r)-6-[ethyl(methyl)carbamoyl]-3-azabicyclo[3.1.0]hex-3-yl}-3-oxa-9-azabicyclo[3.3.1]nonane-9-carboxylate | C 69 and 15 | BV then BW | (400 MHz, METHANOL-$d_4$) δ: 1.09 (t, J = 7.0 Hz, 1 H), 1.22-1.32 (m, 4 H), 1.62 (t, J = 11.9 Hz, 2 H), 1.89-1.99 (m, 2 H), 2.06 (dd, J = 13.1, 5.2 Hz, 2 H), 2.21-2.28 (m, 1 H), 2.54 (d, J = 8.5 Hz, 2 H), 2.92 (s, 1 H), 3.13-3.19 (m, 3 H), 3.35-3.44 (m, 4 H), 3.57 (q, J = 7.3 Hz, 1 H), 3.68 (d, J = 11.0 Hz, 2 H), 3.79-3.92 (m, 2 H), 4.06-4.13 (m, 2 H), 4.17 (q, J = 7.1 Hz, 2 H). | 1 E | m/z 366 (M + H)⁺ (ES⁺), at 3.24 min, 202 nm |
| 10-2 | Isomer 1: ethyl 7-[(1R,5S,6r)-6-(diethylcarbamoyl)-3-azabicyclo[3.1.0]hex-3-yl]-3-oxa-9-azabicyclo[3.3.1]nonane-9-carboxylate | C 69 and 4 | BX then BY | (400 MHz, METHANOL-$d_4$) δ: 0.80-1.01 (m, 2 H), 1.11 (t, J = 7.1 Hz, 2 H), 1.21-1.44 (m, 9 H), 1.49-1.69 (m, 2 H), 1.92-1.95 (m, 2 H), 1.97-2.10 (m, 1 H), 2.26 (t, J = 2.7 Hz, 1 H), 2.28-2.36 (m, 2 H), 2.52 (d, J = 9.3 Hz, 1 H), 3.18 (d, J = 9.3 Hz, 1 H), 3.35-3.42 (m, 2 H), 3.47-3.68 (m, 4 H), 4.08-4.33 (m, 4 H). | 1 C | m/z 380 (M + H)⁺ (ES⁺), at 3.46 min, 210 nm |
| 10-2 | Isomer 2: ethyl 7-[(1R,5S,6r)-6-(diethylcarbamoyl)-3-azabicyclo[3.1.0]hex-3-yl]-3-oxa-9-azabicyclo[3.3.1]nonane-9-carboxylate | C 69 and 4 | BX then BY | (400 MHz, METHANOL-$d_4$) δ: 1.10 (t, J = 6.8 Hz, 3 H), 1.20-1.38 (m, 6 H), 1.53-1.71 (m, 2 H), 1.91-1.98 (m, 2 H), 2.07 (dd, J = 13.2, 5.4 Hz, 2 H), 2.18-2.26 (m, 1 H), 2.55 (d, J = 9.3 Hz, 2 H), 3.17 (dd, J = 9.3, 5.4 Hz, 2 H), 3.35-3.46 (m, 3 H), 3.54 (q, J = 7.3 Hz, 2 H), 3.68 (d, J = 11.2 Hz, 2 H), 3.79-3.92 (m, 2 H), 4.05-4.14 (m, 2 H), 4.14-4.26 (m, 2 H). | 1 C | m/z 380 (M + H)⁺ (ES⁺), at 3.49 min, 210 nm |
| 10-3 | Isomer 1: methyl 7-[(1R,5S,6r)-6-(diethylcarbamoyl)-3-azabicyclo[3.1.0]hex-3-yl]-3-oxa-9-azabicyclo[3.3.1]nonane-9-carboxylate | C 71 and 4 | BZ then CA | (400 MHz, METHANOL-$d_4$) δ: 1.09 (s, 3 H), 1.20-1.28 (m, 3 H), 1.50-1.60 (m, 2 H), 1.88-1.94 (m, 2 H), 1.95-2.05 (m, 1 H), 2.21-2.26 (m, 1 H), 2.27-2.39 (m, 2 H), 2.45-2.54 (m, 2 H), 3.11-3.20 (m, 2 H), 3.33-3.40 (m, 2 H), 3.46-3.64 (m, 6 H), 3.70 (s, 3 H), 4.16-4.23 (m, 2 H). | 1 E | m/z 366 (M + H)⁺ (ES⁺), at 3.06 min, 202 nm |
| 10-3 | Isomer 2: methyl 7-[(1R,5S,6r)-6-(diethylcarbamoyl)-3-azabicyclo[3.1.0]hex-3-yl]-3-oxa-9-azabicyclo[3.3.1]nonane-9-carboxylate | C 71 and 4 | BZ then CA | (400 MHz, METHANOL-$d_4$) δ: 1.10 (t, J = 7.3 Hz, 3 H), 1.26 (t, J = 7.0 Hz, 3 H), 1.52-1.72 (m, 2 H), 1.90-1.95 (m, 2 H), 2.06 (dd, J = 13.1, 4.6 Hz, 2 H), 2.16-2.28 (m, 1 H), 2.54 (d, J = 9.2 Hz, 2 H), 3.16 (dd, J = 9.5, 6.4 Hz, 2 H), 3.35-3.46 (m, 3 H), 3.49-3.62 (m, 2 H), 3.62-3.71 (m, 2 H), 3.73 (s, 3 H), 3.85 (dd, J = 16.5, 11.6 Hz, 2 H), 4.03-4.10 (m, 2 H). | 1 E | m/z 366 (M + H)⁺ (ES⁺), at 3.07 min, 202 nm |
| 10-4 | Isomer 1: ethyl 7-{(1R,5S,6r)-6-[methyl(propan-2-yl)carbamoyl]-3-azabicyclo[3.1.0]hexan-3-yl}-3-oxa-9-azabicyclo[3.3.1]nonane-9-carboxylate | C 69 and 18 | CB then CC | (400 MHz, METHANOL-$d_4$) δ: 1.10 (d, J = 6.85 Hz, 3 H), 1.23-1.31 (m, 6 H), 1.55-1.67 (m, 2 H), 1.92-2.00 (m, 2 H), 2.19-2.25 (m, 1 H), 2.28-2.39 (m, 2 H), 2.51-2.63 (m, 2 H), 2.77 (s, 1.5 H), 3.00 (s, 1.5 H), 3.17-3.26 (m, 2 H), 3.48-3.56 (m, 2 H), 3.57-3.71 (m, 2 H), 4.10-4.25 (m, 4 H), 4.46-4.54 (m, 1 H), 4.67-4.77 (m, 1 H). | 3 E | m/z 380 (M + H)⁺ (ES⁺), at 2.95 min, 202 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 10-4 | Isomer 2: ethyl 7-{(1R,5S,6r)-6-[methyl(propan-2-yl)carbamoyl]-3-azabicyclo[3.1.0]hexan-3-yl}-3-oxa-9-azabicyclo[3.3.1]nonane-9-carboxylate | C 69 and 18 | CB then CC | (400 MHz, METHANOL-$d_4$) δ: 1.09 (d, J = 6.85 Hz, 3 H), 1.22-1.31 (m, 6 H), 1.55-1.68 (m, 2 H), 1.92-1.98 (m, 2 H), 2.02-2.11 (m, 2 H), 2.17-2.30 (m, 1 H), 2.53-2.65 (m, 2 H), 2.76 (s, 1.5 H), 2.99 (s, 1.5 H), 3.14-3.23 (m, 2 H), 3.62-3.71 (m, 2 H), 3.78-3.90 (m, 2 H), 4.04-4.12 (m, 2 H), 4.12-4.19 (m, 2 H), 4.43-4.51 (m, 1 H), 4.68-4.76 (m, 1 H). | 3 E | m/z 380 $(M + H)^+$ $(ES^+)$, at 2.99 min, 202 nm |
| 10-5 | Isomer 1: methyl 7-((1R,5S,6r)-6-(isopropyl(methyl)carbamoyl)-3-azabicyclo[3.1.0]hexan-3-yl)-3-oxa-9-azabicyclo[3.3.1]nonane-9-carboxylate | C 71 and 18 | CD then CE | (400 MHz, METHANOL-$d_4$) δ: 1.10 (d, J = 7.02 Hz, 3 H), 1.25 (d, J = 6.71 Hz, 3 H), 1.50-1.61 (m, 2 H), 1.89-1.95 (m, 2 H), 1.95-2.05 (m, 1 H), 2.26-2.38 (m, 2 H), 2.46-2.54 (m, 2 H), 2.76 (s, 1.5 H), 3.00 (s, 1.5 H), 3.12-3.19 (m, 2 H), 3.46-3.66 (m, 4 H), 3.70 (s, 3 H), 4.15-4.23 (m, 2 H), 4.45-4.53 (m, 1 H), 4.66-4.76 (m, 1 H). | 3 E | m/z 366 $(M + H)^+$ $(ES^+)$, at 2.70 min, 202 nm |
| 10-5 | Isomer 2: methyl 7-((1R,5S,6r)-6-(isopropyl(methyl)carbamoyl)-3-azabicyclo[3.1.0]hexan-3-yl)-3-oxa-9-azabicyclo[3.3.1]nonane-9-carboxylate | C 71 and 18 | CD then CE | (400 MHz, METHANOL-$d_4$) δ: 1.09 (d, J = 6.71 Hz, 3 H), 1.20-1.27 (m, 3 H), 1.53-1.67 (m, 2 H), 1.90-1.96 (m, 2 H), 2.00 (m, 2 H), 2.17-2.29 (m, 1 H), 2.46-2.55 (m, 2 H), 2.76 (s, 1.5 H), 2.99 (s, 1.5 H), 3.10-3.19 (m, 2 H), 3.61-3.69 (m, 2 H), 3.71 (d, J = 0.92 Hz, 3 H), 3.77-3.89 (m, 2 H), 4.03-4.09 (m, 2 H), 4.43-4.52 (m, 1 H), 4.66-4.76 (m, 1 H). | 3 E | m/z 366 $(M + H)^+$ $(ES^+)$, at 2.71 min, 202 nm |
| 10-6 | Isomer 1: ethyl 7-{(1R,5S,6r)-6-[ethyl(propan-2-yl)carbamoyl]-3-azabicyclo[3.1.0]hex-3-yl}-3-oxa-9-azabicyclo[3.3.1]nonane-9-carboxylate | C 69 and 5 | CF | (400 MHz, METHANOL-$d_4$) δ: 0.85-0.98 (m, 1 H), 1.06-1.18 (m, 4 H), 1.23-1.33 (m, 8 H), 1.49-1.63 (m, 2 H), 1.83-2.09 (m, 3 H), 2.18-2.24 (m, 1 H), 2.25-2.40 (m, 2 H), 2.44-2.56 (m, 2 H), 3.10-3.24 (m, 2 H), 3.35-3.29 (m, 1 H), 3.40-3.65 (m, 5 H), 4.09-4.25 (m, 3 H), 4.39-4.70 (m, 1 H). | 3 E | m/z 394 $(M + H)^+$ $(ES^+)$, at 3.38 min, 202 nm |
| 10-6 | Isomer 2: ethyl 7-{(1R,5S,6r)-6-[ethyl(propan-2-yl)carbamoyl]-3-azabicyclo[3.1.0]hex-3-yl}-3-oxa-9-azabicyclo[3.3.1]nonane-9-carboxylate | C 69 and 5 | CF | (400 MHz, METHANOL-$d_4$) δ: 1.05-1.19 (m, 4 H), 1.19-1.33 (m, 6 H), 1.63 (t, J = 12.2 Hz, 2 H), 1.86-1.98 (m, 2 H), 2.07 (dd, J = 13.1 5.2 Hz, 2 H), 2.15-2.32 (m, 1 H), 2.45-2.61 (m, 2 H), 3.11-3.22 (m, 2 H), 3.26-3.31 (m, 1 H), 3.37 (s, 2 H), 3.41-3.53 (m, 2 H), 3.68 (d, J = 11.6 Hz, 2 H), 3.77-3.95 (m, 2 H), 4.03-4.13 (m, 2 H), 4.17 (q, J = 7.1 Hz, 2 H), 4.39-4.70 (m, 1 H). | 3 E | m/z 394 $(M + H)^+$ $(ES^+)$, at 3.44 min, 202 nm |
| 10-7 | Isomer 1: methyl 7-{(1R,5S,6r)-6-[ethyl(propan-2-yl)carbamoyl]-3-azabicyclo[3.1.0]hexan-3-yl}-3-oxa-9-azabicyclo[3.3.1]nonane-9-carboxylate | C 71 and 5 | CG then CH | (400 MHz, METHANOL-$d_4$) δ: 1.07-1.19 (m, 6 H), 1.22-1.37 (m, 3 H), 1.50-1.65 (m, 2 H), 1.90-1.96 (m, 2 H), 1.95-2.07 (m, 1 H), 2.27-2.40 (m, 2 H), 2.45-2.57 (m, 2 H), 3.11-3.21 (m, 2 H), 3.41-3.66 (m, 6 H), 3.71 (s, 3 H), 4.16-4.26 (m, 2 H), 4.42-4.51 (m, 1 H), 4.59-4.69 (m, 1 H). | 3 E | m/z 380 $(M + H)^+$ $(ES^+)$, at 3.03 min, 202 nm |
| 10-7 | Isomer 2: methyl 7-{(1R,5S,6r)-6-[ethyl(propan-2-yl)carbamoyl]-3-azabicyclo[3.1.0]hexan-3-yl}-3-oxa-9-azabicyclo[3.3.1]nonane-9-carboxylate | C 71 and 5 | CG then CH | (400 MHz, METHANOL-$d_4$) δ: 1.06-1.18 (m, 6 H), 1.23-1.31 (m, 3 H), 1.53-1.67 (m, 2 H), 1.91-1.97 (m, 2 H), 2.00-2.10 (m, 2 H), 2.16-2.28 (m, 1 H), 2.47-2.58 (m, 2 H), 3.11-3.19 (m, 2 H), 3.34-3.50 (m, 2 H), 3.61-3.70 (m, 2 H), 3.71 (s, 3 H), 3.78-3.88 (m, 2 H), 4.03-4.11 (m, 2 H), 4.40-4.49 (m, 1 H) 4.57-4.68 (m, 1 H). | 3 E | m/z 380 $(M + H)^+$ $(ES^+)$, at 3.04 min, 202 nm |
| 10-8 | Isomer 1: ethyl 7-{(1R,5S,6r)-6-[cyclopropyl(methyl)carbamoyl]-3-azabicyclo[3.1.0]hexan-3-yl}-3-oxa-9-azabicyclo[3.3.1]nonane-9-carboxylate | C 69 and 79 | CI then CJ | (400 MHz, METHANOL-$d_4$) δ: 0.78-0.84 (m, 2 H), 0.94-1.00 (m, 2 H), 1.23-1.32 (m, 3 H), 1.51-1.62 (m, 2 H), 1.89-1.94 (m, 2 H), 2.26-2.39 (m, 2 H), 2.48-2.57 (m, 2 H), 2.65-2.69 (m, 1 H), 2.84-2.93 (m, 3 H), 3.10-3.21 (m, 2 H), 3.47-3.71 (m, 6 H), 4.10-4.24 (m, 4 H). | 3 E | m/z 378 $(M + H)^+$ $(ES^+)$, at 2.79 min, 202 nm |
| 10-8 | Isomer 2: ethyl 7-{(1R,5S,6r)-6-[cyclopropyl(methyl)carbamoyl]-3-azabicyclo[3.1.0]hexan-3-yl}-3-oxa-9-azabicyclo[3.3.1]nonane-9-carboxylate | C 69 and 79 | CI then CJ | (400 MHz, METHANOL-$d_4$) δ: 0.76-0.85 (m, 2 H), 0.91-1.03 (m, 2 H), 1.22-1.33 (m, 3 H), 1.54-1.69 (m, 2 H), 1.88-1.97 (m, 2 H), 1.99-2.12 (m, 2 H), 2.48-2.59 (m, 2 H), 2.61-2.67 (m, 1 H), 2.89 (s, 3 H), 3.10-3.20 (m, 2 H), 3.33-3.45 (m, 2 H), 3.61-3.73 (m, 2 H), 3.77-3.89 (m, 2 H), 4.02-4.11 (m, 2 H), 4.11-4.21 (m, 2 H). | 3 E | m/z 378 $(M + H)^+$ $(ES^+)$, at 2.88 min, 202 nm |
| 10-9 | Isomer 1: ethyl 7-{(1R,5S,6r)-6-[cyclopropyl(ethyl)carbamoyl]-3-azabicyclo[3.1.0]hex-3-yl}-3-oxa-9-azabicyclo[3.3.1]nonane-9-carboxylate | C 69 and 19 | CK | (400 MHz, METHANOL-$d_4$) δ: 0.79-0.85 (m, 2 H), 0.97-1.06 (m, 2 H), 1.06-1.17 (m, 3 H), 1.28 (t, J = 7.0 Hz, 3 H), 1.48-1.68 (m, 2 H), 1.91-1.96 (m, 2 H), 2.01 (tt, J = 11.6, 5.8 Hz, 1 H), 2.24-2.43 (m, 2 H), 2.53 (d, J = 9.2 Hz, 2 H), 2.66-2.71 (m, 1 H), 2.83-3.03 (m, 1 H), 3.18 (d, J = 9.2 Hz, 2 H), 3.43 (q, J = 6.9 Hz, 2 H), 3.48-3.69 (m, 4 H) 4.10-4.27 (m, 4 H). | 3 E | m/z 392 $(M + H)^+$ $(ES^+)$, at 3.09 min, 202 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 10-9 | Isomer 2: ethyl 7-{(1R,5S,6r)-6-[cyclopropyl(ethyl)carbamoyl]-3-azabicyclo[3.1.0]hex-3-yl}-3-oxa-9-azabicyclo[3.3.1]nonane-9-carboxylate | C 69 and 19 | CK | (400 MHz, METHANOL-$d_4$) δ: 0.78-0.85 (m, 2 H), 0.97-1.05 (m, 2 H), 1.12 (t, J = 7.0 Hz, 3 H), 1.28 (t, J = 7.0 Hz, 3 H), 1.55-1.71 (m, H), 1.92-1.97 (m, 2 H), 2.06 (dd, J = 12.8, 5.5 Hz, 2 H), 2.56 (d, J = 9.2 Hz, 2 H), 2.63-2.67 (m, 1 H), 2.80-2.92 (m, 1 H), 3.17 (dd, J = 9.5, 4.0 Hz, 2 H), 3.36-3.46 (m, 3 H), 3.63-3.76 (m, 2 H), 3.80-3.92 (m, 2 H), 4.04-4.13 (m, 2 H), 4.17 (q, J = 6.9 Hz, 2 H). | 3 E | m/z 392 (M + H)⁺ (ES⁺), at 3.15 min, 202 nm |
| 10-10 | Isomer 1: methyl 7-{(1R,5S,6r)-6-[cyclopropyl(ethyl)carbamoyl]-3-azabicyclo[3.1.0]hexan-3-yl}-3-oxa-9-azabicyclo[3.3.1]nonane-9-carboxylate | C 71 and 19 | CL then CM | (400 MHz, METHANOL-$d_4$) δ: 0.76-0.86 (m, 2 H), 0.95-1.03 (m, 2 H), 1.06-1.15 (m, 3 H), 1.51-1.63 (m, 2 H), 1.89-1.96 (m, 2 H), 1.98-2.09 (m, 1 H), 2.26-2.39 (m, 2 H), 2.49-2.57 (m, 2 H), 2.63-2.69 (m, 1 H), 2.81-2.90 (m, 1 H), 3.11-3.22 (m, 2 H), 3.36-3.46 (m, 2 H), 3.47-3.66 (m, 4 H), 3.71 (s, 3 H), 3.14-4.24 (m, 2 H). | 3 E | m/z 378 (M + H)⁺ (ES⁺), at 2.80 min, 202 nm |
| 10-10 | Isomer 2: methyl 7-{(1R,5S,6r)-6-[cyclopropyl(ethyl)carbamoyl]-3-azabicyclo[3.1.0]hexan-3-yl}-3-oxa-9-azabicyclo[3.3.1]nonane-9-carboxylate | C 71 and 19 | CL then CM | (400 MHz, METHANOL-$d_4$) δ: 0.77-0.84 (m, 2 H), 0.96-1.03 (m, 2 H), 1.06-1.14 (m, 3 H), 1.56-1.69 (m, 2 H), 1.90-1.97 (m, 2 H), 2.00-2.11 (m, 2 H), 2.54-2.66 (m, 3 H), 2.80-2.88 (m, 1 H), 3.12-3.21 (m, 2 H), 3.35 (s, 1 H), 3.37-3.47 (m, 2 H), 3.62-3.69 (m, 2 H), 3.71 (s, 3 H), 3.77-3.89 (m, 2 H), 4.03-4.12 (m, 2 H). | 3 E | m/z 378 (M + H)⁺ (ES⁺), at 2.83 min, 202 nm |
| 10-11 | Isomer 1: ethyl 7-[(1R,5S,6r)-6-(piperidin-1-ylcarbonyl)-3-azabicyclo[3.1.0]hex-3-yl]-3-oxa-9-azabicyclo[3.3.1]nonane-9-carboxylate | C 69 and 21 | CN then CO | (400 MHz, METHANOL-$d_4$) δ: 1.25-1.34 (m, 4 H), 1.51-1.68 (m, 5 H), 1.71 (d, J = 4.3 Hz, 2 H), 1.94-1.99 (m, 2 H), 2.05-2.17 (m, 1 H), 2.27-2.42 (m, 3 H), 2.61 (d, J = 7.9 Hz, 2 H), 3.23 (d, J = 9.8 Hz, 2 H), 3.51-3.72 (m, 8 H), 4.12-4.27 (m, 4 H). | 3 E | m/z 392 (M + H)⁺ (ES⁺), at 3.16 min, 202 nm |
| 10-11 | Isomer 2: ethyl 7-[(1R,5S,6r)-6-(piperidin-1-ylcarbonyl)-3-azabicyclo[3.1.0]hex-3-yl]-3-oxa-9-azabicyclo[3.3.1]nonane-9-carboxylate | C 69 and 21 | CN then CO | (400 MHz, METHANOL-$d_4$) δ: 1.29 (t, J = 7.0 Hz, 3 H), 1.50-1.75 (m, 7 H), 1.94-2.00 (m, 2 H), 2.08 (dd, J = 12.8, 4.9 Hz, 2 H), 2.24-2.29 (m, 1 H), 2.62 (d, J = 9.2 Hz, 2 H), 3.21 (dd, J = 9.2, 4.3 Hz, 2 H), 3.37 (s, 1 H), 3.42-3.62 (m, 3 H), 3.62-3.74 (m, 4 H), 3.79-3.94 (m, 2 H), 4.06-4.13 m, 2 H), 4.17 (q, J = 7.1 Hz, 2 H). | 3 E | m/z 392 (M + H)⁺ (ES⁺), at 3.19 min, 202 nm |
| 10-12 | Isomer 1: methyl 7-[(1R,5S,6r)-6-(piperidin-1-carbonyl)-3-azabicyclo[3.1.0]hexan-3-yl]-3-oxa-9-azabicyclo[3.3.1]nonane-9-carboxylate | C 71 and 21 | CP then CQ | (400 MHz, METHANOL-$d_4$) δ: 1.48-1.59 (m, 4 H), 1.60-1.66 (m, 2 H), 1.66-1.74 (m, 2 H), 1.89-1.93 (m, 2 H), 1.94-2.06 (m, 1 H), 2.25-2.38 (m, 3 H), 2.46-2.52 (m, 2 H), 3.11-3.18 (m, 2 H), 3.46-3.56 (m, 5 H), 3.57-3.60 (m, 1 H), 3.64-3.69 (m, 2 H), 3.70 (s, 3 H), 4.14-4.24 (m, 2 H). | 3 E | m/z 378 (M + H)⁺ (ES⁺), at 2.80 min, 202 nm |
| 10-12 | Isomer 2: methyl 7-[(1R,5S,6r)-6-(piperidin-1-carbonyl)-3-azabicyclo[3.1.0]hexan-3-yl]-3-oxa-9-azabicyclo[3.3.1]nonane-9-carboxylate | C 71 and 21 | CP then CQ | (400 MHz, METHANOL-$d_4$) δ: 1.47-1.55 (m, 2 H), 1.56-1.66 (m, 4 H), 1.66-1.74 (m, 2 H), 1.89-1.95 (m, 2 H), 2.00-2.09 (m, 2 H), 2.22-2.27 (m, 1 H), 2.47-2.54 (m, 2 H), 3.09-3.16 (m, 2 H), 3.33-3.41 (m, 1 H), 3.49-3.55 (m, 2 H), 3.61-3.69 (m, 4 H), 3.71 (s, 3 H), 3.78-3.88 (m, 2 H), 4.03-4.10 (m, 2 H). | 3 E | m/z 378 (M + H)⁺ (ES⁺), at 2.83 min, 202 nm |
| 10-13 | Isomer 1: ethyl 7-[(1R,5S,6r)-6-(morpholine-4-carbonyl)-3-azabicyclo[3.1.0]hexan-3-yl]-3-oxa-9-azabicyclo[3.3.1]nonane-9-carboxylate | C 69 and 80 | CR then CS | (400 MHz, METHANOL-$d_4$) δ: 1.26 (s, 3 H), 1.62-1.74 (m, 2 H), 2.00-2.09 (m, 2 H), 2.21-2.27 (m, 1 H), 2.28-2.40 (m, 2 H), 2.64-2.87 (m, 2 H), 3.23-3.29 (m, 2 H), 3.35 (s, 2 H), 3.52-3.60 (m, 4 H), 3.61-3.66 (m, 2 H), 3.66-3.70 (m, 2 H), 3.71 (s, 3 H), 4.11-4.19 (m, 2 H), 4.19-4.26 (m, 2 H). | 3 E | m/z 394 (M + H)⁺ (ES⁺), at 2.55 min, 202 nm |
| 10-13 | Isomer 2: ethyl 7-[(1R,5S,6r)-6-(morpholine-4-carbonyl)-3-azabicyclo[3.1.0]hexan-3-yl]-3-oxa-9-azabicyclo[3.3.1]nonane-9-carboxylate | C 69 and 80 | CR then CS | (400 MHz, METHANOL-$d_4$) δ: 1.27 (t, J = 7.09 Hz, 3 H), 1.58-1.72 (m, 2 H), 2.00-2.06 (m, 2 H), 2.07-2.15 (m, 2 H), 2.22-2.27 (m, 1 H), 2.67-2.91 (m, 2 H), 3.22-3.30 (m, 2 H), 3.35 (s, 2 H), 3.53-3.59 (m, 2 H), 3.60-3.66 (m, 2 H), 3.70 (m, 2 H), 3.70 (s, 3 H), 3.80-3.90 (m, 2 H), 4.08-4.19 (m, 4 H). | 3 E | m/z 394 (M + H)⁺ (ES⁺), at 2.59 min, 202 nm |
| 10-14 | Isomer 1: ethyl 7-[(1R,5S,6r)-6-(azepan-1-ylcarbonyl)-3-azabicyclo[3.1.0]hex-3-yl]-3-oxa-9-azabicyclo[3.3.1]nonane-9-carboxylate | C 69 and 24 | CT | (400 MHz, METHANOL-$d_4$) δ: 1.28 (t, J = 7.0 Hz, 3 H), 1.51-1.67 (m, 6 H), 1.71 (dt, J = 11.3, 6.0 Hz, 2 H), 1.76-1.88 (m, 2 H), 1.93-1.97 (m, 2 H), 1.97-2.13 (m, 1 H), 2.20-2.42 (m, 3 H), 2.42-2.59 (m, 2 H), 3.11-3.23 (m, 2 H), 3.49-3.76 (m, 8 H), 4.06-4.28 (m, 4 H). | 3 E | m/z 406 (M + H)⁺ (ES⁺), at 3.48 min, 202 nm |

TABLE 3-continued

| Ex. No. | Name | Synthetic Method and Intermediates Used | Purification Method | ¹H NMR | LC-MS System and Method | LCMS data |
|---|---|---|---|---|---|---|
| 10-14 | Isomer 2: ethyl 7-[(1R,5S,6r)-6-(azepan-1-ylcarbonyl)-3-azabicyclo[3.1.0]hex-3-yl]-3-oxa-9-azabicyclo[3.3.1]nonane-9-carboxylate | C 69 and 24 | CT | (400 MHz, METHANOL-$d_4$) δ: 1.28 (t, J = 7.0 Hz, 3 H), 1.52-1.67 (m, 6 H), 1.71 (dt, J = 11.3, 6.0 Hz, 2 H), 1.81 (quin, J = 5.8 Hz, 2 H), 1.93-1.98 (m, 2 H), 2.06 (dd, J = 12.8, 5.5 Hz, 2 H), 2.23-2.28 (m, 1 H), 2.54 (d, J = 9.2 Hz, 2 H), 3.16 (dd, J = 9.8, 5.5 Hz, 2 H), 3.35-3.46 (m, 1 H), 3.51 (t, J = 6.1 Hz, 2 H), 3.62-3.76 (m, 4 H), 3.79-3.95 (m, 2 H), 4.06-4.13 (m, 2 H), 4.17 (q, J = 7.3 Hz, 2 H). | 3 E | m/z 406 $(M + H)^+$ $(ES^+)$, at 3.58 min, 202 nm |
| 10-15 | Isomer 1: ethyl 7-[(1R,5S,6r)-6-(1-azapiro[3.3]hept-1-ylcarbonyl)-3-azabicyclo[3.1.0]hex-3-yl]-3-oxa-9-azabicyclo[3.3.1]nonane-9-carboxylate | C 69 and 28 | CU | (400 MHz, METHANOL-$d_4$) δ: 1.28 (t, J = 7.0 Hz, 3 H), 1.50-1.78 (m, 2 H), 1.78-1.89 (m, 2 H), 1.90-1.95 (m, 1 H), 1.97-2.12 (m, 3 H), 2.16-2.24 (m, 1 H), 2.25-2.42 (m, 3 H), 2.43-2.58 (m, 3 H), 2.77-3.00 (m, 2 H), 3.11-3.24 (m, 2 H), 3.36-3.42 (m, 1 H), 3.49-3.72 (m, 3 H), 3.75-3.91 (m, 2 H), 4.05-4.26 (m, 5 H). | 3 E | m/z 404 $(M + H)^+$ $(ES^+)$, at 3.34 min, 202 nm |
| 10-15 | Isomer 2: ethyl 7-[(1R,5S,6r)-6-(1-azapiro[3.3]hept-1-ylcarbonyl)-3-azabicyclo[3.1.0]hex-3-yl]-3-oxa-9-azabicyclo[3.3.1]nonane-9-carboxylate | C 69 and 28 | CU | (400 MHz, METHANOL-$d_4$) δ: 1.28 (t, J = 7.0 Hz, 3 H), 1.56-1.89 (m, 4 H), 1.90-1.95 (m, 1 H), 1.96-2.14 (m, 4 H), 2.15-2.31 (m, 1 H), 2.34-2.49 (m, 2 H), 2.49-2.67 (m, 2 H), 2.75-3.04 (m, 2 H), 3.16 (ddd, J = 19.7, 9.6, 4.9 Hz, 2 H), 3.36-3.50 (m, 1 H), 3.62-3.73 (m, 3 H), 3.74-3.92 (m, 3 H), 4.04-4.25 (m, 5 H). | 3 E | m/z 404 $(M + H)^+$ $(ES^+)$, at 3.41 min, 202 nm |
| 11-1 | Isomer 1: ethyl 4-[(1R,5S,6r)-6-(diethylcarbamoyl)-3-azabicyclo[3.1.0]hexan-3-yl]azepane-1-carboxylate | C 82 and 4 | CV then CW | (400 MHz, METHANOL-$d_4$) δ: 1.05 (t, J = 7.09 Hz, 3 H), 1.16-1.26 (m, 6 H), 1.41-1.68 (m, 3 H), 1.75-1.94 (m, 5 H), 2.15 (t, J = 2.93 Hz, 1 H), 2.28-2.36 (m, 1 H), 2.45-2.51 (m, 2 H), 3.05-3.13 (m, 2 H), 3.24-3.36 (m, 4 H), 3.36-3.43 (m, 1 H), 3.44-3.55 (m, 3 H), 4.03-4.13 (m, 2 H). | 3 E | m/z 352 $(M + H)^+$ $(ES^+)$, at 3.41 min, 202 nm |
| 11-1 | Isomer 2: ethyl 4-[(1R,5S,6r)-6-(diethylcarbamoyl)-3-azabicyclo[3.1.0]hexan-3-yl]azepane-1-carboxylate | C 82 and 4 | CV then CW | (400 MHz, METHANOL-$d_4$) δ: 0.97-1.13 (m, 3 H), 1.16-1.27 (m, 6 H), 1.42-1.68 (m, 3 H), 1.76-1.93 (m, 4 H), 2.13-2.17 (m, 1 H), 2.27-2.37 (m, 1 H), 2.44-2.54 (m, 2 H), 3.04-3.14 (m, 2 H), 3.22-3.37 (m, 5 H), 3.37-3.44 (m, 1 H), 3.43-3.56 (m, 3 H), 4.04-4.11 (m, 2 H). | 3 E | m/z 352 $(M + H)^+$ $(ES^+)$, at 3.41 min, 202 nm |
| 11-2 | Isomer 1: ethyl 3-[(1R,5S,6r)-6-(diethylcarbamoyl)-3-azabicyclo[3.1.0]hexan-3-yl]-6-azabicyclo[3.2.1]octane-6-carboxylate | C 85 and 4 | CX | (400 MHz, METHANOL-$d_4$) δ: 1.09 (t, J = 7.02 Hz, 3 H), 1.18-1.33 (m, 7 H), 1.39-1.49 (m, 1 H), 1.53-1.62 (m, 1 H), 1.78-2.01 (m, 4 H), 2.14-2.24 (m, 2 H), 2.27-2.38 (m, 1 H), 2.40-2.54 (m, 3 H), 3.10 (dd, J = 9.61, 5.59 Hz, 2 H), 3.20-3.29 (m, 1 H), 3.29-3.43 (m, 3 H), 3.43-3.61 (m, 2 H), 4.05-4.19 (m, 3 H). | 4 C | m/z 364 $(M + H)^+$ $(ES^+)$, at 3.29 min, 202 nm |
| 11-2 | Isomer 2: ethyl 3-[(1R,5S,6r)-6-(diethylcarbamoyl)-3-azabicyclo[3.1.0]hexan-3-yl]-6-azabicyclo[3.2.1]octane-6-carboxylate | C 85 and 4 | CX | (400 MHz, METHANOL-$d_4$) δ: 1.03-1.14 (m, 3 H), 1.21-1.31 (m, 6 H), 1.50-1.59 (m, 1 H), 1.61-1.77 (m, 2 H), 1.80-1.92 (m, 3 H), 2.01-2.24 (m, 3 H), 2.26-2.37 (m, 2 H), 2.44-2.53 (m, 1 H), 3.10-3.40 (m, 6 H), 3.40-3.56 (m, 2 H), 3.75-3.88 (m, 1 H), 3.94-4.05 (m, 1 H), 4.07-4.24 (m, 2 H). | 4 C | m/z 364 $(M + H)^+$ $(ES^+)$, at 4.36 min, 202 nm |
| 12-1 | Isomer 1: ethyl 5-[(1R,5S,6r)-6-(diethylcarbamoyl)-3-azabicyclo[3.1.0]hexan-3-yl]hexahydrocyclopenta[c]pyrrole-2(1H)-carboxylate | C 88 and 4 | CZ | (400 MHz, METHANOL-$d_4$) δ: 1.08 (t, J = 7.10 Hz, 3 H), 1.24 (t, J = 7.10 Hz, 6 H), 1.27-1.36 (m, 2 H), 1.86-1.94 (m, 2 H), 2.07-2.18 (m, 2 H), 2.21-2.27 (m, 1 H), 2.49 (d, J = 9.31 Hz, 2 H), 2.55-2.72 (m, 3 H), 3.12 (d, J = 9.61 Hz, 2 H), 3.31-3.40 (m, 4 H), 3.41-3.59 (m, 4 H), 4.09 (q, J = 7.02 Hz, 2 H). | 3 E | m/z 364 $(M + H)^+$ $(ES^+)$, at 3.35 min, 202 nm |
| 12-1 | Isomer 2: ethyl 5-[(1R,5S,6r)-6-(diethylcarbamoyl)-3-azabicyclo[3.1.0]hexan-3-yl]hexahydrocyclopenta[c]pyrrole-2(1H)-carboxylate | C 88 and 4 | CZ | (400 MHz, METHANOL-$d_4$) δ: 1.09 (t, J = 7.10 Hz, 3 H), 1.25 (t, J = 7.10 Hz, 6 H), 1.28-1.36 (m, 2 H), 1.88-1.94 (m, 2 H), 2.09-2.18 (m, 2 H), 2.22-2.26 (m, 1 H), 2.50 (d, J = 9.31 Hz, 2 H), 2.56-2.71 (m, 3 H), 3.12 (d, J = 9.61 Hz, 2 H), 3.32-3.40 (m, 4 H), 3.42-3.49 (m, 2 H), 4.53 (q, J = 7.17 Hz, 2 H), 4.10 (q, J = 7.17 Hz, 2 H). | 3 E | m/z 364 $(M + H)^+$ $(ES^+)$, at 3.36 min, 202 nm |

BIOLOGICAL ACTIVITY

Example A

Phospho-ERK1/2 Assays

Functional assays were performed using the Alphascreen Surefire phospho-ERK1/2 assay (Crouch & Osmond, *Comb. Chem. High Throughput Screen,* 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader. $pEC_{50}$ and $E_{max}$ figures were calculated from the resulting data for each receptor subtype and the results are set out in Table 4 below (NT=not tested).

For the vast majority of examples at least two diastereomers exist and these have been separated, unless otherwise stated, using the techniques of reversed phase HPLC, chiral HPLC or chiral SFC. Isomer assignment (Isomer 1, Isomer 2, etc.) is based on the retention time of the compound using the separation technique that was performed in the final purification step. By implication, this could be reversed phase HPLC, chiral HPLC or chiral SFC retention time, and this will vary from compound to compound.

Analytical data for active isomers is reported in Table 3. Data for several weakly active compounds are included in Table 4 to highlight the preference for absolute stereochemistry.

TABLE 4

| Example No. | Muscarinic Activity | | | |
|---|---|---|---|---|
| | $pEC_{50}$ $M_1$ (% Emax cf. ACh) | $pEC_{50}$ $M_2$ (% Emax cf. ACh) | $pEC_{50}$ $M_3$ (% Emax cf. ACh) | $pEC_{50}$ $M_4$ (% Emax cf. ACh) |
| ACh | 8.05 (96) | 7.74 (106) | 8.27 (104) | 7.99 (109) |
| 1-1 | 5.03 (115) | <4.70 (12) | <4.70 (6) | 6.50 (73) |
| 1-2 | 6.88 (110) | NT | NT | 6.02 (81) |
| 1-4 | 5.34 (55) | NT | NT | 6.21 (47) |
| 2-1 Mixture of isomers | <4.70 (22) | <4.70 (7) | <4.70 (0) | 7.11 (86) |
| 2-2 Isomer 1 | 6.41 (69) | NT | NT | 5.62 (43) |
| 2-2 Isomer 2 | 7.10 (101) | <4.70 (8) | < 4.70 (2) | 6.56 (63) |
| 2-3 Isomer 1 | 7.39 (108) | <4.70 (14) | <4.70 (15) | 6.77 (100) |
| 2-3 Isomer 2 | 6.83 (90) | NT | NT | 5.97 (66) |
| 2-4 Isomer 1 | 5.64 (49) | NT | NT | 5.97 (37) |
| 2-4 Isomer 2 | 7.27 (112) | <4.70 (18) | <4.70 (1) | 6.81 (94) |
| 2-5 Isomer 1 | <4.70 (26) | NT | NT | 5.71 (37) |
| 2-5 Isomer 1 | 7.25 (107) | <4.70 (9) | <4.70 (20) | 6.72 (85) |
| 2-6 Isomer 1 | 5.90 (42) | NT | NT | <4.70 (39) |
| 2-7 Isomer 1 | 5.80 (66) | NT | NT | 5.60 (50) |
| 2-8 Isomer 1 | 6.06 (50) | NT | NT | 5.78 (37) |
| 2-8 Isomer 2 | 7.52 (110) | <4.70 (15) | <4.70 (17) | 7.00 (92) |
| 2-9 Isomer 1 | 6.39 (57) | NT | NT | 5.96 (28) |
| 2-10 Isomer 1 | 5.93 (66) | NT | NT | <4.70 (56) |
| 2-11 Mixture of isomers | 7.69 (100) | <4.70 (20) | <4.70 (55) | 7.17 (85) |
| 2-12 Isomer 1 | 4.88 (65) | NT | NT | 6.14 (85) |
| 2-12 Isomer 2 | 6.67 (79) | NT | NT | 6.37 (72) |
| 2-13 Isomer 1 | 6.72 (31) | NT | NT | <4.70 (71) |
| 2-13 Isomer 2 | 6.94 (83) | <4.70 (51) | <4.70 (38) | 6.32 (72) |
| 2-14 Isomer 1 | 6.49 (80) | NT | NT | 5.91 (33) |
| 2-14 Isomer 2 | 7.72 (111) | <4.70 (62) | 4.85 (100) | 7.16 (93) |
| 2-16 Isomer 1 | 7.29 (30) | <4.70 (53) | <4.70 (45) | <4.70 (11) |
| 2-16 Isomer 2 | 7.79 (94) | <4.70 (87) | <4.70 (59) | 7.42 (75) |
| 2-17 Isomer 1 | 6.28 (44) | NT | NT | <4.70 (13) |
| 2-17 Isomer 2 | 7.19 (96) | <4.70 (7) | <4.70 (20) | 6.55 (63) |
| 2-18 Mixture of isomers | <4.70 (11) | NT | NT | 6.04 (34) |
| 2-19 Isomer 2 | 7.88 (93) | <4.70 (16) | <4.70 (35) | 7.43 (95) |
| 2-21 Isomer 1 | 6.34 (67) | NT | NT | 5.92 (43) |
| 2-22 Isomer 2 | 5.76 (95) | NT | NT | 5.67 (71) |
| 2-23 Isomer 2 | 6.79 (129) | NT | NT | 6.45 (95) |
| 2-24 Isomer 1 | 6.03 (76) | NT | NT | 5.79 (53) |
| 2-24 Isomer 2 | 7.47 (115) | <4.70 (11) | 4.73 (47) | 7.30 (102) |
| 2-25 Isomer 2 | 5.89 (37) | NT | NT | 6.36 (35) |
| 2-25 Isomer 4 | 6.49 (65) | <4.70 (24) | <4.70 (4) | 6.82 (48) |
| 2-26 Mixture of isomers | 5.86 (52) | <4.70 (8) | <4.70 (12) | 7.31 (114) |
| 2-27 Mixture of isomers | <4.70 (20) | NT | NT | 5.83 (32) |
| 2-28 Isomer 1 | 6.24 (58) | NT | NT | <4.70 (21) |
| 2-28 Isomer 2 | 7.19 (104) | <4.70 (7) | <4.70 (5) | 7.27 (51) |
| 2-29 Isomer 2 | 6.19 (43) | <4.70 (36) | <4.70 (2) | 7.06 (83) |
| 2-30 Isomer 1 | <4.70 (29) | NT | NT | 6.45 (61) |
| 2-30 Isomer 2 | 6.85 (86) | <4.70 (34) | <4.70 (7) | 7.57 (88) |
| 3-1 Mixture of isomers | <4.70 (21) | <4.70 (4) | <4.70 (2) | 7.89 (62) |
| 3-2 Mixture of isomers | 8.32 (92) | <4.70 (20) | <4.70 (21) | 7.79 (79) |

TABLE 4-continued

| Example No. | Muscarinic Activity | | | |
|---|---|---|---|---|
| | $pEC_{50}$ $M_1$ (% Emax cf. ACh) | $pEC_{50}$ $M_2$ (% Emax cf. ACh) | $pEC_{50}$ $M_3$ (% Emax cf. ACh) | $pEC_{50}$ $M_4$ (% Emax cf. ACh) |
| 4-1 | 6.63 (84) | NT | NT | 6.15 (35) |
| 5-1 Isomer 1 | 5.21 (78) | NT | NT | 6.53 (81) |
| 5-1 Isomer 2 | <4.70 (102) | NT | NT | 6.09 (54) |
| 5-2 Isomer 1 | 7.00 (134) | <4.70 (10) | NT | 5.58 (95) |
| 6-1 Isomer 2 | 6.46 (76) | NT | NT | <4.70 (2) |
| 7-1 Isomer 2 | 5.67 (83) | NT | NT | 5.80 (62) |
| 7-2 Isomer 1 | 6.11 (116) | NT | NT | <4.70 (14) |
| 7-2 Isomer 2 | 6.66 (113) | NT | NT | 4.96 (53) |
| 7-3 Isomer 1 | 6.78 (123) | NT | NT | 5.58 (45) |
| 7-5 Isomer 2 | <4.70 (23) | NT | NT | 6.13 (38) |
| 7-6 Isomer 2 | 5.94 (56) | NT | NT | 6.21 (73) |
| 8-1 Mixture of isomers | 5.78 (53) | NT | NT | 6.26 (61) |
| 8-2 Isomer 2 | 6.20 (134) | NT | NT | 5.20 (52) |
| 8-3 Isomer 1 | 5.83 (104) | NT | NT | 5.49 (29) |
| 8-4 Isomer 1 | 6.13 (89) | NT | NT | <4.70 (4) |
| 8-5 Isomer 1 | 6.89 (106) | <4.70 (6) | <4.70 (6) | 5.72 (47) |
| 8-5 Isomer 2 | 7.05 (39) | <4.70 (2) | <4.70 (5) | <4.70 (12) |
| 8-6 Isomer 1 | 6.07 (31) | NT | NT | <4.70 (2) |
| 8-6 Isomer 2 | 6.45 (39) | NT | NT | <4.70 (2) |
| 8-9 Isomer 1 | 6.43 (99) | NT | NT | <4.70 (7) |
| 8-10 Isomer 1 | 7.87 (117) | <4.70 (7) | <4.70 (21) | 7.13 (52) |
| 8-10 Isomer 2 | 6.03 (123) | NT | NT | <4.70 (16) |
| 9-1 Isomer 1 | 7.04 (93) | <4.70 (19) | <4.70 (21) | 6.06 (57) |
| 9-1 Isomer 2 | 6.01 (93) | NT | NT | <4.70 (24) |
| 9-2 Isomer 1 | 6.56 (102) | NT | NT | 5.87 (41) |
| 9-3 Isomer 1 | 6.40 (106) | NT | NT | 6.12 (60) |
| 10-1 Isomer 1 | 5.94 (110) | NT | NT | <4.70 (24) |
| 10-1 Isomer 1 | 5.76 (78) | NT | NT | <4.70 (15) |
| 10-2 Isomer 2 | 7.15 (113) | <4.70 (25) | <4.70 (10) | 6.04 (62) |
| 10-3 Isomer 1 | 6.67 (96) | NT | NT | 6.24 (73) |
| 10-3 Isomer 2 | 5.75 (81) | NT | NT | <4.70 (25) |
| 10-5 Isomer 1 | 6.30 (99) | NT | NT | 5.91 (81) |
| 10-5 Isomer 2 | 5.66 (101) | NT | NT | 4.90 (90) |
| 10-7 Isomer 1 | 7.42 (99) | NT | NT | 6.79 (69) |
| 10-7 Isomer 2 | 6.83 (100) | NT | NT | 6.23 (64) |
| 10-8 Isomer 1 | 5.99 (116) | NT | NT | 4.84 (47) |
| 10-8 Isomer 2 | 5.65 (85) | NT | NT | 5.67 (32) |
| 10-9 Isomer 2 | 6.57 (105) | NT | NT | 5.47 (38) |
| 10-10 Isomer 1 | NT | NT | NT | NT |
| 10-10 Isomer 2 | NT | NT | NT | NT |
| 10-12 Isomer 2 | 5.99 (99) | NT | NT | 4.85 (86) |
| 10-13 Isomer 1 | 6.51 (104) | <4.70 (24) | <4.70 (68) | 5.95 (64) |
| 10-13 Isomer 2 | 6.43 (101) | <4.70 (24) | <4.70 (22) | 4.99 (59) |
| 11-1 Isomer 1 | 7.98 (97) | NT | NT | 6.90 (84) |
| 11-1 Isomer 2 | 7.43 (94) | NT | NT | 6.33 (62) |
| 11-2 Isomer 1 | 6.41 (37) | NT | NT | <4.70 (3) |
| 11-2 Isomer 2 | 6.93 (113) | <4.70 (5) | <4.70 (3) | 6.02 (65) |
| 12-1 Isomer 1 | 6.21 (49) | NT | NT | <4.70 (6) |
| 12-1 Isomer 2 | 5.94 (49) | NT | NT | <4.70 (8) |

The invention claimed is:

1. A compound of the formula (1):

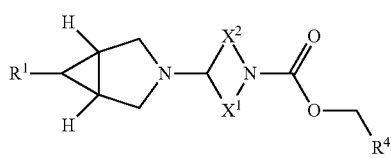

(1)

or a salt thereof, wherein:

$X^1$ and $X^2$ are saturated hydrocarbon groups which together contain a total of five to nine carbon atoms and zero or one oxygen atoms and which link together such that the moiety:

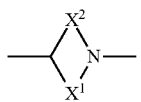

forms a monocyclic or bicyclic ring system optionally substituted with one or more fluorine atoms;

$R^1$ is selected from $OR^5$; $NR^5R^6$; $COR^5$; $COOR^5$; $CONR^5R^6$; $CONR^5OR^6$; $C(=NR^5)R^6$; $C(=NOR^5)R^6$; $OCOR^5$; $NR^7COR^5$; $NR^7CONR^5R^6$; $NR^7COOR^5$; $OCONR^5R^6$; $CH_2OR^5$; $CH_2NR^5R^6$; $CH_2COR^5$; $CH_2COOR^5$; $CH_2CONR^5R^6$; $CH_2CONR^5OR^6$; $CH_2C(=NR^5)R^6$; $CH_2C(=NOR^5)R^6$; $CH_2OCOR^5$; $CH_2NR^7COR^5$; $CH_2NR^7CONR^5R^6$; $CH_2NR^7COOR^5$; $CH_2OCONR^5R^6$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 4, 5- or 6-membered ring containing 0, 1, 2 or 3 heteroatoms selected from O, N and S and oxidized forms thereof;

$R^4$ is H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof; and $R^5$, $R^6$ and $R^7$ are the same or different and each is independently selected from hydrogen, a non-aromatic $C_{1-6}$ hydrocarbon group optionally substituted with one or more fluorine atoms or optionally substituted with a 4, 5- or 6-membered ring containing 0, 1, 2 or 3 heteroatoms selected from O, N and S and oxidized forms thereof, or $R^5$ and $R^6$ can be joined together to form an optionally substituted monocyclic or bicyclic ring containing 0, 1, 2 or 3 heteroatoms selected from O, N and S and oxidized forms thereof.

2. The compound according to claim 1 wherein $R^1$ is selected from $OR^5$; $NR^5R^6$; $COOR^5$; $CONR^5R^6$; $CONR^5OR^6$; $C(=NOR^5)R^6$; $CH_2NR^7COR^5$; a $C_{1-3}$ alkyl group which is optionally substituted with one to three fluorine atoms; and an optionally substituted 4, 5- or 6-membered ring containing 1, or 2 heteroatoms selected from O, N and S and oxidized forms thereof.

3. The compound according to claim 1 wherein $R^1$ is selected from $COOR^5$; $CONR^5R^6$; $CONR^5OR^6$; $C(=NOR^5)R^6$; and an optionally substituted 5-membered ring containing 1, or 2 hetero atoms selected from O, N and S and oxidized forms thereof.

4. The compound according to claim 1 wherein $R^1$ is selected from $COOR^5$ and $CONR^5R^6$.

5. The compound according to claim 1 wherein $R^5$ is selected from hydrogen, a non-aromatic $C_{1-6}$ hydrocarbon group optionally substituted with one or more fluorine atoms or optionally substituted with a 5- or 6-membered ring containing 0, 1, 2 or 3 heteroatoms selected from O, N and S and oxidized forms thereof, or $R^5$ and $R^6$ can be joined together to form an optionally substituted monocyclic or bicyclic ring containing 0, 1, 2 or 3 hetero atoms selected from O, N and S and oxidized forms thereof.

6. The compound according to claim 1 wherein $R^6$ is selected from hydrogen, a non-aromatic $C_{1-6}$ hydrocarbon group optionally substituted with one or more fluorine atoms or optionally substituted with a 4, 5- or 6-membered ring containing 0, 1, 2 or 3 heteroatoms selected from O, N and S and oxidized forms thereof, or $R^5$ and $R^6$ can be joined together to form an optionally substituted monocyclic or bicyclic ring containing 0, 1, 2 or 3 heteroatoms selected from O, N and S and oxidized forms thereof.

7. The compound according to claim 1 wherein $R^1$ is $COOR^5$ wherein $R^5$ is a non-aromatic $C_{1-6}$ hydrocarbon group or $R^1$ is $CONR^5R^6$ wherein $R^5$ is a non-aromatic $C_{1-6}$ hydrocarbon group and $R^6$ is selected from hydrogen and a non-aromatic $C_{1-6}$ hydrocarbon group, or $R^1$ is $CONR^5R^6$ and $R^5$ and $R^6$ are joined together to form an optionally substituted monocyclic or bicyclic ring containing, 0, 1, 2 or 3 heteroatoms selected from O, N and S and oxidized forms thereof, or $R^1$ is $CONR^5OR^6$ wherein $R^5$ is a non-aromatic $C_{1-6}$ hydrocarbon group and $R^6$ is a non-aromatic $C_{1-6}$ hydrocarbon group.

8. The compound according to claim 1 wherein $R^1$ is selected from $NR^5R^6$; $CONR^5R^6$; and $CH_2NR^5R^6$; and $R^5$ and $R^6$ are joined together to form an optionally substituted monocyclic or bicyclic ring containing. 0, 1, 2 or 3 heteroatoms selected from O, N and S and oxidized forms thereof.

9. The compound according to claim 1 wherein $R^1$ is selected from the group consisting of:

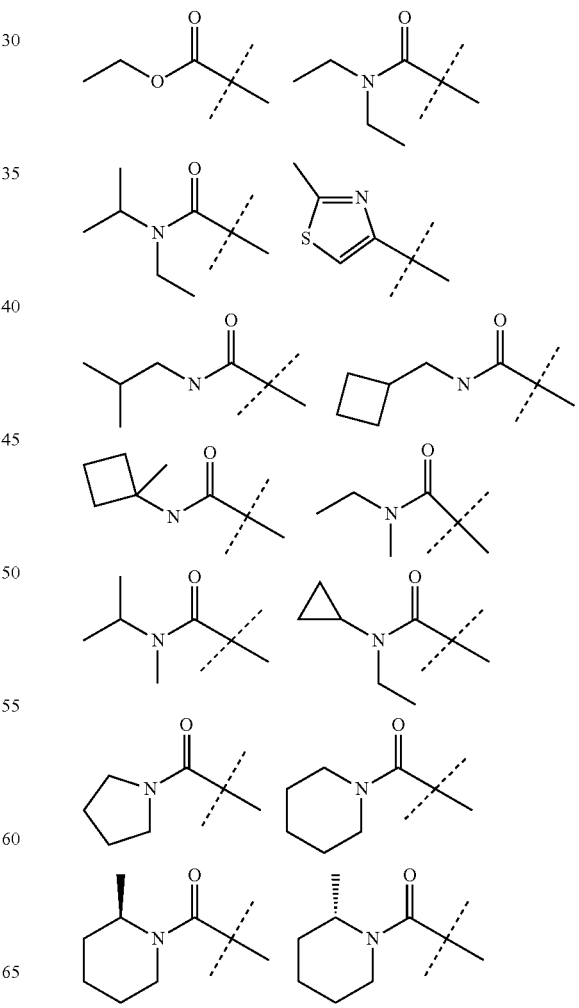

-continued

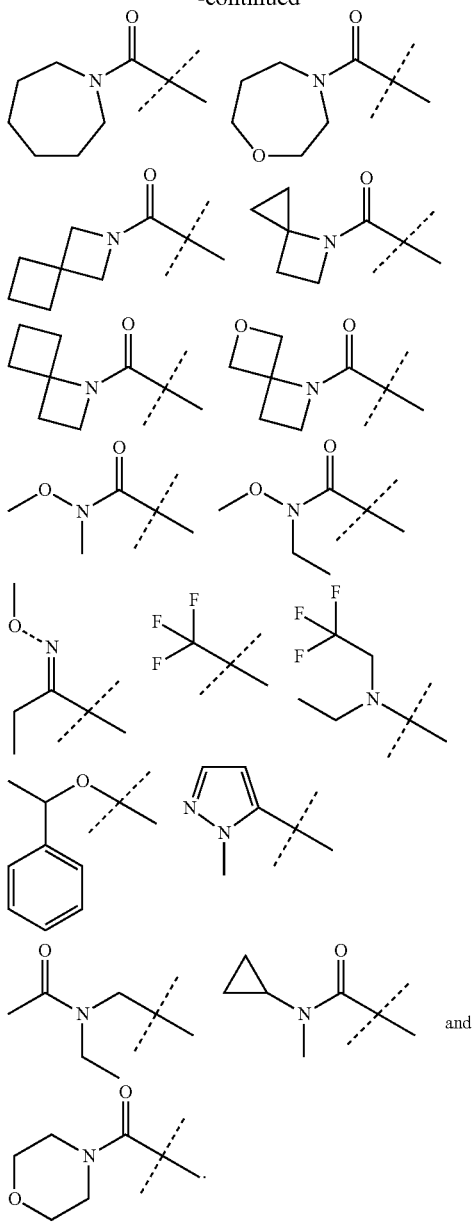

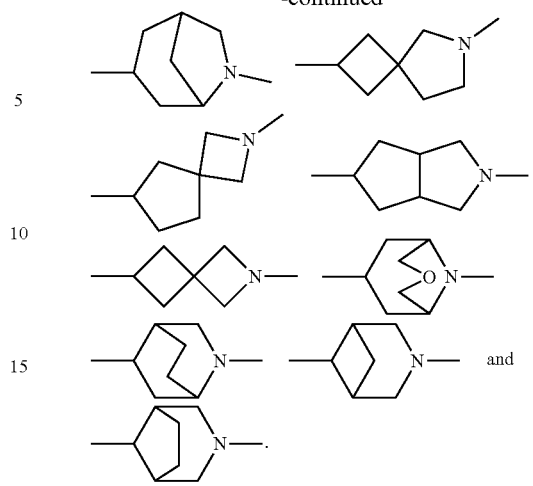

10. The compound according to claim 1 wherein R⁴ is selected from the group consisting of H, methyl, ethyl, ethynyl and 1-propynyl.

11. The compound according to claim 1 wherein the bicyclic ring system formed by the moiety:

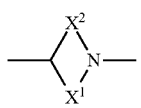

is selected from ring systems below:

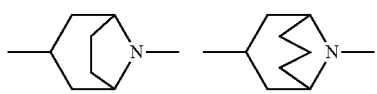

12. The compound according to claim 1 of the formula (2):

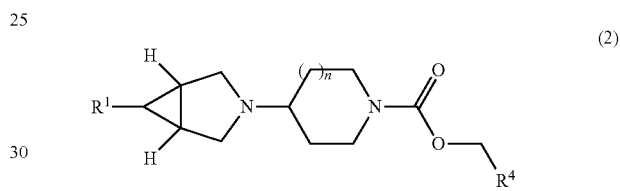

wherein n is 1 or 2.

13. The compound according to claim 1 wherein the compound is selected from the group consisting of:

ethyl 6-[(1R,5S,6r)-6-(ethoxycarbonyl)-3-azabicyclo[3.1.0]hex-3-yl]-2-azaspiro[3.3]heptane-2-carboxylate;

ethyl 6-[(1R,5S,6r)-6-(diethylcarbamoyl)-3-azabicyclo[3.1.0]hex-3-yl]-2-azaspiro[3.3]heptane-2-carboxylate;

ethyl 6-{(1R,5S,6r)-6-[ethyl(propan-2-yl)carbamoyl]-3-azabicyclo[3.1.0]hex-3-yl}-2-azaspiro[3.3]heptane-2-carboxylate;

ethyl 6-[(1R,5S,6r)-6-(2-methyl-1,3-thiazol-4-yl)-3-azabicyclo[3.1.0]hex-3-yl]-2-azaspiro[3.3]heptane-2-carboxylate;

ethyl 2-[(1R,5S,6r)-6-(ethoxycarbonyl)-3-azabicyclo[3.1.0]hex-3-yl]-6-azaspiro[3.4]octane-6-carboxylate;

ethyl 2-{(1R,5S,6r)-6-[(2-methylpropyl)carbamoyl]-3-azabicyclo[3.1.0]hex-3-yl}-6-azaspiro[3.4]octane-6-carboxylate;

ethyl 2-{(1R,5S,6r)-6-[(cyclobutylmethyl)carbamoyl]-3-azabicyclo[3.1.0]hex-3-yl}-6-azaspiro[3.4]octane-6-carboxylate;

ethyl 2-{(1R,5S,6r)-6-[(1-methylcyclobutyl)carbamoyl]-3-azabicyclo[3.1.0]hex-3-yl}-6-azaspiro[3.4]octane-6-carboxylate;

ethyl 2-{(1R,5S,6r)-6-[ethyl(methyl)carbamoyl]-3-azabicyclo[3.1.0]hex-3-yl}-6-azaspiro[3.4]octane-6-carboxylate;

ethyl 2-[(1R,5S,6r)-6-(diethylcarbamoyl)-3-azabicyclo[3.1.0]hex-3-yl]-6-azaspiro[3.4]octane-6-carboxylate;

methyl 2-[(1R,5S,6r)-6-(diethylcarbamoyl)-3-azabicyclo[3.1.0]hex-3-yl]-6-azaspiro[3.4]octane-6-carboxylate;

ethyl 2-{(1R,5S,6r)-6-[methyl(propan-2-yl)carbamoyl]-3-azabicyclo[3.1.0]hex-3-yl}-6-azaspiro[3.4]octane-6-carboxylate;

ethyl 2-{(1R,5S,6r)-6-[ethyl(propan-2-yl)carbamoyl]-3-azabicyclo[3.1.0]hex-3-yl}-6-azaspiro[3.4]octane-6-carboxylate;

methyl 2-{(1R,5S,6r)-6-[ethyl(propan-2-yl)carbamoyl]-3-azabicyclo[3.1.0]hex-3-yl}-6-azaspiro[3.4]octane-6-carboxylate;

ethyl 2-{(1R,5S,6r)-6-[cyclopropyl(ethyl)carbamoyl]-3-azabicyclo[3.1.0]hex-3-yl}-6-azaspiro[3.4]octane-6-carboxylate;

ethyl 2-[(1R,5S,6r)-6-(pyrrolidin-l-ylcarbonyl)-3-azabicyclo[3.1.0]hex-3-yl]-6-azaspiro[3.4]octane-6-carboxylate;

ethyl 2-[(1R,5S,6r)-6-(piperidin-1-ylcarbonyl)-3-azabicyclo[3.1.0]hex-3-yl]-6-azaspiro[3.4]octane-6-carboxylate;

ethyl 2-[(1R,5S,6r)-6-{[(2R)-2-methylpiperidin-1-yl]carbonyl}-3-azabicyclo[3.1.0]hex-3-yl]-6-azaspiro[3.4]octane-6-carboxylate;

ethyl 2-[(1R,5S,6r)-6-{[(2S)-2-methylpiperidin-1-yl]carbonyl}-3-azabicyclo[3.1.0]hex-3-yl]-6-azaspiro[3.4]octane-6-carboxylate;

ethyl 2-[(1R,5S,6r)-6-(azepan-1-ylcarbonyl)-3-azabicyclo[3.1.0]hex-3-yl]-6-azaspiro[3.4]octane-6-carboxylate;

ethyl 2-[(1R,5S,6r)-6-(1,4-oxazepan-4-ylcarbonyl)-3-azabicyclo[3.1.0]hex-3-yl]-6-azaspiro[3.4]octane-6-carboxylate;

ethyl 2-[(1R,5S,6r)-6-(2-azaspiro[3.3]hept-2-ylcarbonyl)-3-azabicyclo[3.1.0]hex-3-yl]-6-azaspiro[3.4]octane-6-carboxylate;

ethyl 2-[(1R,5S,6r)-6-(4-azaspiro[2.3]hex-4-ylcarbonyl)-3-azabicyclo[3.1.0]hex-3-yl]-6-azaspiro[3.4]octane-6-carboxylate;

ethyl 2-[(1R,5S,6r)-6-(1-azaspiro[3.3]hept-1-ylcarbonyl)-3-azabicyclo[3.1.0]hex-3-yl]-6-azaspiro[3.4]octane-6-carboxylate;

methyl 2-[(1R,5S,6r)-6-(1-azaspiro[3.3]hept-1-ylcarbonyl)-3-azabicyclo[3.1.0]hex-3-yl]-6-azaspiro[3.4]octane-6-carboxylate;

ethyl 2-[(1R,5S,6r)-6-(6-oxa-1-azaspiro[3.3]hept-1-ylcarbonyl)-3-azabicyclo[3.1.0]hex-3-yl]-6-azaspiro[3.4]octane-6-carboxylate;

ethyl 2-{(1R,5S,6r)-6-[methoxy(methyl)carbamoyl]-3-azabicyclo[3.1.0]hex-3-yl}-6-azaspiro[3.4]octane-6-carboxylate;

ethyl 2-{(1R,5S,6r)-6-[ethyl(methoxy)carbamoyl]-3-azabicyclo[3.1.0]hex-3-yl}-6-azaspiro[3.4]octane-6-carboxylate;

ethyl 2-[(1R,5S,6r)-6-(N-methoxypropanimidoyl)-3-azabicyclo[3.1.0]hexan-3-yl]-6-azaspiro[3.4]octane-6-carboxylate;

ethyl 2-[6-(trifluoromethyl)-3-azabicyclo[3.1.0]hex-3-yl]-6-azaspiro[3.4]octane-6-carboxylate;

ethyl 2-{(1R,5S,6s)-6-[ethyl(2,2,2-trifluoroethyl)amino]-3-azabicyclo[3.1.0]hexan-3-yl}-6-azaspiro[3.4]octane-6-carboxylate;

ethyl 2-[(1R,5S,6s)-6-(1-phenylethoxy)-3-azabicyclo[3.1.0]hex-3-yl]-6-azaspiro[3.4]octane-6-carboxylate;

ethyl 2-[(1R,5S,6r)-6-(1-methyl-1H-pyrazol-5-yl)-3-azabicyclo[3.1.0]hex-3-yl]-6-azaspiro[3.4]octane-6-carboxylate;

ethyl 2-[(1R,5S,6r)-6-(2-methyl-1,3-thiazol-4-yl)-3-azabicyclo[3.1.0]hex-3-yl]-6-azaspiro[3.4]octane-6-carboxylate;

ethyl 6-[(1R,5S,6r)-6-(ethoxycarbonyl)-3-azabicyclo[3.1.0]hex-3-yl]-2-azaspiro[3.4]octane-2-carboxylate;

ethyl 6-[(1R,5S,6r)-6-(diethylcarbamoyl)-3-azabicyclo[3.1.0]hex-3-yl]-2-azaspiro[3.4]octane-2-carboxylate;

methyl 6-[(1R,5S,6r)-6-(diethylcarbamoyl)-3-azabicyclo[3.1.0]hex-3-yl]-2-azaspiro[3.4]octane-2-carboxylate;

ethyl 6-{(1R,5S,6r)-6-[ethyl(propan-2-yl)carbamoyl]-3-azabicyclo[3.1.0]hex-3-yl}-2-azaspiro[3.4]octane-2-carboxylate;

ethyl 4-[(1R,5S,6r)-6-(diethylcarbamoyl)-3-azabicyclo[3.1.0]hexan-3-yl]piperidine-1-carboxylate;

ethyl 6-[(1R,5S,6r)-6-(ethoxycarbonyl)-3-azabicyclo[3.1.0]hexan-3-yl]-3-azabicyclo[3.1.1]heptane-3-carboxylate;

ethyl 6-[(1R,5S,6r)-6-(diethylcarbamoyl)-3-azabicyclo[3.1.0]hexan-3-yl]-3-azabicyclo[3.1.1]heptane-3-carboxylate;

ethyl 8-[(1R,5S,6r)-6-(diethylcarbamoyl)-3-azabicyclo[3.1.0]hexan-3-yl]-3-azabicyclo[3.2.1]octane-3-carboxylate;

ethyl 3-[(1R,5S,6r)-6-(ethoxycarbonyl)-3-azabicyclo[3.1.0]hex-3-yl]-8-azabicyclo[3.2.1]octane-8-carboxylate;

ethyl 3-{(1R,5S,6r)-6-[ethyl(methyl)carbamoyl]-3-azabicyclo[3.1.0]hex-3-yl}-8-azabicyclo[3.2.1]octane-8-carboxylate;

ethyl 3-[(1R,5S,6r)-6-(diethylcarbamoyl)-3-azabicyclo[3.1.0]hex-3-yl]-8-azabicyclo[3.2.1]octane-8-carboxylate;

ethyl 3-{(1R,5S,6r)-6-[ethyl(propan-2-yl)carbamoyl]-3-azabicyclo[3.1.0]hex-3-yl}-8-azabicyclo[3.2.1]octane-8-carboxylate;

ethyl 3-[(1R,5S ,6r)-6-{[acetyl(ethyl)amino]methyl}-3-azabicyclo[3.1.0]hex-3-yl]-8-azabicyclo[3.2.1]octane-8-carboxylate;

ethyl 3-[(1R,5S,6r)-6-(2-methyl-1,3-thiazol-4-yl)-3-azabicyclo[3.1.0]hex-3-yl]-8-azabicyclo[3.2.1]octane-8-carboxylate;

ethyl 5-[(1R,5S,6r)-6-(ethoxycarbonyl)-3-azabicyclo[3.1.0]hex-3-yl]-2-azabicyclo[2.2.2]octane-2-carboxylate;

ethyl (1S,4S)-5-{(1R,5S,6r)-6-[ethyl(methyl)carbamoyl]-3-azabicyclo[3.1.0]hex-3-yl}-2-azabicyclo[2.2.2]octane-2-carboxylate;

ethyl (1R,4R)-5-{(1R,5S,6r)-6-[ethyl(methyl)carbamoyl]-3-azabicyclo[3.1.0]hexan-3-yl}-2-azabicyclo[2.2.2]octane-2-carboxylate;

ethyl (1S,4S)-5-[(1R,5S,6r)-6-(diethylcarbamoyl)-3-azabicyclo[3.1.0]hexan-3-yl]-2-azabicyclo[2.2.2]octane-2-carboxylate;

ethyl (1R,4R)-5-[(1R,5S,6r)-6-(diethylcarbamoyl)-3-azabicyclo[3.1.0]hexan-3-yl]-2-azabicyclo[2.2.2]octane-2-carboxylate;

methyl 5-[(1R,5S,6r)-6-(diethylcarbamoyl)-3-azabicyclo[3.1.0]hex-3-yl]-2-azabicyclo[2.2.2]octane-2-carboxylate;

ethyl 5-{(1R,5S,6r)-6-[ethyl(propan-2-yl)carbamoyl]-3-azabicyclo[3.1.0]hex-3-yl}-2-azabicyclo[2.2.2]octane-2-carboxylate;

ethyl (1S,4S)-5-{(1R,5S,6r)-6-[cyclopropyl(ethyl)carbamoyl]-3-azabicyclo[3.1.0]hex-3-yl}-2-azabicyclo[2.2.2]octane-2-carboxylate;

ethyl 5-{(1R,5S,6r)-6-[methoxy(methyl)carbamoyl]-3-azabicyclo[3.1.0]hexan-3-yl}-2-azabicyclo[2.2.2]octane-2-carboxylate;

ethyl 5-{(1R,5S,6r)-6-[ethyl(methoxy)carbamoyl]-3-azabicyclo[3.1.0]hex-3-yl}-2-azabicyclo[2.2.2]octane-2-carboxylate;

ethyl 3-{(1R,5S ,6r)-6-[ethyl(methyl)carbamoyl]-3-azabicyclo[3.1.0]hex-3-yl}-9-azabicyclo[3.3.1]nonane-9-carboxylate;

ethyl 3-[(1R,5S,6r)-6-(diethylcarbamoyl)-3-azabicyclo[3.1.0]hex-3-yl]-9-azabicyclo[3.3.1]nonane-9-carboxylate;

methyl 3-[(1R,5S,6r)-6-(diethylcarbamoyl)-3-azabicyclo[3.1.0]hex-3-yl]-9-azabicyclo[3.3.1]nonane-9-carboxylate;

ethyl 7-{(1R,5S ,6r)-6-[ethyl(methyl)carbamoyl]-3-azabicyclo[3.1.0]hex-3-yl}-3-oxa-9-azabicyclo[3.3.1]nonane-9-carboxylate;

ethyl 7-[(1R,5S,6r)-6-(diethylcarbamoyl)-3-azabicyclo[3.1.0]hex-3-yl]-3-oxa-9-azabicyclo[3.3.1]nonane-9-carboxylate;

methyl 7-[(1R,5S,6r)-6-(diethylcarbamoyl)-3-azabicyclo[3.1.0]hex-3-yl]-3-oxa-9-azabicyclo[3.3.1]nonane-9-carboxylate;

ethyl 7-{(1R,5S,6r)-6-[methyl(propan-2-yl)carbamoyl]-3-azabicyclo[3.1.0]hexan-3-yl}-3-oxa-9-azabicyclo[3.3.1]nonane-9-carboxylate;

methyl 7-((1R,5S ,6r)-6-(isopropyl(methyl)carbamoyl)-3-azabicyclo[3.1.0]hexan-3-yl)-3-oxa-9-azabicyclo[3.3.1]nonane-9-carboxylate;

ethyl 7-{(1R,5S ,6r)-6-[ethyl(propan-2-yl)carbamoyl]-3-azabicyclo[3.1.0]hex-3-yl}-3-oxa-9-azabicyclo[3.3.1]nonane-9-carboxylate;

methyl 7-{(1R,5S,6r)-6-[ethyl(propan-2-yl)carbamoyl]-3-azabicyclo[3.1.0]hexan-3-yl}-3-oxa-9-azabicyclo[3.3.1]nonane-9-carboxylate;

ethyl 7-{(1R,5S,6r)-6-[cyclopropyl(methyl)carbamoyl]-3-azabicyclo[3.1.0]hexan-3-yl}-3-oxa-9-azabicyclo[3.3.1]nonane-9-carboxylate;

ethyl 7-{(1R,5S ,6r)-6-[cyclopropyl(ethyl)carbamoyl]-3-azabicyclo[3.1.0]hex-3-yl}-3-oxa-9-azabicyclo[3.3.1]nonane-9-carboxylate;

methyl 7-{(1R,5S,6r)-6-[cyclopropyl(ethyl)carbamoyl]-3-azabicyclo[3.1.0]hexan-3-yl}-3-oxa-9-azabicyclo[3.3.1]nonane-9-carboxylate;

ethyl 7-[(1R,5S,6r)-6-(piperidin-1-ylcarbonyl)-3-azabicyclo[3.1.0]hex-3-yl]-3-oxa-9-azabicyclo[3.3.1]nonane-9-carboxylate;

methyl 7-[(1R,5S,6r)-6-(piperidine-1-carbonyl)-3-azabicyclo[3.1.0]hexan-3-yl]-3-oxa-9-azabicyclo[3.3.1]nonane-9-carboxylate;

ethyl 7-[(1R,5S,6r)-6-(morpholine-4-carbonyl)-3-azabicyclo[3.1.0]hexan-3-yl]-3-oxa-9-azabicyclo[3.3.1]nonane-9-carboxylate;

ethyl 7-[(1R,5S,6r)-6-(azepan-1-ylcarbonyl)-3-azabicyclo[3.1.0]hex-3-yl]-3-oxa-9-azabicyclo[3.3.1]nonane-9-carboxylate;

ethyl 7-[(1R,5S,6r)-6-(1-azaspiro[3.3]hept-1-ylcarbonyl)-3-azabicyclo[3.1.0]hex-3-yl]-3-oxa-9-azabicyclo[3.3.1]nonane-9-carboxylate;

ethyl 4-[(1R,5S,6r)-6-(diethylcarbamoyl)-3-azabicyclo[3.1.0]hexan-3-yl]azepane-1-carboxylate;

ethyl 3-[(1R,5S,6r)-6-(diethylcarbamoyl)-3-azabicyclo[3.1.0]hexan-3-yl]-6-azabicyclo[3.2.1]octane-6-carboxylate; and ethyl 5-[(1R,5S,6r)-6-(diethylcarbamoyl)-3-azabicyclo[3.1.0]hexan-3-yl]hexahydrocyclopenta[c]pyrrole-2(1H)-carboxylate, or salts thereof.

14. A pharmaceutical composition comprising a compound as defined in claim 1 and a pharmaceutically acceptable excipient.

15. The compound according to claim 13 which is methyl 6-[(1R,5S,6r)-6-(diethylcarbamoyl)-3-azabicyclo[3.1.0]hex-3-yl]-2-azaspiro[3.4]octane-2-carboxylate or a salt thereof.

16. The compound according to claim 13 which is ethyl 6-[(1R,5S,6r)-6-(diethylcarbamoyl)-3-azabicyclo[3.1.0]hex-3-yl]-2-azaspiro[3.4]octane-2-carboxylate or a salt thereof.

17. The compound according to claim 13 which is methyl 7-{(1R,5S,6r)-6-[ethyl(propan-2-yl)carbamoyl]-3-azabicyclo[3.1.0]hexan-3-yl}-3-oxa-9-azabicyclo[3.3.1]nonane-9-carboxylate or a salt thereof.

* * * * *